United States Patent
Hansen et al.

(10) Patent No.: US 7,144,898 B2
(45) Date of Patent: Dec. 5, 2006

(54) INDOLE DERIVATIVES FOR THE TREATMENT OF DEPRESSION AND ANXIETY

(75) Inventors: Marvin Martin Hansen, Indianapolis, IN (US); John Xiaoqiang He, Fishers, IN (US); Nicholas Allan Honigschmidt, Brownsburg, IN (US); Daniel James Koch, Indianapolis, IN (US); Todd Jonathan Kohn, Fishers, IN (US); Vincent Patrick Rocco, Indianapolis, IN (US); Patrick Gianpietro Spinazze, Avon, IN (US); Kumiko Takeuchi, Indianapolis, IN (US)

(73) Assignee: Eli Lilly and Company, Indianapolis, IN (US)

( * ) Notice: Subject to any disclaimer, the term of this patent is extended or adjusted under 35 U.S.C. 154(b) by 431 days.

(21) Appl. No.: 10/149,476

(22) PCT Filed: Dec. 6, 2000

(86) PCT No.: PCT/US00/32430

§ 371 (c)(1),
(2), (4) Date: Sep. 30, 2002

(87) PCT Pub. No.: WO01/46181

PCT Pub. Date: Jun. 28, 2001

(65) Prior Publication Data

US 2004/0006229 A1    Jan. 8, 2004

Related U.S. Application Data

(60) Provisional application No. 60/172,748, filed on Dec. 20, 1999.

(51) Int. Cl.
*A11K 31/445*    (2006.01)

(52) U.S. Cl. .................... 514/319; 514/277; 546/201; 546/202; 546/192; 546/195; 546/184

(58) Field of Classification Search ................ 544/289; 514/183, 319, 277; 546/202, 201, 192, 195, 546/184
See application file for complete search history.

(56) References Cited

U.S. PATENT DOCUMENTS

| | | | |
|---|---|---|---|
| 3,929,793 A | 12/1975 | Popelak et al. | |
| 4,304,915 A | 12/1981 | Berthold | |
| 5,300,498 A * | 4/1994 | Shutske | 514/218 |
| 5,576,321 A * | 11/1996 | Krushinski et al. | 514/254.09 |
| 5,627,196 A | 5/1997 | Audia et al. | |
| 5,789,402 A * | 8/1998 | Audia et al. | 514/212.02 |
| 5,912,256 A * | 6/1999 | Koch et al. | 514/323 |
| 6,242,450 B1 * | 6/2001 | Koch et al. | 514/255.04 |

FOREIGN PATENT DOCUMENTS

| | | |
|---|---|---|
| EP | 025111 | 3/1981 |
| EP | 722941 | 7/1996 |
| EP | 976747 | 2/2000 |
| WO | WO00/06166 | 2/2000 |
| WO | WO00/71517 | 11/2000 |

\* cited by examiner

*Primary Examiner*—James O. Wilson
*Assistant Examiner*—Jason H. Johnsen
(74) *Attorney, Agent, or Firm*—Danica Hostettler; Paul J. Gaylo

(57) ABSTRACT

The present invention provides compounds of formula (I): which are useful for treating depression, anxiety, and alleviating the symptoms caused by withdrawal or partial withdrawal from the use of tobacco or of nicotine.

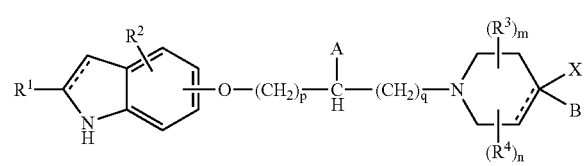

19 Claims, No Drawings

INDOLE DERIVATIVES FOR THE TREATMENT OF DEPRESSION AND ANXIETY

This application claims the benefit of Patent Cooperation Treaty Application No. PCT/US00/32430, filed 6 Dec. 2000, and U.S. patent application Ser. No. 60/172,748, filed 20 Dec. 1999, the contents of which are herein incorporated by reference.

Pharmaceutical researchers have discovered that the neurons of the brain which contain monoamines are of extreme importance in a great many physiological processes which very strongly affect many psychological and personality-affecting processes as well. In particular, serotonin (5-hydroxytryptamine; 5-HT) has been found to be a key to a very large number of processes which affect both physiological and psychological functions. Drugs which influence the function of serotonin in the brain are accordingly of great importance and are now used for a surprisingly large number of different therapies.

The early generations of serotonin-affecting drugs tended to have a variety of different physiological functions, considered from both the mechanistic and therapeutic points of view. For example, many of the tricyclic antidepressant drugs are now known to be active as inhibitors of serotonin reuptake, and also to have anticholinergic, antihistaminic or anti-α-adrenergic activity. More recently, it has become possible to study the function of drugs at individual receptors in vitro or ex vivo, and it has also been realized that therapeutic agents free of extraneous mechanisms of action are advantageous to the patient.

The present invention provides compounds which have highly selective activity as antagonists and partial agonists of the serotonin $1_A$ receptor and a second activity as inhibitors of reuptake of serotonin. The best-known pharmaceutical with the latter efficacy is fluoxetine, and the importance of its use in the treatment of depression and other conditions is extremely well documented and publicized. Artigas, *TIPS*, 14, 262 (1993), have suggested that the efficacy of a reuptake inhibitor may be decreased by the activation of serotonin $1_A$ receptors with the resultant reduction in the firing rate of serotonin neurons. Accordingly, present research in the central nervous system is focusing on the effect of combining reuptake inhibitors with compounds which affect the 5-$HT_{1A}$ receptor.

Compounds exhibiting both serotonin reuptake inhibition activity and 5-$HT_{1A}$ antagonist activity have been described, for example in U.S. Pat. No. 5,576,321, issued Nov. 19, 1996. It has been found that compounds of the present invention are potent serotonin reuptake inhibitors and antagonists of the 5-$HT_{1A}$ receptor.

The present invention provides compounds of formula I:

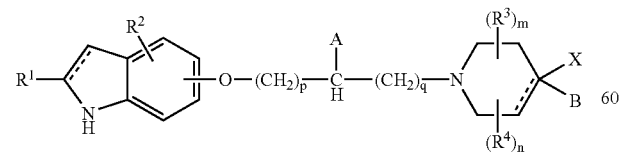

formula I wherein
A is hydrogen or OH:
B is selected from the group consisting of:

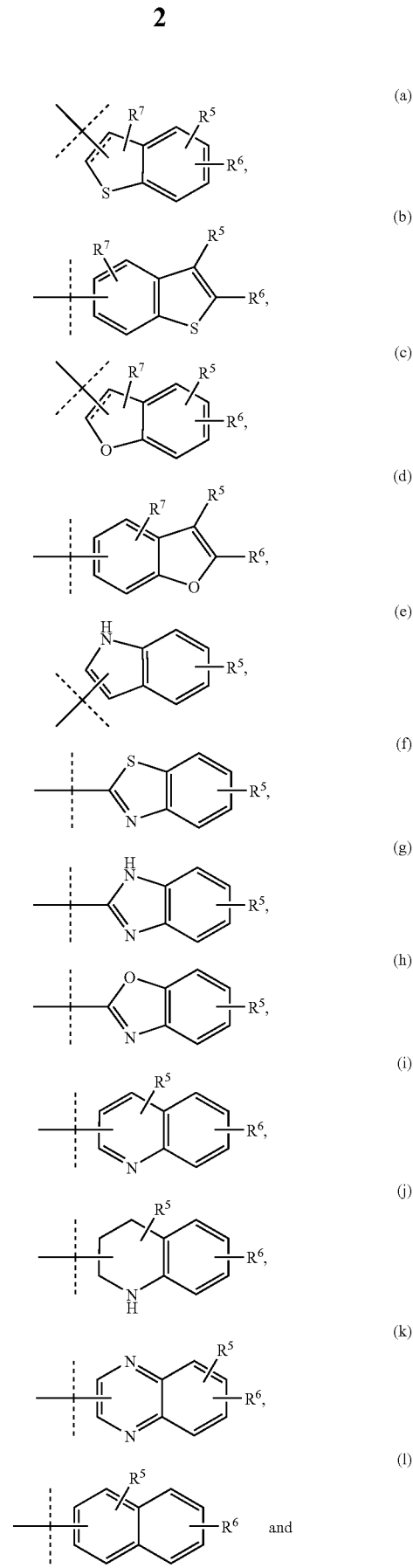

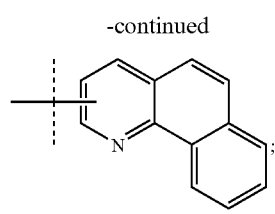

(m)

- - - - represents a single or a double bond;

X is hydrogen, OH or $C_1$–$C_6$ alkoxy when - - - - represents a single bond in the piperidine ring, and X is nothing when - - - - represents a double bond in the piperidine ring;

$R^1$ is hydrogen, F, $C_1$–$C_{20}$ alkyl, —C(=O)$NR^8R^9$, or CN;

$R^2$ is hydrogen, F, Cl, Br, I, OH, $C_1$–$C_6$ alkyl or $C_1$–$C_6$ alkoxy;

$R^3$ and $R^4$ are each independently hydrogen or $C_1$–$C_4$ alkyl;

$R^5$ and $R^6$ are each independently hydrogen, F, Cl, Br, I, OH, $C_1$–$C_6$ alkyl, $C_1$–$C_6$ alkoxy, halo($C_1$–$C_6$)alkyl, phenyl, —C(=O)$NR^8R^9$, $NO_2$, $NH_2$, CN, or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, $NO_2$, $NH_2$, CN, and phenyl;

$R^7$ is hydrogen, F, Cl, Br, I, OH, $C_1$–$C_6$ alkyl or ($C_1$–$C_6$ alkyl)$NR^8R^9$;

$R^8$ and $R^9$ are each independently hydrogen or $C_1$–$C_{10}$ alkyl;

m is 0, 1, or 2;

n is 0, 1, or 2;

p is 0, 1, 2, 3 or 4; and q is 0, 1, 2 or 3; or a pharmaceutically acceptable salt thereof;

with the proviso that if both $R^3$ and $R^4$ represent hydrogen, then $R^1$ is F, $C_1$–$C_{20}$ alkyl, —C(=O)$NR^8R^9$, or CN.

The present invention further provides a method of inhibiting the reuptake of serotonin and antagonizing the 5-$HT_{1A}$ receptor which comprises administering to a patient an effective amount of a compound of formula I.

More particularly, the present invention provides a method for alleviating the symptoms caused by withdrawal or partial withdrawal from the use of tobacco or of nicotine; a method of treating anxiety; and a method of treating a condition chosen from the group consisting of depression, hypertension, cognitive disorders, Alzheimer's disease, psychosis, sleep disorders, gastric motility disorders, sexual dysfunction, brain trauma, memory loss, eating disorders and obesity, substance abuse, obsessive-compulsive disease, panic disorder, and migraine; which methods comprise administering to a patient an effective amount of a compound of formula I.

In addition, the present invention provides a method of potentiating the action of a serotonin reuptake inhibitor comprising administering to a patient an effective amount of a compound of formula I in combination with an effective amount of a serotonin reuptake inhibitor.

In addition, the invention provides pharmaceutical compositions of compounds of formula I, including the hydrates thereof, comprising, as an active ingredient, a compound of formula I in combination with a pharmaceutically acceptable carrier, diluent or excipient. This invention also encompasses novel intermediates, and processes for the synthesis of the compounds of formula I.

According to another aspect, the present invention provides the use of a compound of formula I, or a pharmaceutically acceptable salt thereof as defined hereinabove for the manufacture of a medicament for inhibiting the reuptake of serotonin and antagonizing the 5-$HT_{1A}$ receptor.

According to yet another aspect, the present invention provides the use of a compound of formula I or a pharmaceutically acceptable salt thereof as defined hereinabove for inhibiting the reuptake of serotonin and antagonizing the 5-$HT_{1A}$ receptor.

In addition, compounds of the present invention can be inhibitors of serotonin reuptake, dopamine reuptake, and norepinephrine reuptake.

It is understood that the compounds of formula Ia:

formula Ia

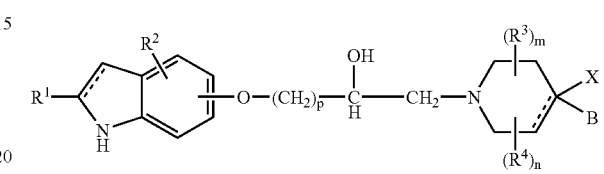

are included within the scope of the present invention wherein the substituents are defined as herein.

It is further understood that the compounds of formula Iaa:

formula Iaa

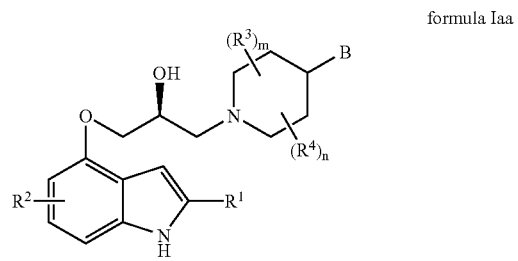

are included within the scope of the present invention wherein the substituents are defined as herein.

As used herein, the terms "Me", "Et", "Pr", "i-Pr", "Bu" and "t-Bu" refer to methyl, ethyl, propyl, isopropyl, butyl and tert-butyl respectively.

As used herein, the terms "Halo", "Halide" or "Hal" refer to a chlorine, bromine, iodine or fluorine atom, unless otherwise specified herein.

As used herein the term "$C_1$–$C_4$ alkyl" refers to a straight or branched, monovalent, saturated aliphatic chain of 1 to 4 carbon atoms and includes, but is not limited to methyl, ethyl, n-propyl, isopropyl, n-butyl, isobutyl and the like.

As used herein the term "$C_1$–$C_6$ alkyl" refers to a straight or branched, monovalent, saturated aliphatic chain of 1 to 6 carbon atoms and includes, but is not limited to methyl, ethyl, n-propyl, isopropyl, n-butyl, isobutyl, t-butyl, n-pentyl, n-hexyl, and the like.

As used herein the term "$C_1$–$C_{10}$ alkyl" refers to a straight or branched, monovalent, saturated aliphatic chain of 1 to 10 carbon atoms and includes, but is not limited to methyl, ethyl, propyl, isopropyl, n-butyl, isobutyl, tertiary butyl, pentyl, isopentyl, hexyl, 2,3-dimethyl-2-butyl, heptyl, 2,2-dimethyl-3-pentyl, 2-methyl-2-hexyl, octyl, 4-methyl-3-heptyl and the like.

As used herein the term "$C_1$–$C_{20}$ alkyl" refers to a straight or branched, monovalent, saturated aliphatic chain of 1 to 20 carbon atoms and includes, but is not limited to, methyl, ethyl, propyl, isopropyl, butyl, isobutyl, t-butyl, pentyl, isopentyl, hexyl, 3-methylpentyl, 2-ethylbutyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-nonadecyl, n-eicosyl and the like.

As used herein the term "halo($C_1$–$C_6$)alkyl" refers to a straight or branched alkyl chain having from one to six carbon atoms with 1, 2 or 3 halogen atoms attached to it. Typical halo($C_1$–$C_6$)alkyl groups include chloromethyl, 2-bromoethyl, 1-chloroisopropyl, 3-fluoropropyl, 2,3-dibromobutyl, 3-chloroisobutyl, iodo-t-butyl, trifluoromethyl and the like. The term "halo($C_1$–$C_6$)alkyl" includes within its definition the term "halo($C_1$–$C_4$)alkyl".

As used herein the term "$C_1$–$C_6$ alkoxy" refers to a straight or branched alkyl chain having from one to six carbon atoms attached to an oxygen atom. Typical $C_1$–$C_6$ alkoxy groups include methoxy, ethoxy, propoxy, isopropoxy, butoxy, t-butoxy, pentoxy and the like. The term "$C_1$–$C_6$ alkoxy" includes within its definition the term "$C_1$–$C_4$ alkoxy".

The designation "◂▬" refers to a bond that protrudes forward out of the plane of the page.

The designation "⋯▮" refers to a bond that protrudes backward out of the plane of the page.

This invention includes the hydrates and the pharmaceutically acceptable salts of the compounds of formula I. A compound of this invention can possess a sufficiently basic functional group which can react with any of a number of inorganic and organic acids, to form a pharmaceutically acceptable salt.

The term "pharmaceutically acceptable salt" as used herein, refers to salts of the compounds of formula I which are substantially non-toxic to living organisms. Typical pharmaceutically acceptable salts include those salts prepared by reaction of the compounds of the present invention with a pharmaceutically acceptable mineral or organic acid. Such salts are also known as acid addition salts. Such salts include the pharmaceutically acceptable salts listed in *Journal of Pharmaceutical Science,* 66, 2–19 (1977) which are known to the skilled artisan.

Acids commonly employed to form acid addition salts are inorganic acids such as hydrochloric acid, hydrobromic acid, hydroiodic acid, sulfuric acid, phosphoric acid, and the like, and organic acids such as p-toluenesulfonic, methanesulfonic acid, benzenesulfonic acid, oxalic acid, p-bromophenylsulfonic acid, carbonic acid, succinic acid, citric acid, benzoic acid, acetic acid, and the like. Examples of such pharmaceutically acceptable salts are the sulfate, pyrosulfate, bisulfate, sulfite, bisulfite, phosphate, monohydrogenphosphate, dihydrogenphosphate, metaphosphate, pyrophosphate, bromide, iodide, acetate, propionate, decanoate, caprate, caprylate, acrylate, ascorbate, formate, hydrochloride, dihydrochloride, isobutyrate, caproate, heptanoate, propiolate, propionate, phenylpropionate, salicylate, oxalate, malonate, succinate, suberate, sebacate, fumarate, malate, maleate, hydroxymaleate, mandelate, nicotinate, isonicotinate, cinnamate, hippurate, nitrate, phthalate, teraphthalate, butyne-1,4-dioate, butyne-1,4-dicarboxylate, hexyne-1,4-dicarboxylate, hexyne-1,6-dioate, benzoate, chlorobenzoate, methylbenzoate, hydroxybenzoate, methoxybenzoate, dinitrobenzoate, o-acetoxybenzoate, naphthalene-2-benzoate, phthalate, p-toluenesulfonate, p-bromobenzenesulfonate, p-chlorobenzenesulfonate, xylenesulfonate, phenylacetate, trifluoroacetate, phenylpropionate, phenylbutyrate, citrate, lactate, α-hydroxybutyrate, glycolate, tartrate, benzenesulfonate, methanesulfonate, ethanesulfonate, propanesulfonate, hydroxyethanesulfonate, naphthalene-1-sulfonate, napthtalene-2-sulfonate, mandelate, tartarate, and the like. Preferred pharmaceutically acceptable acid addition salts are those formed with mineral acids such as hydrochloric acid and hydrobromic acid, and those formed with organic acids such as maleic acid, oxalic acid and methanesulfonic acid.

It should be recognized that the particular counterion forming a part of any salt of this invention is usually not of a critical nature, so long as the salt as a whole is pharmacologically acceptable and as long as the counterion does not contribute undesired qualities to the salt as a whole. It is further understood that such salts may exist as a hydrate.

As used herein, the term "stereoisomer" refers to a compound made up of the same atoms bonded by the same bonds but having different three-dimensional structures which are not interchangeable. The three-dimensional structures are called configurations. As used herein, the term "enantiomer" refers to two stereoisomers whose molecules are nonsuperimposable mirror images of one another. The term "chiral center" refers to a carbon atom to which four different groups are attached. As used herein, the term "diastereomers" refers to stereoisomers which are not enantiomers. In addition, two diastereomers which have a different configuration at only one chiral center are referred to herein as "epimers". The terms "racemate", "racemic mixture" or "racemic modification" refer to a mixture of equal parts of enantiomers.

The term "enantiomeric enrichment" as used herein refers to the increase in the amount of one enantiomer as compared to the other. A convenient method of expressing the enantiomeric enrichment achieved is the concept of enantiomeric excess, or "ee", which is found using the following equation:

$$ee = \frac{E^1 - E^2}{E^1 + E^2} \times 100$$

wherein $E^1$ is the amount of the first enantiomer and $E^2$ is the amount of the second enantiomer. Thus, if the initial ratio of the two enantiomers is 50:50, such as is present in a racemic mixture, and an enantiomeric enrichment sufficient to produce a final ratio of 50:30 is achieved, the ee with respect to the first enantiomer is 25%. However, if the final ratio is 90:10, the ee with respect to the first enantiomer is 80%. An ee of greater than 90% is preferred, an ee of greater than 95% is most preferred and an ee of greater than 99% is most especially preferred. Enantiomeric enrichment is readily determined by one of ordinary skill in the art using standard techniques and procedures, such as gas or high performance liquid chromatography with a chiral column. Choice of the appropriate chiral column, eluent and conditions necessary to effect separation of the enantiomeric pair is well within the knowledge of one of ordinary skill in the art. In addition, the enantiomers of compounds of formulas I or Ia can be resolved by one of ordinary skill in the art using standard techniques well known in the art, such as those described by J. Jacques, et al., "Enantiomers, Racemates, and Resolutions", John Wiley and Sons, Inc., 1981.

Some of the compounds of the present invention have one or more chiral centers and may exist in a variety of stereoisomeric configurations. As a consequence of these chiral centers, the compounds of the present invention occur as racemates, mixtures of enantiomers and as individual enantiomers, as well as diastereomers and mixtures of diastereomers. All such racemates, enantiomers, and diastereomers are within the scope of the present invention.

The terms "R" and "S" are used herein as commonly used in organic chemistry to denote specific configuration of a chiral center. The term "R" (rectus) refers to that configuration of a chiral center with a clockwise relationship of group priorities (highest to second lowest) when viewed along the bond toward the lowest priority group. The term "S" (sinister) refers to that configuration of a chiral center with a counterclockwise relationship of group priorities (highest to second lowest) when viewed along the bond toward the lowest priority group. The priority of groups is based upon their atomic number (in order of decreasing atomic number). A partial list of priorities and a discussion of stereochemistry is contained in "Nomenclature of Organic Compounds: Principles and Practice", (J. H. Fletcher, et al., eds., 1974) at pages 103–120.

The specific stereoisomers and enantiomers of compounds of formula (I) can be prepared by one of ordinary skill in the art utilizing well known techniques and processes, such as those disclosed by Eliel and Wilen, "Stereochemistry of Organic Compounds", John Wiley & Sons, Inc., 1994, Chapter 7, Separation of Stereoisomers. Resolution. Racemization, and by Collet and Wilen, "Enantiomers, Racemates, and Resolutions", John Wiley & Sons, Inc., 1981. For example, the specific stereoisomers and enantiomers can be prepared by stereospecific syntheses using enantiomerically and geometrically pure, or enantiomerically or geometrically enriched starting materials. In addition, the specific stereoisomers and enantiomers can be resolved and recovered by techniques such as chromatography on chiral stationary phases, enzymatic resolution or fractional recrystallization of addition salts formed by reagents used for that purpose.

As used herein, the term "SRI" refers to serotonin reuptake inhibitor.

As used herein the term "serotonin" is equivalent to and interchangeable with the terms "5-HT" or "5-hydroxytryptamine".

As used herein, "Pg" refers to a protecting group on the amine which is commonly employed to block or protect the amine while reacting other functional groups on the compound. Examples of protecting groups (Pg) used to protect the amino group and their preparation are disclosed by T. W. Greene, "Protective Groups in Organic Synthesis," John Wiley & Sons, 1981, pages 218–287. Choice of the protecting group used will depend upon the substituent to be protected and the conditions that will be employed in subsequent reaction steps wherein protection is required, and is well within the knowledge of one of ordinary skill in the art. Preferred protecting groups are t-butoxycarbonyl also known as a BOC protecting group, and benzyloxycarbonyl also known as a Cbz protecting group.

The compounds of formula I can be prepared by techniques and procedures readily available to one of ordinary skill in the art. For example, various starting materials and general procedures which may be employed by one of ordinary skill in the art in the preparation of compounds of formula I are described in U.S. Pat. No. 3,929,793, issued Dec. 30, 1975, U.S. Pat. No. 4,304,915, issued Dec. 8, 1981, U.S. Pat. No. 4,288,442, issued Sep. 8, 1981, U.S. Pat. No. 4,361,562, issued Nov. 30, 1982, U.S. Pat. No. 4,460,586, issued Jul. 17, 1984, U.S. Pat. No. 4,704,390, issued Nov. 3, 1987, U.S. Pat. No. 4,935,414, issued Jun. 19, 1990, U.S. Pat. No. 5,013,761, issued May 7, 1991, and U.S. Pat. No. 5,614,523, issued Mar. 25, 1997. More specifically, compounds of formula I can be prepared by following the procedures as set forth in Schemes I through IV. All substituents, unless otherwise indicated, are previously defined. The reagents and starting materials are readily available to one of ordinary skill in the art. More specifically, Schemes I through II provide general syntheses of various intermediate piperidines.

Scheme I

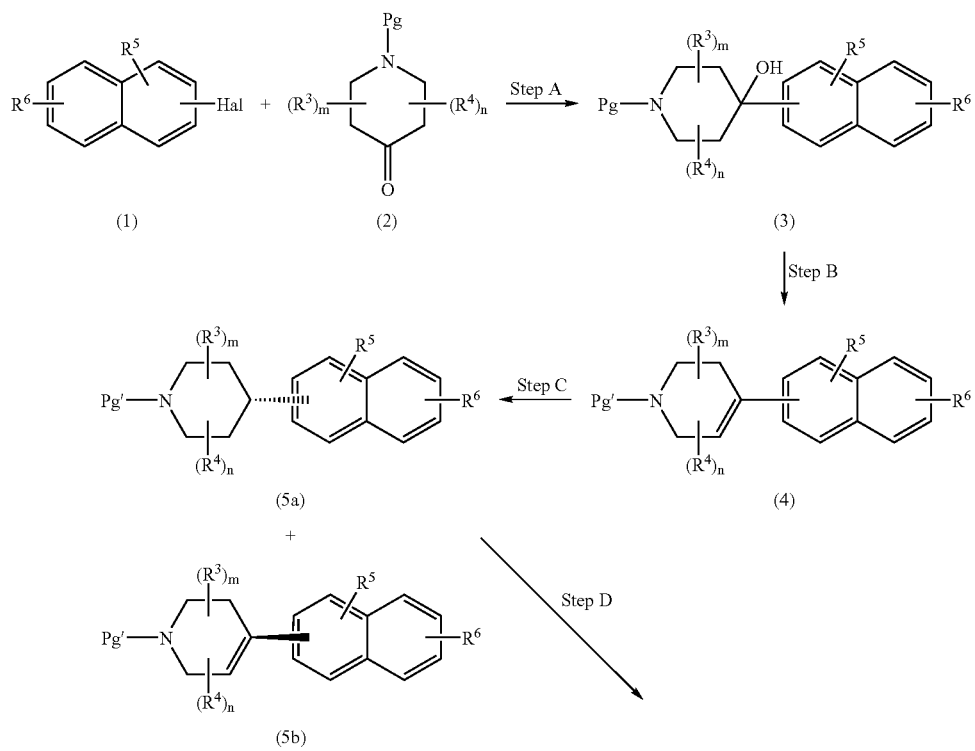

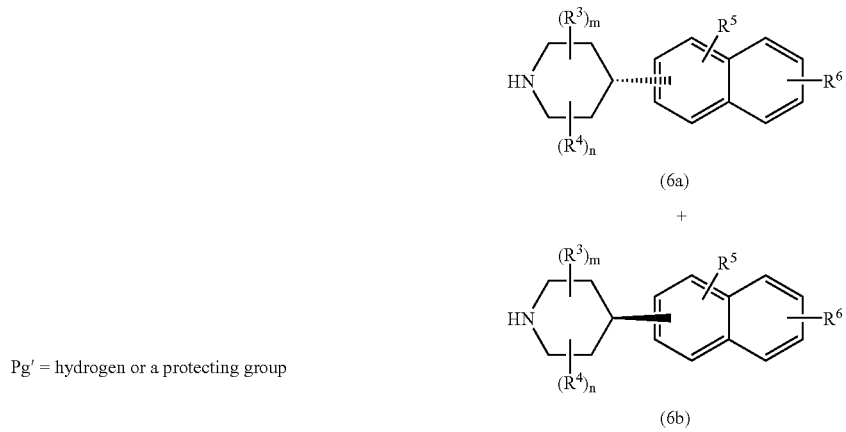

(6a)

+

(6b)

Pg' = hydrogen or a protecting group

In Scheme I, step A, compound (1) is added to piperidone (2) under conditions well known in the art, to provide the alcohol (3). For example, an appropriately substituted naphthalene, such as 2-bromonaphthalene, 1-bromo-5-methoxy-naphthalene, 2-bromo-7-methoxy-naphthalene, 6-iodo-1-methoxy-naphthalene, and the like, is dissolved in a suitable organic solvent, such as tetrahydrofuran, and cooled to about −78° C. To this stirring solution is added an excess of a suitable base, such as t-butyllithium. The mixture is stirred for about 1 to 3 hours, and about 1.0 to about 1.1 equivalents of the piperidone (2) are added. The reaction is allowed to warm to room temperature and the alcohol (3) is isolated and purified by techniques well known in the art. For example, the mixture is diluted with water and extracted with a suitable organic solvent, such as ethyl acetate. The organic extracts are combined, washed with brine, dried over anhydrous sodium sulfate, filtered and concentrated under vacuum. The crude alcohol can then be purified by flash chromatography on silica gel with a suitable eluent, such as ethyl acetate/hexanes to provide the purified alcohol (3). Alternatively, the crude isolated alcohol (3) can be carried directly onto the next step.

The piperidones (2) are readily available to one of ordinary skill in the art utilizing known starting materials. For example, I. V. Micovic, et al., *J. Chem. Soc., Perkin Trans.*, 1(16), 2041–2050 (1996) teach the preparation of variously substituted piperidine-2,4-diones. Such piperidine-2,4-diones can be selectively protected, alkylated, and reduced under conditions well known in the art to provide the desired piperidone (2). For example, compounds of the formula (2a')

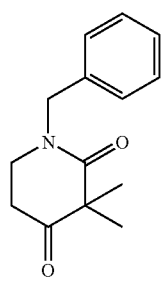

(2a')

can be prepared in a manner analogous to the procedure described by Micovic et al. Above, which can then be reduced to provide the 2,2-disubstituted-N-protected-4-piperidone (2a").

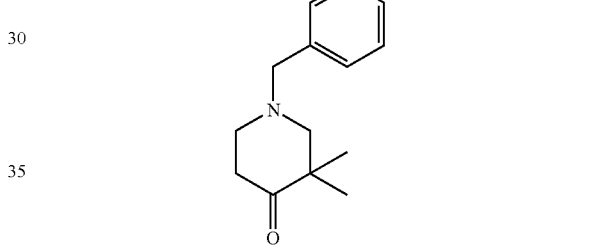

(2a")

In Scheme I, step B, the alcohol (3) is dehydrated under standard conditions to provide the 1,2,5,6-tetrahydropyridine (4) wherein Pg' is maintained as a protecting group and does not represent hydrogen. For example, the alcohol (3) is dissolved in a suitable organic solvent, such as toluene, and treated with an excess of a suitable acid, such as p-toluenesulfonic acid monohydrate. The reaction mixture is heated at reflux for about 6 to 12 hours and then cooled. The 1,2,5,6-tetrahydropyridine is then isolated and purified under conditions well known in the art. For example, the cooled reaction mixture is basified with 2 N sodium hydroxide and extracted with a suitable organic solvent, such as ethyl acetate. The organic extracts are combined, washed with brine, dried over anhydrous sodium sulfate, filtered and concentrated under vacuum. The crude residue is then purified by flash chromatography on silica gel with a suitable eluent, such as methanol/methylene chloride to provide the purified 1,2,5,6-tetrahydropyridine (4).

Alternatively, in Scheme I, step B, the alcohol (3) can be dehydrated and deprotected concomitantly under standard conditions to provide the compound (4) wherein Pg' is hydrogen. For example, the alcohol (3) wherein the protecting group is N-t-butoxycarbonyl is dissolved in a suitable organic solvent, such as dry dichloromethane, and the solution is cooled to about 0° C. To this solution is added excess trifluoroacetic acid and the reaction mixture is stirred at about 0° C. for about 15 h. The reaction is then quenched at room temperature with saturated aqueous NaHCO₃ solution.

The product is then isolated by techniques well known in the art, such as extraction and then purified by flash chromatography. For example, the mixture is extracted with a suitable organic solvent, such as dichloromethane, the combined organic extracts are dried over anhydrous magnesium sulfate, filtered and concentrated under vacuum to provide the crude compound (4). This material can be purified by flash chromatography on silica gel with a suitable eluent, such as ethyl acetate/hexanes.

In Scheme I, step C, the 1,2,5,6-tetrahydropyridine (4) is hydrogenated under conditions well known in the art to provide a mixture of piperidines (5a) and (5b). For example, the 1,2,5,6-tetrahydropyridine (4) is dissolved in a suitable organic solvent, such as ethanol and treated with a suitable catalyst, such as 5% palladium on carbon. The mixture is then placed under an atmosphere of hydrogen and stirred for about 12 hours at room temperature. The reaction mixture is then filtered to remove the catalyst and the filtrate is concentrated under vacuum to provide a mixture of isomers (5a) and (5b). It is readily appreciated by one of ordinary skill in the art that various isomers may exist at this step wherein the R groups ($R^3$ and $R^4$) can be either cis or trans to the naphthyl group. It is further recognized that these isomers may be separated from one another by techniques well known in the art, such as flash chromatography, radial chromatography or high performance liquid chromatography on silica gel with a suitable eluent, such as methanol/methylene chloride. Alternatively, the mixture of isomers may be carried on to the next step or the separated isomers may individually be carried onto the next step.

In Scheme I, step D, wherein Pg' is a protecting group and not hydrogen, the piperidines (5a) and (5b) are deprotected under conditions well known to one of ordinary skill in the art to provide piperidines (6a) and (6b). For example, when Pg is a methyl group, the piperidines (5a) and (5b) are dissolved in a suitable organic solvent, such as dichloroethane and cooled to about 0° C. The cooled solution is then treated with an excess of 1-chloroethylchloroformate. The reaction is then allowed to warm to room temperature and then heated at reflux for about 12 hours. After cooling, the solvent is then removed under vacuum and the residue is dissolved in a suitable organic solvent, such as methanol. The solution is then heated at reflux for about 2 to 4 hours, cooled to room temperature, and then concentrated under vacuum. The residue is treated with water and a suitable organic solvent, such as ethyl acetate. The phases are separated and the aqueous phase is extracted with ethyl acetate. The organic extracts, including the first organic phase, are combined, rinsed with brine, dried over anhydrous sodium sulfate, filtered and concentrated under vacuum to provide the crude piperidines (6a) and (6b). The mixture can then be separated into purified individual stereoisomers if they were not already separated in step C using similar techniques, such as flash chromatography, radial chromatography or high performance chromatography on silica gel with a suitable eluent, such as methanol/methylene chloride.

It is readily appreciated by one of ordinary skill in the art that the sequence of steps of dehydration, deprotection, and reduction can be varied depending upon the protecting groups utilized and the ultimate products desired. The conditions required for varying the sequence are well within the knowledge of one of ordinary skill in the art.

Scheme IA

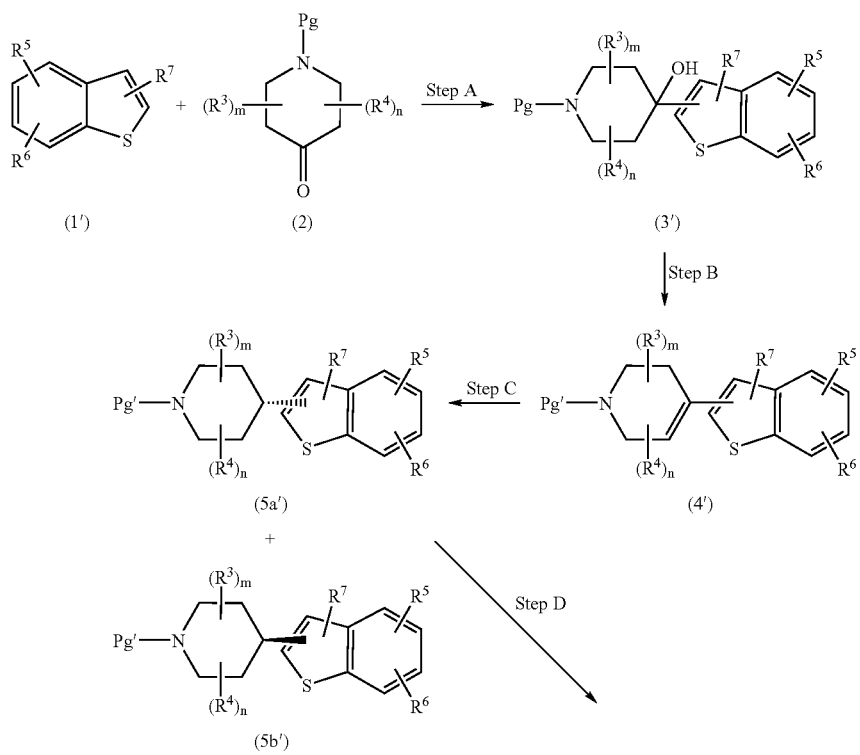

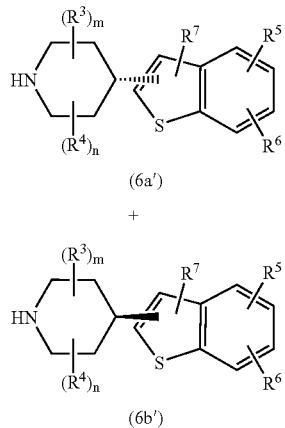
In Scheme IA, the steps A through D are carried out in a manner analogous to the procedures set forth in Scheme I, steps A through D respectively.
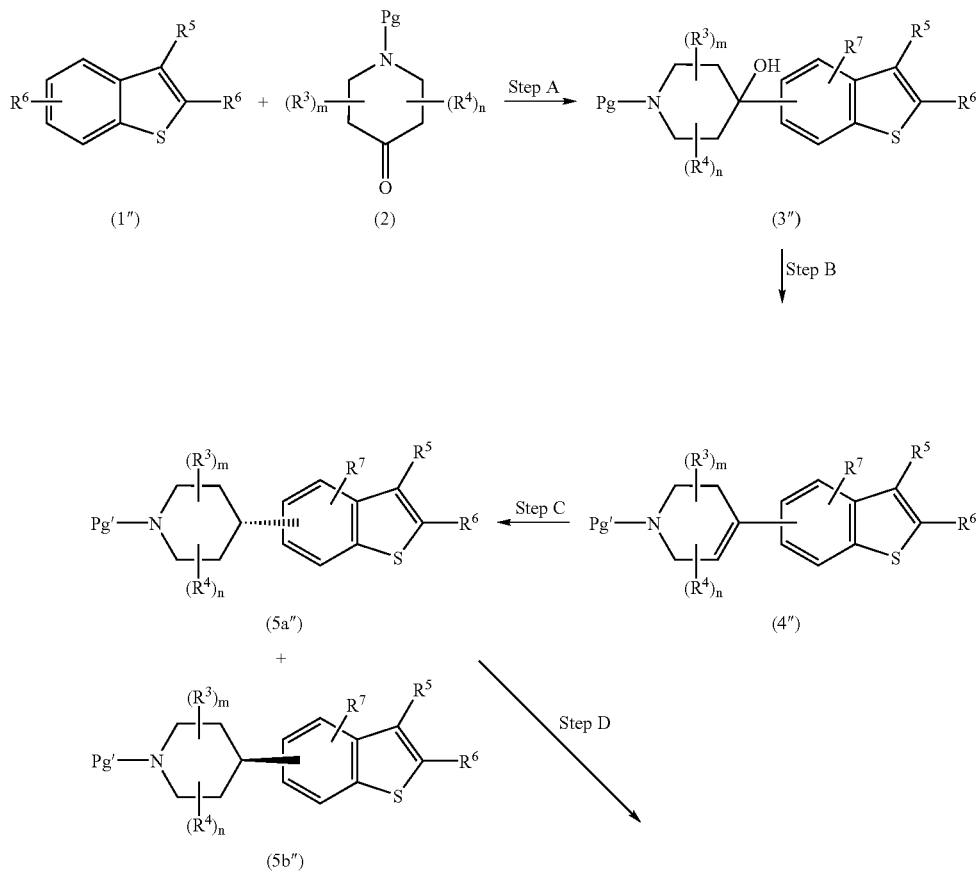

-continued

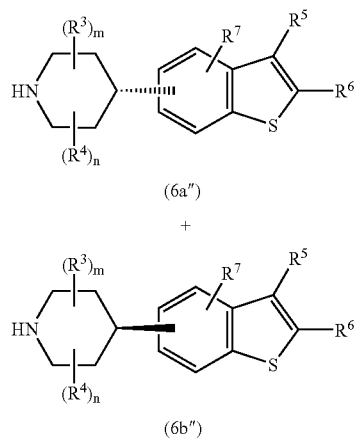

In Scheme IAA, the steps A through D are carried out in a manner analogous to the procedures set forth in Scheme I, steps A through D respectively.

Scheme IB

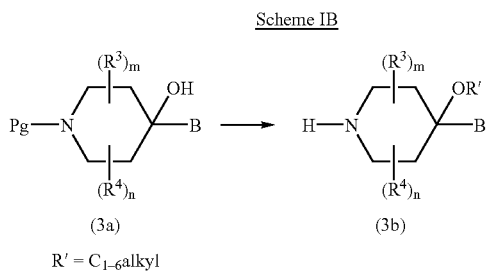

R' = C$_{1-6}$alkyl

In Scheme IB, alcohol (3a) is alkylated under standard conditions to provide the ether (3b). For example, alcohol (3a), wherein the protecting group is N-t-butoxycarbonyl, is dissolved in a suitable organic solvent, such as dry MeOH and the solution is cooled to about 0° C. To this solution is added excess trifluoroacetic acid. The reaction mixture is then stirred at room temperature for about one to 6 days. The reaction is then quenched at room temperature with saturated aqueous NaHCO$_3$ solution, extracted with a suitable organic solvent such as dichloromethane, the combined organic extracts are dried over anhydrous magnesium sulfate, filtered and concentrated under vacuum to provide the crude ether (3b). The crude ether (3b) can then be purified by flash chromatography on silica gel with a suitable eluent, such as 7% (10% conc. NH$_4$OH in MeOH)/CH$_2$Cl$_2$.

Scheme IC

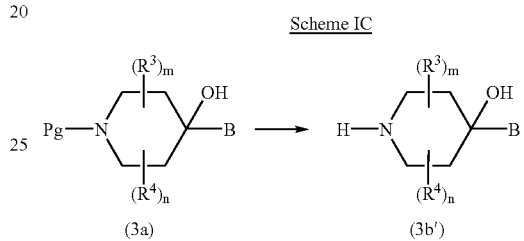

In Scheme IC, alcohol (3a) can be deprotected without dehydration under standard conditions well known in the art, through appropriate choice of protecting groups, to provide the deprotected alcohol (3b'). For example, the alcohol (3a), wherein the protecting group is a —CH$_2$CH=CH$_2$ group, is dissolved in a suitable solvent, such as aqueous ethanol (10% H$_2$O). The solution is then treated with chlorotris (triphenylphosphine) rhodium(I) (Wilkinson's catalyst) and approximately 50% of the solvent is then distilled off over a period of about 1 hour. An additional 65 mL of solvent and 45 mg of Wilkinson's catalyst is added and the reaction mixture is refluxed for about 1 hour and then the solvent is again distilled off to about 50% volume. The reaction mixture is then evaporated and the residue is purified using silica gel chromatography with a suitable eluent, such as dichloromethane/20% methanol, 2% anhydrous ammonia in dichloromethane gradient, to provide the purified deprotected alcohol (3b').

Scheme II

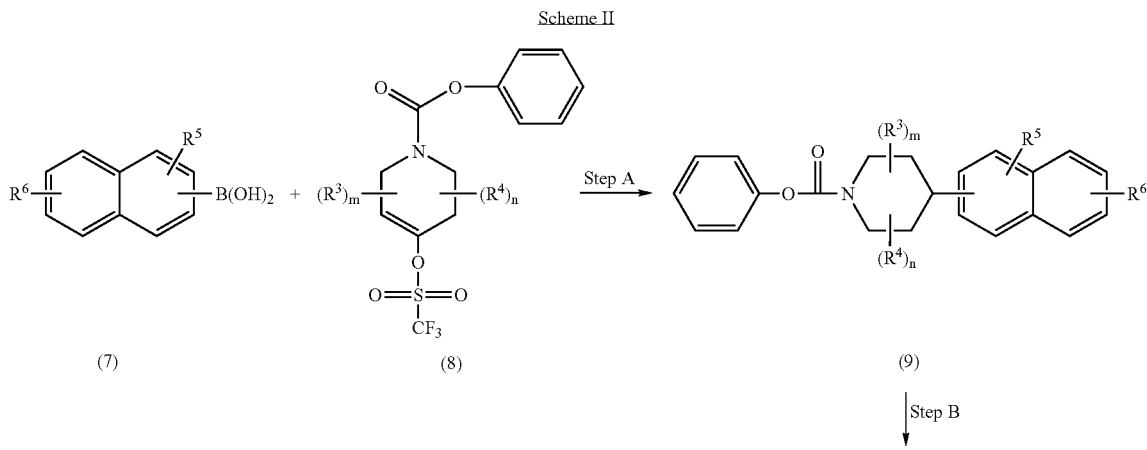

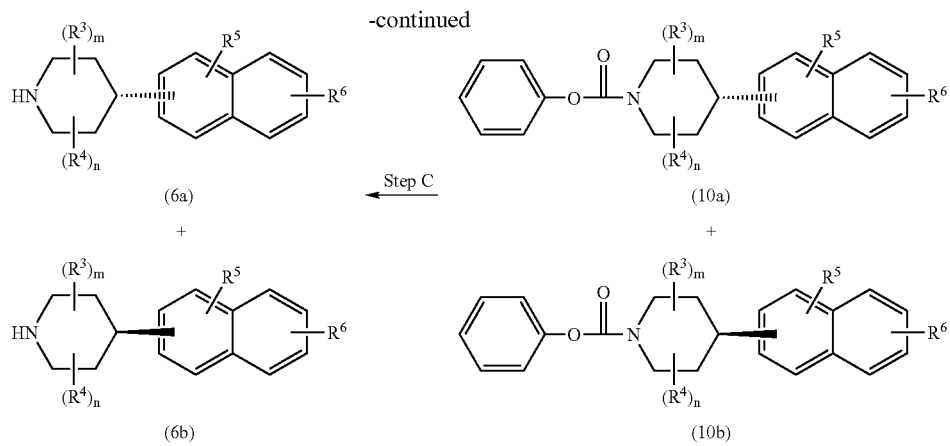

In Scheme II, step A, a naphthylboronic acid (7), such as 2-naphthylboronic acid is combined with the 1,2,5,6-tetrahydropyridine (8) to provide the coupled compound (9). For example, about 1 to 1.5 equivalents of a naphthylboronic acid (7) is combined with about 1 equivalent of 1,2,5,6-tetrahydropyridine (8), about 2 equivalents of lithium chloride, a catalytic amount of tetrakis(triphenylphosphine)palladium(0) in a mixture of 2 M aqueous sodium carbonate and tetrahydrofuran. The mixture is heated at reflux for about 12 hours and then cooled to room temperature. The reaction is then treated with 2 N sodium hydroxide and extracted with a suitable organic solvent, such as ethyl acetate. The organic extracts are combined, rinsed with brine, dried over anhydrous sodium sulfate, filtered and concentrated under vacuum. The crude residue is then purified by flash chromatography on silica gel with a suitable eluent such as ethyl acetate/hexanes to provide the compound (9).

In Scheme II, step B, the compound (9) is hydrogenated under standard conditions to provide the piperidines (10a) and (10b). For example, the compound (9) is dissolved in a suitable organic solvent, such as methanol, treated with a suitable catalyst, such as 5% palladium on carbon and stirred under an atmosphere of hydrogen for about 12 hours at room temperature. The reaction mixture is then filtered to remove the catalyst and the filtrate is concentrated under vacuum to provide piperidines (10a) and (10b). As noted in Scheme I, step C, it is readily appreciated by one of ordinary skill in the art that various isomers may exist at this particular step wherein the R groups ($R^3$ or $R^4$) can be either cis or trans to the naphthyl group. It is further recognized that these isomers may be separated from one another by techniques well known in the art, such as flash chromatography, radial chromatography or high performance liquid chromatography on silica gel with a suitable eluent, such as methanol/methylene chloride. Alternatively, the mixture of isomers may be carried on to the next step or the separated isomers may individually be carried onto the next step.

In Scheme II, step C, the piperidines (10a) and (10b) are deprotected under conditions well known in the art to provide the piperidines (6a) and (6b). For example, piperidines (10a) and (10b) are dissolved in a suitable solvent mixture, such as 50% water/isopropanol and treated with an excess of a suitable base, such as potassium hydroxide. The reaction mixture is then heated at reflux for about 1 to 3 days and then cooled to room temperature. 2 N sodium hydroxide is added and the reaction is extracted with a suitable organic solvent, such as ethyl acetate. The organic extracts are combined, rinsed with brine, dried over anhydrous sodium sulfate, filtered and concentrated under vacuum. The crude residue is then purified by flash chromatography on silica gel with a suitable eluent, such as methanol/methylene chloride to provide the purified piperidines (6a) and (6b). The mixture can then be separated into individual stereoisomers if they were not already separated in step C using similar techniques, such as flash chromatography, radial chromatography or high performance chromatography on silica gel with a suitable eluent, such as methanol/methylene chloride.

It is readily appreciated by one of ordinary skill in the art that compounds (4), (4') and (9) can be deprotected prior to reduction and the unsaturated deprotected piperidines can be used directly in Schemes III and IV.

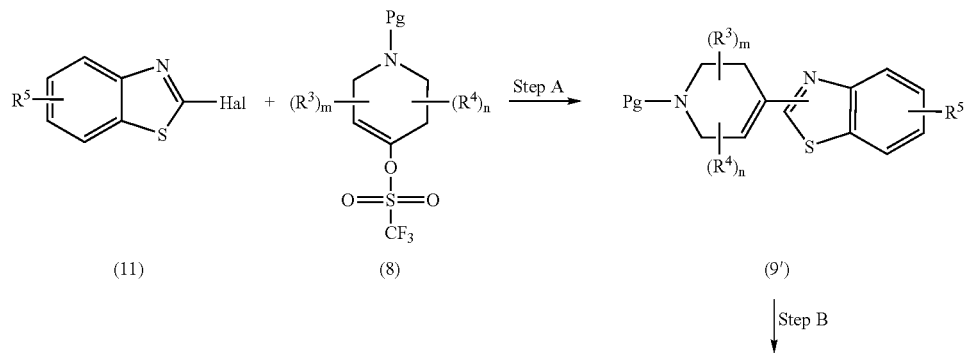

-continued

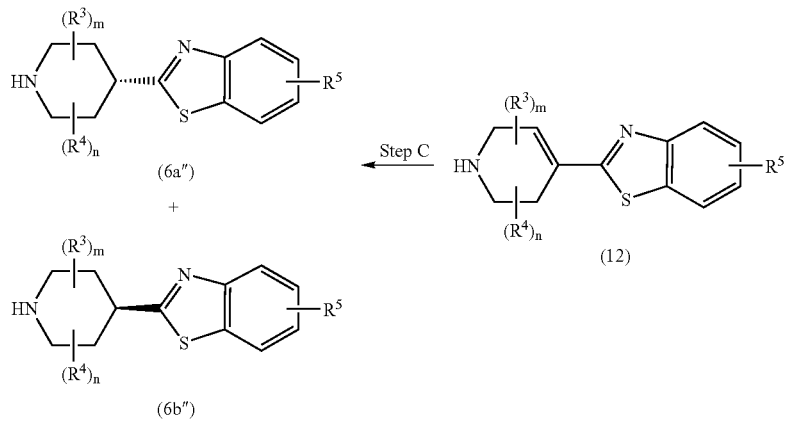

In Scheme IIA, step A, a 2-halo-benzothiazole (11), such as 2-chloro-4-fluorobenzothiazole, is combined with the 1,2,5,6-tetrahydropyridine (8), to provide the coupled compound (9'). For example, about 1 equivalent of a 2-halo-benzothiazole (11) is combined with about 1.2 equivalents of 1,2,5,6-tetrahydropyridine (8), about 1 equivalent of bis(trimethyltin), about 3 equivalents of lithium chloride, and a catalytic amount of tetrakis(triphenylphosphine)palladium(0) in a suitable organic solvent, such as 1,4-dioxane. The mixture is heated at reflux for about 20 hours and then cooled to about 20° C. The reaction is then treated with saturated potassium fluoride and ethyl acetate, and stirred for about 2 hours. The organic phase is separated, washed with brine, dried over anhydrous sodium sulfate, filtered and concentrated under vacuum. The crude residue is then purified by flash chromatography on silica gel with a suitable eluent such as ethyl acetate/hexanes to provide the compound (9').

In Scheme IIA, Step B, the compound (9') is deprotected under standard conditions to provide the compound (12). For example, the compound (9') is dissolved in a suitable organic solvent, such as dichloromethane, cooled to about 0° C. and treated with an excess of trifluoroacetic acid. The mixture is then stirred for about 30 minutes, then warmed to about 20° C. and stirred for an additional 20 minutes. The mixture is then diluted with 2 N sodium hydroxide and extracted with a suitable organic solvent, such as ethyl acetate. The organic extracts are combined, dried over anhydrous sodium sulfate, filtered and concentrated under vacuum to provide the crude compound (12). Compound (12) can then be purified by flash chromatography on silica gel with a suitable eluent, such as (dichloromethane/10% methanol 1% ammonium hydroxide in dichloromethane gradient elution) to provide the purified compound (12).

In Scheme IIA, step C, the compound (12) is hydrogenated under standard conditions to provide the cis and trans isomers (6a") and (6b"). For example, the compound (12) is dissolved in a suitable organic solvent, such as ethanol and treated with a catalytic amount of platinum oxide. The mixture is then hydrogenated under 1 atmosphere for about 20 hours, filtered and the filtrate concentrated under vacuum to provide the cis and trans isomers (6a") and (6b"). The compounds can then be separated using standard techniques well known to one of ordinary skill in the art, such as recrystallization techniques, flash chromatography or chiral chromatography.

It is readily appreciated by one of ordinary skill in the art that piperidines of structure (16) [see Schemes III and IV below], wherein B represents:

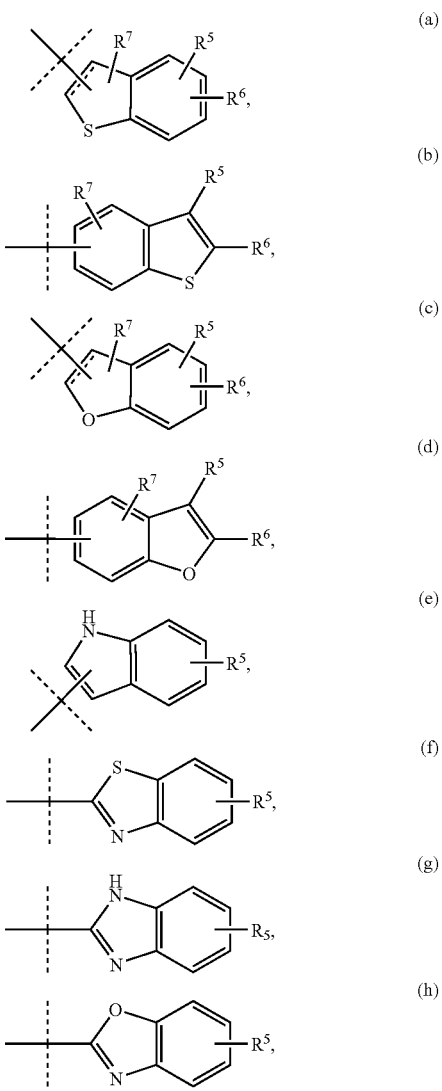

-continued

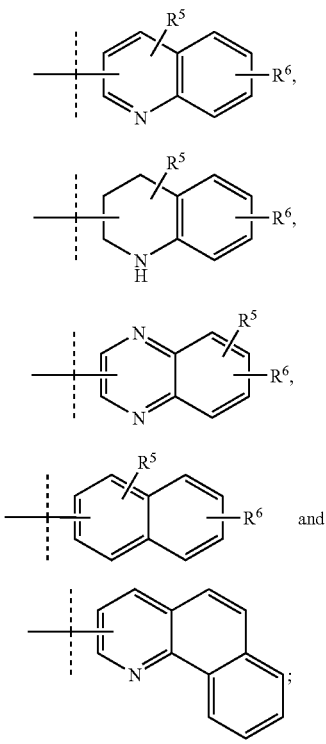

can be prepared under standard conditions, such as in a manner analogous to the procedures set forth in Schemes I through IIA for preparation of the piperidines described therein.

Compounds of formula I are prepared following generally the procedure set forth in Scheme III. All substituents, unless otherwise indicated, are previously defined. The reagents and starting materials are readily available to one of ordinary skill in the art.

Scheme III

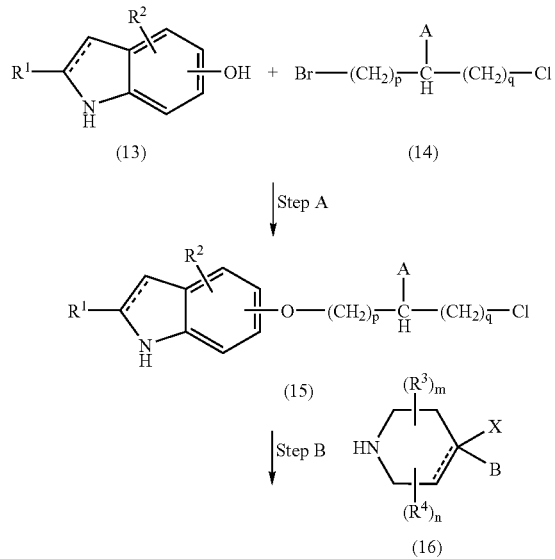

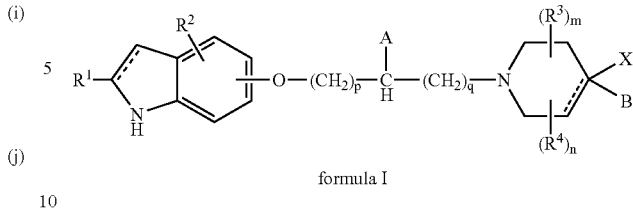

formula I

In Scheme III, step A, the compound (13) is coupled with the compound (14) under standard conditions well known in the art, to provide the compound (15). For example, the compound (13) is dissolved in a suitable organic solvent, such as DMF, and treated with about one equivalent of a suitable base, such as sodium hydride. To the stirring solution is added about 1.1 equivalents of compound (14) and the reaction is stirred at about −10° C. to room temperature, for about 20 minutes to about 1 hour. Compound (15) is then isolated and purified by techniques well known in the art, such as extraction techniques and flash chromatography. For example, the reaction mixture is diluted with water and extracted with a suitable organic solvent, such as ethyl acetate. The organic extracts are combined, dried over anhydrous magnesium sulfate, filtered and concentrated under vacuum to provide the crude material. The crude material can be purified by flash chromatography on silica gel with a suitable eluent, such as ethyl acetate/hexanes.

In Scheme III, step, B the compound (15) is coupled with the piperidine (16) under standard conditions well known in the art to provide the compound of formula I. For example, the compound (15) is dissolved in a suitable organic solvent, such as dimethylformamide with about one equivalent of a suitable neutralizing agent, such as sodium bicarbonate. To this mixture is added about one equivalent of a piperidine (16) and the mixture is heated at about 70° C. to 90° C. for about 4 hours to 12 hours. The compound of formula I is then isolated and purified by techniques well known in the art, such as extraction techniques and flash chromatography. For example, the reaction mixture is diluted with water and extracted with a suitable organic solvent, such as ethyl acetate. The organic extracts are combined, washed with water and brine, dried over anhydrous magnesium sulfate, filtered and concentrated under vacuum to provide the crude material. The crude material can be purified by flash chromatography on silica gel with a suitable eluent, such as ethyl acetate/hexanes.

Compounds of formula Ia are prepared following generally the procedure set forth in Scheme IV. All substituents, unless otherwise indicated, are previously defined. The reagents and starting materials are readily available to one of ordinary skill in the art.

Scheme IV

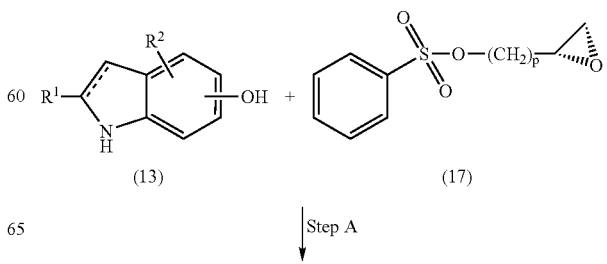

Step A

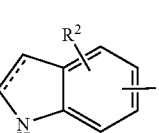

(18)

+

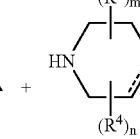

(16)

Step B

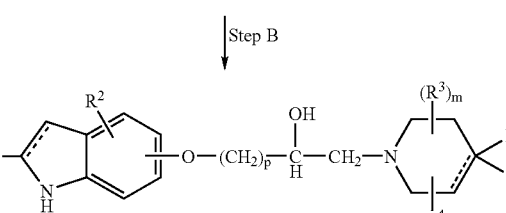

formula Ia

In Scheme IV, step A, the compound of structure (13) is coupled with the epoxide (17) to provide the epoxide (18). For example, compound (13) is dissolved in a suitable organic solvent, such as dimethylformamide and cooled to 0° C. About 1.1 equivalents of sodium hydride is added to the solution which is then stirred for about one hour. A solution of one equivalent of the epoxide (17) in dimethylformamide is then added dropwise to the solution. The reaction mixture is then stirred for about 1 to 24 hours at 0° C. It is then quenched with water. The resulting solution is then extracted with a suitable organic solvent, such as ethyl acetate. The organic layers are combined, washed with water, dried over anhydrous magnesium sulfate, filtered and concentrated to provide the crude epoxide (18). The crude product can be purified by crystallization with a suitable solvent, such as dichloromethane or by flash chromatography on silica gel with a suitable eluent, such as dichloromethane/hexanes.

In Scheme IV, step B, the epoxide (18) is opened with the substituted piperidine of structure (16) under standard conditions well known in the art, such as those disclosed by Krushinski, et al. in U.S. Pat. No. 5,576,321, issued Nov. 19, 1996, to provide the compound of formula Ia. For example, an epoxide (18), such as (S)-(+)-4-(oxiranylmethoxy)-1H-indole, is dissolved in a suitable organic solvent, such as methanol, and treated with about one equivalent of piperidine (16). The solution is then heated at reflux for about 8 to 12 hours and then cooled to room temperature. The reaction mixture is then concentrated under vacuum and the crude residue is purified and the resulting stereoisomers separated from each other by techniques well known in the art, such as flash chromatography, radial chromatography or high performance liquid chromatography on silica gel with a suitable eluent, such as methanol/methylene chloride.

The following examples are illustrative only and represent typical syntheses of the compounds of formula I and formula Ia as described generally above. The reagents and starting materials are readily available to one of ordinary skill in the art. As used herein, the following terms have the meanings indicated: "eq" or "equiv." refers to equivalents; "Ig" refers to grams; "mg" refers to milligrams; "L" refers to liters; "mL" refers to milliliters; "µL" refers to microliters; "mol" refers to moles; "mmol" refers to millimoles; "psi" refers to pounds per square inch; "min" refers to minutes; "h" or "hr" refers to hours; "° C." refers to degrees Celsius; "TLC" refers to thin layer chromatography; "HPLC" refers to high performance liquid chromatography; "$R_f$" refers to retention factor; "$R_t$" refers to retention time; "δ" refers to parts per million down-field from tetramethylsilane; "THF" refers to tetrahydrofuran; "DMF" refers to N,N-dimethylformamide; "DMSO" refers to methyl sulfoxide; "LDA" refers to lithium diisopropylamide; "mp" refers to melting point; "aq" refers to aqueous; "n-BuLi" refers to n-butyllithium; "EtOAc" refers to ethyl acetate; "iPrOAc" refers to isopropyl acetate; "MeOH" refers to methanol; "EtOH" refers to ethanol; "PPA" refers to polyphosphoric acid; "MTBE" refers to tert-butyl methyl ether, and "RT" refers to room temperature.

Preparation 1

Preparation of 1-Bromo-5-methoxy-naphthalene

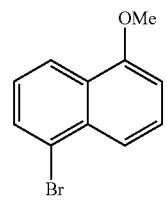

Preparation of 5-Bromo-3,4-dihydro-1(2H)-naphthalenone and 7-bromo-3,4-dihydro-1(2H)-naphthalenone.

Anhydrous AlCl$_3$ (66.67 g, 0.50 mol, 99.99%) under N$_2$ was stirred vigorously as 1-tetralone (29.83 g, 0.20 mol) was added dropwise over ~7 min. The evolved HCl gas was scrubbed through 5 N NaOH. The resulting mixture was a dark brown oil that exothermed to 75° C. When the temperature had cooled to 50° C., Br$_2$ was added dropwise over 15 min. The mixture, which had cooled further to 40° C., was heated to 80° C. for 5 min, then poured into a mixture of ice (600 g) and 12 N HCl (80 mL). All the ice melted, leaving a cool dark mixture which was diluted with H$_2$O (200 mL) and extracted with CH$_2$Cl$_2$ (200 mL, 100 mL). The combined extracts were dried with MgSO$_4$ and concentrated in vacuo (30–60° C.) to a dark brown oil (45.6 g; theory=45.02 g).

Chromatography over silica gel 60 with 8:1 heptane:THF did not prove effective, but two passes through the Biotage™ radially pressured silica gel cartridges using 9:1 heptane:MTBE as eluent produced acceptably pure fractions.

5-Bromo-3,4-dihydro-1(2H)-naphthalenone was isolated as an orange oil (12.27 g, 28.3%). HPLC showed an apparent wide divergence in absorbances at 230 nm for the two regioisomers, and was therefore not reliable for a potency check. TLC on silica gel (4:1 heptane:MTBE) confirmed modest contamination with 7-bromo-3,4-dihydro-1(2H)-naphthalenone.

7-Bromo-3,4-dihydro-1(2H)-naphthalenone was isolated as a yellowish-white solid (15.48 g, 35.8%); mp 69.5–75° C. (lit 74–75° C.). $^1$H NMR (CDCl$_3$) corresponded to the literature description, plus a trace of heptane and an undefined by-product. TLC showed it to be cleaner than 5-bromo-3,4-dihydro-1(2H)-naphthalenone.

A third fraction of orange oil (9.06 g, 20.9%) was isolated. TLC showed it to be a nearly 1:1 ratio of 5-bromo-3,4-dihydro-1(2H)-naphthalenone, and 7-bromo-3,4-dihydro-1(2H)-naphthalenone.

Preparation of 2,5-Dibromo-3,4-dihydro-1(2H)-naphthalenone.

A clear yellow solution of 5-bromo-3,4-dihydro-1(2H)-naphthalenone(12.09 g, 53.7 mmol) in freshly opened Et$_2$O (220 mL) under an N$_2$ atmosphere was chilled to –5° C. HCl was bubbled in subsurface for 1 min, causing no visible change. The dropwise addition of a solution of Br$_2$ (8.58 g, 53.7 mmol) in CH$_2$Cl$_2$ (20 mL) and Et$_2$O (2 mL) to the vigorously stirring solution of 5-bromo-3,4-dihydro-1(2H)-naphthalenone over 2 h (each drop was allowed to fully decolorize before adding the next) produced a product mixture that assayed by HPLC. Peak area showed 79.4% title compound, 9.5% unreacted 5-bromo-3,4-dihydro-1(2H)-naphthalenone, 0.6% unidentified, and 9.4% 2,2',5-tribromo-1-tetralone. The addition of H$_2$O produced a top light brown organic phase, and a clear, colorless bottom aqueous phase which was separated. After drying with MgSO$_4$, the organic layer was concentrated in vacuo at room temperature to give the crude intermediate title compound as a light brown oil (16.08 g, 98.5%).

Preparation of 5-Bromo-1-naphthalenol.

The crude mixture of 2,5-dibromo-1-tetralone (16.08 g, 52.9 mmol,), LiCl (5.61 g, 132 mmol), and 120 mL of dry DMF were combined under an N$_2$ atmosphere and heated to reflux (~155° C.). The mixture turned dark brown. HPLC showed complete consumption of the starting material in just 0.5 h. After cooling to room temperature, the mixture was diluted with 1 N HCl (200 mL) and extracted three times with Et$_2$O (100 mL, 25 mL, 25 mL). The Et$_2$O layers were combined to give a brown hazy mixture (some emulsion). After stirring with decolorizing carbon (10 g, Calgon ADP) and filtration through hyflo supercel, a clear light yellow solution was obtained. This solution was extracted with 3 N NaOH (100 mL, 25 mL), leaving the non-naphtholic byproducts behind. The brown NaOH extracts were combined, acidified to pH 1 with conc. HCl, and extracted with CH$_2$Cl$_2$ (100 mL, 25 mL). The combined CH$_2$Cl$_2$ layers formed a deep red solution. After stirring with decolorizing carbon (5 g, Darco G-60) and filtration through hyflo supercel, the solution was again light yellow. An equal volume of heptane was added, and the CH$_2$Cl$_2$ was distilled away. When the temperature reached 75° C., gray precipitate became evident. This increased substantially on cooling to room temperature. Following filtration and drying in vacuo at 50° C., a product mixture of gray solid (5.92 g, 50.2%) was obtained. HPLC showed this to be a mixture of 7-bromo-1-naphthol (48.3%) and 5-bromo-1-naphthol (50.8%). However, $^1$H NMR (CDCl$_3$) integration showed that the actual ratio was about 9/1 5-Br/7-Br. Preparative reverse phase HPLC gave one peak of 5-bromo-1-naphthol as a white solid (3.22 g, 27.3%).

Preparation of Final Title Compound.

Purified 5-bromo-1-naphthol (3.22 g, 14.4 mmol), was dissolved in CH$_3$CN (50 mL), giving a clear and nearly colorless solution. Dimethylsulfate (2.72 g, 21.6 mmol, 1.5 equiv), K$_2$CO$_3$ (3.0 g, 21.6 mmol), and tetrabutylammonium bromide (TBAB, 20 mg) as phase transfer catalyst were added, and the resulting mixture was stirred for 16 h. HPLC revealed no detectable starting material, when H$_2$O (50 mL) was added. The inorganic salt promptly dissolved, followed immediately by crystallization of the product. Following filtration, an H$_2$O wash (50 mL) of the cake, and drying in vacuo at 50° C., provided the final title compound as a light tan crystalline solid (3.07 g, 90.0%): mp 68.5–69.5° C. Satisfactory elemental analysis was obtained when block dried at 60° C. HPLC of 99.6%.

Preparation 2

Preparation of 2-Bromo-7-methoxy-naphthalene

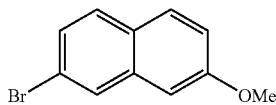

Preparation of 7-Bromo-2-naphthalenol.

Triphenyl phosphine (89.7 g, 0.342 mol) and acetonitrile (350 mL) were combined in a 1-L flask under N$_2$ atmosphere. The mixture was cooled to 10° C. Bromine (17.6 mL, 0.342 mol) was added dropwise over 10 minutes. The cooling bath was removed and 2,7-dihydroxynaphthalene (50.0 g, 0.312 mol) was added along with 350 mL of CH$_3$CN rinse. The resulting yellow tan mixture was heated at reflux for 3 hours. Acetonitrile was distilled off under a water aspirator pressure over 2 hours, resulting in a grayish white solid. The solid was heated to 280° C. over 30 minutes giving a black liquid. The liquid was heated to 310° C. over 20 minutes and the temperature was maintained at 310° C. for an additional 15 minutes until gas evolution ceased. The black mixture was cooled to room temperature. Chromatography yielded 34.5 g of the intermediate title compound as an off-white solid which was 87% pure by HPLC (43% yield).

Preparation of Final Title Compound.

2-Bromo-7-hydroxynaphthalene (34.1 g, 0.134 mol), DMF (290 mL) and powdered potassium carbonate (31.8 g, 0.230 mol) were combined in a 500-mL flask under N$_2$ atmosphere. Methyl iodide (14.3 mL, 0.230 mol) was added at once and the dark yellow mixture was stirred vigorously at room temperature for 3 ¾ hours. Water (290 mL) was added dropwise over 15 minutes to induce crystallization. The mixture was stirred at room temperature for 1 hour. The product was filtered off and washed with 200 mL of a 1:1 mixture of DMF and water. The solid was dried in vacuo at 50° C. to yield 32.6 g of pale yellow solid (HPLC: 89%). The solid was dissolved in 300 mL of boiling MeOH. The hot solution was filtered, then placed in a freezer overnight. The resulting crystals were filtered and washed with 100 mL of cold MeOH. The solid was dried in vacuo at 50° C. to give 27.0 g of pale yellow solid (HPLC: 95%). The solid was dissolved in 100 mL of boiling i-PrOH then allowed to cool to room temperature. The resulting solid was filtered and washed with 100 mL of i-PrOH. The solid was dried in vacuo at 50° C. to yield 22.8 g of final title compound as pale yellow crystals.

Preparation 3

Preparation of 6-Iodo-1-methoxy-naphthalene

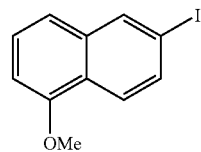

Preparation of 5-Bromo-2-naphthalenecarboxylic acid.

2-Naphthoic acid (50;0 g, 0.290 mol), glacial acetic acid (250 mL), bromine (15 mL, 0.291 mol) and iodine (1.3 g, 0.005 mol) were combined in a flask under $N_2$ atmosphere. The mixture was heated at reflux for 35 minutes then cooled to room temperature. The thick yellow mixture was stirred at room temperature for 1 hour. The mixture was filtered and the pale orange solid was rinsed with ~100 mL of the filtrate. The solid was dried in vacuo at 55° C. overnight to yield 55.5 g of pale orange solid. The solid was slurried in 275 mL of 1 N NaOH for 30 minutes. The solid was filtered off and rinsed 3 times with 50 mL portions of the filtrate. The solid was air dried in the hood over the weekend to yield 46.7 g of solid. The solid was added to 220 mL of water. Concentrated HCl (15 mL) was added to obtain pH of 1.3 and the mixture was stirred for 4 hours. The solid was filtered off and washed with 200 mL of water. The solid was dried in vacuo at 50° C. to give 37.6 g of intermediate title compound as white crystals (HPLC: 90% with 9% 2-naphthoic acid, 46% yield).

Preparation of 5-Bromo-2-naphthalenecarboxylic acid, Methyl Ester.

5-Bromo-2-naphthoic acid (17.33 g, 69 mmol) and 250 mL of MeOH were combined in a flask under $N_2$ atmosphere. Thionyl chloride (5.84 mL, 80 mmol) was added dropwise over 15 minutes at a temperature of 25–30° C., resulting in a pale yellow mixture. The mixture was heated at reflux for 3 ¼ hours. The resulting yellow solution was concentrated in vacuo to 137.4 g of solution then placed in a freezer overnight. The resulting thick mixture was filtered and the solid was washed with 100 mL of cold MeOH. The solid was dried in vacuo at 50° C. to give 11.39 g of the intermediate title compound as white crystals. A second crop was filtered and washed with 100 mL of cold MeOH. The solid was dried to 1.31 g of white crystals. Yield: 69%, 2 crops.

Preparation of 5-Methoxy-2-naphthoic acid.

A 25% solution of sodium methoxide in MeOH (63 mL, 0.258 mol) was added to a 500-mL flask under $N_2$ atmosphere. Cupric iodide (recrystallized, 4.19 g, 22 mmol), 160 mL of pyridine, 160 mL of MeOH and methyl 5-bromo-2-naphthoate (11.39 g, 43 mmol) were added to the flask to give a yellow green mixture. The mixture was heated at reflux for 30 hours. The mixture was cooled to room temperature and water (850 mL) was added resulting in a rust colored mixture with pH of 12.8. The pH was adjusted to 1.0 by addition of concentrated HCl, resulting in a white precipitate. The mixture was cooled to 10° C., filtered, and the solid was washed with cold water. The solid was dried to 11.03 g white crystals. The solid was taken up in 200 mL of EtOAc and 150 mL of water. The pH of the mixture was 3.5. The pH was adjusted to 10.0 by addition of 5 N NaOH and maintained for 4 hours. The EtOAc was removed by concentration in vacuo, then the pH was adjusted to 1.0 by addition of concentrated HCl. The mixture was placed in a freezer overnight. The mixture was filtered and the solid was washed with water until the filtrate stream was colorless. The solid was dried in vacuo at 50° C. to give 9.77 g of off-white solid. The solid was added to 50 mL of 2.5 N NaOH and the thick orange mixture was stirred for 3 hours. The pH was adjusted to 1.0 with concentrated HCl. The mixture was filtered and the solid was washed with water. The solid was dried to 9.43 g of off-white solid. The solid was dissolved in 200 mL of boiling MeOH and the hot solution was filtered, then cooled to room temperature. Water (300 mL) was added, and the mixture was stirred at room temperature for 2 hours. The solid was filtered off and washed with 100 mL of a 1:1 mixture of MeOH and water. The solid was dried in vacuo at 50° C. to give 7.18 g of the intermediate title compound as a white solid (HPLC: 97%, 83% yield).

Preparation of 5-Methoxy-2-naphthylamine.

5-Methoxy-2-naphthoic acid (3.17 g, 15.7 mmol), $CH_2Cl_2$ (38 mL) and DMF (3.04 mL, 39.2 mmol) were combined in a 50-mL flask under a $N_2$ atmosphere. Oxalyl chloride (2.73 mL, 31.3 mmol) was added dropwise over 30 minutes at 20 to 23° C. The resulting yellow solution was stirred at room temperature for 15 minutes. The solution was then concentrated in vacuo to give 6.48 g of yellow solid which was slightly wet with DMF. The solid was dissolved in $CH_3CN$ (157 mL) and added dropwise over 35 minutes to a solution of sodium azide (2.55 g, 39.2 mmol) in 24 mL of water, and rinsed in with an additional 25 mL of $CH_3CN$. Analysis of the resulting yellow mixture by HPLC after 5 minutes showed 15% acyl chloride remaining. Water (15 mL) was added to give an orange mixture and to promote acyl azide formation. The mixture was heated at reflux for 1 hour and 40 minutes. The mixture was cooled to room temperature. Sodium hydroxide (50 mL, 2 N solution) was added and the resulting yellow mixture was stirred at room temperature overnight. The mixture was concentrated in vacuo to yield 102.0 g of brown gum plus liquid. The mixture was extracted with 50 mL of $CH_2Cl_2$. The $CH_2Cl_2$ layer was dried over $Na_2SO_4$, filtered and concentrated in vacuo to provide 1.83 g of the intermediate title compound as a brown oil (HPLC: 91%, 61% yield).

Preparation of Final Title Compound.

2-Amino-5-methoxynaphthalene (1.78 g, 9.35 mmol), 5 mL of concentrated $HCl_{(aq)}$, 5 mL of water and 10 g of ice were combined in a flask. The tan orange mixture was cooled to 5° C. A chilled solution of sodium nitrite (0.75 g, 10.8 mmol) in 4 mL of water was added over 5 minutes, keeping the temperature below 10° C. The mixture was stirred at 5° C. for 30 minutes. A solution of potassium iodide (1.71 g, 10.3 mmol) in 10.5 mL of water was added, the bath was removed and the orange solution plus black solid was stirred at room temperature. Analysis by HPLC showed that more KI was needed. Potassium iodide (7.2 g, 43.4 mmol), 100 mL of $CH_3CN$ and 50 mL of acetone were added, and the mixture was stirred for 22 hours at room temperature. The mixture was extracted with 150 mL of $Et_2O$. The $Et_2O$ phase was washed successively with 200 mL of 5% $NaHSO_{3(aq)}$, 200 mL of 5% $NaHCO_{3(aq)}$, 200 mL of water and 200 mL of saturated NaCl solution. The $Et_2O$ phase was dried over $Na_2SO_4$, filtered and concentrated in vacuo to 2.21 g of dark brown solid (HPLC: 69.5%). The solid was adsorbed onto 8.0 g of silica gel 60 in $CH_2Cl_2$ then concentrated to a powder. The powder was slurried in hexanes and chromatographed on 100 g of silica gel 60 at atmospheric pressure, eluting with hexanes. The desired final title compound was collected (1.33 g, 50% yield) as a white solid after concentration of the appropriate fractions.

Preparation 4

Preparation of
N-t-Butyloxycarbonyl-2-methyl-4-piperidone

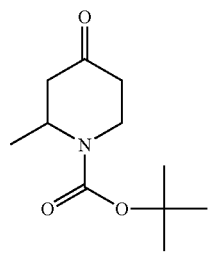

A solution of the following protected amine;

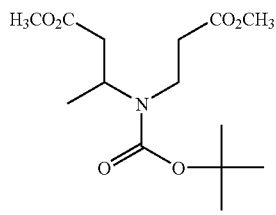

(145 g, prepared in a manner analogous to the procedures described by Hall, H. K. Jr., *J. Am. Chem. Soc.*, 79, 5444 (1957) and Harper, N. J.; Beckett, A. H.; Balon, A. D. J., *J. Chem. Soc.*, 2704 (1960)) dissolved in THF (200 mL) was added dropwise over one hour to a cooled solution of potassium t-butoxide (58.9 g) in THF (500 mL). The mixture was stirred at 0° C. for 2.5 hours and then warmed to room temperature over 1 hours while stirring. Another 50 mL of 1.0 M potassium t-butoxide in THF was added. After one hour, the solvent was removed under vacuum and the residue was dissolved in ethyl acetate (1 L). The organic solution was washed with saturated ammonium chloride (2×500 mL) which was back extracted with ethyl acetate (2×500 mL). The organic extracts were combined, dried over anhydrous magnesium sulfate, filtered and concentrated under vacuum to provide 120.6 g of the crude material as an oil. This oil was then treated with 5 N HCl (700 mL) at reflux for about 14.5 hours. After cooling, the solution was rinsed with a mixture of ethyl acetate/diethyl ether (1:1, 2×300 mL). The aqueous layer was then concentrated to provide the piperidone salt of structure:

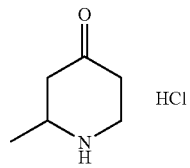

The above piperidone salt was then dissolved in water (200 mL) and THF (250 mL). The solution was then cooled to 0° C. and treated with 50% sodium hydroxide (35 mL), followed by dropwise addition of tert-butoxycarbonyl anhydride (106.7 g) in THF (100 mL) over one hour period. The ice bath was then removed and the solution was stirred at room temperature for about 4 days. The pH was adjusted to about 8 to 9. The THF was then removed under vacuum and the mixture was taken up in ethyl acetate (500 mL). The layers were separated and the aqueous layer was extracted with ethyl acetate (2×500 mL). The organic extracts were combined, washed with brine (300 mL), dried over anhydrous magnesium sulfate, filtered and concentrated under vacuum. The residue was purified by chromatography on silica gel (ethyl acetate/hexanes) to provide 36.81 g of the title compound.

Preparation 5

Preparation of
N-t-Butyloxycarbonyl-2,2-dimethyl-4-piperidone

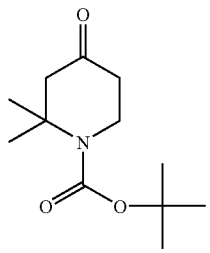

In a manner analogous to the procedure described in preparation 4 above, the title compound was prepared from the following starting material;

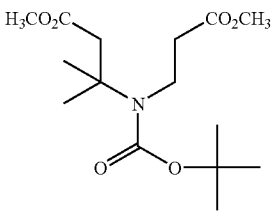

Preparation 6

Preparation of N-Benzyl-3,3-dimethyl-4-piperidone

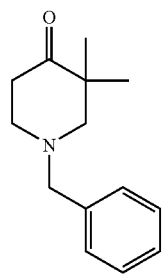

In a 1 liter 3-neck flask equipped with a mechanical stirrer, an addition funnel and a calcium chloride drying tube was added a 37% weight solution of formaldehyde (168.5 mL, 2.25 mole) dissolved in 500 mL of absolute ethanol.

The resulting solution was cooled in an ice-water bath to 10° C., and benzylamine (109 mL, 1 mole) was added dropwise over a one hour period. In a separate 3-liter 3-neck flask equipped with a mechanical stirrer, an addition funnel and two condensers was added 3-methyl-2-butanone (113 mL, 1.06 mole) dissolved in 500 ml of absolute ethanol and concentrated hydrogen chloride (92 mL, 1.11 mole). The resulting solution was brought to reflux and the formaldehyde/benzylamine solution is added dropwise over a 2 hour period. This solution was heated at reflux overnight, and then cooled to ambient temperature. Diisopropylethylamine (142.2 g, 1.1 mole) and formaldehyde (22.46 mL, 0.3 mole) were added and the resulting solution was heated to reflux for six hours, and then cooled to ambient temperature. The solution was quenched with potassium hydroxide (61.6 g, 1.1 mole) in 200 mL of water, and then extracted 3 times with 500 ml ethyl acetate. The organic layers were concentrated under vacuum to give 225 g of a red oil. The crude oil was dissolved in 1 liter of methylene chloride. This solution was carefully poured over 1 kg of silica gel on a sintered glass filter. The silica gel was washed with 4 L of methylene chloride. The methylene chloride was concentrated under vacuum to provide 142 g of a yellow oil which was crystallized in a freezer overnight. Yield=65.4%. MS(ion spray)=218.3(M+1)

Preparation 7

Preparation of:

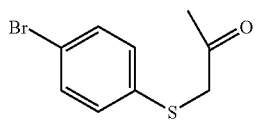

To 24.1 g (0.12 mol) of 4-bromothiophenol was added 168 mL of H$_2$O and 5.6 g (0.13 mol) of NaOH beads. To the resulting slurry was added 11.8 g (0.12 mol) of chloroacetone over 10 min. After 2.5 h, the product was removed by filtration and rinsed with H$_2$O. After drying under vacuum at 35° C. for 3 days, 29.5 g (99%) of title compound was obtained as an off-white solid.

Preparation 8

Preparation of 5-bromo-3-methylbenzo[b]thiophene

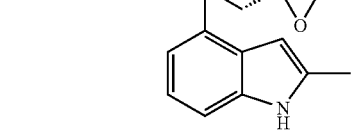

Amberlyst-15 resin (10 g) was slurried in 75 mL of chlorobenzene and the mixture was heated to reflux. Solvent was distilled and fresh solvent was added at an equal rate until 100 mL of solvent had been collected. A solution of 10.0 g (0.041 mol) of the ketone prepared in preparation 7 above in 50 mL of chlorobenzene was added dropwise over 3 h. Solvent was removed by distillation during the addition and 80 mL of additional chlorobenzene was added to maintain a constant volume. The mixture was allowed to cool room temperature and filtered. The resin was rinsed with 50 mL of chlorobenzene and the filtrate was evaporated to 9.38 g (100%) of title compound.

EXAMPLE 1

Preparation of (2S)-(–)-3-[(2R,4R)-4-(6-Methoxybenzo[b]thiophen-2-yl)-2-methylpiperidinyl]-1-(1H-2-methylindol-4-yl)oxy-2-2-propanol oxalate

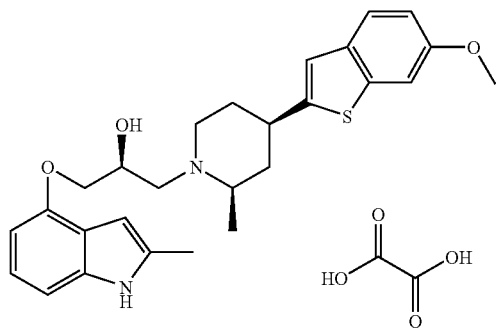

Preparation of (2S)-4-Glycidyloxy-2-methylindole.

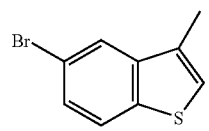

Scheme IV, Step A: To a solution of 4-hydroxy-2-methylindole (19.91 g, 135 mmol), dissolved in DMF (200 mL) at 0° C., was added sodium hydride (80% dispersion in mineral oil, 4.26 g, 142.0 mmol). The green suspension was stirred for 1 h. A solution of (S)-glycidyl nosylate (35.06 g, 135.2 mmol) in 70 mL of DMF was then added dropwise via a cannula and stirred for 10 min. The reaction mixture was stored in the freezer for 15 h, stirred at 0° C. for 4 h, and quenched with 500 mL of H$_2$O. The resulting solution was then extracted with (3×300 mL) EtOAc. The organic layers were washed with (5×300 mL) H$_2$O, dried over MgSO$_4$, filtered and concentrated. The crude product was crystallized from CH$_2$Cl$_2$ and rinsed with pentane. The mother liquor was concentrated and purified by silica gel chromatography (25% hexanes/CH$_2$Cl$_2$). The materials were combined to give the intermediate title compound as yellow crystals (21.24 g, 77%). IR (KBr) 3473, 1096 cm$^{-1}$. Ion Spray MS 204.2 (M+H)$^+$, 202.3 (M–H)$^-$. C$_{12}$H$_{13}$NO$_2$

| analysis: | calculated | found |
|---|---|---|
| C | 70.92 | 71.16 |
| H | 6.45 | 6.51 |
| N | 6.89 | 6.93 |

Preparation of (±)N-t-Butoxycarbonyl-4-hydroxy-4-(6-methoxybenzo[b]thiophen-2-yl)-2-methylpiperidine.

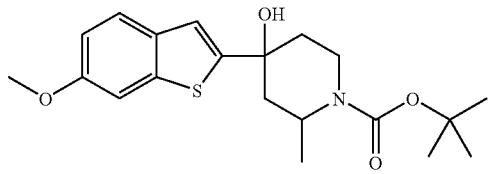

Scheme IA, Step A: To a solution of 6-methoxybenzo[b]thiophene (5.0 g, 30.4 mmol) in dry THF (60 mL) at −78° C. was added 1.6 M n-BuLi in hexanes (20.9 mL, 33.44 mmol). The solution was stirred at −78° C. for 90 min. The N-t-butoxycarbonyl-2-methyl-4-piperidone (3.89 g, 18.24 mmol) dissolved in THF (40 mL) was added via a cannula at −78° C. The reaction mixture was stirred at −78° C. for 3 h. The reaction was then quenched with 75 mL of saturated aqueous NaCl solution. The mixture was extracted with (1×75 mL, 2×125 mL) EtOAc. The combined organic layers were dried over $CaCl_2$ and filtered. The filtrate was concentrated and purified by medium pressure chromatography (30% $Et_2O$/hexanes) to give the intermediate title compound as a yellow foam (1.798 g, 26%). IR (KBr) 3009, 2978 cm⁻. Ion Spray MS 378 (M+H)⁺; 436 (M+$CH_3COO^-$)⁻.

Preparation of (±)-cis-4-(6-Methoxybenzo[b]thiophen-2-yl)-2-methylpiperidine.

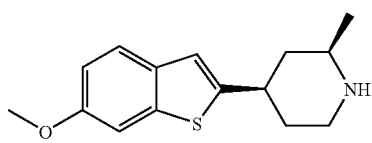

Scheme IA, Steps B and C: To a solution of N-t-butoxycarbonyl-4-hydroxy-4-(6-methoxybenzo[b]thiophen-2-yl)-2-methylpiperidine (1.734 g, 4.59 mmol) in dry $CH_2Cl_2$ (13 mL) at 0° C. was added 5.8 mL of trifluoroacetic acid. The resulting purple solution was stirred at 0° C. for 16 h. The reaction was then quenched at 0° C. with saturated aqueous $NaHCO_3$ solution (75 mL). The mixture was extracted with (2×150 mL) $CH_2Cl_2$. The combined organic layers were dried over $CaCl_2$, filtered, and concentrated. The residue was partitioned between saturated aqueous $NaHCO_3$ and $CH_2Cl_2$ and the layers were separated. The organic layer was dried over $MgSO_4$ and concentrated to yield 0.9 g of crude regioisomeric olefins. To a solution of the crude olefins (0.90 g) in a mixture of ethanol (29.7 mL) and 2,2,2-trifluoroethanol (10 mL) was added 10% Pd/C (1.00 g). The black slurry was stirred vigorously at room temperature under hydrogen (balloon pressure) for one day. The black slurry was then filtered through a pad of Celite and washed with ethanol. The filtrate was concentrated and the residue was purified by flash chromatography [4.5% (2.0 M $NH_3$ in MeOH)/$CH_2Cl_2$] to give the intermediate title compound as green powder (0.321 g, 35%). IR (KBr) 2936, 1478, 839 cm⁻¹. Ion Spray 262.1 (M+H)⁺. $C_{15}H_{19}NOS$

| analysis: | calculated | found |
|---|---|---|
| C | 68.93 | 69.18 |
| H | 7.33 | 7.05 |
| N | 5.36 | 5.17 |

Preparation of (±)-trans-4-(6-Methoxybenzo[b]thiophen-2-yl)-2-methylpiperidine.

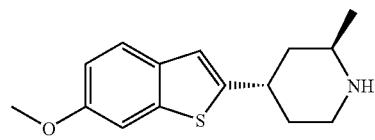

Scheme IA, Steps B and C: To a solution of N-t-butoxycarbonyl-4-hydroxy-4-(6-methoxybenzo[b]thiophen-2-yl)-2-methylpiperidine (1.734 g, 4.59 mmol) in dry $CH_2Cl_2$ (13 mL) at 0° C. was added 5.8 mL of trifluoroacetic acid. The resulting purple solution was stirred at 0° C. for 16 h. The reaction was quenched at 0° C. with saturated aqueous $NaHCO_3$ solution (75 mL). The mixture was extracted (2×150 mL) with $CH_2Cl_2$. The combined organic layers were dried over $CaCl_2$, filtered, and the filtrate was concentrated. The residue was partitioned between saturated aqueous $NaHCO_3$ and $CH_2Cl_2$. The layers were separated, and the organic layer was dried over $MgSO_4$ and concentrated to give 0.9 g of crude regioisomeric olefins. To a solution of the crude olefins (0.90 g) in a mixture of ethanol (29.7 mL) and 2,2,2-trifluoroethanol (10 mL) was added 10% Pd/C (1.00 g). The black slurry was stirred vigorously at room temperature under hydrogen (balloon pressure) for one day. The black slurry was filtered through a pad of Celite and washed with ethanol. The filtrate was then concentrated and the residue was purified by flash chromatography [4.5% (2.0 M $NH_3$ in MeOH)/$CH_2Cl_2$] to provide the intermediate title compound as a yellow/green oil (0.2295 g, 25%). IR (KBr) 2936, 1478, 840 cm⁻¹. Ion Spray 262.1 (M+H)⁺.

Preparation of the Final Title Compound.
Scheme IV, Step B: A solution of (±)-cis-4-(6-methoxybenzo[b]thiophen-2-yl)-2-methylpiperidine (0.118 g, 0.451 mmol) and (2S)-4-glycidyloxy-2-methylindole (0.092 g, 0.451 mmol) in MeOH (6 mL) was heated at reflux for 15 h and then cooled and evaporated. The residue was purified by silica gel chromatography [3% (2.0 M $NH_3$ in MeOH)/$CH_2Cl_2$] to give the free base of the final title compound as a yellow oil (0.0708 g, 34%). The oxalate salt was prepared with 1 eq. of oxalic acid in EtOAc. mp 108° C. (dec.). IR (KBr) 3473, 1058 cm⁻¹. Ion Spray MS 465 (M+H)⁺; 463 (M−H)⁻. $[\alpha]_D = -40$ (c 0.60, $CHCl_3$). $C_{27}H_{32}N_2O_3S \cdot 0.4 CH_2Cl_2$

| analysis: | calculated | found |
|---|---|---|
| C | 65.99 | 66.12 |
| H | 6.64 | 6.86 |
| N | 5.61 | 5.52 |

EXAMPLE 2

Preparation of (2S)-(−)-3-[(2S,4S)-4-(6-Methoxy-benzo[b]thiophen-2-yl)-2-methylpiperidinyl]-1-(1H-2-methylindol-4-yl)oxy-2-propanol oxalate

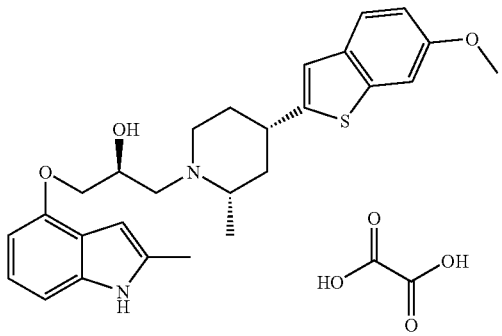

Scheme IV, Step B: A solution of (±)-cis-4-(6-methoxy-benzo[b]thiophen-2-yl)-2-methylpiperidine (0.118 g, 0.451 mmol, prepared in example 1) and (2S)-4-glycidyloxy-2-methylindole (0.092 g, 0.451 mmol, prepared in example 1) in MeOH (6 mL) was heated at reflux for 15 h and then cooled and evaporated. The residue was purified by silica gel chromatography [3% (2.0 M $NH_3$ in MeOH)/$CH_2Cl_2$] to give the free base of the title compound as a yellow oil (0.0664 g, 32%). The oxalate salt was prepared with 1 eq. of oxalic acid in EtOAc. mp 117.9° C. (dec.). IR (KBr) 3473, 1058 $cm^{-1}$. Ion Spray MS 465 $(M+H)^+$; 463 $(M-H)^-$. $[\alpha]_D=-7.52$ (c 0.532, $CHCl_3$). $C_{27}H_{32}N_2O_3S \cdot C_2H_2O_4 \cdot 0.2C_4H_8O_2$

| analysis: | calculated | found |
|---|---|---|
| C | 62.50 | 62.23 |
| H | 6.28 | 6.25 |
| N | 4.89 | 4.70 |

EXAMPLE 3

Preparation of (2S)-(−)-3-[(2S,4R)-4-(6-Methoxy-benzo[b]thiophen-2-yl)-2-methylpiperidinyl]-1-(1H-2-methylindol-4-yl)oxy-2-propanol oxalate

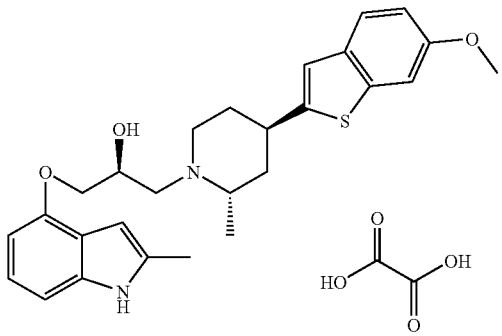

Scheme IV, Step B: A solution of (±)-trans-4-(6-methoxy-benzo[b]thiophen-2-yl)-2-methylpiperidine (0.103 g, 0.394 mmol, prepared in example 1) and (2S)-4-glycidyloxy-2-methylindole (0.801 g, 0.394 mmol, prepared in example 1) in MeOH (6 mL) was heated at reflux for 18 h and then cooled and evaporated. The residue was purified by silica gel chromatography [5% (2.0 M $NH_3$ in MeOH)/$CH_2Cl_2$] to give the free base of the title compound as a white foam (0.0608 g, 33%). The oxalate salt was prepared as in example 1. mp 109.8° C. (dec.). IR (KBr) 3473, 1058 $cm^{-1}$. Ion Spray MS 465 $(M+H)^+$; 463 $(M-H)^-$. $[\alpha]_D=-28.17$ (c 0.497, $CHCl_3$). $C_{27}H_{32}N_2O_3S \cdot C_2H_2O_4$

| analysis: | calculated | found |
|---|---|---|
| C | 62.80 | 62.95 |
| H | 6.18 | 6.19 |
| N | 5.05 | 4.76 |

EXAMPLE 4

Preparation of (2S)-(−)-3-[(2R,4S)-4-(6-Methoxy-benzo[b]thiophen-2-yl)-2-methylpiperidinyl]-1-(1H-2-methylindol-4-yl)oxy-2-propanol oxalate

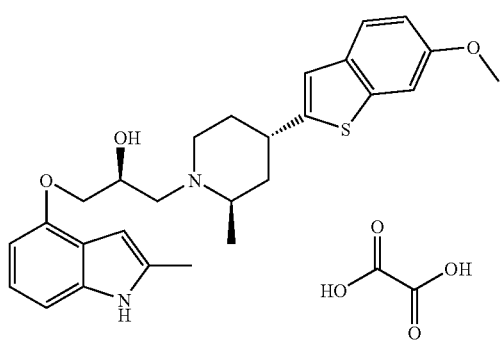

Scheme IV, Step B: A solution of (±)-trans-4-(6-methoxy-benzo[b]thiophen-2-yl)-2-methylpiperidine (0.103 g, 0.394 mmol, prepared in example 1) and (2S)-4-glycidyloxy-2-methylindole (0.801 g, 0.394 mmol, prepared in example 1) in MeOH (6 mL) was heated at reflux for 18 h and then cooled and evaporated. The residue was purified by silica gel chromatography [5% (2.0 M $NH_3$ in MeOH)/$CH_2Cl_2$] to give the free base of the title compound as an amorphous white solid (0.084 g, 46%). The oxalate salt was prepared as in example 1. mp 117.5° C. (dec.). IR (KBr) 3473, 1058 $cm^{-1}$. Ion Spray MS 465 $(M+2H)^+$; 463 $(M-H)^-$. $[\alpha]_D=-11.59$ (c 0.345, $CHCl_3$). $C_{27}H_{32}N_2O_3S \cdot C_2H_2O_4$

| analysis: | calculated | found |
|---|---|---|
| C | 62.80 | 61.14 |
| H | 6.18 | 5.97 |
| N | 5.05 | 5.04 |

EXAMPLE 5

Preparation of (2S)-(−)-3-[(2R, 4R)-4-(4-Methoxy-benzo[b]thiophen-2-yl)-2-methylpiperidinyl]-1-(1H-2-methylindol-4-yl)oxy-2-propanol oxalate

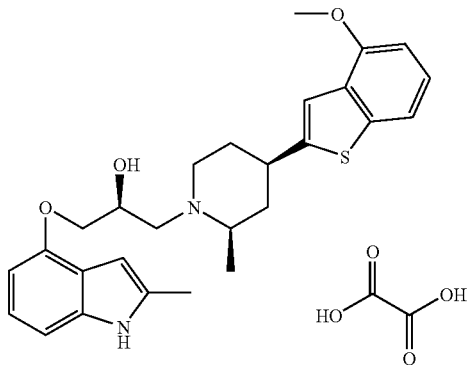

Scheme IV, Step B: A solution of (±)-cis-4-(4-methoxy-benzo[b]thiophen-2-yl)-2-methylpiperidine (0.607 g, 2.32 mmol, prepared in a manner analogous to the preparation of (±)-cis-4-(6-methoxybenzo[b]thiophen-2-yl)-2-methylpiperidine in example 1) and (2S)-4-glycidyloxy-2-methylindole (0.472 g, 2.32 mmol, prepared in example 1) in MeOH (30 mL) was heated at reflux for 15 h and then cooled and evaporated. The residue was purified by silica gel chromatography [1% (2.0 M $NH_3$ in MeOH)/$CH_2Cl_2$] to give the free base of the title compound as a green foam (0.4758 g, 44%). The oxalate salt was prepared as in example 1. mp 124.5° C. (dec.). IR (KBr) 3473, 1049 $cm^{-1}$. Ion Spray MS 465 $(M+H)^+$; 463 $(M-H)^-$. $[\alpha]_D=-29.25$ (c 0.547, $CHCl_3$). $C_{27}H_{32}N_2O_3S \cdot C_2H_2O_4$

| analysis: | calculated | found |
|---|---|---|
| C | 62.80 | 62.53 |
| H | 6.18 | 6.38 |
| N | 5.05 | 4.97 |

EXAMPLE 6

Preparation of (2S)-3-[(2S,4S)-4-(4-Methoxybenzo[b]thiophen-2-yl)-2-methylpiperidinyl]-1-(1H-2-methylindol-4-yl)oxy-2-propanol oxalate

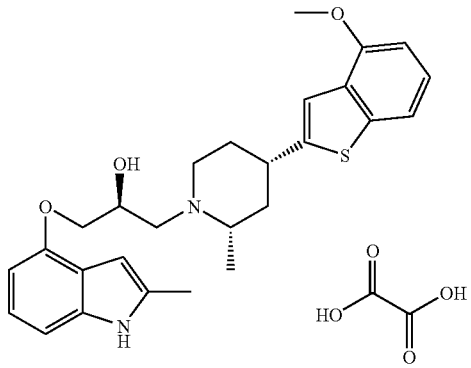

Scheme IV, Step B: A solution of (±)-cis-4-(4-methoxy-benzo[b]thiophen-2-yl)-2-methylpiperidine (0.607 g, 2.32 mmol, prepared in a manner analogous to the preparation of (±)-cis-4-(6-methoxybenzo[b]thiophen-2-yl)-2-methylpiperidine in example 1) and (2S)-4-glycidyloxy-2-methylindole (0.472 g, 2.32 mmol, prepared in example 1) in MeOH (30 mL) was heated at reflux for 15 h and then cooled and evaporated. The residue was purified by silica gel chromatography [1% (2.0 M $NH_3$ in MeOH)/$CH_2Cl_2$] to give the free base of the title compound as a green powder (0.431 g, 40%). The oxalate salt was prepared as in example 1. mp 117.8° C. (dec.). IR (KBr) 3473, 1049 $cm^{-1}$. Ion Spray MS 465 $(M+H)^+$; 463 $(M-H)^-$. $[\alpha]_D=0.00$ (c 0.593, $CHCl_3$). $C_{27}H_{32}N_2O_3S \cdot C_2H_2O_4$

| analysis: | calculated | found |
|---|---|---|
| C | 62.80 | 62.55 |
| H | 6.18 | 6.27 |
| N | 5.05 | 5.13 |

EXAMPLE 7

Preparation of (2S)-(−)-3-[(2S,4R)-4-(4-Methoxy-benzo[b]thiophen-2-yl)-2-methylpiperidinyl]-1-(1H-2-methylindol-4-yl)oxy-2-propanol oxalate

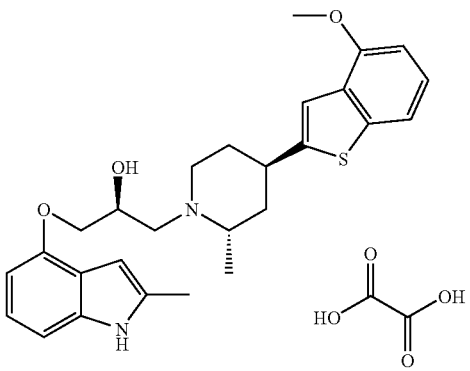

Scheme IV, Step B: A solution of (±)-trans-4-(4-methoxy-benzo[b]thiophen-2-yl)-2-methylpiperidine (0.123 g, 0.470 mmol, prepared in a manner analogous to the preparation of (±)-trans-4-(6-methoxybenzo[b]thiophen-2-yl)-2-methylpiperidine in example 1) and (2S)-4-glycidyloxy-2-methylindole (0.96 g, 0.47 mmol, prepared in example 1) in MeOH (7 mL) was heated at reflux for 15 h and then cooled and evaporated. The residue was purified by silica gel chromatography [3% (2.0 M $NH_3$ in MeOH)/$CH_2Cl_2$] to give the free base of the title compound as a yellow foam (0.101 g, 46%). The oxalate salt was prepared with 1 eq. of oxalic acid in EtOAc. mp 114.9° C. (dec.). IR (KBr) 3473, 1050 $cm^{-1}$. Ion Spray MS 465 $(M+H)^+$; 463 $(M-H)^-$. $[\alpha]_D=-23.39$ (c 0.513, $CHCl_3$). $C_{27}H_{32}N_2O_3S$

| analysis: | calculated | found |
|---|---|---|
| C | 69.8 | 69.97 |
| H | 6.94 | 7.05 |
| N | 6.03 | 6.00 |

Preparation of (2S)-(−)-3-[(2S,4R)-4-(4-Methoxybenzo[b]thiophen-2-yl)-2-methylpiperidinyl]-1-(1H-2-methylindol-4-yl)oxy-2-propanol hydrochloride.

A solution of (±)-trans-4-(4-methoxybenzo[b]thiophen-2-yl)-2-methylpiperidine (0.852 g, 3.262 mmol) and (2S)-4-glycidyloxy-2-methylindole (0.96 g, 3.262 mmol) in methanol (45 mL) was heated at reflux for 20 h and then cooled and evaporated. The residue was purified by silica gel chromatography [1 to 6% (2.0 M NH$_3$ in MeOH)/CH$_2$Cl$_2$, to give the free amine as a yellow foam (0.743 g, 49%). The hydrochloride salt was prepared with 1 eq. of 1.0 M HCl in diethyl ether using EtOAc (10 mL) as the solvent. Ion Spray MS 465 (M+H)$^+$; 523 (M+CH$_3$COO$^-$)$^-$. C$_{27}$H$_{32}$N$_2$O$_3$S.0.6H$_2$O

| analysis: | calculated | found |
|---|---|---|
| C | 63.35 | 63.13 |
| H | 6.73 | 6.60 |
| N | 5.47 | 5.50 |

EXAMPLE 8

Preparation of (2S)-(−)-3-[(2R,4S)-4-(4-Methoxybenzo[b]thiophen-2-yl)-2-methylpiperidinyl]-1-(1H-2-methylindol-4-yl)oxy-2-propanol oxalate

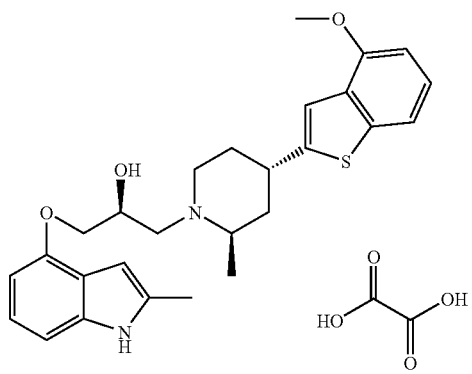

Scheme IV, Step B: A solution of (±)-trans-4-(4-methoxybenzo[b]thiophen-2-yl)-2-methylpiperidine (0.123 g, 0.470 mmol, prepared in a manner analogous to the preparation of (±)-trans-4-(6-methoxybenzo[b]thiophen-2-yl)-2-methylpiperidine in example 1) and (2S)-4-glycidyloxy-2-methylindole (0.96 g, 0.47 mmol, prepared in example 1) in MeOH (7 mL) was heated at reflux for 15 h and then cooled and evaporated. The residue was purified by silica gel chromatography [3% (2.0 M NH$_3$ in MeOH)/CH$_2$Cl$_2$] to give the free base of the title compound as a green oil (0.106 g, 49%). The oxalate salt was prepared with 1 eq. of oxalic acid in EtOAc. mp 123.5° C. (dec.). IR (KBr) 3473, 1050 cm$^{-1}$. Ion Spray MS 465 (M+H)$^+$; 463 (M−H)$^-$. [α]$_D$=−13.64 (c 0.44, CHCl$_3$). C$_{27}$H$_{32}$N$_2$O$_3$S.C$_2$H$_2$O$_4$

| analysis: | calculated | found |
|---|---|---|
| C | 62.80 | 62.63 |
| H | 6.18 | 6.37 |
| N | 5.05 | 5.00 |

EXAMPLE 9

Preparation of 4-[(2S)-(−)-2-Hydroxy-3-[(2R,4R)-(6-methoxybenzo[b]thiophen-2-yl)-2-methylpiperidinyl]propoxy]indole-2-carboxamide oxalate

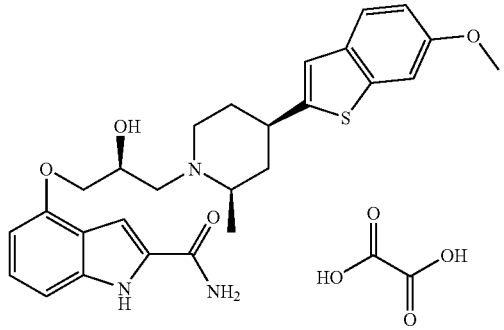

Scheme IV, Step B: A solution of (±)-cis-4-(6-methoxybenzo[b]thiophenyl)-2-methylpiperidine (0.123 g, 0.470 mmol, prepared in example 1) and (2S)-4-glycidyloxy-2-indolecarboxamide (0.270 g, 1.16 mmol, prepared in a manner analogous to the preparation of (2S)-4-glycidyloxy-2-methylindole in example 1) in MeOH (15 mL) was heated at reflux for 8 h and then cooled and allowed to stir for 4 days. The solution was then heated at reflux overnight, cooled, and the solvent was evaporated. The residue was purified by silica gel chromatography [2% (2.0 M NH$_3$ in MeOH)/CH$_2$Cl$_2$] to give the free base of the title compound as a yellow solid (0.308 g, 57%). The oxalate salt was prepared with 1 eq. of oxalic acid in EtOAc. mp 109.5° C. (dec.). IR (KBr) 1668 cm$^{-1}$. Ion Spray MS 494 (M+H)$^+$; 492 (M−H)$^-$. [α]$_D$=−20.91 (c 0.574, CHCl$_3$). C$_{27}$H$_{31}$N$_3$O$_4$S.C$_2$H$_2$O$_4$

| analysis: | calculated | found |
|---|---|---|
| C | 59.68 | 59.80 |
| H | 5.70 | 5.96 |
| N | 7.20 | 6.96 |

EXAMPLE 10

Preparation of 4-[(2S)-(−)-2-Hydroxy-3-[(2S,4S)-(6-methoxybenzo[b]thiophen-2-yl)-2-methylpiperidinyl]propoxy]indole-2-carboxamide oxalate

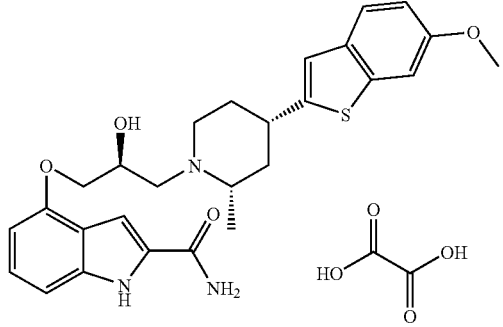

Scheme IV, Step B: A solution of (±)-cis-4-(6-methoxybenzo[b]thiophenyl)-2-methylpiperidine (0.123 g, 0.470 mmol, prepared in example 1) and (2S)-4-glycidyloxy-2-indolecarboxamide (0.270 g, 1.16 mmol, prepared in a manner analogous to the preparation of (2S)-4-glycidyloxy-2-methylindole in example 1) in MeOH (15 mL) was heated at reflux for 8 h and then cooled and allowed to stir for 4 days. The solution was then heated at reflux overnight, cooled, and the solvent was evaporated. The residue was purified by silica gel chromatography [2% (2.0 M $NH_3$ in MeOH)/$CH_2Cl_2$] to give the free base of the title compound as a white solid (0.2069 g, 38.2%). The oxalate salt was prepared with 1 eq. of oxalic acid in EtOAc. mp 130.8° C. (dec.). IR (KBr) 1668 $cm^{-1}$. Ion Spray MS 494 $(M+H)^+$; 492 $(M-H)^-$. $[\alpha]_D=-3.91$ (C 0.512, $CHCl_3$). $C_{27}H_{31}N_3O_4S.0.1CH_2Cl_2.0.3H_2O$

| analysis: | calculated | found |
|---|---|---|
| C | 64.12 | 63.84 |
| H | 6.32 | 6.40 |
| N | 8.27 | 8.09 |

EXAMPLE 11

Preparation of 4-[(2S)-(−)-2-Hydroxy-3-[(2S,4R)-(6-methoxybenzo[b]thiophen-2-yl)-2-methylpiperidinyl]propoxy]indole-2-carboxamide oxalate

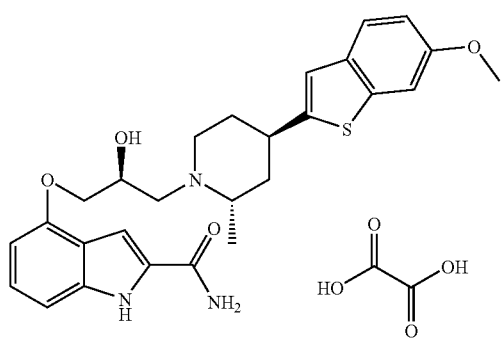

Scheme IV, Step B: A solution of (±)-trans-4-(6-methoxybenzo[b]thiophenyl)-2-methyl piperidine (0.221 g, 0.845 mmol, prepared in example 1) and (2S)-4-glycidyloxy-2-indolecarboxamide (0.196 g, 0.845 mmol, prepared in a manner analogous to the preparation of (2S)-4-glycidyloxy-2-methylindole in example 1) in MeOH (12.0 mL) was heated at reflux for 8 h and then cooled and allowed to stir for 4 days. The solution was then heated at reflux overnight, cooled, and the solvent was evaporated. The residue was purified by silica gel chromatography [2% (2.0 M $NH_3$ in MeOH)/$CH_2Cl_2$] to give the free base of the title compound as a yellow solid (0.1684 g, 40%). The oxalate salt was prepared with 1 eq. of oxalic acid in EtOAc. mp 116.8° C. (dec.). IR (KBr) 3454, 1668 $cm^{-1}$. Ion Spray MS 494 $(M+H)^+$; 492 $(M-H)^-$. $[\alpha]_D=-16.98$ (c 0.589, $CHCl_3$). $C_{27}H_{31}N_3O_4S.0.1C_4H_8O_2.0.6H_2O.C_2H_2O_4$

| analysis: | calculated | found |
|---|---|---|
| C | 58.53 | 58.28 |
| H | 5.86 | 5.81 |
| N | 6.96 | 7.01 |

EXAMPLE 12

Preparation of 4-[(2S)-(−)-2-Hydroxy-3-[(2R,4S-(6-methoxybenzo[b]thiophen-2-yl)-2-methylpiperidinyl]propoxy]indole-2-carboxamide oxalate

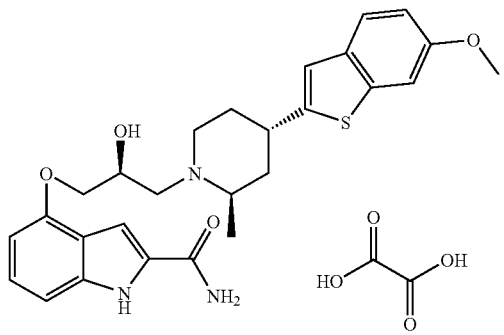

Scheme IV, Step B: A solution of (±)-trans-4-(6-methoxybenzo[b]thiophenyl)-2-methyl piperidine (0.221 g, 0.845 mmol, prepared in example 1) and (2S)-4-glycidyloxy-2-indolecarboxamide (0.196 g, 0.845 mmol, prepared in a manner analogous to the preparation of (2S)-4-glycidyloxy-2-methylindole in example 1) in MEOH (12.0 mL) was heated at reflux for 8 h and then cooled and allowed to stir for 4 days. The solution was then heated at reflux overnight, cooled, and the solvent was evaporated. The residue was purified by silica gel chromatography [2% (2.0 M $NH_3$ in MeOH)/$CH_2Cl_2$] to give the free base of the title compound as a yellow solid (0.1461 g, 35%). The oxalate salt was prepared with 1 eq. of oxalic acid in EtOAc. mp 113.2° C. (dec.). IR (KBr) 1668 $cm^{-1}$. Ion Spray MS 494 $(M+H)^+$; 492 $(M-H)^-$. $[\alpha]_D=-19.8$ (c 0.505, $CHCl_3$). $C_{27}H_{31}N_3O_4S.C_2H_2O_4.0.1C_4H_8O_2.0.6H_2O$

| analysis: | calculated | found |
|---|---|---|
| C | 58.53 | 58.18 |
| H | 5.85 | 5.74 |
| N | 6.97 | 6.94 |

EXAMPLE 13

Preparation of (2S)-(−)-1-(1H-2-Methylindol-4-yl)oxy-3-[(2R,4R)-2-methyl-4-(4-methylbenzo[b]thiophen-2-yl)piperidinyl]-2-propanol oxalate

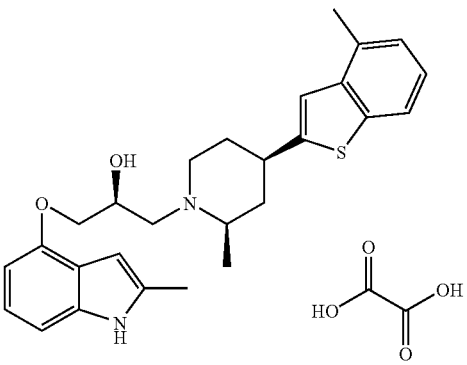

Scheme IV, Step B: A solution of (±)-cis-4-(4-methylbenzo[b]thiophen-2-yl)-2-methylpiperidine (0.191 g, 0.778.

mmol, prepared in a manner analogous to the preparation of (±)-cis-4-(6-methoxybenzo[b]thiophen-2-yl)-2-methylpiperidine in example 1) and (2S)-4-glycidyloxy-2-methylindole (0.158 g, 0.778 mmol, prepared in example 1) in MeOH (10 mL) was heated at reflux for 15 h and then cooled and evaporated. The residue was purified by silica gel chromatography [1.5% (2.0 M NH$_3$ in MeOH)/CH$_2$Cl$_2$] to give the free base of the title compound as a yellow foam (0.1332 g, 38%). The oxalate salt was prepared with 1 eq. of oxalic acid in EtOAc. mp 106.5° C. (dec.). IR (KBr) 3473 cm$^{-1}$. Ion Spray MS 449 (M+H)$^+$; 447 (M−H)$^−$. [α]$_D$=−32.79 (c 0.4269, CHCl$_3$). C$_{27}$H$_{32}$N$_2$O$_2$S.C$_2$H$_2$O$_4$

| analysis: | calculated | found |
|---|---|---|
| C | 64.66 | 64.49 |
| H | 6.36 | 6.60 |
| N | 5.20 | 5.35 |

EXAMPLE 14

Preparation of (2S)-(−)-1-(1H-2-Methylindol-4-yl)oxy-3-[(2S,4S)-2-methyl-4-(4-methylbenzo[b]thiophen-2-yl)piperidinyl]-2-propanol oxalate

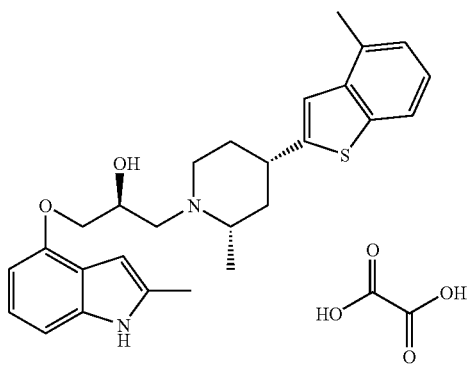

Scheme IV, Step B: A solution of (±)-cis-4-(4-methyl-benzo[b]thiophen-2-yl)-2-methylpiperidine (0.191 g, 0.778 mmol, prepared in a manner analogous to the preparation of (±)-cis-4-(6-methoxybenzo[b]thiophen-2-yl)-2-methylpiperidine in example 1) and (2S)-4-glycidyloxy-2-methylindole (0.158 g, 0.778 mmol, prepared in example 1) in MeOH (10 mL) was heated at reflux for 15 h and then cooled and evaporated. The residue was purified by silica gel chromatography [1.5% (2.0 M NH$_3$ in MeOH)/CH$_2$Cl$_2$] to give the free base of the title compound as a white foam (0.1405 g, 40%). The oxalate salt was prepared with 1 eq. of oxalic acid in EtOAc. mp 84.3° C. (dec.). IR (KBr) 3473 cm$^{-1}$. Ion Spray MS 449 (M+H)$^+$; 447 (M−H)$^−$. [α]$_D$=−4.48 (c 0.4464, CHCl$_3$). C$_{27}$H$_{32}$N$_2$O$_2$S

| analysis: | calculated | found |
|---|---|---|
| C | 72.29 | 72.58 |
| H | 7.19 | 7.20 |
| N | 6.24 | 6.43 |

EXAMPLE 15

Preparation of (2S)-(−)-1-(1H-2-Methylindol-4-yl)oxy-3-[(2S,4R)-2-methyl-4-(4-methylbenzo[b]thiophen-2-yl)piperidinyl]-2-propanol oxalate

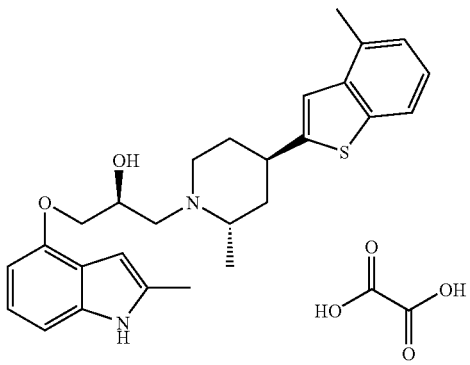

Scheme IV, Step B: A solution of (±)-trans-4-(4-methyl-benzo[b]-thiophenyl)-2-methylpiperidine (0.100 g, 0.407 mmol, prepared in a manner analogous to the preparation of (±)-trans-4-(6-methoxybenzo[b]thiophen-2-yl)-2-methylpiperidine in example 1) and (2S)-4-glycidyloxy-2-methylindole (0.083 g, 0.407 mmol, prepared in example 1) in MeOH (6 mL) was heated at reflux for 15 h and then cooled and evaporated. The residue was purified by silica gel chromatography [1.5% (2.0 M NH$_3$ in MeOH)/CH$_2$Cl$_2$] to give the free base of the title compound as a yellow solid (0.0768 g, 42%). The oxalate salt was prepared with 1 eq. of oxalic acid in EtOAc. mp 121.3° C. (dec.). IR (KBr) 3473 cm$^{-1}$. Ion Spray MS 449 (M+H)$^+$; 447 (M−H)$^−$. [α]$_D$=−25.42 (c 0.5507, CHCl$_3$). C$_{27}$H$_{32}$N$_2$O$_2$S

| analysis: | calculated | found |
|---|---|---|
| C | 72.29 | 72.07 |
| H | 7.19 | 7.32 |
| N | 6.24 | 6.45 |

EXAMPLE 16

Preparation of (2S)-(−)-1-(1H-2-methylindol-4-yl)oxy-3-[(2R,4S)-2-Methyl-4-(4-methylbenzo[b]thiophen-2-yl)piperidinyl]-2-propanol oxalate

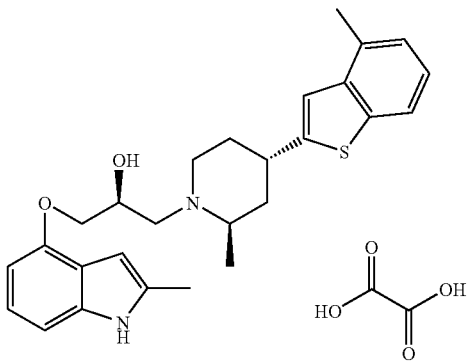

Scheme IV, Step B: A solution of (±)-trans-4-(4-methyl-benzo[b]thiophenyl)-2-methylpiperidine (0.100 g, 0.407 mmol, prepared in a manner analogous to the preparation of (±)-trans-4-(6-methoxybenzo[b]thiophen-2-yl)-2-methylpiperidine in example 1) and (2S)-4-glycidyloxy-2-methylindole (0.083 g, 0.407 mmol, prepared in example 1) in MeOH (6 mL) was heated at reflux for 15 h and then cooled and evaporated. The residue was purified by silica gel chromatography [1.5% (2.0 M $NH_3$ in MeOH)/$CH_2Cl_2$] to give the free base of the title compound as a green solid (0.0818 g, 45%). The oxalate salt was prepared with 1 eq. of oxalic acid in EtOAc. mp 109.1° C. (dec.). IR (KBr) 3473 $cm^{-1}$. Ion Spray MS 449 $(M+H)^+$; 447 $(M-H)^-$. $[\alpha]_D = -18.61$ (c 0.5374, $CHCl_3$). $C_{27}H_{32}N_2O_2S \cdot C_2H_2O_4 \cdot 1.0H_2O \cdot 0.2C_4H_8O_2$

| analysis: | calculated | found |
|---|---|---|
| C | 62.32 | 61.96 |
| H | 6.60 | 6.57 |
| N | 4.88 | 5.14 |

EXAMPLE 17

Preparation of (2S)-(−)-3-[(2R,4R)-4-(5-Chlorobenzo[b]thiophen-2-yl)-2-methylpiperidinyl]-1-(1H-2-methylindol-4-yl)oxy-2-propanol oxalate

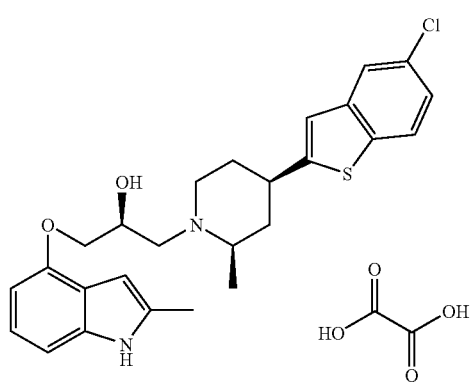

Scheme IV, Step B: A solution of (±)-cis-4-(5-chlorobenzo[b]thiophen-2-yl)-2-methylpiperidine (0.1885 g, 0.709 mmol, prepared in a manner analogous to the preparation of (±)-cis-4-(6-methoxybenzo[b]thiophen-2-yl)-2-methylpiperidine in example 1) and (2S)-4-glycidyloxy-2-methylindole (0.144 g, 0.709 mmol, prepared in example 1) in MeOH (10 mL) was heated at reflux for 15 h and then cooled and evaporated. The residue was purified by silica gel chromatography [4% (2.0 M $NH_3$ in MeOH)/$CH_2Cl_2$] to give the free base of the title compound as a yellow solid (0.1473 g, 44%) The oxalate salt was prepared with 1 eq. of oxalic acid in EtOAc. mp 82.1° C. (dec.). IR (KBr) 3473 $cm^{-1}$. Ion Spray MS 469 $(M+H)^+$; 467 $(M-H)^-$. $[\alpha]_D = -28.07$ (c 0.4988, $CHCl_3$). $C_{26}H_{29}ClN_2O_2S \cdot C_2H_2O_4$

| analysis: | calculated | found |
|---|---|---|
| C | 60.15 | 59.85 |
| H | 5.59 | 5.57 |
| N | 5.01 | 4.77 |

EXAMPLE 18

Preparation of (2S)-(−)-3-[(2S,4S)-4-(5-Chlorobenzo[b]thiophen-2-yl)-2-methylpiperidinyl]-1-(1H-2-methylindol-4-yl)oxy-2-propanol oxalate.

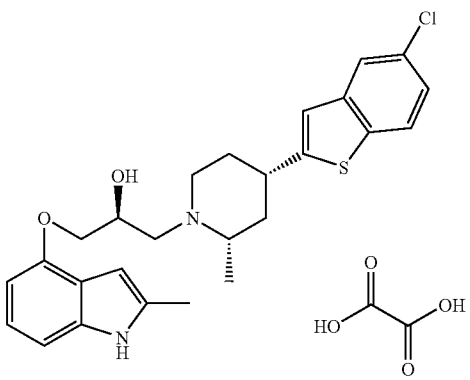

Scheme IV, Step B: A solution of (±)-cis-4-(5-chlorobenzo[b]thiophen-2-yl)-2-methylpiperidine (0.1885 g, 0.709 mmol, prepared in a manner analogous to the preparation of (±)-cis-4-(6-methoxybenzo[b]thiophen-2-yl)-2-methylpiperidine in example 1) and (2S)-4-glycidyloxy-2-methylindole (0.144 g, 0.709 mmol, prepared in example 1) in MeOH (10 mL) was heated at reflux for 15 h and then cooled and evaporated. The residue was purified by silica gel chromatography [4% (2.0 M $NH_3$ in MeOH)/$CH_2Cl_2$] to give the free base of the title compound as a transparent oil (0.0429 g, 13%). The oxalate salt was prepared with 1 eq. of oxalic acid in EtOAc. mp 105.0° C. (dec.). IR (KBr) 3473 $cm^{-1}$. Ion Spray MS 469 $(M+H)^+$; 467 $(M-H)^-$. $[\alpha]_D = -11.59$ (C0.345, $CHCl_3$). $C_{26}H_{29}ClN_2O_2S \cdot C_2H_2O_4$

| analysis: | calculated | found |
|---|---|---|
| C | 60.15 | 60.32 |
| H | 5.59 | 5.78 |
| N | 5.01 | 5.04 |

EXAMPLE 19

Preparation of (2S)-(−)-3-[(2S,4R)-4-(5-Chlorobenzo[b]thiophen-2-yl)-2-methylpiperidinyl]-1-(1H-2-methylindol-4-yl)oxy-2-propanol oxalate.

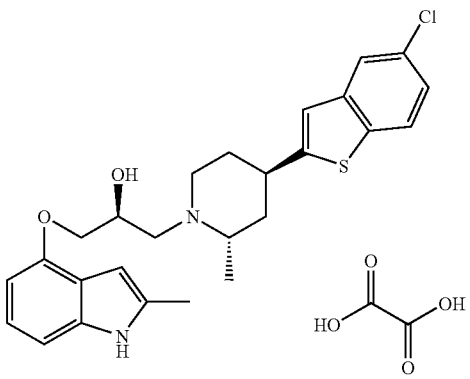

Scheme IV, Step B: A solution of (±)-trans-4-(5-chlorobenzo[b]thiophen-2-yl)-2-methylpiperidine (0.1443 g, 0.542 mmol, prepared in a manner analogous to the preparation of (±)-trans-4-(6-methoxybenzo[b]thiophen-2-yl)-2-methylpiperidine in example 1) and (2S)-4-glycidyloxy-2- methylindole (0.110 g, 0.542 mmol, prepared in example 1) in MeOH (8 mL) was heated at reflux for 15 h and then cooled and evaporated. The residue was purified by silica gel chromatography [4% (2.0 M NH$_3$ in MeOH)/CH$_2$Cl$_2$] to give the free base of the title compound as a white foam (0.109 g, 43%). The oxalate salt was prepared with 1 eq. of oxalic acid in EtOAc. mp 88.5° C. (dec.). IR (KBr) 3473 cm$^{-1}$. Ion Spray MS 469 (M+H)$^+$; 467 (M−H)$^-$. [α]$_D$=−21.33 (c 0.4689, CHCl$_3$). C$_{26}$H$_{29}$ClN$_2$O$_2$S.C$_2$H$_2$O$_4$

| analysis: | calculated | found |
|---|---|---|
| C | 60.15 | 60.02 |
| H | 5.59 | 5.87 |
| N | 5.01 | 4.80 |

EXAMPLE 20

Preparation of (2S)-(−)-3-[(2R,4S)-4-(5-Chlorobenzo[b]thiophen-2-yl)-2-methylpiperidinyl]-1-(1H-2-methylindol-4-yl)oxy-2-propanol oxalate

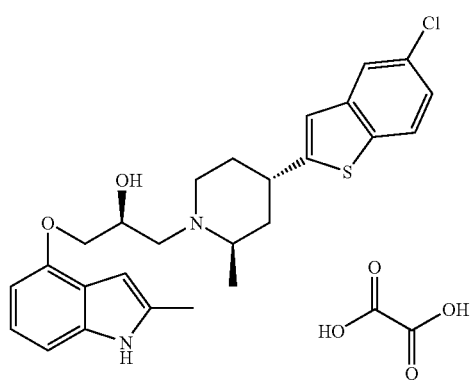

Scheme IV, Step B: A solution of (±)-trans-4-(5-chlorobenzo[b]thiophen-2-yl)-2-methylpiperidine (0.1443 g, 0.542 mmol, prepared in a manner analogous to the preparation of (±)-trans-4-(6-methoxybenzo[b]thiophen-2-yl)-2-methylpiperidine in example 1) and (2S)-4-glycidyloxy-2-methylindole (0.110 g, 0.542 mmol, prepared in example 1) in MeOH (8 mL) was heated at reflux for 15 h and then cooled and evaporated. The residue was purified by silica gel chromatography [4% (2.0 M NH$_3$ in MeOH)/CH$_2$Cl$_2$] to give the free base of the title compound as a white foam (0.0925 g, 36%). The oxalate salt was prepared with 1 eq. of oxalic acid in EtOAc. mp 98.5° C. (dec.). IR (KBr) 3473 cm$^{-1}$. Ion Spray MS 469 (M+H)$^+$; 467 (M−H)$^-$. [α]$_D$=−28.06 (c 0.4689, CHCl$_3$). C$_{26}$H$_{29}$ClN$_2$O$_2$S.C$_2$H$_2$O$_4$

| analysis: | calculated | found |
|---|---|---|
| C | 60.15 | 60.17 |
| H | 5.59 | 5.83 |
| N | 5.01 | 5.17 |

EXAMPLE 21

Preparation of (2S)-(−)-3-[4-(4-Methylbenzo[b]thiophen-2-yl)piperidinyl]-1-(1H-2-methylindol-4-yl)oxy-2-propanol oxalate

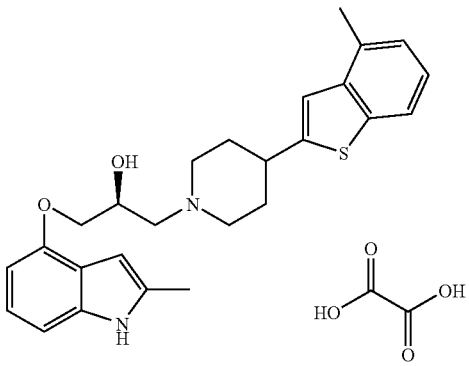

Scheme IV, Step B: A solution of 4-(4-methylbenzo[b]thiophen-2-yl)piperidine (0.1609 g, 0.695 mmol, prepared in a manner analogous to the preparation of (±)-cis-4-(6-methoxybenzo[b]thiophen-2-yl)-2-methylpiperidine in example 1) and (2S)-4-glycidyloxy-2-methylindole (0.141 g, 0.695 mmol, prepared in example 1) in MeOH (10 mL) was heated at reflux for 15 h and then cooled and evaporated. The residue was purified by silica gel chromatography [1% (2.0 M NH$_3$ in MeOH)/CH$_2$Cl$_2$] to give the free base of the title compound as a green oil (0.237 g, 79%). The oxalate salt was prepared with 1 eq. of oxalic acid in EtOAc. mp 101.9–105.5° C. (dec.). IR (KBr) 3473, 3008, 2943, 1246 cm$^{-1}$. Ion Spray MS 435 (M+H)$^+$; 433 (M−H)$^-$. [α]$_D$=−19.61 (c 0.51, CHCl$_3$). C$_{26}$H$_{30}$N$_2$O$_2$S.C$_2$H$_2$O$_4$

| analysis: | calculated | found |
|---|---|---|
| C | 64.10 | 63.84 |
| H | 6.15 | 6.17 |
| N | 5.34 | 5.10 |

EXAMPLE 22

Preparation of (2S)-(−)-3-[4-(4-Methoxybenzo[b]thiophen-2-yl)piperidinyl]-1-(1H-2-methylindol-4-yl)oxy-2-propanol oxalate

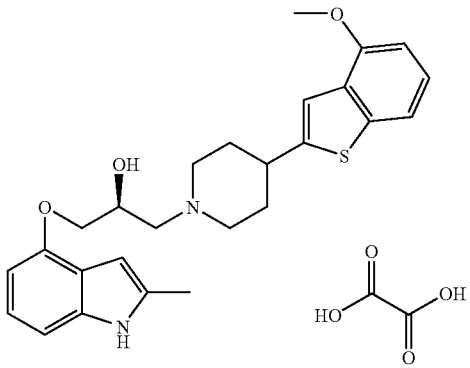

Scheme IV, Step B: A solution of 4-(4-methoxybenzo[b]thiophen-2-yl)piperidine (0.050 g, 0.202 mmol, prepared in a manner analogous to the preparation of (±)-cis-4-(6-methoxybenzo[b]thiophen-2-yl)-2-methylpiperidine in example 1) and (2S)-4-glycidyloxy-2-methylindole (0.0410 g, 0.202 mmol, prepared in example 1) in MeOH (3 mL) was heated at reflux for 21 h, cooled and evaporated. The residue was purified by silica gel chromatography [3.0% (2.0 M NH$_3$ in EtOH)/CH$_2$Cl$_2$] then the lower boiling solvents was azeotropically removed with xylenes to give the free base of the title compound as a green oil (0.0923 g, 99.9%). The oxalate salt was prepared with 1 eq. of oxalic acid in EtOAc. IR (KBr) 3473, 3008, 2942, 1247 cm$^{-1}$. Ion Spray MS 451.2 (M+H)$^+$; 449.2 (M−H)$^-$. [α9 $_D$=−16.0 (c 0.500, CHCl$_3$). C$_{26}$H$_{30}$N$_2$O$_3$S.C$_2$H$_2$O$_4$

| analysis: | calculated | found |
|---|---|---|
| C | 62.21 | 61.94 |
| H | 5.97 | 6.07 |
| N | 5.18 | 5.15 |

EXAMPLE 23

Preparation of (2S)-3-[4-(6-Methylbenzo[b]thiophen-2-yl)piperidinyl]-1-(1H-2-methylindol-4-yl)oxy-2-propanol oxalate

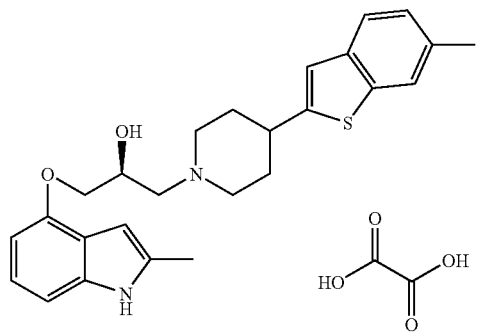

Preparation of N-t-Butoxycarbonyl-4-hydroxy-4-(6-methylbenzo[b]thiophen-2-yl)piperidine.

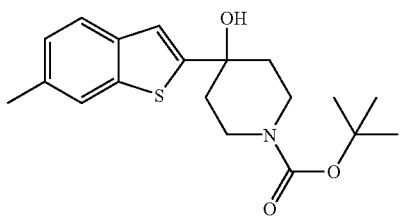

Scheme IA, Step A: To a solution of 6-methylbenzo[b]thiophene (1.25 g, 8.43 mmol) in dry THF (20 mL) at −78° C. was added 1.6 M n-BuLi in hexanes (6.32 mL, 10.1 mmol). The solution was stirred at −78° C. for 40 min. 1-t-Butoxycarbonyl-4-piperidone (1.84 g, 9.27 mmol) dissolved in THF (10 mL) was added via a cannula at −78° C. The reaction mixture was stirred at −78° C. for 3 h. The reaction was then quenched with 50 mL of water. The mixture was extracted (3×75 mL) with EtOAc. The combined organic layers were dried over MgSO$_4$ and filtered. The filtrate was concentrated to an oil and allowed to stand 3 days in which time the material crystallized. The crystals were rinsed with a mixture of EtOAc/hexanes to give the intermediate title compound as yellow crystals (2.13 g, 72.6%). IR (KBr) 1681, 1429, 1246 cm$^{-1}$. FD+MS 347.0 (M).

Preparation of 4-(6-Methylbenzo[b]thiophen-2-yl)piperidine.

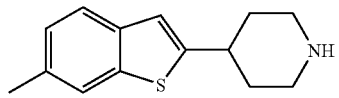

Scheme IA, Steps B and C: To a solution of N-t-butoxycarbonyl-4-hydroxy-4-(6-methylbenzo[b]thiophen-2-yl)piperidine (2.14 g, 6.15 mmol) in dry CH$_2$Cl$_2$ (17.5 mL) at 0° C. was added 7.8 mL of trifluoroacetic acid. The resulting burgundy solution was stirred at 0° C. for 15 h. The reaction was then quenched at room temperature with saturated aqueous NaHCO$_3$ solution (200 mL). The resulting precipitate was dissolved with 200 mL H$_2$O and was extracted (1×600 mL, 2×300 mL) with CH$_2$Cl$_2$. The combined organic layers were dried over MgSO$_4$, filtered and concentrated to give 0.99 g of crude regioisomeric olefins. To the mixture of olefins (0.99 g) in a mixture of ethanol (36 mL) and 2,2,2-trifluoroethanol (12.0 mL) was added 10% Pd/C (4.69 g). The black slurry was stirred vigorously at room temperature under hydrogen (balloon pressure) for three days. The black slurry was then filtered through a pad of Celite. The filtrate was concentrated and the residue was purified by flash chromatography [5% (2.0 M NH$_3$ in MeOH)/CH$_2$Cl$_2$] to give the intermediate title compound as a white solid (0.1192 g, 12.1%). IR (KBr) 2941, 1473, 839 cm$^{-1}$. Ion Spray 232.2 (M+H)$^+$.

Preparation of Final Title Compound.

Scheme IV, Step B: A solution of 4-(6-methylbenzo[b]thiophen-2-yl)piperidine (0.0457 g, 0.197 mmol) and (2S)-4-glycidyloxy-2-methylindole (0.0401 g, 0.1975 mmol, prepared in example 1) in MeOH (3 mL) was heated at reflux for 15 h and then cooled and evaporated. The residue was purified by silica gel chromatography [1% (2.0 M NH$_3$ in MeOH)/CH$_2$Cl$_2$] to give the free base of the final title compound as a yellow foam (0.0743 g, 87%). The oxalate salt was prepared with 1 eq. of oxalic acid in EtOAc. mp 120.9° C. (dec.). IR (KBr) 3473, 3008, 2943, 1247 cm$^{-1}$. Ion Spray MS 435 (M+H)$^+$; 433 (M−H)$^-$. C$_{26}$H$_{30}$N$_2$O$_2$S.C$_2$H$_2$O$_4$.0.9H$_2$O

| analysis: | calculated | found |
|---|---|---|
| C | 62.18 | 61.92 |
| H | 6.30 | 6.62 |
| N | 5.18 | 5.43 |

EXAMPLE 24

Preparation of (2S)-(−)-1-(1H-2-Methylindol-4-yl)oxy-3-[(2R,4R)-2-methyl-4-(6-methylbenzo[b]thiophen-2-yl)piperidinyl]-2-propanol oxalate

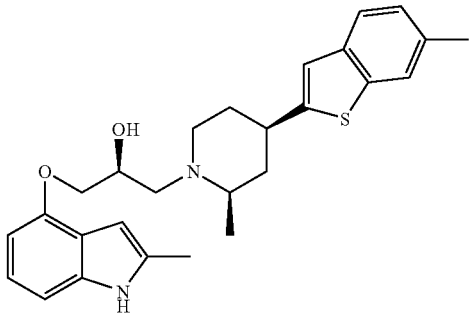

-continued

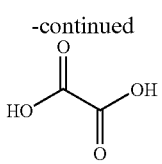

Preparation of N-t-Butoxycarbonyl-4-hydroxy-2-methyl-4-(6-methylbenzo[b]thiophen-2-yl)piperidine.

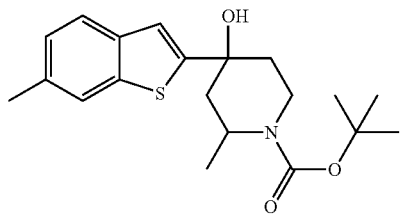

Scheme IA, Step A: To a solution of 6-methylbenzo[b]thiophene (6.11 g, 41.21 mmol) in dry THF (90 mL) at −78° C. was added 1.6 M n-BuLi in hexanes (30.9 mL, 49.4 mmol). The solution was stirred at −78° C. for 40 min. The N-t-butoxycarbonyl-2-methyl-4-piperdone (5.27 g, 24.7 mmol) dissolved in THF (47 mL) was added via a cannula at −78° C. The reaction mixture as stirred at −78° C. for 3 h. The reaction was then quenched with 200 mL of water. The mixture was extracted (3×200 mL) with EtOAc. The combined organic layers were dried over $MgSO_4$ and filtered. The filtrate was concentrated and run through a column of silica gel (17% EtOAc/hexanes) to give the intermediate title compound with some unreacted N-t-butoxycarbonyl-2-methyl-4-piperidone as an orange oil (6.75 g, 45%). IR (KBr) 1680, 1418, 1366, 1158 $cm^{-1}$. Ion Spray MS 420 $(M+CH_3COO^-)^-$.

Preparation of (±)-cis-2-Methyl-4-(6-methylbenzo[b]thiophen-2-yl)piperidine.

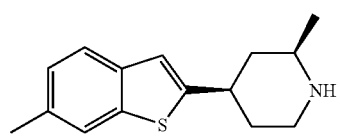

Scheme IA, Steps B and C: To a solution of N-t-butoxycarbonyl-4-hydroxy-2-methyl-4-(6-methylbenzo[b]thiophen-2-yl)piperidine (6.68 g, 18.47 mmol) in dry $CH_2Cl_2$ (52.0 mL) at 0° C. was added 23.45 mL of trifluoroacetic acid. The resulting purple solution was stirred at 0° C. for 15 h. The reaction was then quenched at room temperature with saturated aqueous $NaHCO_3$ solution (200 mL). The mixture was extracted (3×100 mL) with $CH_2Cl_2$. The combined organic layers were dried over $MgSO_4$, filtered and concentrated to yield 4.15 g of crude regioisomeric olefins. The material was run through a column of silica gel [3% (2.0 M $NH_3$ in MeOH)/$CH_2Cl_2$] to give a crude orange amorphous solid (2.36 g). To the mixture of olefins (2.33 g) in a mixture of ethanol (82.0 mL) and 2,2,2-trifluoroethanol (27 mL) was added 10% Pd/C (10.62 g). The black slurry was stirred vigorously at room temperature under hydrogen (balloon pressure) for three days. The black slurry was filtered through a pad of Celite and washed with MeOH. The filtrate was concentrated and the residue was purified by flash chromatography [4% (2.0 M $NH_3$ in MeOH)/$CH_2Cl_2$] to give the intermediate title compound as a white solid (0.2442 g, 10.3%). IR (KBr) 2928, 1473, 839 $cm^{-1}$. Ion Spray 246.3 $(M+H)^+$.

Preparation of (±)-trans-2-Methyl-4-(6-methylbenzo[b]thiophen-2-yl)piperidine.

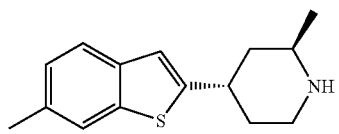

Scheme IA, Steps B and C: To a solution of N-t-butoxycarbonyl-4-hydroxy-2-methyl-4-(6-methylbenzo[b]thiophen-2-yl)piperidine (6.68 g, 18.47 mmol) in dry $CH_2Cl_2$ (52.0 mL) at 0° C. was added 23.45 mL of trifluoroacetic acid. The resulting purple solution was stirred at 0° C. for 15 h. The reaction was then quenched at room temperature with saturated aqueous $NaHCO_3$ solution (200 mL). The mixture was extracted (3×100 mL) with $CH_2Cl_2$. The combined organic layers were dried over $MgSO_4$, filtered and concentrated to yield 4.15 g of crude regioisomeric olefins. The material was run through a column of silica gel 3% (2.0 M $NH_3$ in MeOH)/$CH_2Cl_2$] to give a crude orange semi-solid (2.36 g). To the mixture of olefins (2.33 g) in a mixture of ethanol (82.0 mL) and 2,2,2-trifluoroethanol (27 mL) was added 10% Pd/C (10.62 g). The black slurry was stirred vigorously at room temperature under hydrogen (balloon pressure) for three days. The black slurry was filtered through a pad of Celite and washed with MeOH. The filtrate was then concentrated and the residue was purified by flash chromatography [4% (2.0 M $NH_3$ in MeOH)/$CH_2Cl_2$] to give the intermediate title compound as an orange solid (0.2017 g, 8.5%). IR (KBr) 2925, 1473, 840 $cm^{-1}$. Ion Spray 246.3 $(M+H)^+$.

Preparation of Final Title Compound.

Scheme IV, Step B: A solution of (±)-cis-2-methyl-4-(6-methylbenzo[b]thiophen-2-yl)piperidine (0.1034 g, 0.421 mmol) and (2S)-4-glycidyloxy-2-methylindole (0.0899 g, 0.442.0 mmol, prepared in example 1) in MeOH (6 mL) was heated at reflux for 15 h and then cooled and evaporated. The residue was purified by silica gel chromatography [1.25% (2.0 M $NH_3$ in MeOH)/$CH_2Cl_2$] to give the free base of the final title compound as off-white crystals (0.0539 g, 28%). The oxalate salt was prepared with 1 eq. of oxalic acid in EtOAc. mp 95.4° C. (dec.). IR (KBr) 3473, 3007, 2923, 1246, 1098 $cm^{-1}$. Ion Spray MS 449 $(M+H)^+$; 447 $(M-H)^-$. $[\alpha]_D = -25.16$ (c 0.477, $CHCl_3$). $C_{27}H_{32}N_2O_2S \cdot C_2H_2O_4$

| analysis: | calculated | found |
|---|---|---|
| C | 64.66 | 64.50 |
| H | 6.36 | 6.31 |
| N | 5.20 | 5.39 |

EXAMPLE 25

Preparation of (2S)-(−)-1-(1H-2-Methylindol-4-yl)oxy-3-[(2S,4S)-2-methyl-4-(6-methylbenzo[b]thiophen-2-yl)piperidinyl]-2-propanol oxalate

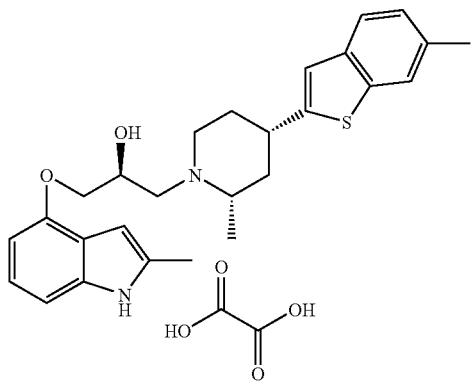

Scheme IV, Step B: A solution of (±)-cis-2-methyl-4-(6-methylbenzo[b]thiophen-2-yl)piperidine (0.1034 g, 0.421 mmol, prepared in example 25) and (2S)-4-glycidyloxy-2-methylindole (0.0899 g, 0.442.0 mmol, prepared in example 1) in MeOH (6 mL) was heated at reflux for 15 h and then cooled and evaporated. The residue was purified by silica gel chromatography [1.25% (2.0 M NH$_3$ in MeOH)/CH$_2$Cl$_2$] to give the free base of the title compound as off-white crystals (0.0468 g, 24.7%). The oxalate salt was prepared with 1 eq. of oxalic acid in EtOAc. mp 98.0° C. (dec.). IR (KBr) 3473, 3007, 2932, 1246, 1097 cm$^{-1}$. Ion Spray MS 449 (M+H)$^+$; 447 (M−H)$^-$. [α]$_D$=−6.96 (c 0.575, CHCl$_3$). C$_{27}$H$_{32}$N$_2$O$_2$S.C$_2$H$_2$O$_4$.1.0H$_2$O

| analysis: | calculated | found |
|---|---|---|
| C | 62.57 | 62.33 |
| H | 6.52 | 6.34 |
| N | 5.03 | 5.11 |

EXAMPLE 26

Preparation of (2S)-(−)-1-(1H-2-Methylindol-4-yl)oxy-3-[(2S,4R)-2-methyl-4-(6-methylbenzo[b]thiophen-2-yl)piperidinyl]-2-propanol oxalate

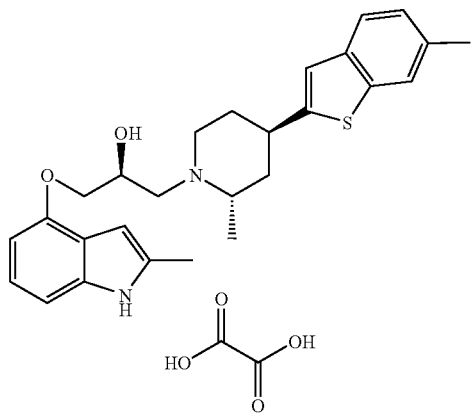

Scheme IV, Step B: A solution of (±)-trans-2-methyl-4-(6-methylbenzo[b]thiophen-2-yl)piperidine (0.0743 g, 0.302 mmol, prepared in example 25) and (2S)-4-glycidyloxy-2-methylindole (0.0646 g, 0.317 mmol, prepared in example 1) in MeOH (4 mL) was heated at reflux for 15 h and then cooled and evaporated. The residue was purified by silica gel chromatography [1.75% (2.0 M NH$_3$ in MeOH)/CH$_2$Cl$_2$] to give the free base of the title compound as an off-white solid (0.0274 g, 20%). The oxalate salt was prepared with 1 eq. of oxalic acid in EtOAc. mp 95.6° C. (dec.). Ion Spray MS 449 (M+H)$^+$; 447 (M−H)$^-$. [α]$_D$=−23.58 (c 0.424, CHCl$_3$). C$_{27}$H$_{32}$N$_2$O$_2$S.0.1H$_2$O

| analysis: | calculated | found |
|---|---|---|
| C | 72.00 | 71.84 |
| H | 7.21 | 7.60 |
| N | 6.22 | 6.13 |

EXAMPLE 27

Preparation of (2S)-(−)-1-(1H-2-Methylindol-4-yl)oxy-3-[(2R,4S)-2-methyl-4-(6-methylbenzo[b]thiophen-2-yl)piperidinyl]-2-propanol oxalate

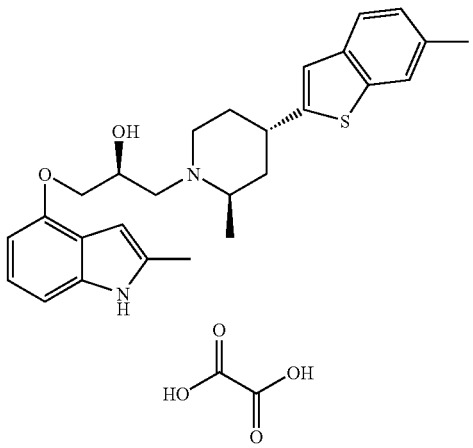

Scheme IV, Step B: A solution of (±)-trans-2-methyl-4-(6-methylbenzo[b]thiophen-2-yl)piperidine (0.0743 g, 0.302 mmol, prepared in example 25) and (2S)-4-glycidyloxy-2-methylindole (0.0646 g, 0.317 mmol, prepared in example 1) in MeOH (4 mL) was heated at reflux for 15 h and then cooled and evaporated. The residue was purified by silica gel chromatography [1.75% (2.0 M NH$_3$ in MeOH)/CH$_2$Cl$_2$] to give the free base of the title compound as a green oil (0.0407 g, 30%). The oxalate salt was prepared with 1 eq. of oxalic acid in EtOAc. mp 96.5° C. (dec.). Ion Spray MS 449 (M+H)$^+$; 447 (M−H)$^-$. [α]$_D$=−16.35 (c 0.363, CHCl$_3$). C$_{27}$H$_{32}$N$_2$O$_2$S.C$_2$H$_2$O$_4$.0.6H$_2$O

| analysis: | calculated | found |
|---|---|---|
| C | 63.39 | 63.07 |
| H | 6.46 | 6.29 |
| N | 5.10 | 5.39 |

EXAMPLE 28

Preparation of (2S)-1-(1H-Indol-4-yl)oxy-3-[(2R,4R)-2-methyl-4-(6-methylbenzo[b]thiophen-2-yl)piperidinyl]-2-propanol oxalate

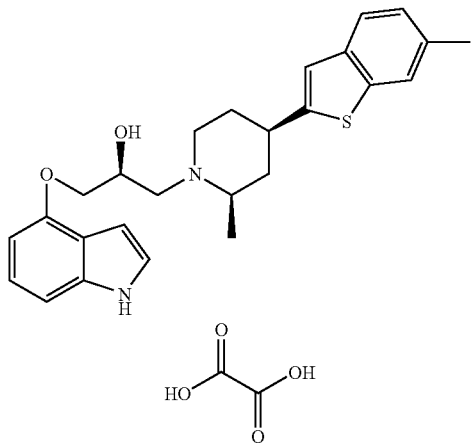

Scheme IV, Step B: A solution of (±)-cis-2-methyl-4-(6-methylbenzo[b]thiophen-2-yl)piperidine (0.11 g, 0.44 mmol, prepared in example 25) and (2S)-4-glycidyloxyindole (0.0874 g, 0.462.0 mmol) in MeOH (6 mL) was heated at reflux for 8 h and then cooled and allowed to stir at room temperature for 2 days. The solution was then heated at reflux for 4 h and then cooled and evaporated. The residue was purified by silica gel chromatography [1% (2.0 M $NH_3$ in $MeOH)/CH_2Cl_2$] to give the free base of the title compound as an off-white solid (0.0397 g, 20%). The oxalate salt was prepared with 1 eq. of oxalic acid in EtOAc. mp 96.8° C. (dec.). Ion Spray MS 435 (M+H)$^+$; 433 (M−H)$^-$. $C_{26}H_{30}N_2O_2S$

| analysis: | calculated | found |
|---|---|---|
| C | 71.86 | 71.87 |
| H | 6.96 | 7.05 |
| N | 6.45 | 6.18 |

EXAMPLE 29

Preparation of (2S)-1-(1H-Indol-4-yl)oxy-3-[(2S,4S)-2-methyl-4-(6-methylbenzo[b]thiophen-2-yl)piperidinyl]-2-propanol oxalate

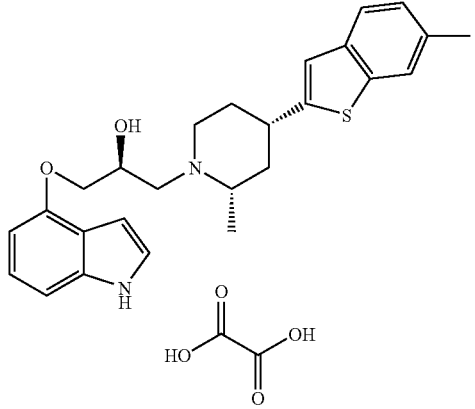

Scheme IV, Step B: A solution of (±)-cis-2-methyl-4-(6-methylbenzo[b]thiophen-2-yl)piperidine (0.11 g, 0.44 mmol, prepared in example 25) and (2S)-4-glycidyloxyindole (0.0874 g, 0.462.0 mmol) in MeOH (6 mL) was heated at reflux for 8 h and then cooled and allowed to stir at room temperature for 2 days. The solution was then heated at reflux for 4 h and then cooled and evaporated. The residue was purified by silica gel chromatography [1% (2.0 M $NH_3$ in $MeOH)/CH_2Cl_2$] to give the free base of the title compound as an off-white solid (0.0174 g, 9%). The oxalate salt was prepared with 1 eq. of oxalic acid in EtOAc. mp 89.5° C. (dec.). Ion Spray MS 435 (M+H)$^+$; 433 (M−H)$^-$. $C_{26}H_{30}N_2O_2S.C_2H_2O_4.0.4H_2O.0.1C_4H_8O_2$

| analysis: | calculated | found |
|---|---|---|
| C | 63.09 | 63.15 |
| H | 6.26 | 6.63 |
| N | 5.18 | 4.79 |

EXAMPLE 30

Preparation of (2S)-1-(1H-Indol-4-yl)oxy-3-[(2S,4R)-2-methyl-4-(6-methylbenzo[b]thiophen-2-yl)piperidinyl]-2-propanol oxalate

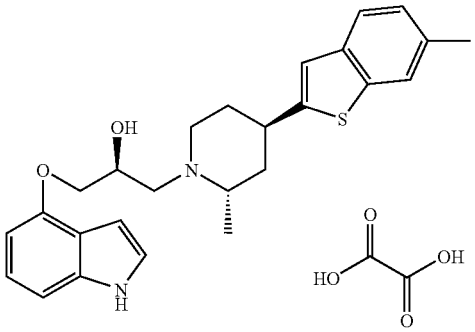

Scheme IV, Step B: A solution of (±)-trans-2-methyl-4-(6-methylbenzo[b]thiophen-2-yl)piperidine (0.070 g, 0.28 mmol, prepared in example 25) and (2S)-4-glycidyloxyindole (0.056 g, 0.300 mmol) in MeOH (4 mL) was heated at reflux for 8 h and then cooled and allowed to stir at room temperature for 2 days. The solution was then heated at reflux for 4 h and then cooled and evaporated. The residue was purified by silica gel chromatography [1% (2.0 M $NH_3$ in $MeOH)/CH_2Cl_2$] to give the free base of the title compound as a white solid (0.0122 g, 10%). The oxalate salt was prepared with 1 eq. of oxalic acid in EtOAc. mp 91° C. (dec.). Ion Spray MS 435 (M+H)$^+$; 433 (M−H)$^-$. $C_{26}H_{30}N_2O_2S.C_2H_2O_4.1.0H_2O$

| analysis: | calculated | found |
|---|---|---|
| C | 61.97 | 61.73 |
| H | 6.32 | 6.23 |
| N | 5.16 | 4.77 |

EXAMPLE 31

Preparation of (2S)-1-(1H-Indol-4-yl)oxy-3-[(2R,4S)-2-methyl-4-(6-methylbenzo[b]thiophen-2-yl)piperidinyl]-2-propanol oxalate

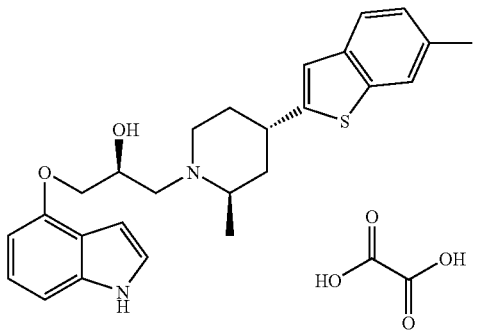

Scheme IV, Step B: A solution of (±)-trans-2-methyl-4-(6-methylbenzo[b]thiophen-2-yl)piperidine (0.070 g, 0.28 mmol, prepared in example 25) and (2S)-4-glycidyloxyindole (0.056 g, 0.300 mmol) in MeOH (4 mL) was heated at reflux for 8 h and then cooled and allowed to stir at room temperature for 2 days. The solution was then heated at reflux for 4 h and then cooled and evaporated. The residue was purified by silica gel chromatography [1% (2.0 M $NH_3$ in MeOH)/$CH_2Cl_2$] to give the free base of the title compound as a white solid (0.0103 g, 10%). The oxalate salt was prepared with 1 eq. of oxalic acid in EtOAc. mp 94.5° C. (dec.). Ion Spray MS 435 $(M+H)^+$; 433 $(M-H)^-$. $C_{26}H_{30}N_2O_2S \cdot C_2H_2O_4 \cdot 0.2H_2O$

| analysis: | calculated | found |
|---|---|---|
| C | 63.66 | 63.46 |
| H | 6.18 | 6.27 |
| N | 5.30 | 4.91 |

EXAMPLE 32

Preparation of (2S)-(+)-3-[4-(5-Chlorobenzo[b]thiophen-2-yl)piperidinyl]-1-(1H-2-methylindol-4-yl)oxy-2-propanol oxalate

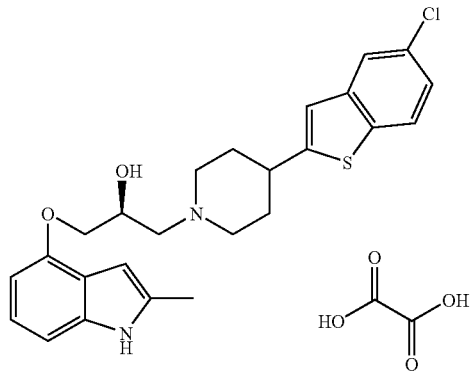

Scheme IV, Step B: A solution of the 4-(5-chlorobenzo[b]thiophen-2-yl)piperidine (192.5 mg, 0.76 mmol) and (2S)-4-glycidyloxy-2-methylindole (155.4 mg, 0.76 mmol, prepared in example 1) in MeOH (7 mL) was heated at reflux for 5.5 h. The reaction mixture was concentrated and flash chromatographed [2% (10% conc. $NH_4OH$ in MeOH)/$CH_2Cl_2$) to afford the free base of the title compound (316.4 mg, 91%) The oxalate salt was prepared with an equivalent amount of oxalic acid in EtOAc. IR ($CHCl_3$) 3394 $cm^{-1}$. Ion Spray MS 455.1 $(M^+)$. $[\alpha]_D=3.64$ (c 0.55, MeOH). $C_{25}H_{27}ClN_2O_2S$

| analysis: | calculated | found |
|---|---|---|
| C | 65.99 | 66.17 |
| H | 5.98 | 5.87 |
| N | 6.16 | 6.16 |

EXAMPLE 33

Preparation of (2S)-3-[4-(5-Chlorobenzo[b]thiophen-2-yl)-2-methyl-1,2,3,6-tetrahydropyridyl]-1-(1H-indol-4-yl)oxy-2-propanols oxalate

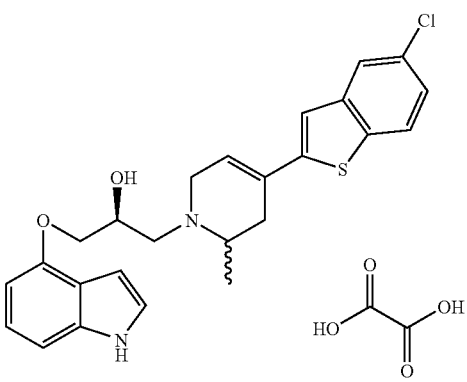

Preparation of 4-(5-Chlorobenzo[b]thiophen-2-yl)-2-methyl-1,2,3,6-tetrahydropyridine and 4-(5-Chlorobenzo[b]thiophen-2-yl)-2-methyl-1,2,5,6-tetrahydropyridine.

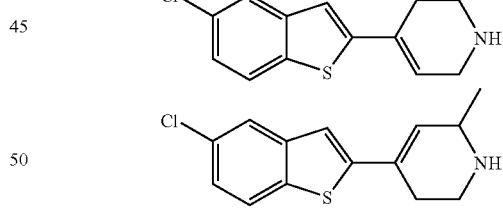

Scheme IA, Step A: A solution of 5-chlorobenzo[b]thiophene (505.4 mg, 3.0 mmol) in dry THF (10 mL) at −78° C. is treated with 1.6 M n-BuLi in hexanes (2.2 mL, 3.3 mmol) for 1 h. To this is cannulated N-t-butoxycarbonyl-4-(2-methyl)piperidone (3.3 mmol) in THF (5 mL) and the reaction mixture is stirred at −78° C. for 2h, warmed to room temperature and stirred for an additional 1 h. The reaction is then quenched with 40 mL of saturated aqueous $NaHCO_3$ solution. The mixture is then extracted with (3×50 mL) EtOAc. The organic layers are washed with 40 mL of brine, combined, dried over $MgSO_4$ and concentrated. Purification with flash chromatography (25% EtOAc/hexanes) affords the intermediate title compound which is carried on to the next step.

Scheme IA, Step B: To a solution of N-t-butoxycarbonyl-4-(5-chlorobenzo[b]thiophen-2-yl)-4-(2-methyl)piperidinol (2.4 mmol) in dry $CH_2Cl_2$ (6 mL) at 0° C. is added 3 mL of trifluoroacetic acid. The resulting solution is stirred at 0° C. for 1.5 h. The reaction is then quenched at room temperature with saturated aqueous $NaHCO_3$ solution (80 mL). The mixture is extracted with (3×250 mL) $CH_2Cl_2$. The combined organic layers are washed with 150 mL of brine and dried over $MgSO_4$. The filtrate is then concentrated and the residue is purified and intermediate title compounds partially separated by flash chromatography [8% (10% conc. $NH_4OH$ in $MeOH)/CH_2Cl_2$]. Ion Spray MS 264.0 $(M+H)^+$. $C_{14}H_{14}ClNS$.

Preparation of ( )-cis- and ( )-trans-4-(5-Chlorobenzo[b]thiophen-2-yl)-2-methylpiperidine.

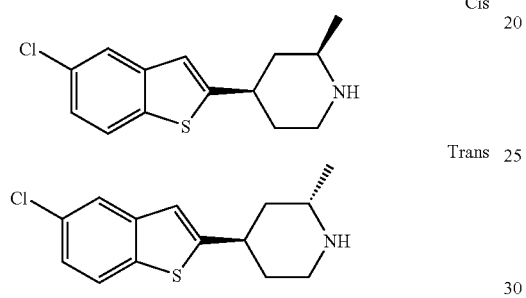

Scheme IA, Step C: A solution of 4-(5-chlorobenzo[b]thiophen-2-yl)-2-methyl-1,2,3,6-tetrahydropyridine and 4-(5-chlorobenzo[b]thiophen-2-yl)-2-methyl-1,2,5,6-tetrahydropyridine (816.8 mg, 3.1 mmol) in 32 mL of 3:1 mixture of ethanol and 2,2,2-trifluoroethanol was stirred vigorously at room temperature under hydrogen (balloon pressure) in the presence of 10% Pd/C (820 mg) for 4 days. The black slurry was then filtered through a Celite pad to remove the catalyst which was thoroughly washed with THF. The filtrate and washings were combined, concentrated, and flash chromatographed [8% (10% conc. $NH_4OH$ in $MeOH/CH_2Cl_2$] to yield the cis intermediate title compound (396.5 mg, 48%) and trans intermediate title compound (220.7 mg, 27%).

Cis compound: IR (KBr) 3447, 3290 $cm^{-1}$. Ion Spray MS 266.0 $(M+H)^+$. $C_{14}H_{16}ClNS$

| analysis: | calculated | found |
|---|---|---|
| C | 63.26 | 63.04 |
| H | 6.07 | 5.85 |
| N | 5.27 | 5.47 |

Trans compound: IR (KBr) 3434, 3256 $cm^{-1}$. Ion Spray MS 266.0 $(M+H)^+$. $C_{14}H_{16}ClNS$

| analysis: | calculated | found |
|---|---|---|
| C | 63.26 | 63.73 |
| H | 6.07 | 6.52 |
| N | 5.27 | 5.32 |

Preparation of Final Title Compound.

Scheme IV, Step B: A solution of 4-(5-chlorobenzo[b]thiophen-2-yl)-2-methyl-1,2,3,6-tetrahydropyridine (123.4 mg, 0.47 mmol) and (S)-4-(oxiranylmethoxy)indole (88.5 mg, 0.47 mmol) in MeOH (5 mL) was heated at reflux for 2.5 days. The mixture was concentrated and the residue was flash chromatographed [2% (10% conc. $NH_4OH$ in MeOH)/$CH_2Cl_2$] to afford the free base of the title compound. The oxalate salt was prepared with an equivalent amount of oxalic acid in EtOAc. Ion Spray MS 453 $(M)^+$. $C_{25}H_{25}ClN_2O_2S.(CO_2H)_2.0.9EtOAc$

| analysis: | calculated | found |
|---|---|---|
| C | 59.06 | 59.34 |
| H | 5.54 | 5.46 |
| N | 4.50 | 4.45 |

EXAMPLE 34

Preparation of (2S)-3-[4-(5-Chlorobenzo[b]thiophen-2-yl)-2-methyl-1,2,5,6-tetrahydropyridyl]-1-(1H-indol-4-yl)oxy-2-propanols oxalate

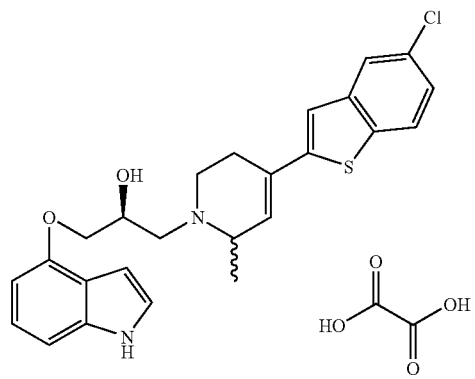

Scheme IV, Step B: A solution of 4-(5-chlorobenzo[b]thiophen-2-yl)-2-methyl-1,2,5,6-tetrahydropyridine (147.3 mg, 0.56 mmol, prepared in example 33) and (S)-4-(oxiranylmethoxy)indole (105.7 mg, 0.56 mmol) in MeOH (5 mL) was heated at reflux for 12 hr. The mixture was concentrated and the residue was flash chromatographed [2% (10% conc. $NH_4OH$ in MeOH)/$CH_2Cl_2$] to afford the free base of the title compound. The oxalate salt was prepared with an equivalent amount of oxalic acid in EtOAc (89% yield). IR (KBr) 3402, 1584, 1509, 1502 $cm^{-1}$. Ion Spray MS 453.0 $(M)^+$. $C_{25}H_{25}ClN_2O_2S.0.3EtOAc$

| analysis: | calculated | found |
|---|---|---|
| C | 65.64 | 65.61 |
| H | 5.76 | 5.72 |
| N | 5.84 | 5.87 |

EXAMPLE 35

Preparation of (2S)-(−)-3-[(2R,4R)-4-(5-Chlorobenzo[b]thiophen-2-yl)-2-methylpiperidinyl]-1-(1H-indol-4-yl)oxy-2-propanol oxalate (A) and (2S)-(+)-3-[(2S,4S)-4-(5-Chlorobenzo[b]thiophen-2-yl)-2-methylpiperidinyl]-1-(1H-indol-4-yl)oxy-2-propanol oxalate (B)

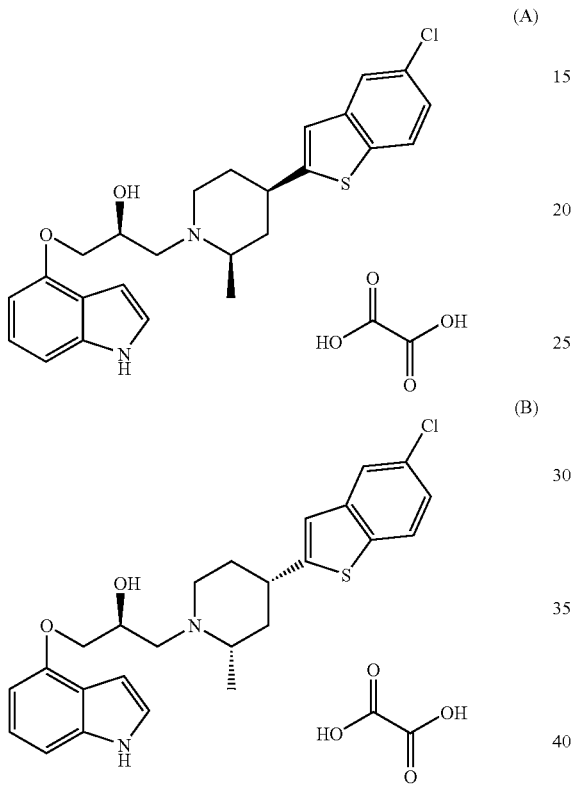

Scheme IV, Step B: A solution of ( )-cis-4-(5-chlorobenzo[b]thiophen-2-yl)-2-methylpiperidine (390.2 mg, 1.47 mmol, prepared in example 33) and (S)-4-(oxiranylmethoxy)indole (277.8 mg, 1.47 mmol) in MeOH (15 mL) was heated at reflux for 30 h. The mixture was concentrated and flash chromotagraphed [2% (2.0 M $NH_3$ in MeOH)/$CH_2Cl_2$] to afford the free base to title compound A (309.2 mg, 46%) and the free base of title compound B (303.5 mg, 45%). The oxalate salt of each compound was prepared with an equivalent amount of oxalic acid in EtOAc in quantitative yield.

Compound A: IR (KBr) 3406 cm$^{-1}$. Ion Spray MS 455.0 (M)$^+$. [ ]$_D$=−11.93 (c 0.50, MeOH). $C_{25}H_{27}ClN_2O_2S \cdot 0.8 (CO_2H)_2 \cdot 0.3 EtOAc$

| analysis: | calculated | found |
|---|---|---|
| C | 60.33 | 60.51 |
| H | 5.65 | 5.42 |
| N | 5.06 | 4.69 |

Compound B: IR (KBr) 3407 cm$^{-1}$. Ion Spray MS 455.0 (M)$^+$. [α]$_D$=30.84 (c 0.45, MeOH). $C_{25}H_{27}ClN_2O_2S$

| analysis: | calculated | found |
|---|---|---|
| C | 65.99 | 66.15 |
| H | 5.98 | 6.04 |
| N | 6.16 | 5.91 |

EXAMPLE 36

Preparation of (2S)-3-[(2S,4R)-4-(5-Chlorobenzo[b]thiophen-2-yl)-2-methylpiperidinyl]-1-(1H-indol-4-yl)oxy-2-propanol oxalate (A) and (2S)-(+)-3-[(2R,4S)-4-(5-Chlorobenzo[b]thiophen-2-yl)-2-methylpiperidinyl]-1-(1H-indol-4-yl)oxy-2-propanol oxalate (B)

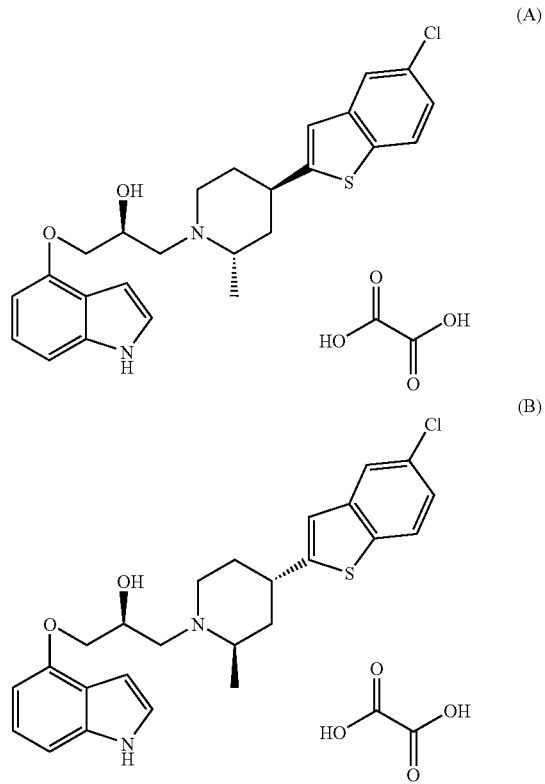

Scheme IV, Step B: A solution of ( )-trans-4-(5-chlorobenzo[b]thiophen-2-yl)-2-methylpiperidine (214.7 mg, 0.81 mmol, prepared in example 33) and (S)-4-(oxiranylmethoxy)indole (152.8 mg, 0.81 mmol) in MeOH (10 mL) was heated at reflux for 24 hr. The mixture was concentrated and flash chromotagraphed [2% (2.0 M $NH_3$ in MeOH)/$CH_2Cl_2$] to afford the free base of compound A (152.3 mg, 41%) and compound B (133.7 mg, 36%). The oxalate salt of each compound was prepared with an equivalent amount of oxalic acid in EtOAc in quantitative yield.

Compound A: IR (KBr) 3377 cm$^{-1}$. Ion Spray MS 455.0 (M)$^+$. [α]$_D$=0.00 (C 0.50, MeOH). C$_{25}$H$_{27}$ClN$_2$O$_2$S

| analysis: | calculated | found |
|---|---|---|
| C | 65.99 | 66.0 |
| H | 5.98 | 6.16 |
| N | 6.16 | 6.07 |

Compound B: IR (KBr) 3403 cm$^{-1}$. Ion Spray MS 455.0 (M)$^+$. [α]$_D$=12.1 (c 0.50, MeOH). C$_{25}$H$_{27}$ClN$_2$O$_2$S

| analysis: | calculated | found |
|---|---|---|
| C | 65.99 | 66.21 |
| H | 5.98 | 5.97 |
| N | 6.16 | 6.13 |

EXAMPLE 37

Preparation of (2S)-(−)-1-(1H-Indol-4-yl)oxy-3-[(2R,4R)-4-(4-methylbenzo[b]thiophen-2-yl)-2-methylpiperidinyl]-2-propanol oxalate (A) and (2S)-(+)-1-(1H-Indol-4-yl)oxy-3-[(2S,4S)-4-(4-methylbenzo[b]thiophen-2-yl)-2-methylpiperidinyl]-2-propanol oxalate (B)

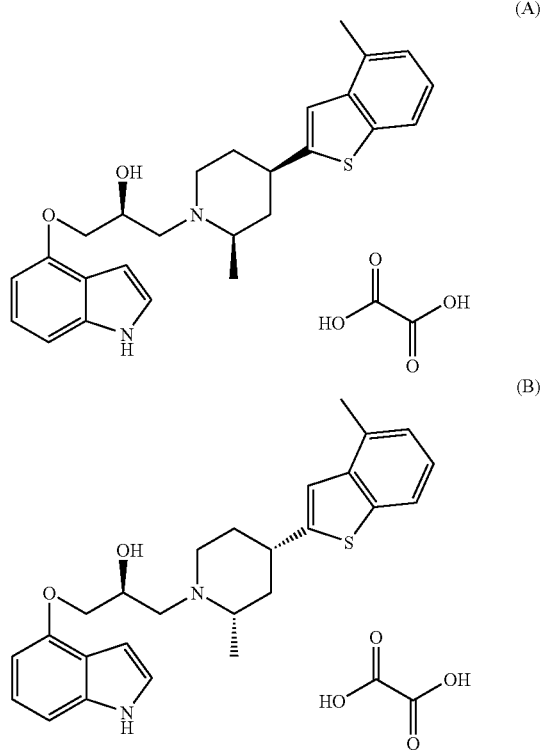

Preparation of ( )-cis-and ( )-trans-4-(4-Methylbenzo[b]thiophen-2-yl)-2-methylpiperidine.

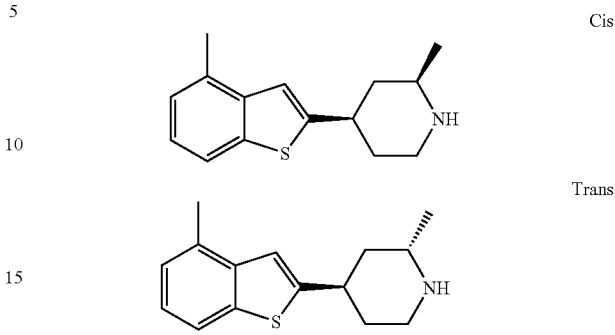

Scheme IV, Steps A, B and C: The title compounds were prepared in three steps in a manner analogous to the procedure described in example 33 to provide the intermediate title cis-compound (22% in 3 steps) and the intermediate trans-compound (9.7% in three steps). Ion Spray MS 246.1 (M+H)$^+$.

Preparation of Final Title Compound.

Scheme IV, Step B: A solution of ( )-cis-4-(4-methylbenzo[b]thiophen-2-yl)-2-methylpiperidine (200.7 mg, 0.82 mmol) and (S)-4-(oxiranylmethoxy)indole (200.7 mg, 0.82 mmol) in MeOH (8 mL) was heated at reflux for 8 h. The mixture was concentrated and flash chromatographed [3% (2.0 M NH$_3$ in MeOH)/CH$_2$Cl$_2$] to afford the free base of compound A (138.9 mg, 39%) and the free base of compound B (159.3 mg, 45%). The oxalate salt of each compound was prepared with an equivalent amount of oxalic acid in EtOAc in quantitative yield.

Compound 1: IR (KBr) 3411 cm$^{-1}$. Ion Spray MS 435.1 (M+H)$^+$; 433.1 (M−H)$^+$. [α]$_D$=−11.63 (c 0.34, MeOH). C$_{26}$H$_{30}$N$_2$O$_2$S.0.9(CO$_2$H)$_2$.0.2EtOAc

| analysis: | calculated | found |
|---|---|---|
| C | 64.42 | 64.52 |
| H | 6.31 | 5.54 |
| N | 5.25 | 4.89 |

Compound 2: IR (KBr) 3414 cm$^{-1}$. Ion Spray MS 435.1 (M+H)$^+$; 433.1 (M−H)$^+$. [α]$_D$=20.00 (c 0.50, MeOH). C$_{26}$H$_{30}$N$_2$O$_2$S.0.9(CO$_2$H)$_2$.0.6EtOAc

| analysis: | calculated | found |
|---|---|---|
| C | 63.80 | 63.93 |
| H | 6.49 | 6.88 |
| N | 4.93 | 4.72 |

EXAMPLE 38

Preparation of (2S)-1-(1H-Indol-4-yl)oxy-3-[(2S, 4R)-4-(4-methylbenzo[b]thiophen-2-yl)-2-methylpiperidinyl]-2-propanol oxalate (A) and (2S)-(−)-1-(1H-Indol-4-yl)oxy-3-[(2R,4S)-4-(4-methylbenzo[b]thiophen-2-yl)-2-methylpiperidinyl]-2-propanol oxalate (B)

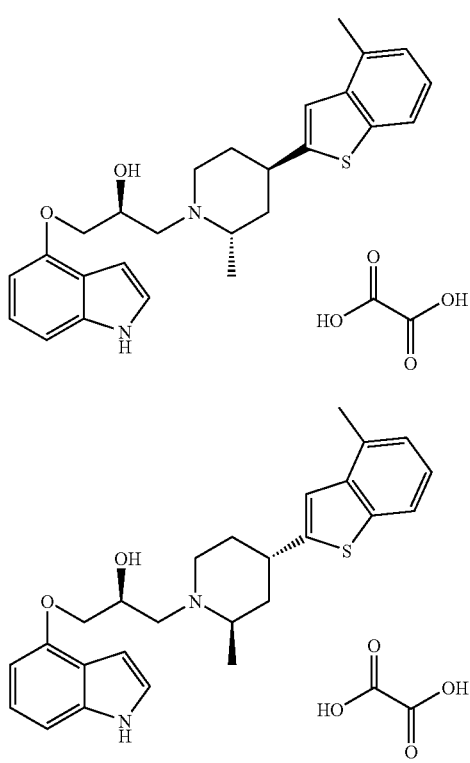

Scheme IV, Step B: A solution of ( )-trans-4-(4-methylbenzo[b]thiophen-2-yl)-2-methylpiperidine (88.4 mg, 0.36 mmol, prepared in example 37) and (S)-4-(oxiranylmethoxy)indole (71.6 mg, 0.36 mmol) in MeOH (4 mL) was heated at reflux for 6–7 hr. The mixture was concentrated and flash chromotographed [2% (2.0 M NH$_3$ in MeOH)/CH$_2$Cl$_2$] to afford the free base of compound A (78.3 mg, 50%) and the free base of compound B (74.0 mg, 47%). The oxalate salt of each compound was prepared with an equivalent amount of oxalic acid in EtOAc in quantitative yield.

Compound A: Ion Spray MS 435.0 (M+H)$^+$; 433.0 (M−H)$^+$. [α]$_D$=0.00 (c 0.28, MeOH). C$_{26}$H$_{30}$N$_2$O$_2$S.(CO$_2$H)$_2$. 0.2EtOAc

| analysis: | calculated | found |
|---|---|---|
| C | 63.79 | 63.57 |
| H | 6.25 | 6.56 |
| N | 5.17 | 4.79 |

Compound B: IR (KBr) 3414 cm$^{-1}$. Ion Spray MS 435.1 (M+H)$^+$; 433.1 (M−H)$^+$. [α]$_D$=−13.84 (c 0.29, MeOH). C$_{26}$H$_{30}$N$_2$O$_2$S.(CO$_2$H)$_2$.0.7EtOAc

| analysis: | calculated | found |
|---|---|---|
| C | 63.09 | 62.71 |
| H | 6.46 | 6.64 |
| N | 4.78 | 4.62 |

EXAMPLE 39

Preparation of (2S)-(−)-3-[(2R,4R)-4-(4,5-Dimethoxybenzo[b]thiophen-2-yl)-2-methylpiperidinyl]-1-(1H-indol-4-yl)oxy-2-propanol oxalate (A) and (2S)-3-[(2S,4S)-4-(4,5-Dimethoxybenzo[b]thiophen-2-yl)-2-methylpiperidinyl]-1-(1H-indol-4-yl)oxy-2-propanol oxalate (B)

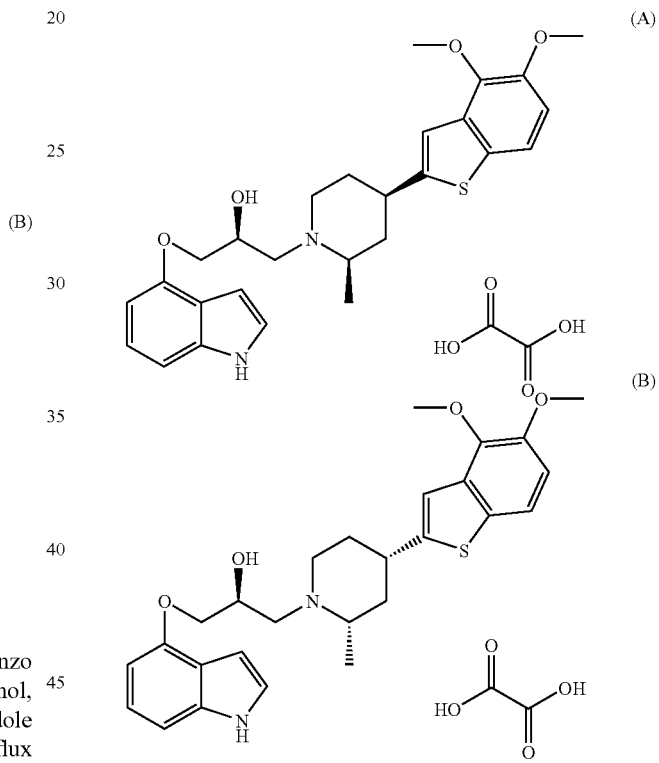

Preparation of ( )-cis- and ( )-trans-4-(4,5-Dimethoxybenzo[b]thiophen-2-yl)-2-methylpiperidine.

Cis
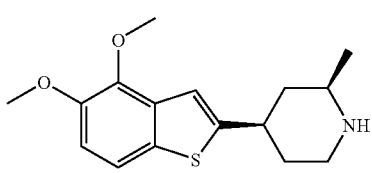

Trans
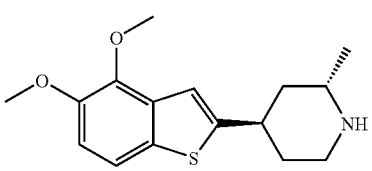

Scheme IA, Steps A, B and C: The intermediate title compounds were prepared in 3 steps in a manner analogous to the procedure described in example 33 to provide the cis-piperidine (61% in 3 steps) and trans-piperidine (12% in 3 steps). Ion Spray MS 292.0 (M+H)+.

Preparation of Final Title Compound.

Scheme IV, Step B: A solution of the ( )-cis-4-(4,5-dimethoxybenzo[b]thiophen-2-yl)-2-methylpiperidine (385.7 mg, 1.3 mmol) and (S)-4-(oxiranylmethoxy)indole (263.0 mg, 1.3 mmol) in MeOH (13 mL) was heated at reflux for 8 h. The mixture was concentrated and flash chromotagraphed [3% (2.0 M $NH_3$ in MeOH)/$CH_2Cl_2$] to afford the free base of compound A (48.1 mg, 7.6%), free base of compound B (50.8 mg, 8.0%), a byproduct (2S)-1-(1H-indol-4-yl)oxy-3-methoxy-2-propanol (153.3 mg, 52%) and recovered cis-piperidine (104.7 mg, 27%). The oxalate salt of each compound was prepared with an equivalent amount of oxalic acid in EtOAc in quantitative yield.

Compound A: Ion Spray MS 481.0 (M+H)+; 479.1 (M−H)−. $[\alpha]_D$=−12.93 (c 0.46, MeOH). $C_{27}H_{32}N_2O_4S \cdot 0.6(CO_2H)_2 \cdot 0.7EtOAc$

| analysis: | calculated | found |
|---|---|---|
| C | 62.44 | 62.75 |
| H | 6.56 | 6.58 |
| N | 4.70 | 6.36 |

Compound B: Ion Spray MS 481.0 (M+H)+; 479.0 (M−H)−. $[\alpha]_D$=0.00 (c 0.13, MeOH).

EXAMPLE 40

Preparation of (2S)-(−)-3-[(2S,4R)-4-(4,5-Dimethoxybenzo[b]thiophen-2-yl)-2-methylpiperidinyl]-1-(1H-indol-4-yl)oxy-2-propanol oxalate (A) and (2S)-3-[(2R,4S)-4-(4,5-Dimethoxybenzo[b]thiophen-2-yl)-2-methylpiperidinyl]-1-(1H-indol-4-yl)oxy-2-propanol oxalate (B)

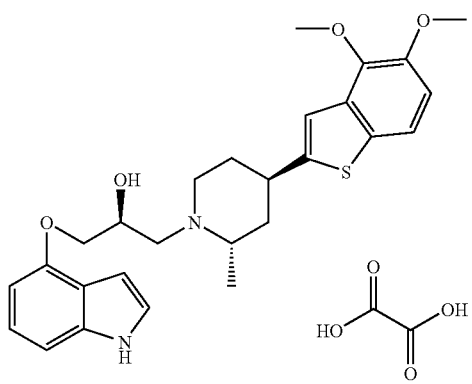
(A)

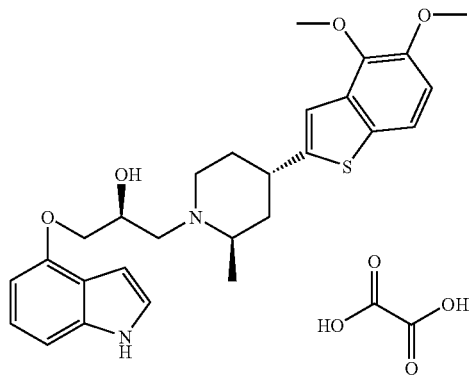
(B)

Scheme IV, Step B: A solution of ( )-trans-4-(4,5-Dimethoxybenzo[b]thiophen-2-yl)-2-methylpiperidine (82.0 mg, 0.28 mmol, prepared in example 39) and (S)-4-(oxiranylmethoxy)indole (55.9 mg, 0.30 mmol) in MeOH (3 mL) was heated at reflux for 6–7 hr. The mixture was concentrated and flash chromatagraphed [2% (2.0 M $NH_3$ in MeOH)/$CH_2Cl_2$] to afford the free base of compound A (57.3 mg, 42%) and the free base of compound B (64.3 mg, 48%). The oxalate salt of each compound was prepared with an equivalent amount of oxalic acid in EtOAc in 98 and 88% yield, respectively.

Compound A: Ion Spray MS 481.0 (M+H)+; 479.0 (M−H)−. $[\alpha]_D$=−5.24 (c 0.38, MeOH). $C_{27}H_{32}N_2O_4S \cdot 0.8(CO_2H)_2 \cdot 0.5EtOAc$

| analysis: | calculated | found |
|---|---|---|
| C | 61.59 | 61.68 |
| H | 6.35 | 6.13 |
| N | 4.36 | 4.36 |

Compound B: Ion Spray MS 481.0 (M+H)+; 479.0 (M−H)−. $[\alpha]_D$=0.00 (c 0.37, MeOH). $C_{27}H_{32}N_2O_4S \cdot 1.0(CO_2H)_2$

| analysis: | calculated | found |
|---|---|---|
| C | 61.04 | 61.07 |
| H | 6.01 | 6.29 |
| N | 4.91 | 4.64 |

EXAMPLE 41

Preparation of (2S)-(−)-3-[(2R,4R)-[4-(4-Chlorobenzo[b]thiophen-2-yl)-2-methylpiperidinyl]-1-(1H-Indol-4-yl)oxy-2-propanol oxalate (A) and (2S)-3-[(2S,4S)-[4-(4-Chlorobenzo[b]thiophen-2-yl)-2-methylpiperidinyl]-1-(1H-Indol-4-yl)oxy-2-propanol oxalate (B)

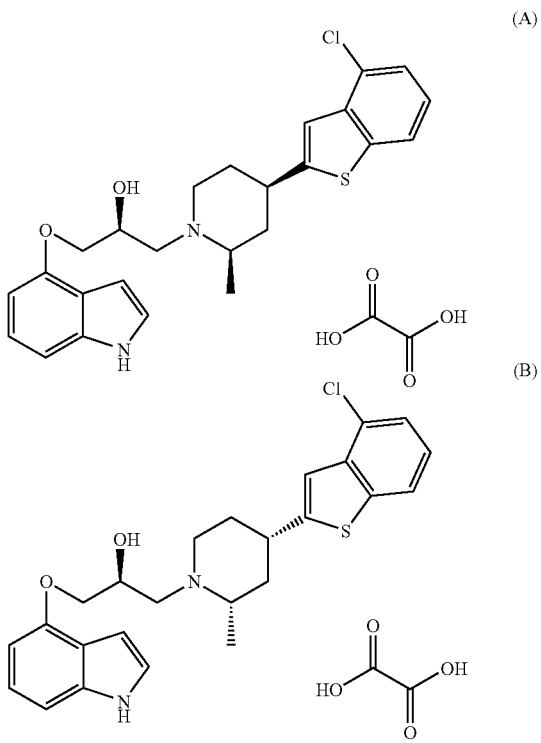

Preparation of 4-Chlorobenzo[b]thiophene and 6-Chlorobenzo[b]thiophene.

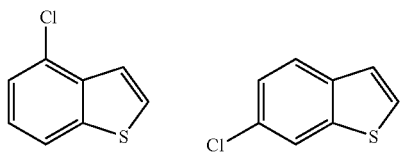

A mixture of 3-chlorobenzenethiol (9.9 g, 68.5 mmol), K₂CO₃ (11.35 g, 82.1 mmol), and bromoacetaldehyde diethyl acetal (8.1 mL, 68.5 mmol) in acetone (250 mL) was stirred at room temperature for 24 h. The base and the salt formed were removed by filtration with ethereal rinse. The filtrate and washings were combined, concentrated, taken up in 250 mL of Et₂O, and washed with 200 mL each of 0.5 N KOH and brine. The aqueous layers were back-extracted with 2×250 mL of Et₂O. Combined organic layers were dried over MgSO₄, concentrated, and dried under vacuum.

To a heated and vigorously stirred biphasic solution of polyphosphoric acid (PPA) (ca. 35 g) and chlorobenzene (350 mL) was added dropwise the crude acetal in 100 mL of chlorobenzene over 2.5 h period. After heating at reflux for 1.25 h, the mixture was stirred overnight while allowed to cool to room temperature. The organic layer was separated by decantation, concentrated, taken up in EtOAc (300 mL), and washed with 200 mL each of saturated aqueous NaHCO₃ and brine. The PPA layer was dissolved in H₂O (ca. 500 mL) and extracted with 3×300 mL of EtOAc which was washed with the saturated aqueous NaHCO₃ and brine used above. Combined organic layers were dried over MgSO₄, concentrated, and purified by PrepLC 500A with hexanes as eluent to yield 4-chlorobenzo[b]thiophene (4.269 g, 40%) and 6-chlorobenzo[b]thiophene (5.896 g, 51%) which was contaminated with 3-chlorobenzenedisulfide. FDMS 168(M)⁺.

Preparation of (N-t-Butoxycarbonyl-4-(4-chlorobenzo[b]thiophen-2-yl-2-methyl-4-piperidinol.

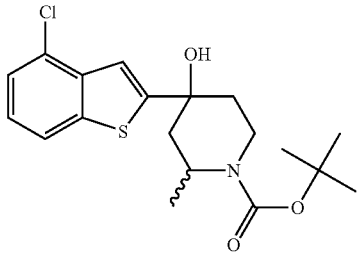

Scheme IA, Step A: A solution of 4-chlorobenzo[b]thiophene (1.6315 g, 9.67 mmol) in dry THF (20 mL) at −78° C. was treated with 1.6 M n-BuLi in hexanes (7.9 mL, 12.6 mmol) for 1 h. To this was cannulated (N-t-butoxycarbonyl-2-methyl-4-piperidone (420152, 3.2063 g, 15.0 mmol) in THF (15 mL) and the reaction mixture was stirred at −78° C. for 2h and then overnight while allowed to warm to −5° C. The reaction was quenched with 50 mL of saturated aqueous NaHCO3 solution and the mixture was extracted with EtOAc (3×100 mL). The organic layers were washed with 50 mL of brine, combined, dried over MgSO₄ and concentrated. Purification by PrepLC 500A (0–15% EtOAc/hexanes) afforded unreacted 4-chlorobenzo[b]thiophene (1.2646 g, 78%), the intermediate title compound (566.9 mg, 15%), and unreacted piperidone (2.4304 g, 76%). Ion Spray MS 382 (M+H)⁺.

Preparation of ( )-cis- and ( )-trans-4-(4-Chlorobenzo[b]thiophen-2-yl)-2-methylpiperidine.

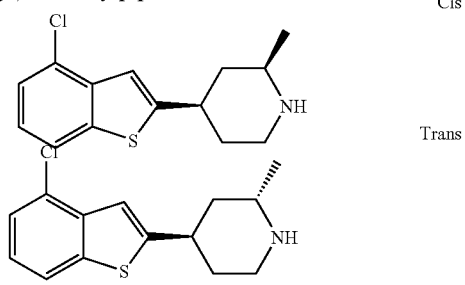

Scheme IA, Steps B and C: The intermediate title compounds were prepared in two steps from the piperidinol (N-t-butoxycarbonyl-4-(4-chlorobenzo[b]thiophen-2-yl)-2-methyl-4-piperidinol in two steps in a manner analogous to the procedure described in example 33: ( )-cis-4-(4-chlorobenzo[b]thiophen-2-yl)-2-methylpiperidine (32%) and ( )-trans-4-(4-chlorobenzo[b]thiophen-2-yl)-2-methylpiperidine (8%). Also obtained was dechlorinated 4-(benzo[b]thiophen-2-yl)-2-methylpiperidine (8%). Ion Spray MS 266.0 (M+H)⁺.

Preparation of Final Title Compound.

Scheme IV, Step B: The title compounds were prepared in a manner analogous to the procedure described in example 40 from ( )-cis-4-(4-chlorobenzo[b]thiophen-2-yl)-2-methylpiperidine and (S)-4-(oxiranylmethoxy)indole: Compound A (28%) and Compound B (23%). The oxalate salt of each compound was prepared with an equivalent amount of oxalic acid in EtOAc in quantitative yield.

Compound A: Ion Spray MS 455.0 (M)⁺; 454.2 (M–H)⁻. [α]$_D$=–13.67 (c 0.44, MeOH). $C_{25}H_{27}ClN_2O_2S \cdot 1.0(CO_2H)_2 \cdot 1.0EtOAc$

| analysis: | calculated | found |
|---|---|---|
| C | 58.81 | 58.65 |
| H | 5.89 | 6.27 |
| N | 4.42 | 4.32 |

Compound B: Ion Spray MS 455.0 (M)⁺; 479.0. [α]$_D$=0.00 (c 0.47, MeOH). $C_{25}H_{27}ClN_2O_2S \cdot 0.9(CO_2H)_2 \cdot 1.0EtOAc$

| analysis: | calculated | found |
|---|---|---|
| C | 59.27 | 59.53 |
| H | 5.94 | 6.34 |
| N | 4.49 | 4.51 |

EXAMPLE 42

Preparation of (2S)-(–)-3-[(2S,4R)-[4-(4-Chlorobenzo[b]thiophen-2-yl)-2-methylpiperidinyl]-1-(1H-Indol-4-yl)oxy-2-propanol oxalate (A) and (2S)-(–)-3-[(2R,4S)-[4-(4-Chlorobenzo[b]thiophen-2-yl)-2-methylpiperidinyl]-1-(1H-Indol-4-yl)oxy-2-propanol oxalate (B)

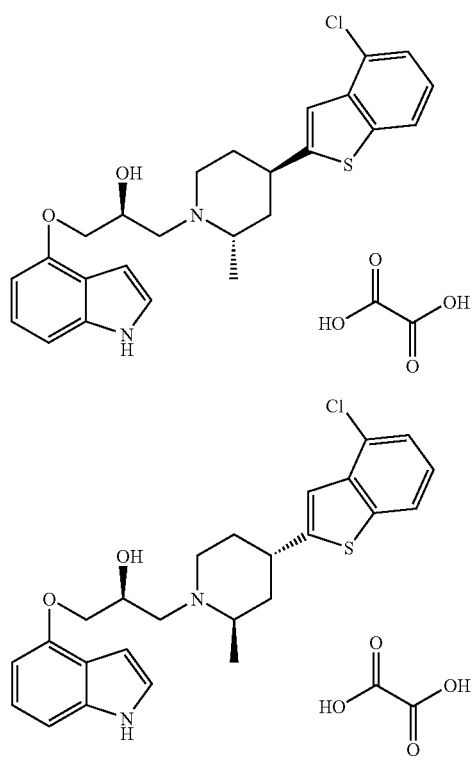

Scheme IV, Step B: The title compounds were prepared from ( )-trans-4-(4-chlorobenzo[b]thiophen-2-yl)-2-methylpiperidine (prepared in example 41) and (S)-4-(oxiranylmethoxy)indole in a manner analogous to the procedure described in example 40: compound A (340%) and compound B (24%). The oxalate salt of each compound was prepared with an equivalent amount of oxalic acid in EtOAc in quantitative yield.

Compound A: Ion Spray MS 455.0 (M)⁺. [α]$_D$=–6.43 (c 0.31, MeOH). $C_{25}H_{27}ClN_2O_2S \cdot 1.0(CO_2H)_2 \cdot 0.7EtOAc$

| analysis: | calculated | found |
|---|---|---|
| C | 58.99 | 58.70 |
| H | 5.75 | 6.10 |
| N | 4.62 | 4.86 |

Compound B: Ion Spray MS 455.0 (M)⁺; 479.0. [α]$_D$=–6.76 (c 0.30, MeOH). $C_{25}H_{27}ClN_2O_2S \cdot 1.8(CO_2H)_2 \cdot 0.9EtOAc$

| analysis: | calculated | found |
|---|---|---|
| C | 55.54 | 55.18 |
| H | 5.47 | 5.84 |
| N | 4.02 | 4.30 |

EXAMPLE 43

Preparation of (2S)-(–)-3-[(2R,4R)-4-(6-Chlorobenzo[b]thiophen-2-yl)-2-methylpiperidinyl]-1-(1H-indol-4-yl)oxy-2-propanol oxalate (A) and (2S)-(+)-3-[(2S,4S)-4-(6-Chlorobenzo[b]thiophen-2-yl)-2-methylpiperidinyl]-1-(1H-indol-4-yl)oxy-2-propanol oxalate (B).

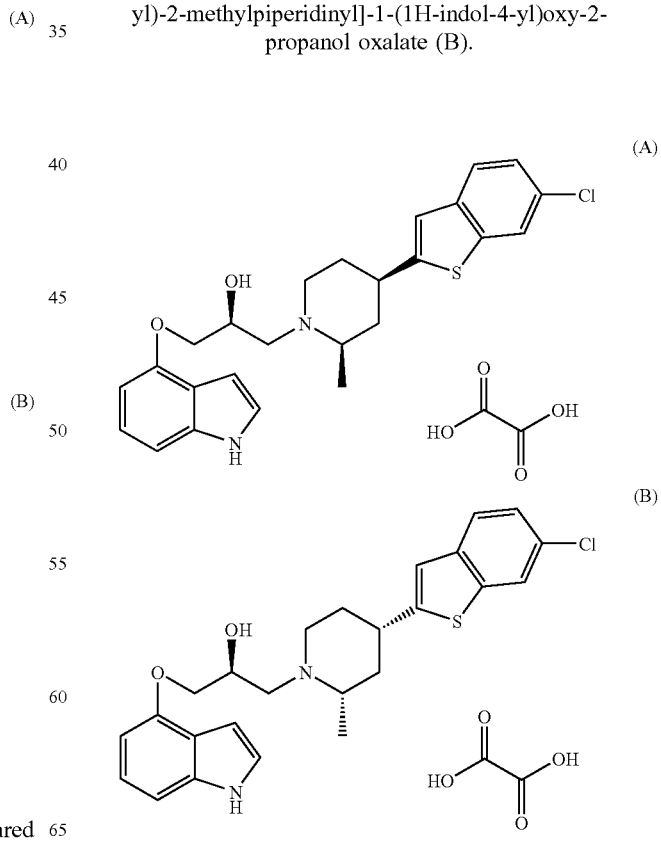

Preparation of N-t-Butoxycarbonyl-4-(6-chlorobenzo[b]thiophen-2-yl)-4-piperidinol.

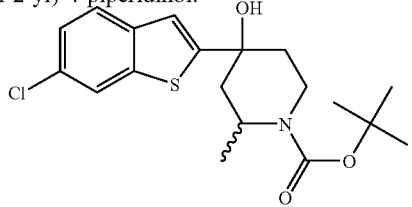

Scheme IA, Step A: A solution of 6-chlorobenzo[b]thiophene (3.3424 g, 19.8 mmol, prepared in example 41) in dry THF (90 mL) at −78° C. was treated with 1.6 M n-BuLi in hexanes (12.5 mL, 20.0 mmol) for 1 h. To this was cannulated (N-t-butoxycarbonyl-2-methyl-4-piperidone (420152, 2.6672 g, 12.5 mmol) in THF (10 mL) and the reaction mixture was stirred at −78° C. for 3 h. The cold bath was removed and the reaction was quenched after 10 min with 100 mL of saturated aqueous $NaHCO_3$ solution and the mixture was extracted with EtOAc (3×250 mL). The organic layers were washed with 100 mL of brine, combined, dried over $MgSO_4$ and concentrated. Purification by PrepLC 500A (0–30% $Et_2O$/hexanes) afforded unreacted 6-chlorobenzo[b]thiophene (2.0047 g, 60%) N-t-butoxycarbonyl-4-(4-chlorobenzo[b]thiophen-2-yl)-2-methyl-4-piperidinol (0.2528 g, 3.3%, resulted from the 4-chloro contamination in the starting 6-chlorobenzo[b]thiophene), unreacted piperidone (0.4184 g, 16%) and the intermediate title piperidinol (2.7510 g, 36%). Ion Spray MS 382.0 $(M+H)^+$.

Preparation of ( )-cis- and ( )-trans-4-(4-Chlorobenzo[b]thiophen-2-yl)-2-methylpiperidine.

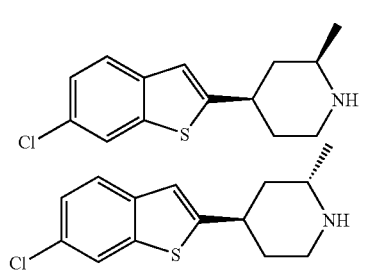

Scheme IA, Steps B and C: The title compounds were prepared in two steps from N-t-butoxycarbonyl-4-(6-chlorobenzo[b]thiophen-2-yl)-4-piperidinol in a manner analogous to the procedure described in example 33: ( )-cis-4-(4-chlorobenzo[b]thiophen-2-yl)-2-methylpiperidine (39%) and ( )-trans4-(4-chlorobenzo[b]thiophen-2-yl)-2-methylpiperidine (20%). Also obtained was 4-(6-chlorobenzo[b]thiophen-2-yl)-2-methyltetrahydropyridines (5%). Ion Spray MS 266.0 $(M+H)^+$. $C_{14}H_{16}ClNS$ (trans-isomer).

| analysis: | calculated | found |
|---|---|---|
| C | 63.26 | 63.00 |
| H | 6.07 | 6.21 |
| N | 5.27 | 5.09 |

Preparation of Final Title Compound.

Scheme IV, Step B: The title compounds were prepared from ( )-cis-4-(4-chlorobenzo[b]thiophen-2-yl)-2-methylpiperidine and (S)-4-(oxiranylmethoxy)indole in a manner analogous to the procedure described in example 40: Compound A (44%) and compound B (44%). The oxalate salt of each isomer was prepared with an equivalent amount of oxalic acid in EtOAc in quantitative yield.

Compound A: IR (KBr) 3406, 3350 $cm^{-1}$. Ion Spray MS 455.0 $(M)^+$. $[\alpha]_D$=−5.28 (c 0.38, MeOH). $C_{25}H_{27}ClN_2O_2S.0.1CH_2Cl_2$

| analysis: | calculated | found |
|---|---|---|
| C | 65.04 | 65.03 |
| H | 5.92 | 5.93 |
| N | 6.04 | 5.87 |

Compound B: IR (KBr) 3405 $cm^{-1}$. Ion Spray MS 455.0 $(M)^+$. $[\alpha]_D$=31.58 (c 0.57, MeOH). $C_{25}H_{27}ClN_2O_2S$

| analysis: | calculated | found |
|---|---|---|
| C | 65.99 | 65.99 |
| H | 5.98 | 5.97 |
| N | 6.16 | 5.89 |

EXAMPLE 44

Preparation of (2S)-3-[(2S,4R)-4-(6-Chlorobenzo[b]thiophen-2-yl)-2-methylpiperidinyl]-1-(1H-indol-4-yl)oxy-2-propanol oxalate (A) and (2S)-(+)-3-[(2R,4S)-4-(6-Chlorobenzo[b]thiophen-2-yl)-2-methylpiperidinyl]-1-(1H-indol-4-yl)oxy-2-propanol oxalate (B)

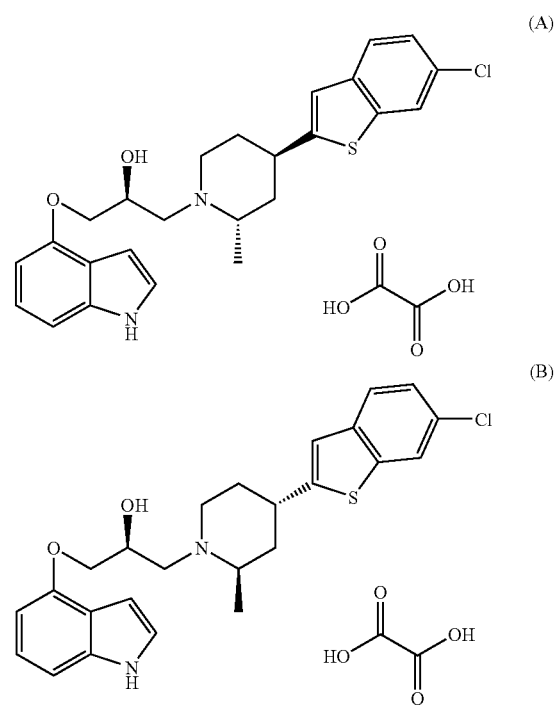

Scheme IV, Step B: The title compounds were prepared from ( )-trans-4-(4-chlorobenzo[b]thiophen-2-yl)-2-methylpiperidine (prepared in example 43) and (S)-4-(oxiranylmethoxy)indole in a manner analogous to the procedure described in example 43: Compound A (42%) and compound B (42%). The oxalate salt of each compound was prepared with an equivalent amount of oxalic acid in EtOAc in quantitative yield.

Compound A: $[\alpha]_D$ (could not be determined due to solubility problem). IR (KBr) 3406 cm$^{-1}$. Ion Spray MS 455.0 (M)$^+$. $C_{25}H_{27}ClN_2O_2S$

| analysis: | calculated | found |
|---|---|---|
| C | 65.99 | 66.22 |
| H | 5.98 | 5.74 |
| N | 6.16 | 5.86 |

Compound B: IR (KBr) 3406 cm$^{-1}$. Ion Spray MS 455.0 (M)$^+$. $[\alpha]_D=+10.19$ (c 0.59, MeOH). $C_{25}H_{27}ClN_2O_2S.0.8 (CO_2H)_2.0.7EtOAc$

| analysis: | calculated | found |
|---|---|---|
| C | 59.98 | 60.03 |
| H | 5.86 | 6.04 |
| N | 4.76 | 4.37 |

EXAMPLE 45

Preparation of (2S)-(−)-1-(1H-Indol-4-yl)oxy-3-[(2R,4R)-4-(6-methoxybenzo[b]thiophen-2-yl)-2-methylpiperidinyl]-2-propanol oxalate

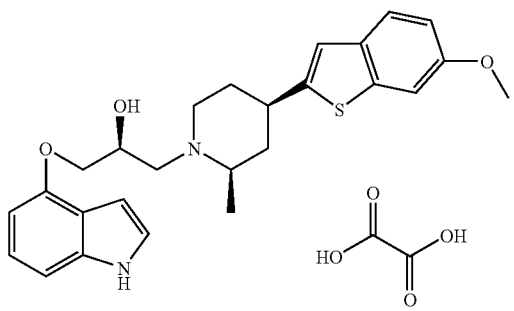

Preparation of N-t-Butoxycarbonyl-4-(6-methoxybenzo[b]thiophen-2-yl)-2-methyl-4-piperidinol.

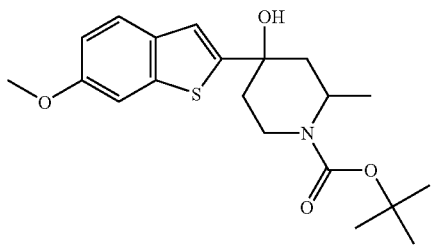

Scheme IA, Step A: To a solution of 6-methoxybenzo[b]thiophene (1.93 g, 11.7 mmol) in dry THF (55 mL) at −78° C. was added 1.6 M n-BuLi in hexanes (8.06 mL, 12.9 mmol). The solution was stirred at −78° C. for 45 min. N-t-Butoxycarbonyl-2-methyl-4-piperidone (1.50 g, 7.03 mmol) dissolved in THF (40 mL) was added via a cannula at −78° C. The reaction mixture was stirred at −78° C. for 3 h. The reaction was then quenched with 55 mL of saturated aqueous NH$_4$Cl solution. The mixture was extracted (1×400 mL) with EtOAc. The combined organic layers were then dried over MgSO$_4$ and filtered. The filtrate was concentrated and purified by medium pressure chromatography (20% EtOAc/hexanes) to give the intermediate title compound as a white foam (1.82 g, 69%). IR (KBr) 3422 (br), 1690, 1666 cm$^{-1}$. FDMS m/e=378 (M$^+$).

Preparation of (±)-cis-4-(6-Methoxybenzo[b]thiophen-2-yl)-2-methylpiperidine.

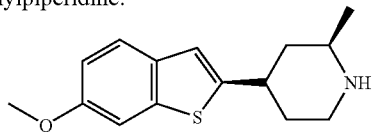

Scheme IA, Steps B and C: To a solution of N-t-butoxycarbonyl-4-(6-methoxybenzo[b]thiophen-2-yl)-2-methyl-4-piperidinol (1.80 g, 4.77 mmol) in dry CH$_2$Cl$_2$ (14 mL) at 0° C. was added 6 mL of trifluoroacetic acid. The resulting purple solution was stirred at 0° C. for 1.5 h. The reaction was then quenched at room temperature with saturated aqueous NaHCO$_3$ solution (150 mL). The mixture was extracted (1×300 mL) with CH$_2$Cl$_2$. The combined organic layers were dried over MgSO$_4$ and concentrated to yield 1.13 g of crude regioisomeric olefins. To a solution of the crude olefins (1.13 g) in a 3:1 mixture of ethanol (36 mL) and 2,2,2-trifluoroethanol (12 mL) was added 10% Pd/C (1.30 g). The black slurry was stirred vigorously at room temperature under hydrogen (balloon pressure) for 9 days. The black slurry was then filtered over a pad of diatomaceous earth and washed with ethanol. The filtrate was then concentrated, and the residue was purified by silica gel chromatography [6.5% (2.0 M NH$_3$ in MeOH)/CH$_2$Cl$_2$] to provide the intermediate title compound as a light brown solid (0.461 g, 40%). mp (oxalate) 248–250° C. Ion Spray MS 262 (M+H)$^+$.

Preparation of (±)-trans-4-(6-Methoxybenzo[b]thiophen-2-yl)-2-methylpiperidine.

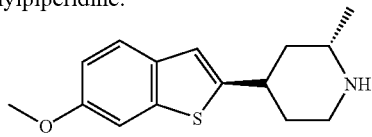

Scheme IA, Steps B and C: To a solution of N-t-butoxycarbonyl-4-(6-methoxybenzo[b]thiophen-2-yl)-2-methyl-4-piperidinol (1.80 g, 4.77 mmol) in dry CH$_2$Cl$_2$ (14 mL) at 0° C. was added 6 mL of trifluoroacetic acid. The resulting purple solution was stirred at 0° C. for 1.5 h. The reaction was then quenched at room temperature with saturated aqueous NaHCO$_3$ solution (150 mL). The mixture was extracted (1×300 mL) with CH$_2$Cl$_2$. The combined organic layers were dried over MgSO$_4$ and concentrated to yield 1.13 g of crude regioisomeric olefins. To a solution of the crude olefins (1.13 g) in a 3:1 mixture of ethanol (36 mL) and 2,2,2-trifluoroethanol (12 mL) was added 10% Pd/C (1.30 g). The black slurry was stirred vigorously at room temperature under hydrogen (balloon pressure) for 9 days. The black slurry was then filtered over a pad of diatomaceous earth and washed with ethanol. The filtrate was then concentrated, and the residue was purified by silica gel chromatography [6.5% 2.0 M NH$_3$ in MeOH)/CH$_2$Cl$_2$] to give (±)-trans-4-(6-methoxybenzo[b]thiophen-2-yl)-2-methylpiperidine as a light brown oil (0.257 g, 23%). Ion Spray MS 262 (M+H)$^+$.

Preparation of Final Title Compound.

Scheme IV, Step B: A solution of (±)-cis-2-methyl-4-(6-methoxybenzo[b]thiophen-2-yl)piperidine (0.200 g, 0.765 mmol) and (S)-4-(oxiranylmethoxy)indole (0.145 g, 0.765 mmol) in MeOH (10 mL) was heated at reflux for 28 h and then cooled and evaporated. The residue was purified using silica gel chromatography [1% (2.0 M $NH_3$ in MeOH)/$CH_2Cl_2$] to give the free base of the final title compound as a white foam (0.133 g, 39%). The oxalate salt was prepared with 1 equiv. of oxalic acid in EtOAc. mp 124–127° C. IR (KBr) 3406, 3350 (br) $cm^{-1}$. Ion Spray MS 451 (M+H)$^+$; 449 (M−H)$^-$; 509 (M+$CH_3COO^-$)$^-$. $[α]_D$ =−4.25 (c 0.47, MeOH). $C_{26}H_{30}N_2O_3S$

| analysis: | calculated | found |
|---|---|---|
| C | 69.30 | 69.47 |
| H | 6.71 | 6.62 |
| N | 6.22 | 6.07 |

EXAMPLE 46

Preparation of (2S)-(+)-1-(1H-indol-4-yl)oxy-3-[(2S,4S)-4-(6-methoxybenzo[b]thiophen-2-yl)-2-methylpiperidinyl]-2-propanol oxalate

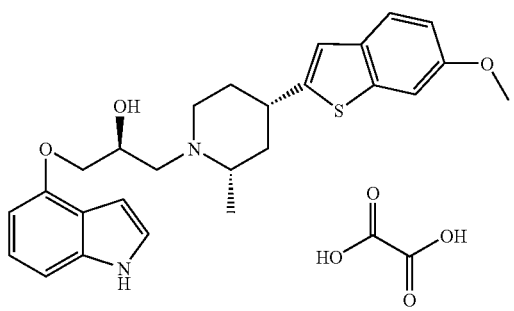

Scheme IV, Step B: A solution of (±)-cis-2-methyl-4-(6-methoxybenzo[b]thiophen-2-yl)piperidine (0.200 g, 0.765 mmol, prepared in example 45) and (S)-4-(oxiranylmethoxy)indole (0.145 g, 0.765 mmol) in MeOH (10 mL) was heated at reflux for 28 h and then cooled and evaporated. The residue was purified using silica gel chromatography [1% (2.0 M $NH_3$ in MeOH)/$CH_2Cl_2$] to give the title compound as a white foam (0.087 g, 25%). The oxalate salt was prepared with 1 equiv. of oxalic acid in EtOAc. mp 119–121° C. IR (KBr) 3411, 3350 (br) $cm^{-1}$. Ion Spray MS 451 (M+H)$^+$; 449 (M−H)$^-$; 509 (M+$CH_3COO^-$)$^-$. $[α]D$ =7.68 (c 0.52, MeOH). $C_{26}H_{30}N_2O_3S$

| analysis: | calculated | found |
|---|---|---|
| C | 69.30 | 69.50 |
| H | 6.71 | 6.71 |
| N | 6.22 | 6.22 |

EXAMPLE 47

Preparation of (2S)-1-(1H-Indol-4-yl)oxy-3-[(2S,4R)-4-(6-methoxybenzo[b]thiophen-2-yl)-2-methylpiperidinyl]-2-propanol

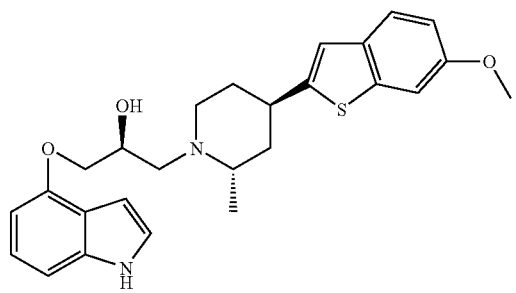

Scheme IV, Step B: A solution of (±)-trans-2-methyl-4-(6-methoxybenzo[b]thiophen-2-yl)piperidine (0.200 g, 0.765 mmol, prepared in example 45) and (S)-4-(oxiranylmethoxy)indole (0.145 g, 0.765 mmol) in MeOH (10 mL) was heated at reflux for 26 h and then cooled. The reaction mixture was filtered and washed with MeOH to give the title compound as a white solid (0.138.1 g, 40%). mp 179–182° C. IR (KBr) 3355 (br) $cm^{-1}$. Ion Spray MS 451 (M+H)$^+$; 449 (M−H)$^-$; 509 (M+$CH_3COO^-$)$^-$. $[α]_D$ =0 (c 0.44, DMSO). $C_{26}H_{30}N_2O_3S$

| analysis: | calculated | found |
|---|---|---|
| C | 69.30 | 69.28 |
| H | 6.71 | 6.54 |
| N | 6.22 | 6.18 |

EXAMPLE 48

Preparation of (2S)-(+)-1-(1H-Indol-4-yl)oxy-3-[(2R,4S)-4-(6-methoxybenzo[b]thiophen-2-yl)-2-methylpiperidinyl]-2-propanol oxalate

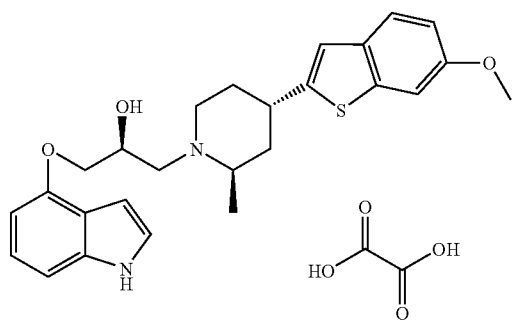

Scheme IV, Step B: A solution of (±)-trans-2-methyl-4-(6-methoxybenzo[b]thiophen-2-yl)piperidine (0.200 g, 0.765 mmol) and (S)-4-(oxiranylmethoxy)indole (0.145 g, 0.765 mmol) in MeOH (10 mL) was heated at reflux for 26 h and then cooled and filtered. The filtrate was concentrated and purified using silica gel chromatography [2% (2.0 M NH$_3$ in MeOH)/CH$_2$Cl$_2$] to give the free base of the title compound as a white foam (0.136 g, 39%). The oxalate salt was prepared with 1 equiv. of oxalic acid in EtOAc. mp 66–68° C. IR (KBr) 3403, 3350 (br) cm$^{-1}$. Ion Spray MS 451 (M+H)$^+$; 449 (M–H)$^-$; 509 (M+CH$_3$COO$^-$)$^-$. [α]$_D$=11.27 (c 0.36, MeOH). C$_{26}$H$_{39}$N$_2$O$_3$S

| analysis: | calculated | found |
|---|---|---|
| C | 69.30 | 69.17 |
| H | 6.71 | 6.42 |
| N | 6.22 | 6.08 |

EXAMPLE 49

Preparation of (2S)-(–)-1-(1H-Indol-4-yl)oxy-3-[(2R,4R)-2-methyl-4-(4-trifluoromethylbenzo[b]thiophen-2-yl)piperidinyl]-2-propanol oxalate

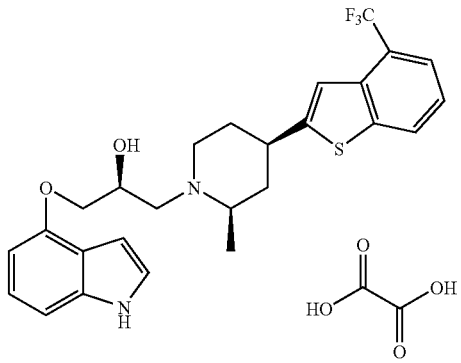

Preparation of N,N-Dimethyl-2-hydroxy-2-(2-trifluoromethylphenyl)thioacetamide.

To a solution of lithium diisopropylamide (2.0 M in heptane) (34.5 mL, 68.9 mmol) in 100 mL of dry THF (100 mL) cooled to –78° C. was added 2-trifluoromethylbenzaldehyde (7.58 mL, 57.4 mmol) and N,N-dimethylthioformamide (4.89 mL, 57.4 mmol) dissolved in 150 mL of dry THF via a cannula over a period of 10 min. The reaction mixture was stirred at –78° C. for 15 min, then warmed to 0° C., and quenched with saturated aqueous NH$_4$Cl solution (300 mL). The mixture was extracted with (3×1.0 L) with EtOAc. The combined organic layers were dried over MgSO$_4$ and concentrated. The residue was purified by medium pressure chromatography (silica gel, 25% EtOAc/hexanes) and then recrystallized from EtOAc/hexanes to give the intermediate title compound as an off-white solid (3.18 g, 21%). mp 112–115° C. IR (KBr) 3350 (br), 3239 cm$^{-1}$. Ion Spray MS 264 (M+H)$^+$; 246 (M–H$_2$O)$^+$; 322 (M+CH$_3$COO$^-$)$^-$.

Preparation of 2-Dimethylamino-4-trifluoromethylbenzo[b]thiophene.

N,N-Dimethyl-2-hydroxy-2-(2-trifluoromethylphenyl)thioacetamide (3.18 g, 12.1 mmol) was dissolved in Eaton's reagent (7.5% w/w P$_2$O$_5$/methanesulfonic acid) (21.2 mL). The reaction mixture was heated to 80° C. and stirred for 45 min. The reaction was quenched by pouring the reaction mixture slowly into cooled (0° C.) 5.0 N NaOH (75 mL). The mixture was extracted (2×300 mL) with EtOAc. The combined organic layers were dried over MgSO$_4$, concentrated, and the residue was purified by medium pressure chromatography (8% Et$_2$O/hexanes) to give the intermediate title compound as a yellow solid (0.816 g, 28%). mp 70–73° C. Ion Spray MS 246 (M+H)$^+$.

Preparation of 4-Trifluoromethylthianapthen-2-one.

2-Dimethylamino-4-trifluoromethylbenzo[b]thiophene (0.795 g, 3.24 mmol) was dissolved in a 1:1 mixture of THF/1.0 N HCl (30 mL). The biphasic mixture was stirred vigorously and heated at reflux for 4.5 days. The reaction mixture was then cooled to room temperature and the layers were separated. The aqueous layer was extracted (2×100 mL) with Et$_2$O. The combined organic layers were dried over MgSO$_4$ and concentrated. The residue was then purified by silica gel chromatography (1% Et$_2$O/hexanes) to give the intermediate title compound as a yellow oil (0.528 g, 75%). IR (CHCl$_3$) 1720 cm$^{-1}$. Ion Spray MS 217 (M–H)$^-$.

Preparation of 4-Trifluoromethylbenzo[b]thiophene.

To a solution of 4-trifluoromethylthianapthen-2-one (0.509 g, 2.33 mmol) in CH$_2$Cl$_2$ (23 mL) was added dropwise 1.0 M diisobutylaluminum hydride in toluene (2.57 mL, 2.57 mmol) at 0° C. The solution was stirred at 0° C. for 15 min. The reaction was quenched with conc. HCl (15 mL). This mixture was then stirred vigorously for 2 h. The layers were separated, and the organic layer was dried over MgSO$_4$, concentrated, and the residue was purified by silica gel chromatography (100% hexanes) to give the intermediate title compound as a clear liquid (0.300 g, 65%). IR (CHCl$_3$) 1313 cm$^{-1}$. FDMS m/e=216 (M+14)$^+$;

Preparation of N-t-Butoxycarbonyl-2-methyl-4-(4-trifluoromethylbenzo[b]thiophen-2-yl)-4-piperidinol.

Scheme IA, Step A: To a solution of 4-trifluoromethylbenzo[b]thiophene (0.440 g, 2.18 mmol) in dry THF (10 mL) at –78° C. was added 1.6 M n-BuLi in hexanes (1.50 mL, 2.39 mmol). The solution was stirred at –78° C. for 30 min. N-t-Butoxycarbonyl-2-methyl-4-piperidone (0.464 g, 2.18 mmol) dissolved in THF (5 mL) was added via a cannula at –78° C. The reaction mixture was warmed to room temperature over 18 h. The reaction was then quenched with 50 mL of saturated aqueous NH$_4$Cl solution. The mixture was extracted (3×100 mL) with EtOAc. The combined organic layers were then dried over MgSO$_4$, concentrated and purified by silica gel chromatography (10% EtOAc/hexanes) to give the intermediate title compound as a white foam (0.617 g, 68%). IR (KBr) 3416 (br), 1663 cm$^{-1}$. Ion Spray MS 416 (M+H)$^+$; 298 (M–(BOC+H$_2$O))$^+$; 342 (M–73)$^+$ (base peak); 890 (2M+CH$_3$COO).

Preparation of (±)-trans-4-Hydroxy-2-methyl-4-(4-trifluoromethylbenzo[b]thiophen-2-yl)piperidine.

Scheme IC: To a solution of N-t-butoxycarbonyl-2-methyl-4-(4-trifluoromethylbenzo[b]thiophen-2-yl)-4-piperidinol (0.611 g, 1.47 mmol) in dry CH$_2$Cl$_2$ (5 mL) at 0° C. was added 2 mL of trifluoroacetic acid. The resulting brown solution was stirred at 0° C. for 2 h. The reaction was then quenched at room temperature with saturated aqueous NaHCO$_3$ solution (30 mL). The mixture was extracted (1×60 mL) with CH$_2$Cl$_2$. The combined organic layers were dried over MgSO$_4$ and concentrated to yield 0.418 g of the crude deprotected product. To a solution of the piperidine (0.418 g) in a 3:1 mixture of ethanol (12 mL) and 2,2,2-trifluoroethanol (4 mL) was added 10% Pd/C (0.450 g). The black slurry was stirred vigorously at room temperature under hydrogen (balloon pressure) for 6 h. The black slurry was then filtered over a pad of diatomaceous earth and washed with ethanol. The filtrate was then concentrated, and the residue was purified by silica gel chromatography [7% (2.0 M NH$_3$ in MeOH)/CH$_2$Cl$_2$] to give the intermediate title compound as a white foam (0.127 g, 27%). mp 182–184° C. IR (KBr) 3300 (br), 3150 (br) cm$^{-1}$. Ion Spray MS 316 (M+H)$^+$; 298 (M–H$_2$O)$^+$.

Preparation of (±)-trans-2-Methyl-4-(4-trifluoromethyl-benzo[b]thiophen-2-yl)piperidine.

Scheme IA, Steps B and C: To a solution of N-t-butoxy-carbonyl-2-methyl-4-(4-trifluoromethylbenzo[b]thiophen-2-yl)-4-piperidinol (0.611 g, 1.47 mmol) in dry CH$_2$Cl$_2$ (5 mL) at 0° C. was added 2 mL of trifluoroacetic acid. The resulting brown solution was stirred at 0° C. for 2 h. The reaction was then quenched at room temperature with saturated aqueous NaHCO$_3$ solution (30 mL). The mixture was extracted (1×60 mL) with CH$_2$Cl$_2$. The combined organic layers were dried over MgSO$_4$ and concentrated to yield 0.418 g of the crude deprotected product. To a solution of the piperidine (0.418 g) in a 3:1 mixture of ethanol (12 mL) and 2,2,2-trifluoroethanol (4 mL) was added 10% Pd/C (0.450 g). The black slurry was stirred vigorously at room temperature under hydrogen (balloon pressure) for 6 h. The black slurry was then filtered over a pad of diatomaceous earth and washed with ethanol. The filtrate was then concentrated and the residue was purified by silica gel chromatography [7% (2.0 M NH$_3$ in MeOH)/CH$_2$Cl$_2$] to give the intermediate title compound as an off-white foam (0.044 g, 10%). Ion Spray MS 300 (M+H)$^+$.

Preparation of (±)-cis-2-Methyl-4-(4-trifluoromethylbenzo[b]thiophen-2-yl)piperidine.

Scheme IA, Steps B and C: To a solution of N-t-butoxy-carbonyl-2-methyl-4-(4-trifluoromethylbenzo[b]thiophen-2-yl)-4-piperidinol (0.611 g, 1.47 mmol) in dry CH$_2$Cl$_2$ (5 mL) at 0° C. was added 2 mL of trifluoroacetic acid. The resulting brown solution was stirred at 0° C. for 2 h. The reaction was then quenched at room temperature with saturated aqueous NaHCO$_3$ solution (30 mL). The mixture was extracted (1×60 mL) with CH$_2$Cl$_2$. The combined organic layers were dried over MgSO$_4$ and concentrated to yield 0.418 g of the crude deprotected product. To a solution of the piperidine (0.418 g) in a 3:1 mixture of ethanol (12 mL) and 2,2,2-trifluoroethanol (4 mL) was added 10% Pd/C (0.450 g). The black slurry was stirred vigorously at room temperature under hydrogen (balloon pressure) for 6 h. The black slurry was then filtered over a pad of diatomaceous earth and washed with ethanol. The filtrate was then concentrated and the residue was purified by silica gel chromatography [7% (2.0 M NH$_3$ in MeOH)/CH$_2$Cl$_2$] to give the intermediate title compound as an off-white foam (0.140 g, 32%). mp 106–108° C. IR (KBr) 3400 (br), 3228 cm$^{-1}$. Ion Spray MS 300 (M+H)$^+$.

Preparation of Final Title Compound.

Scheme IV, Step B: A solution of (±)-cis-2-methyl-4-(4-trifluoromethylbenzo[b]thiophen-2-yl)piperidine (0.133 g, 0.444 mmol) and (S)-4-(oxiranylmethoxy)indole (0.084 g, 0.444 mmol) in MeOH (7 mL) was heated at reflux for 26 h and then cooled and evaporated. The residue was purified using silica gel chromatography [1.5% (2.0 M NH$_3$ in MeOH)/CH$_2$Cl$_2$] to give the free base of the final title compound as a white foam (0.101 g, 47%). The oxalate salt was prepared with 1 equiv. of oxalic acid in EtOAc. mp (oxalate) 102–105° C. IR (KBr) 3407, 3350 (br) cm$^{-1}$. Ion Spray MS 489 (M+H)$^+$; 487 (M−H)$^-$. [α]$_D$=−7.19 (c 0.56, MeOH). C$_{26}$H$_{27}$F$_3$N$_2$O$_2$S

| analysis: | calculated | found |
|---|---|---|
| C | 63.92 | 63.67 |
| H | 5.57 | 5.79 |
| N | 5.73 | 5.76 |

EXAMPLE 50

Preparation of (2S)-(+)-1-(1H-Indol-4-yl)oxy-3-[(2S,4S)-2-methyl-4-(4-trifluoromethylbenzo[b]thiophen-2-yl)piperidinyl]-2-propanol oxalate

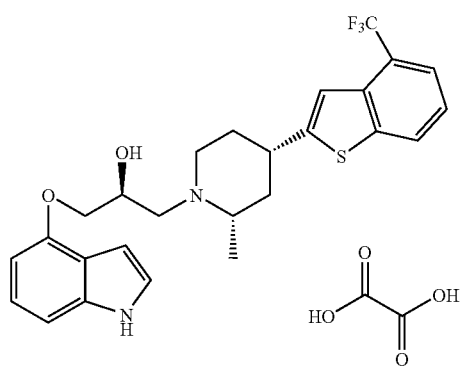

Scheme IV, Step B: A solution of (±)-cis-2-methyl-4-(4-trifluoromethylbenzo[b]thiophen-2-yl)piperidine (0.133 g, 0.444 mmol, prepared in example 49) and (S)-4-(oxiranyl-methoxy)indole (0.084 g, 0.444 mmol) in MeOH (7 mL) was heated at reflux for 26 h and then cooled and evaporated. The residue was purified using silica gel chromatography [1.5% (2.0 M NH$_3$ in MeOH)/CH$_2$Cl$_2$] to give the free base of the title compound as a white foam (0.090 g, 41%). The oxalate salt was prepared with 1 equiv. of oxalic acid in EtOAc. mp (oxalate) 115–119° C. IR (KBr) 3407, 3350 (br) cm$^{-1}$. Ion Spray MS 489 (M+H)$^+$; 487 (M−H)$^-$; 547 (M+CH$_3$COO$^-$)$^-$. [α]$_D$=6.10 (c 0.33, MeOH). C$_{26}$H$_{27}$F$_3$N$_2$O$_2$S

| analysis: | calculated | found |
|---|---|---|
| C | 63.92 | 63.73 |
| H | 5.57 | 5.46 |
| N | 5.73 | 5.49 |

EXAMPLE 51

Preparation of (2S)-1-(1H-Indol-4-yl)oxy-3-[(2S,4R)-2-methyl-4-(4-trifluoromethylbenzo[b]thiophen-2-yl)piperidinyl]-2-propanol oxalate

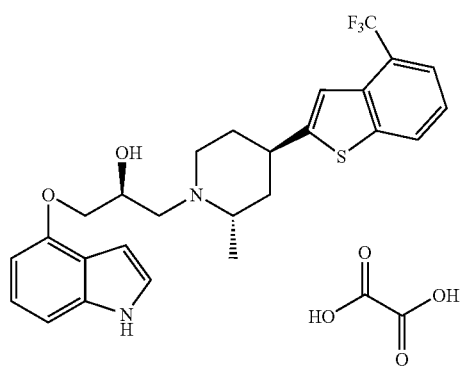

Scheme IV, Step B: A solution of (±)-trans-2-methyl-4-(4-trifluoromethylbenzo[b]thiophen-2-yl)piperidine (0.040 g, 0.132 mmol, prepared in example 49) and (S)-4-(oxiranylmethoxy)indole (0.025 g, 0.132 mmol) in MeOH (2 mL) was heated at reflux for 19 h and then cooled and evaporated. The residue was purified using silica gel chromatography [1.5% (2.0 M $NH_3$ in MeOH)/$CH_2Cl_2$] to give the free base of the title compound as an off-white foam (0.022 g, 34%). The oxalate salt was prepared with 1 equiv. of oxalic acid in EtOAc. mp (oxalate) 82–26° C. Ion Spray MS 489 (M+H)$^+$; 487 (M−H)$^−$; 547 (M+$CH_3COO^−$)$^−$. $C_{26}H_{27}F_3N_2O_2S.0.2CH_2Cl_2$

| analysis: | calculated | found |
|---|---|---|
| C | 62.24 | 62.52 |
| H | 5.46 | 5.72 |
| N | 5.54 | 5.20 |

EXAMPLE 52

Preparation of (2S)-1-(1H-Indol-4-yl)oxy-3-[(2R,4S)-2-methyl-4-(4-trifluoromethylbenzo]b]thiophen-2-yl)piperidinyl]-2-propanol oxalate

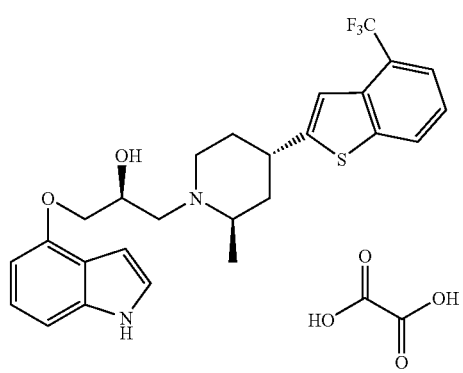

Scheme IV, Step B: A solution of (±)-trans-2-methyl-4-(4-trifluoromethylbenzo[b]thiophen-2-yl)piperidine (0.040 g, 0.132 mmol, prepared in example 49) and (S)-4-(oxiranylmethoxy)indole (0.025 g, 0.132 mmol) in MeOH (2 mL) was heated at reflux for 19 h and then cooled and evaporated. The residue was purified using silica gel chromatography [1.5% (2.0 M $NH_3$ in MeOH)/$CH_2Cl_2$] to give the free base of the title compound as an off-white foam (0.023 g, 35%). The oxalate salt was prepared with 1 equiv. of oxalic acid in EtOAc. mp (oxalate) 83–87° C. Ion Spray MS 489 (M+H)$^+$; 487 (M−H)$^−$. $C_{26}H_{27}F_3N_2O_2S.0.3C_6H_{14}$

| analysis: | calculated | found |
|---|---|---|
| C | 64.91 | 65.00 |
| H | 6.11 | 6.15 |
| N | 5.45 | 5.15 |

EXAMPLE 53

Preparation of (2S)-3-[(2R,4S)-4-Hydroxy-2-methyl-4-(4-trifluoromethylbenzo[b]thiophen-2-yl)piperidinyl]-1-(1H-indol-4-yl)oxy-2-propanol oxalate

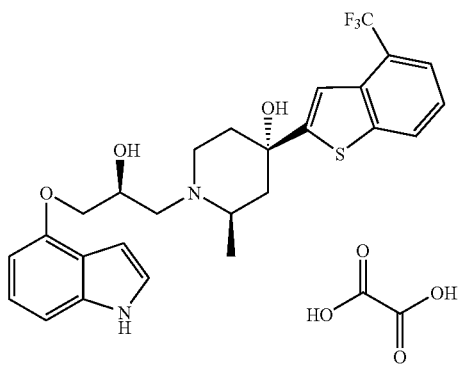

Scheme IV, Step B: A solution of (±)-trans-4-hydroxy-2-methyl-4-(4-trifluoromethylbenzo[b]thiophen-2-yl)piperidine (0.106 g, 0.336 mmol, prepared in example 49) and (S)-4-(oxiranylmethoxy)indole (0.064 g, 0.336 mmol) in MeOH (5 mL) was heated at reflux for 24 h and then cooled and evaporated. The residue was purified using silica gel chromatography [4% (2.0 M $NH_3$ in MeOH)/$CH_2Cl_2$] to give the free base of the title compound as a white foam (0.061 g, 36%). The oxalate salt was prepared with 1 equiv. of oxalic acid in EtOAc. mp (oxalate) 110° C. (dec.). IR (KBr) 3405, 3350 (br) cm$^{-1}$. Ion Spray MS 505 (M+H)$^+$; 487 (M−$H_2O$)$^+$; 503 (M−H)$^−$; 563 (M+$CH_3COO^−$)$^−$. $[\alpha]_D=0$ (c 0.34, MeOH). $C_{26}H_{27}F_3N_2O_3S.C_2H_2O_4$

| analysis: | calculated | found |
|---|---|---|
| C | 56.56 | 56.32 |
| H | 4.92 | 5.14 |
| N | 4.71 | 4.46 |

EXAMPLE 54

Preparation of (2S)-3-[(2S,4R)-4-Hydroxy-2-methyl-4-(4-trifluoromethylbenzo[b]thiophen-2-yl)piperidinyl]-1-(1H-indol-4-yl)oxy-2-propanol oxalate

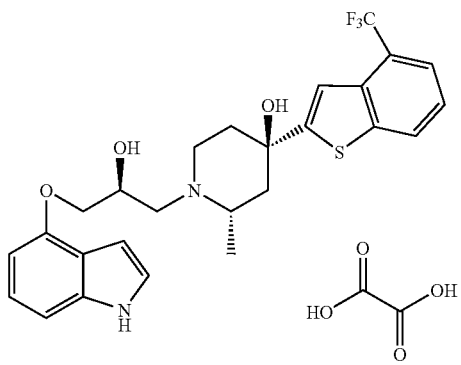

Scheme IV, Step B: A solution of (±)-trans-4-hydroxy-2-Methyl-4-(4-trifluoromethylbenzo[b]thiophen-2-yl)piperidine (0.106 g, 0.336 mmol, prepared in example 49) and (S)-4-(oxiranylmethoxy)indole (0.064 g, 0.336 mmol) in MeOH (5 mL) was heated at reflux for 24 h and then cooled and evaporated. The residue was purified using silica gel chromatography [4% (2.0 M $NH_3$ in $MeOH$)/$CH_2Cl_2$] to give the free base of the title compound as a white foam (0.066 g, 39%). The oxalate salt was prepared with 1 equiv. of oxalic acid in EtOAc. mp (oxalate) 103–105° C. IR (KBr) 3404, 3350 (br) $cm^{-1}$. Ion Spray MS 505 $(M+H)^+$; 487 $(M-H_2O)^+$; 503 $(M-H)^-$; 563 $(M+CH_3COO^-)^-$. $[\alpha]_D = -5.19$ (c 0.39, MeOH). $C_{26}H_{27}F_3N_2O_3S \cdot C_2H_2O_4$

| analysis: | calculated | found |
|---|---|---|
| C | 56.56 | 56.39 |
| H | 4.92 | 5.04 |
| N | 4.71 | 4.43 |

EXAMPLE 55

Preparation of (2S)-3-[4-(4-Fluorobenzo[b]thiophen-2-yl)piperidinyl]-1-(1H-2-methylindol-4-yl)oxy-2-propanol oxalate

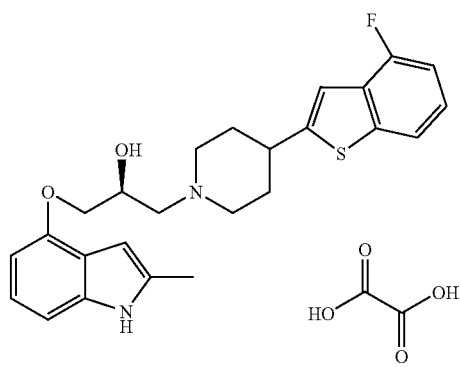

Preparation of 3-Fluorobenzenethioacetaldehyde diethyl acetal.

The title compound was prepared in 95% crude yield from 3-flourobenzenethiol in a manner analogous to the procedure of Graham, S. L., et. al. *J. Med. Chem.* 1989,32, 2548–2554.

Preparation of 4- and 6-Fluorobenzo[b]thiophene.

To a biphasic mixture of polyphosphoric acid (PPA; 22.5 g) and 210 mL of dry chlorobenzene heated to reflux was added dropwise 3-fluorobenzenethioacetaldehyde diethyl acetal (10.0 g, 40.9 mmol) in 40 mL of chlorobenzene over a period of 45 min. The dark green biphasic mixture was heated at reflux for an additional hour. The reaction mixture was cooled to room temperature and the organic layer was decanted off the PPA layer. The PPA layer was cooled to 0° C. and diluted with 200 mL of $H_2O$. This aqueous layer was extracted; with $CH_2Cl_2$ (2×400 mL). The combined organic layers dried over $MgSO_4$ and concentrated under reduced pressure. The residue was purified by medium pressure chromatography to give 4- and 6-fluorobenzo[b]thiophene as a green oil (5.12 g, 82%). FDMS m/e=152 $(M^+)$.

Preparation of N-t-Butoxycarbonyl-4-(4-fluorobenzo[b]thiophen-2-yl)-4-piperidinol.

Scheme IA, Step A: To a solution of 4- and 6-fluorobenzo[b]thiophene (1.70 g, 11.2 mmol) in dry THF (50 mL) at −78° C. was added 1.6 M n-BuLi in hexanes (9.08 mL, 14.5 mmol). The solution was stirred at −78° C. for 35 min. N-t-butoxycarbonyl-4-piperidone (2.67 g, 15.6 mmol) dissolved in THF (10 mL) was added via a cannula at −78° C. The reaction mixture was kept at −78° C. for 1.5 h, then allowed to warm to room temperature. The reaction was quenched with 150 mL of saturated aqueous $NH_4Cl$ solution. The mixture was then extracted (3×300 mL) with EtOAc. The combined organic layers were dried over $MgSO_4$ and filtered. The filtrate was concentrated and purified by medium pressure chromatography (silica gel, 20% EtOAc/hexanes) to give the intermediate title compound as a white foam (0.525 g, 13%). IR ($CHCl_3$) 3350 (br), 1683, 1244 $cm^{-1}$. Ion Spray MS 352 $(M+H)^+$; 234 $(M-(BOC+H_2O)^+$; 278 $(M-73)^+$ (base peak); 410 $(M+CH_3COO^-)^-$.

Preparation of 4-(4-Fluorobenzo[b]thiophen-2-yl)-1,2,5,6-tetrahydropyridine.

Scheme IA, Step B: To a solution of N-t-butoxycarbonyl-4-(4-fluorobenzo[b]thiophen-2-yl)-4-piperidinol (0.507 g, 1.44 mmol) in dry $CH_2Cl_2$ (5 mL) at 0° C. was added 2 mL of trifluoroacetic acid. The solution was stirred at 0° C. for 1.5 h. The reaction was then quenched at room temperature with saturated aqueous $NaHCO_3$ solution (25 mL). The mixture was extracted (3×50 mL) with $CH_2Cl_2$. The combined organic layers were dried over $MgSO_4$ and concentrated to give the intermediate title compound as a brown semi-solid (0.316 g, 94% (crude)). mp 83–86° C. Ion Spray MS 234 $(M+H)^+$.

Preparation of 4-(4-Fluorobenzo[b]thiophen-2-yl)piperidine.

Scheme IA, Step C: To a solution of 4-(4-fluorobenzo[b]thiophen-2-yl)-1,2,5,6-tetrahydropyridine (0.239 g, 1.03 mmol) in a 3:1 mixture of ethanol (9 mL) and 2,2,2-trifluoroethanol (3 mL) was added 10% Pd/C (0.250 g). The black slurry was stirred vigorously at room temperature under hydrogen (balloon pressure) for 8 h. The black slurry was then filtered over a pad of diatomaceous earth and washed with ethanol. The filtrate was concentrated, and the residue was purified by silica gel chromatography [8% (10% conc. $NH_4OH$ in MeOH)/$CH_2Cl_2$] to give the intermediate title compound as a yellow semi-solid (0.127 g, 53%). IR (KBr) 3432 (br), 3252, 3216, 1234 $cm^{-1}$. Ion Spray MS 236 $(M+H)^+$.

Preparation of Final Title Compound.

Scheme IV, Step B: A solution of 4-(4-fluorobenzo[b]thiophen-2-yl)piperidine (0.021 g, 0.089 mmol) and (2S)-4-glycidyloxy-2-methylindole (0.018 g, 0.089 mmol) in MeOH (2 mL) was heated at reflux for 6 h and then cooled and evaporated. The residue was purified using silica gel chromatography [2% (10% conc. $NH_4OH$ in MeOH)/$CH_2Cl_2$] to give the free base of the final title compound as an off-white foam (0.029 g, 73%). The oxalate salt was prepared with 1 equiv. of oxalic acid in EtOAc. mp (oxalate) 156–159° C. (dec.). Ion Spray MS 439 $(M+H)^+$; 437 $(M-H)^-$; 497 $(M+CH_3COO^-)^-$. $C_{25}H_{27}FN_2O_2S \cdot C_2H_2O_4$

| analysis: | calculated | found |
|---|---|---|
| C | 61.35 | 61.17 |
| H | 5.53 | 5.29 |
| N | 5.30 | 5.01 |

EXAMPLE 56

Preparation of (2S)-3-[(2R,4R)-4-(4-Fluorobenzo[b]thiophen-2-yl)-2-methylpiperidinyl]-1-(1H-indol-4-yl)oxy-2-propanol oxalate

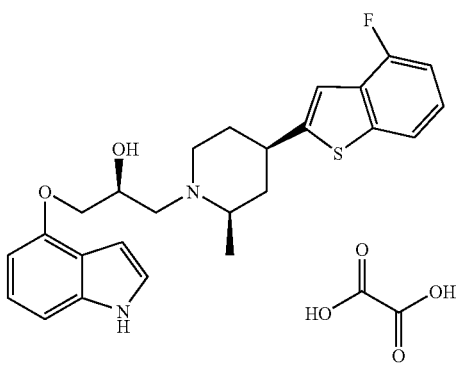

Preparation of N-t-Butoxycarbonyl-4-(4-fluorobenzo[b]thiophen-2-yl)-2-methyl-4-piperidinol.

Scheme IA, Step A: To a solution of 4- and 6-fluorobenzo[b]thiophene (12.4 g, 81.7 mmol, prepared in example 55) in dry THF (415 mL) at −78° C. was added 1.6 M n-BuLi in hexanes (56.4 mL, 90.2 mmol). The solution was stirred at −78° C. for 1.5 h. N-t-butoxycarbonyl-2-methyl-4-piperidone (15.7 g, 73.5 mmol) dissolved in THF (40 mL) was added via a cannula at −78° C. The reaction mixture was stirred at −78° C. for 4 h. The reaction was then quenched with 300 mL of saturated aqueous NH$_4$Cl solution. The mixture was extracted (2×500 mL) with EtOAc. The combined organic layers were then dried over MgSO$_4$ and filtered. The filtrate was concentrated and purified by medium pressure chromatography (15% EtOAc/hexanes) to give the title compound as a white foam (3.66 g, 14%). $^1$HNMR (CDCl$_3$) 7.54 (d, J=8.8 Hz, 1H), 7.25 (s, 1H), 7.22 (m, 1H), 6.96 (dd, J=9.0, 8.1, 1H), 4.31 (dist t, 1H), 3.85 (m, 1H), 3.18 (dt, J=13.0, 2.9 Hz, 1H), 2.02–1.82 (m, 1H), 1.64 (dd, J=14.2, 6.8, 1H), 1.54–1.44 (m, 11H), 1.28 (d, J=6.8 Hz, 3H)

Preparation of (±)-cis4-(4-Fluorobenzo[b]thiophen-2-yl)-2-methylpiperidine.

Scheme IA, Steps B and C: To a solution of N-t-butoxycarbonyl-4-(4-fluorobenzo[b]thiophen-2-yl)-2-methyl-4-piperidinol (1.47 g, 4.02 mmol) in dry CH$_2$Cl$_2$ (12 mL) at 0° C. was added 5 mL of trifluoroacetic acid. The solution was stirred at 0° C. for 2 h. The reaction was then quenched at room temperature with saturated aqueous NaHCO$_3$ solution (70 mL). The mixture was extracted (2×150 mL) with CH$_2$Cl$_2$. The combined organic layers were dried over MgSO$_4$ and concentrated to yield 0.880 g of the crude regioisomeric olefins. To a solution of the crude olefins (0.880 g) in a 3:1 mixture of ethanol (30 mL) and 2,2,2-trifluoroethanol (10 mL) was added 10% Pd/C (0.900 g). The black slurry was stirred vigorously at room temperature under hydrogen (balloon pressure) for 15 h. The black slurry was then filtered over a pad of diatomaceous earth and washed with ethanol. The filtrate was concentrated, and the residue was purified by silica gel chromatography [7% (2.0 M NH$_3$ in MeOH)/CH$_2$Cl$_2$] to give the intermediate title compound as a white solid (0.227 g, 23%). mp 63–65° C. Ion Spray MS 251 (M+2H)$^+$.

Preparation of (±)-trans-4-(4-Fluorobenzo[b]thiophen-2-yl)-2-methylpiperidine.

Scheme IA, Steps B and C: To a solution of N-t-butoxycarbonyl-4-(4-fluorobenzo[b]thiophen-2-yl)-2-methyl-4-piperidinol (1.47 g, 4.02 mmol) in dry CH$_2$Cl$_2$ (12 mL) at 0° C. was added 5 mL of trifluoroacetic acid. The solution was stirred at 0° C. for 2 h. The reaction was then quenched at room temperature with saturated aqueous NaHCO$_3$ solution (70 mL). The mixture was extracted (2×150 mL) with CH$_2$Cl$_2$. The combined organic layers were dried over MgSO$_4$ and concentrated to yield 0.880 g of the crude regioisomeric olefins. To a solution of the crude olefins (0.880 g) in a 3:1 mixture of ethanol (30 mL) and 2,2,2-trifluoroethanol (10 mL) was added 10% Pd/C (0.900 g). The black slurry was stirred vigorously at room temperature under hydrogen (balloon pressure) for 15 h. The black slurry was then filtered over a pad of diatomaceous earth and washed with ethanol. The filtrate was concentrated, and the residue was purified by silica gel chromatography [7% (2.0 M NH$_3$ in MeOH)/CH$_2$Cl$_2$] to give the intermediate title compound as a white solid (0.128 g, 13%). Ion Spray MS 250 (M+H)$^+$.

Preparation of Final Title Compound.

Scheme IV, Step B: A solution of (±)-cis-4-(4-fluorobenzo[b]thiophen-2-yl)-2-methylpiperidine (0.068 g, 0.273 mmol) and (S)-4-(oxiranylmethoxy)indole (0.052 g, 0.273 mmol) in MeOH (4 mL) was heated at reflux for 22 h and then cooled and evaporated. The residue was purified using silica gel chromatography [1–1.5% (2.0 M NH$_3$ in MeOH)/CH$_2$Cl$_2$] to provide the free base of the final title compound as a white foam (0.046 g, 38%). The oxalate salt was prepared with 1 equiv. of oxalic acid in EtOAc. IR (KBr) 3407, 3300 (br), 1237 cm$^{-1}$. Ion Spray MS 439 (M+H)$^+$; 437 (M−H)$^-$; 497 (M+CH$_3$COO$^-$)$^-$. C$_{25}$H$_{27}$FN$_2$O$_2$S

| analysis: | calculated | found |
|---|---|---|
| C | 68.47 | 68.68 |
| H | 6.21 | 6.40 |
| N | 6.39 | 6.48 |

EXAMPLE 57

Preparation of (2S)-3-[(2S,4S)-4-(4-Fluorobenzo[b]thiophen-2-yl)-2-methylpiperidinyl]-1-(1H-indol-4-yl)oxy-2-propanol oxalate

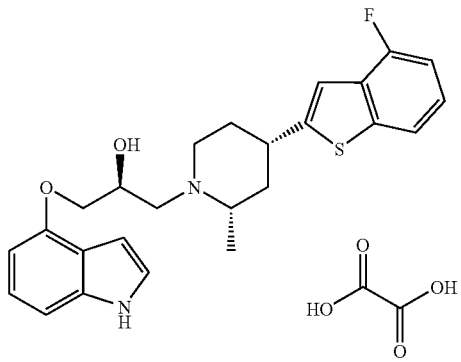

Scheme IV, Step B: A solution of (±)-cis-4-(4-fluorobenzo[b]thiophen-2-yl)-2-methylpiperidine (0.068 g, 0.273 mmol, prepared in example 56) and (S)-4-(oxiranylmethoxy)indole (0.052 g, 0.273 mmol) in MeOH (4 mL) was heated at reflux for 22 h and then cooled and evaporated. The residue was purified using silica gel chromatography [1–1.5% (2.0 M $NH_3$ in $MeOH$)/$CH_2Cl_2$] to give the free base of the title compound as a white foam (0.048 g, 40%). The oxalate salt was prepared with 1 equiv. of oxalic acid in EtOAc. IR (KBr) 3406, 3300 (br), 1237 $cm^{-1}$. Ion Spray MS 439 $(M+H)^+$; 437 $(M-H)^-$. $C_{25}H_{27}FN_2O_2S$

| analysis: | calculated | found |
|---|---|---|
| C | 68.47 | 68.37 |
| H | 6.21 | 6.41 |
| N | 6.39 | 6.45 |

EXAMPLE 58

Preparation of (2S)-3-[(2S,4R)-4-(4-Fluorobenzo[b]thiophen-2-yl)-2-methylpiperidinyl]-1-(1H-indol-4-yl)oxy-2-propanol oxalate

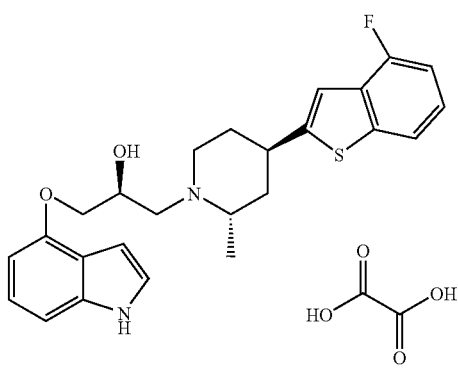

Scheme IV, Step B: A solution of (±)-trans-4-(4-fluorobenzo[b]thiophen-2-yl)-2-methylpiperidine (0.123 g, 0.494 mmol, prepared in example 56) and (S)-4-(oxiranylmethoxy)indole (0.094 g, 0.494 mmol) in MeOH (6 mL) was heated at reflux for 12 h and then cooled and evaporated. The residue was purified using silica gel chromatography [1.4% (2.0 M $NH_3$ in MeOH)/$CH_2Cl_2$] to give the free base of the title compound as a white foam (0.093 g, 43%). The oxalate salt was prepared with 1 equiv. of oxalic acid in EtOAc. Ion Spray MS 439 $(M+H)^+$; 437 $(M-H)^-$. $[\alpha]_D=0$ (c 0.41, MeOH). $C_{25}H_{27}FN_2O_2S \cdot C_2H_2O_4$

| analysis: | calculated | found |
|---|---|---|
| C | 61.35 | 61.44 |
| H | 5.53 | 5.80 |
| N | 5.30 | 5.32 |

EXAMPLE 59

Preparation of (2S)-(+)-3-[(2R,4S)-4-(4-Fluorobenzo[b]thiophen-2-yl)-2-methylpiperidinyl]-1-(1H-indol-4-yl)oxy-2-propanol oxalate

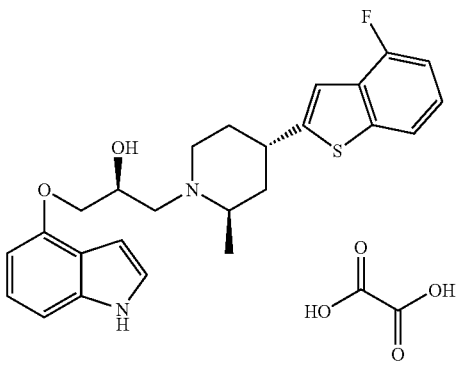

Scheme IV, Step B: A solution of (±)-trans-4-(4-fluorobenzo[b]thiophen-2-yl)-2-methylpiperidine (0.123 g, 0.494 mmol, prepared in example 56) and (S)-4-(oxiranylmethoxy)indole (0.094 g, 0.494 mmol) in MeOH (6 mL) was heated at reflux for 12 h and then cooled and evaporated. The residue was purified using silica gel chromatography [1.4% (2.0 M $NH_3$ in MeOH)/$CH_2Cl_2$] to give the free base of the title compound as a white foam (0.069 g, 32%). The oxalate salt was prepared with 1 equiv. of oxalic acid in EtOAc. mp (oxalate) 127–130° C. Ion Spray MS 439 $(M+H)^+$; 437 $(M-H)^-$. $[\alpha]_D=12.93$ (c 0.46, MeOH). $C_{25}H_{27}FN_2O_2S$

| analysis: | calculated | found |
|---|---|---|
| C | 68.47 | 68.73 |
| H | 6.21 | 6.40 |
| N | 6.39 | 6.46 |

EXAMPLE 60

Preparation of (2S)-3-[(2R,4R)-4-(4-Fluorobenzo[b]thiophen-2-yl)-2-methylpiperidinyl]-1-(1H-2-methylindol-4-yl)oxy-2-propanol oxalate

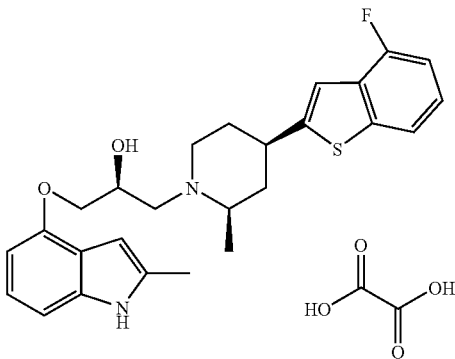

Scheme IV, Step B: A solution of (±)-cis-4-(4-fluorobenzo[b]thiophen-2-yl)-2-methylpiperidine (0.200 g, 0.802 mmol, prepared in example 56) and (2S)-4-glycidyloxy-2-methylindole (0.163 g, 0.802 mmol) in MeOH (10 mL) was heated at reflux for 16 h and then cooled and evaporated. The residue was purified using silica gel chromatography [1% (2.0 M NH$_3$ in MeOH)/CH$_2$Cl$_2$] to give the free base of the title compound as a white foam (0.155 g, 43%). The oxalate salt was prepared with 1 equiv. of oxalic acid in EtOAc. IR (CHCl$_3$) 3474, 1245 cm$^{-1}$. Ion Spray MS 453 (M+H)$^+$; 451 (M–H)$^-$. [α]$_D$=0 (c 0.52, MeOH). C$_{26}$H$_{29}$FN$_2$O$_2$S

| analysis: | calculated | found |
|---|---|---|
| C | 69.00 | 69.29 |
| H | 6.46 | 6.26 |
| N | 6.19 | 6.28 |

EXAMPLE 61

Preparation of (2S)-(+)-3-[(2S,4S)-4-(4-Fluorobenzo[b]thiophen-2-yl)-2-methylpiperidinyl]-1-(1H-2-methylindol-4-yl)oxy-2-propanol oxalate

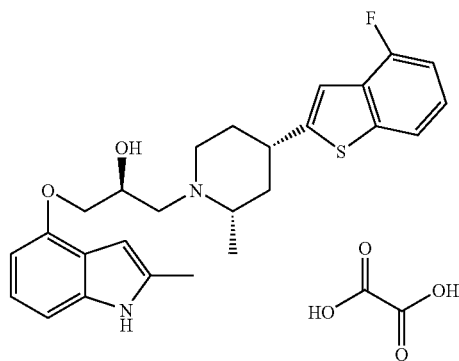

Scheme IV, Step B: A solution of (±)-cis-4-(4-fluorobenzo[b]thiophen-2-yl)-2-methylpiperidine (0.200 g, 0.802 mmol) and (2S)-4-glycidyloxy-2-methylindole (0.163 g, 0.802 mmol) in MeOH (10 mL) was heated at reflux for 16 h and then cooled and evaporated. The residue was purified using silica gel chromatography [1% (2.0 M NH$_3$ in MeOH)/CH$_2$Cl$_2$] to give the free base of the title compound as a white foam (0.131 g, 36%). The oxalate salt was prepared with 1 equiv. of oxalic acid in EtOAc. IR (CHCl$_3$) 3474, 1243 cm$^{-1}$. Ion Spray MS 453 (M+H)$^+$; 451 (M–H)$^-$. [α]$_D$=31.37 (c 0.51, MeOH). C$_{26}$H$_{29}$FN$_2$O$_2$S

| analysis: | calculated | found |
|---|---|---|
| C | 69.00 | 69.23 |
| H | 6.46 | 6.16 |
| N | 6.19 | 6.20 |

EXAMPLE 62

Preparation of (2S)-(+)-3-[4-(4,6-Dimethylbenzo[b]thiophen-2-yl)piperidinyl]-1-(1H-2-methylindol-4-yl)oxy-2-propanol oxalate

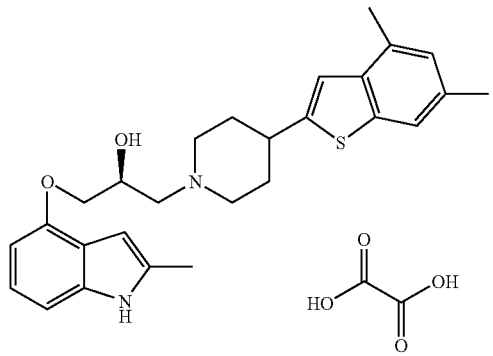

Preparation of 3,5-Dimethylbenzenethioacetaldehyde diethyl acetal.

The title compound was prepared in 95% crude yield from 3,5-dimethylbenzenethiol in a manner analogous to the procedure described by Graham, S. L., et. al. *J. Med. Chem.* 1989, 32, 2548–2554.

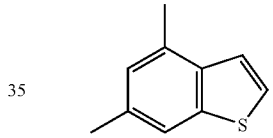

Preparation of 4,6-Dimethylbenzo[b]thiophene.

To a biphasic mixture of polyphosphoric acid (PPA; 21.6 g) and 200 mL of dry chlorobenzene heated to reflux was added dropwise 3,5-dimethylbenzenethioacetaldehyde diethyl acetal (10.0 g, 39.3 mmol) in 30 mL of chlorobenzene over a period of 1 h. The dark green biphasic mixture was heated at reflux for an additional h. The reaction mixture was cooled to room temperature and the organic layer was decanted off the PPA layer. The PPA layer was cooled to 0° C. and diluted with 150 mL of H$_2$O. This aqueous layer was extracted with Et$_2$O (3×500 mL). The combined organic layers were dried over MgSO$_4$ and concentrated under reduced pressure. The residue was purified by medium pressure chromatography to give the intermediate title compound as a yellow oil (4.69 g, 74%). FDMS m/e=162 (M$^+$).

Preparation of 4-(4,6-Dimethylbenzo[b]thiophen-2-yl)-1,2,5,6-tetrahydropyridine.

Scheme IA, Steps A and B: To a solution of 4,6-dimethylbenzo[b]-thiophene (0.750 g, 4.62 mmol) in dry THF (25 mL) at –78° C. was added 1.6 M n-BuLi in hexanes (3.18 mL, 5.08 mmol). The solution was stirred at –78° C. for 1 h. N-t-butoxycarbonyl-4-piperidone (0.921 g, 4.62 mmol) dissolved in THF (5 mL) was added via a cannula at –78° C. The reaction mixture was allowed to warm slowly to room temperature over 19 h. The reaction was quenched with saturated aqueous NH$_4$Cl solution (55 mL). The mixture was then extracted (3×125 mL) with EtOAc. The combined organic layers were dried over MgSO$_4$ and filtered. The filtrate was concentrated to give a crude tertiary alcohol intermediate (1.66 g). To a solution of the crude tertiary alcohol intermediate (1.66 g, 4.59 mmol) in dry CH$_2$Cl$_2$ (16 mL) at 0° C. was added 7 mL of trifluoroacetic acid. The resulting purple solution was stirred at 0° C. for 1 h 15 min. The reaction was then quenched at 0° C. with saturated aqueous NaHCO$_3$ solution (80 mL). The mixture was extracted (2×150 mL) with CH$_2$Cl$_2$. The combined organic layers were dried over MgSO$_4$, concentrated, and the residue was purified by silica gel chromatography (4% (10% conc. NH$_4$OH in MeOH)/CH$_2$Cl$_2$] to give the intermediate title compound as an orange solid (0.440 g, 39%). IR (CHCl$_3$) 3428 (br) cm$^{-1}$. Ion Spray MS 244 (M+H)$^+$; 215 (M−28)$^+$ (base peak).

Preparation of 4-(4,6-Dimethylbenzo[b]thiophen-2-yl)piperidine.

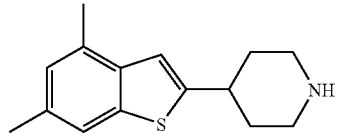

Scheme IA, Step C: To a solution of 4-(4,6-dimethylbenzo[b]thiophen-2-yl)-1,2,5,6-tetrahydropyridine (0.435 g, 1.79 mmol) in a 3:1 mixture of ethanol (13.5 mL) and 2,2,2-trifluoroethanol (4.5 mL) was added 10% Pd/C (0.450 g). The black slurry was stirred vigorously at room temperature under hydrogen (balloon pressure) for 22 h. The black slurry was then filtered over a pad of diatomaceous earth and washed with ethanol. The filtrate was then concentrated, and the residue was purified by silica gel chromatography (5% (2.0 M NH$_3$ in MeOH)/CH$_2$Cl$_2$] to give the intermediate title compound as an off-white solid (0.253 g, 58%). mp 83–88° C. Ion Spray MS 246 (M+H)$^+$; 290 (M+Cl)$^-$.

Preparation of Final Title Compound.

Scheme IV, Step B: A solution of 4-(4,6-dimethylbenzo[b]thiophen-2-yl)piperidine (0.100 g, 0.408 mmol) and (2S)-4-glycidyloxy-2-methylindole (0.083 g, 0.408 mmol) in MeOH (5 mL) was heated at reflux for 10 h and then cooled and evaporated. The residue was purified using silica gel chromatography [1.5% (2.0 M NH$_3$ in MeOH)/CH$_2$Cl$_2$] to give the free base of the final title compound as a white foam (0.138 g, 75%). The oxalate salt was prepared with 1 equiv. of oxalic acid in EtOAc. mp (oxalate) 110–113° C. (dec.). IR (CHCl$_3$) 3474, 3350 (br) cm$^{-1}$. Ion Spray MS 449 (M+H)$^+$; 447 (M−H)$^-$; 507 (M+CH$_3$COO$^-$)$^-$. [α]$_D$=9.83 (c 0.41, MeOH). C$_{27}$H$_{27}$NO$_4$S

| analysis: | calculated | found |
|---|---|---|
| C | 72.29 | 72.06 |
| H | 7.19 | 6.91 |
| N | 6.24 | 6.35 |

EXAMPLE 63

Preparation of (2S)-(−)-3-[(2R,4R)-4-(4,6-Dimethylbenzo[b]thiophen-2-yl)-2-methylpiperidinyl]-1-(1H-2-methylindol-4-yl)oxy-2-propanol oxalate

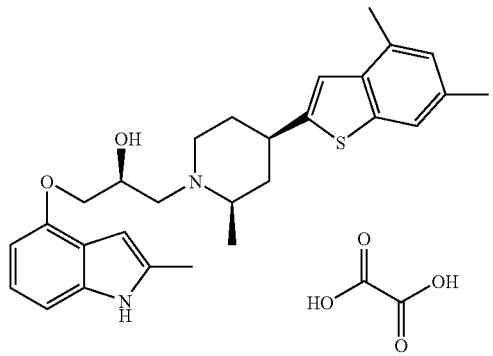

Preparation of N-t-Butoxycarbonyl-4-(4,6-dimethylbenzo[b]thiophen-2-yl)-2-methyl-4-piperidinol.

Scheme IA, Step A: To a solution of 4,6-dimethylbenzo[b]thiophene (3.71 g, 22.9 mmol) in dry THF (115 mL) at −78° C. was added 1.6 M n-BuLi in hexanes (15.7 mL, 25.2 mmol). The solution was stirred at −78° C. for 1 h. N-t-butoxycarbonyl-2-methyl-4-piperidone (4.39 g, 20.6 mmol) dissolved in THF (10 mL) was added via a cannula at −78° C. The reaction mixture was allowed to warm to room temperature over 19 h. The reaction was then quenched with 240 mL of saturated aqueous NH$_4$Cl solution. The mixture was extracted (3×500 mL) with EtOAc. The combined organic layers were dried over MgSO$_4$ and filtered. The filtrate was concentrated and purified by medium pressure chromatography (silica gel, 10% EtOAc/hexanes) to give the intermediate title compound as a yellow foam (4.11 g, 37%). IR (CHCl$_3$) 3550 (br), 1680 cm$^{-1}$. Ion Spray MS 376 (M+H)$^+$; 302 (M−74)$^+$ (base peak); 434 (M+CH$_3$COO$^-$)$^-$. $^1$HNMR (CDCl$_3$) 7.42 (s, 1H), 7.14 (s, 1H), 6.94 (s, 1H), 4.45 (br m, 1H), 4.03–4.09 (br m, 1H), 3.35 (br t, 1H), 2.51 (s, 3H), 2.39 (s, 3H), 2.19 (dd, J=14.7, 6.8 Hz, 1H), 1.92–2.09 (m, 3H), 1.59 (s, 1H), 1.47 (s, 9H), 1.39 (d, J=7.3 Hz, 3H).

Preparation of (±)-cis-4-(4,6-Dimethylbenzo[b]thiophen-2-yl)-2-methylpiperidine.

Scheme IA, Steps B and C: To a solution of N-t-butoxycarbonyl-4-(4,6-dimethylbenzo[b]thiophen-2-yl)-2-methyl-4-piperidinol (4.11 g, 10.9 mmol) in dry CH$_2$Cl$_2$ (38 mL) at 0° C. was added 17 mL of trifluoroacetic acid. The resulting purple solution was stirred at 0° C. for 1 h 15 min. The reaction was then quenched at room temperature with saturated aqueous NaHCO$_3$ solution (180 mL). The mixture was extracted (2×300 mL) with CH$_2$Cl$_2$. The combined organic layers were dried over MgSO$_4$ and concentrated to yield 3.43 g of crude regioisomeric olefins. To a solution of the crude olefins (3.43 g) in a 3:1 mixture of ethanol (100 mL) and 2,2,2-trifluoroethanol (33 mL) was added 10% Pd/C (3.25 g). The black slurry was stirred vigorously at room temperature under hydrogen (balloon pressure) for 16 h. The black slurry was then filtered over a pad of diatomaceous earth and washed with ethanol. The filtrate was concentrated, and the residue was purified by medium pressure chromatography (silica gel, 4–5% (2.0 M NH$_3$ in MeOH)/CH$_2$Cl$_2$] to give the intermediate title compound as an orange oil (1.44 g, 51%). mp 52–57° C. Ion Spray MS 260 (M+H)$^+$.

Preparation of (±)-trans-4-(4,6-Dimethylbenzo[b]thiophen-2-yl)-2-methylpiperidine.

Scheme IA, Steps B and C: To a solution of N-t-butoxy-carbonyl-4-(4,6-dimethylbenzo[b]thiophen-2-yl)-2-methyl-4-piperidinol (4.11 g, 10.9 mmol) in dry CH$_2$Cl$_2$ (38 mL) at 0° C. was added 17 mL of trifluoroacetic acid. The resulting purple solution was stirred at 0° C. for 1 h 15 min. The reaction was then quenched at room temperature with saturated aqueous NaHCO$_3$ solution (180 mL). The mixture was extracted (2×300 mL) with CH$_2$Cl$_2$. The combined organic layers were dried over MgSO$_4$ and concentrated to yield 3.43 g of crude regioisomeric olefins. To a solution of the crude olefins (3.43 g) in a 3:1 mixture of ethanol (100 mL) and 2,2,2-trifluoroethanol (33 mL) was added 10% Pd/C (3.25 g). The black slurry was stirred vigorously at room temperature under hydrogen (balloon pressure) for 16 h. The black slurry was then filtered over a pad of diatomaceous earth and washed with ethanol. The filtrate was concentrated, and the residue was purified by medium pressure chromatography (silica gel, 4–5% (2.0 M NH$_3$ in MeOH)/CH$_2$Cl$_2$] to give the intermediate title compound as an orange oil (0.490 g, 17%). mp 59–64° C. Ion Spray MS 260 (M+H)$^+$.

Preparation of Final Title Compound.

Scheme IV, Step B: A solution of (±)-cis-4-(4,6-dimethylbenzo[b]thiophen-2-yl)-2-methylpiperidine (0.200 g, 0.771 mmol) and (2S)-4-glycidyloxy-2-methylindole (0.157 g, 0.771 mmol) in MeOH (10 mL) was heated at reflux for 16 h and then cooled and evaporated. The residue was purified using silica gel chromatography [1% (2.0 M NH$_3$ in MeOH)/CH$_2$Cl$_2$] to give the free base of the title compound as an off-white foam (0.146 g, 41%). The oxalate salt was prepared with 1 equiv. of oxalic acid in EtOAc. mp (oxalate) 109–112° C. (dec.). IR (CHCl$_3$) 3474, 3350 (br) cm$^{-1}$. Ion Spray MS 463 (M+H)$^+$, 461 (M–H)$^-$. [α]$_D$=−7.09 (c 0.56, MeOH). C$_{28}$H$_{34}$N$_2$O$_2$S·0.1 CH$_2$Cl$_2$

| analysis: | calculated | found |
|---|---|---|
| C | 71.63 | 71.86 |
| H | 7.32 | 7.26 |
| N | 5.95 | 6.07 |

EXAMPLE 64

Preparation of (2S)-(+)-3-[(2S,4S)-4-(4,6-Dimethyl-benzo[b]thiophen-2-yl)-2-methylpiperidinyl]-1-(1H-2-methylindol-4-yl)oxy-2-propanol oxalate

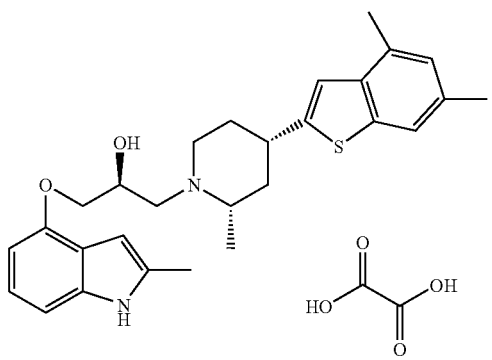

Scheme IV, Step B: A solution of (±)-cis-4-(4,6-dimethylbenzo[b]thiophen-2-yl)-2-methylpiperidine (0.200 g, 0.771 mmol, prepared in example 63) and (2S)-4-glycidyloxy-2-methylindole (0.157 g, 0.771 mmol) in MeOH (10 mL) was heated at reflux for 16 h and then cooled and evaporated. The residue was purified using silica gel chromatography [1% (2.0 M NH$_3$ in MeOH)/CH$_2$Cl$_2$] to give the free base of the title compound as an off-white foam (0.079 g, 22%). The oxalate salt was prepared with 1 equiv. of oxalic acid in EtOAc. IR (CHCl$_3$) 3474, 3350 (br) cm$^{-1}$. Ion Spray MS 463 (M+H)$^+$; 461 (M–H)$^+$. [α]$_D$=25.21 (c 0.56, MeOH). C$_{26}$H$_{30}$N$_2$O$_3$S·C$_2$H$_2$O$_4$

| analysis: | calculated | found |
|---|---|---|
| C | 65.20 | 65.25 |
| H | 6.57 | 6.62 |
| N | 5.07 | 5.05 |

EXAMPLE 65

Preparation of (2S)-3-[(2S,4R)-4-(4,6-Dimethyl-benzo[b]thiophen-2-yl)-2-methylpiperidinyl]-1-(1H-2-methylindol-4-yl)oxy-2-propanol oxalate

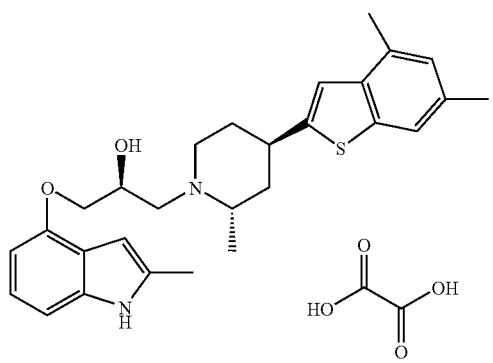

Scheme IV, Step B: A solution of (±)-trans-4-(4,6-dimethylbenzo[b]thiophen-2-yl)-2-methylpiperidine (0.200 g, 0.771 mmol, prepared in example 63) and (2S)-4-glycidyloxy-2-methylindole (0.157 g, 0.771 mmol) in MeOH (10 mL) was heated at reflux for 16 h and then cooled and evaporated. The residue was purified using silica gel chromatography [1% (2.0 M NH$_3$ in MeOH)/CH$_2$Cl$_2$] to give the title propanol as an off-white foam (0.149 g, 42%). The oxalate salt was prepared with 1 equiv. of oxalic acid in EtOAc. mp (oxalate) 139–142° C. (dec.). IR (CHCl$_3$) 3474, 3350 (br) cm$^{-1}$. Ion Spray MS 463 (M+H)$^+$; 461 (M–H)$^-$. [α]$_D$=0 (C 0.51, MeOH). C$_{28}$H$_{34}$N$_2$O$_2$S·0.2CH$_2$Cl$_2$

| analysis: | calculated | found |
|---|---|---|
| C | 70.62 | 70.88 |
| H | 7.23 | 6.96 |
| N | 5.84 | 5.83 |

EXAMPLE 66

Preparation of (2S)-(+)-3-[(2R,4S)-4-(4,6-Dimethyl-benzo[b]thiophen-2-yl)-2-methylpiperidinyl]-1-(1H-2-methylindol-4-yl)oxy-2-propanol oxalate

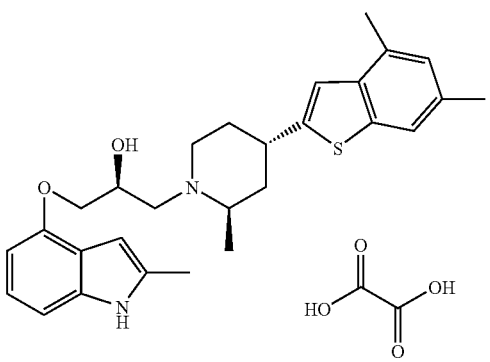

Scheme IV, Step B: A solution of (±)-trans-4-(4,6-dimethylbenzo[b]thiophen-2-yl)-2-methylpiperidine (0.200 g, 0.771 mmol, prepared in example 63) and (2S)-4-glycidyloxy-2-methylindole (0.157 g, 0.771 mmol) in MeOH (10 mL) was heated at reflux for 16 h and then cooled and evaporated. The residue was purified using silica gel chromatography [1% (2.0 M $NH_3$ in MeOH)/$CH_2Cl_2$] to give the free base of the title compound as an off-white foam (0.1401 g, 28%). The oxalate salt was prepared with 1 equiv. of oxalic acid in EtOAc. mp (oxalate) 143–146° C. (dec.). IR ($CHCl_3$) 3474, 3350 (br) $cm^{-1}$. Ion Spray MS 463 $(M+H)^+$; 461 $(M-H)^-$. $[\alpha]_D$=11.80 (c 0.51, MeOH). $C_{28}H_{34}N_2O_2S \cdot C_2H_2O_4$

| analysis: | calculated | found |
|---|---|---|
| C | 65.20 | 64.82 |
| H | 6.57 | 6.26 |
| N | 5.07 | 4.93 |

EXAMPLE 67

Preparation of (2S)-(−)-3-[(2R,4R)-4-(4,6-Dimethyl-benzo[b]thiophen-2-yl)-2-methylpiperidinyl]-1-(1H-indol-4-yl)oxy-2-propanol oxalate

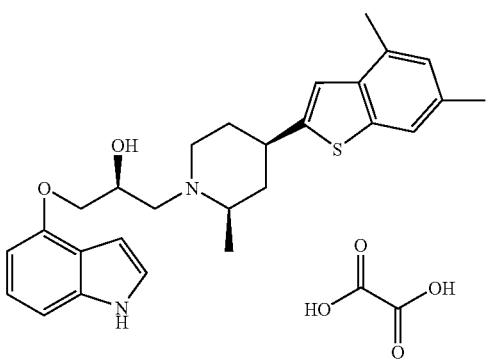

Scheme IV, Step B: A solution of (±)-cis-4-(4,6-dimethylbenzo[b]thiophen-2-yl)-2-methylpiperidine (0.200 g, 0.771 mmol, prepared in example 63) and (S)-4-(oxiranylmethoxy)indole (0.146 g, 0.771 mmol) in MeOH (10 mL) was heated at reflux for 6 h and then cooled and evaporated. The residue was purified using silica gel chromatography [1% (2.0 M $NH_3$ in MeOH)/$CH_2Cl_2$] to give the free base of the title compound as a white foam (0.151 g, 44%). The oxalate salt was prepared with 1 equiv. of oxalic acid in EtOAc. IR ($CHCl_3$) 3482, 3350 (br) $cm^{-1}$. Ion Spray MS 449 $(M+H)^+$; 447 $(M-H)^-$. $[\alpha]_D$=−10.05 (c 0.60, MeOH). $C_{27}H_{32}N_2O_2S \cdot 1.1C_2H_2O_4 \cdot 0.1C_4H_8O_2$

| analysis: | calculated | found |
|---|---|---|
| C | 63.89 | 63.86 |
| H | 6.34 | 5.95 |
| N | 5.03 | 4.84 |

EXAMPLE 68

Preparation of (2S)-(+)-3-[(2S,4S)-4-(4,6-Dimethyl-benzo[b]thiophen-2-yl)-2-methylpiperidinyl]-1-(1H-indol-4-yl)oxy-2-propanol oxalate

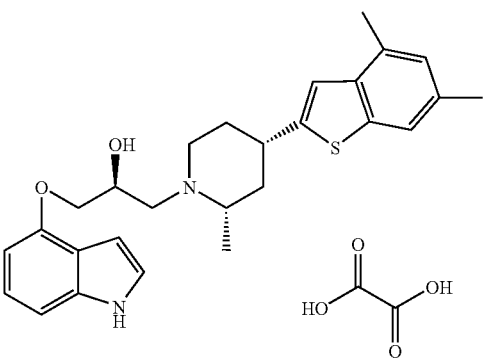

Scheme IV, Step B: A solution of (±)-cis-4-(4,6-dimethylbenzo[b]thiophen-2-yl)-2-methylpiperidine (0.200 g, 0.771 mmol, prepared in example 63) and (S)-4-(oxiranylmethoxy)indole (0.146 g, 0.771 mmol) in MeOH (10 mL) was heated at reflux for 6 h and then cooled and evaporated. The residue was purified using silica gel chromatography [1% (2.0 M $NH_3$ in MeOH)/$CH_2Cl_2$] to give the free base of the title compound as a white foam (0.156 g, 45%). The oxalate salt was prepared with 1 equiv. of oxalic acid in EtOAc. IR ($CHCl_3$) 3482, 3350 (br) $cm^{-1}$. Ion Spray MS 449 $(M+H)^+$; 447 $(M-H)^-$. $[\alpha]_D$=30.17 (c 0.53, MeOH). $C_{27}H_{32}N_2O_2S \cdot 0.2H_2O$

| analysis: | calculated | found |
|---|---|---|
| C | 71.71 | 71.52 |
| H | 7.22 | 7.61 |
| N | 6.19 | 6.09 |

EXAMPLE 69

Preparation of (2S)-3-[(2S,4R)-4-(4,6-Dimethyl-benzo[b]thiophen-2-yl)-2-methylpiperidinyl]-1-(1H-indol-4-yl)oxy-2-propanol oxalate

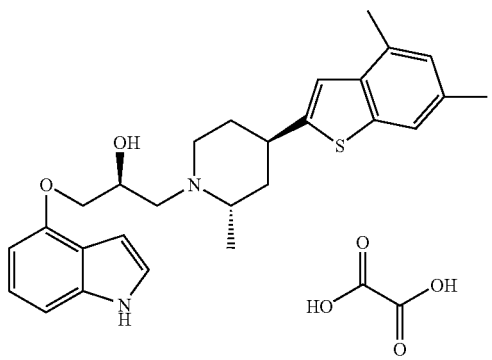

Scheme IV, Step B: A solution of (±)-trans-4-(4,6-dimethylbenzo[b]thiophen-2-yl)-2-methylpiperidine (0.200 g, 0.771 mmol, prepared in example 63) and (S)-4-(oxiranylmethoxy)indole (0.146 g, 0.771 mmol) in MeOH (10 mL) was heated at reflux for 6 h and then cooled and evaporated. The residue was purified using silica gel chromatography [1% (2.0 M $NH_3$ in MeOH)/$CH_2Cl_2$] to give the free base of the title compound as a white foam (0.149 g, 43%). The oxalate salt was prepared with 1 equiv. of oxalic acid in EtOAc. mp (oxalate) 117–120° C. IR ($CHCl_3$) 3482, 3350 (br) $cm^{-1}$. Ion Spray MS 449 $(M+H)^+$; 447 $(M-H)^-$. $[\alpha]_D=0$ (c 0.47, MeOH). $C_{27}H_{32}N_2O_2S$

| analysis: | calculated | found |
|---|---|---|
| C | 72.29 | 72.49 |
| H | 7.19 | 6.89 |
| N | 6.24 | 6.48 |

EXAMPLE 70

Preparation of (2S)-(+)-3-[(2R,4S)-4-(4,6-Dimethyl-benzo[b]thiophen-2-yl)-2-methylpiperidinyl]-1-(1H-indol-4-yl)oxy-2-propanol oxalate

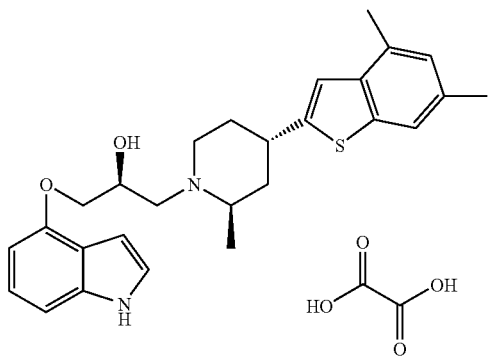

Scheme IV, Step B: A solution of (±)-trans-4-(4,6-dimethylbenzo[b]-thiophen-2-yl)-2-methylpiperidine (0.200 g, 0.771 mmol, prepared in example 63) and (S)-4-(oxiranylmethoxy)indole (0.146 g, 0.771 mmol) in MeOH (10 mL) was heated at reflux for 6 h and then cooled and evaporated. The residue was purified using silica gel chromatography [1% (2.0 M $NH_3$ in MeOH)/$CH_2Cl_2$] to give the free base of the title compound as a white foam (0.092 g, 27%). The oxalate salt was prepared with 1 equiv. of oxalic acid in EtOAc. mp (oxalate) 147–150° C. (dec.). IR ($CHCl_3$) 3482, 3350 (br) $cm^{-1}$. Ion Spray MS 449 $(M+H)^+$; 447 $(M-H)^-$. $[\alpha]_D=15.98$ (c 0.50, MeOH). $C_{27}H_{32}N_2O_2S$

| analysis: | calculated | found |
|---|---|---|
| C | 72.29 | 72.05 |
| H | 7.19 | 7.40 |
| N | 6.24 | 6.32 |

EXAMPLE 71

Preparation of (2S)-(−)-3-[(2R,4R)-4-(4,6-Dimethoxybenzo[b]thiophen-2-yl)-2-methylpiperidinyl]-1-(1H-2-methylindol-4-yl)oxy-2-propanol oxalate

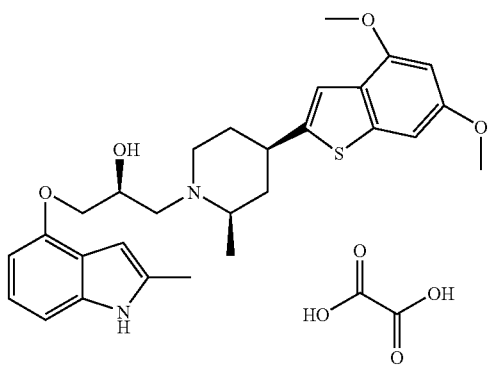

Preparation of N,N-Dimethyl-2-(2,4-dimethoxyphenyl)-2-hydroxythioacetamide.

To a solution of lithium diisopropylamide (108 mmol) in 400 mL of dry THF cooled to −78° C. was added 2,4-dimethoxybenzaldehyde (15.00 g, 90.3 mmol) and N,N-dimethylthioformamide (7.69 mL, 90.3 mmol) dissolved in 55 mL of dry THF via a cannula over a period of 10 min. The reaction mixture was stirred at −78° C. for 30 min then warmed to 0° C. and quenched with saturated aqueous $NH_4Cl$ solution (450 mL). The mixture was extracted with (3×1 L) EtOAc. The combined organic layers were dried over $MgSO_4$ and concentrated. The residue was then recrystallized from EtOAc/hexanes to give the intermediate title compound as a tan solid (12.9 g, 50%). IR ($CHCl_3$) 3250 (br) $cm^{-1}$. FDMS m/e=255 $(M^+)$. $^1$HNMR ($CDCl_3$) 7.24 (d, J=8.3 Hz, 1H), 6.43 (d, J=2.2 Hz, 1H), 6.41 (dd, J=8.3, 2.2 Hz, 1H), 5.70 (s, 1H), 3.86 (s, 3H), 3.77 (s, 3H), 3.47 (s, 3H), 3.02 (s, 3H).

Preparation of 4,6-Dimethoxy-2-dimethylaminobenzo[b]thiophene.

N,N-Dimethyl-2-(2,4-dimethoxyphenyl)-2-hydroxythioacetamide (12.0 g, 47.0 mmol) was dissolved in Eaton's reagent (7.5% w/w $P_2O_5$/$MeSO_3H$) (80 mL). The reaction mixture was heated to 80° C. and stirred for 1 h 20 min. The reaction was quenched by pouring the reaction mixture slowly into cooled (0° C.) 5.0 N NaOH (280 mL). The mixture was extracted (3×750 mL) with EtOAc. The combined organic layers were then dried over $MgSO_4$, concentrated, and the residue was purified by medium pressure chromatography (silica gel, 8% Et₂O/hexanes) to give the intermediate title compound as a light yellow oil (2.34 g, 21%). IR (CHCl₃) 1369, 958 cm⁻¹. Ion Spray MS 238 (M+H)⁺ (base peak); 223 (M−CH₂)⁺; 207 (M−2CH₂)⁺. ¹HNMR (CDCl3) 6.73 (d, J=2.0 Hz, 1H), 6.35 (d, J=2.0 Hz, 1H), 6.05 (br s, 1H), 3.87 (s, 3H), 3.81 (s, 3H), 2.94 (s, 6H).

Preparation of 4,6-Dimethoxythianapthen-2-one.

4,6-Dimethoxy-2-dimethylaminobenzo[b]thiophene (2.32 g, 9.76 mmol) was dissolved in a 1:1 mixture of THF/1.0 N HCl (70 mL). The biphasic mixture was stirred vigorously and heated at reflux for 2 h. The reaction mixture was then cooled to room temperature and the layers were separated. The aqueous layer was extracted (2×125 mL) with EtOAc. The combined organic layers were dried over MgSO₄ and concentrated to give the intermediate title compound as a white solid (2.05 g, quantitative yield). mp 135–137° C. IR (CHCl₃) 1716 cm⁻¹. Ion Spray MS 211 (M+H)⁺; 183 (M−27)⁺ (base peak).

Preparation of 4,6-Dimethoxybenzo[b]thiophene.

To a solution of 4,6-dimethoxythianapthen-2-one (2.01 g, 9.57 mmol) in CH₂Cl₂ (100 mL) was added dropwise 1.0 M diisobutylaluminum hydride in toluene (10.5 mL, 10.5 mmol) at 0° C. The solution was stirred at 0° C. for 15 min. The reaction was quenched with conc. HCl (60 mL). This mixture was then stirred vigorously for 1 h. The layers were separated, and the organic layer was dried over MgSO₄ and concentrated. The residue was purified by medium pressure chromatography (100% hexanes) to give the intermediate title compound as a white solid (1.10 g, 59%). mp 78–80° C. IR (CHCl₃) 1149, 1046 cm⁻¹. Ion Spray MS 195 (M+H)⁺.

Preparation of N-t-Butoxycarbonyl-4-(4,6-dimethoxybenzo[b]thiophen-2-yl)-2-methyl-4-piperidinol.

Scheme IA, Step A: To a solution of 4,6-dimethoxybenzo[b]thiophene (1.07 g, 5.52 mmol) in dry THF (30 mL) at −78° C. was added 1.6 M n-BuLi in hexanes (3.80 mL, 6.07 mmol). The solution was stirred at −78° C. for 45 min. N-t-butoxycarbonyl-2-methyl-4-piperidone (1.18 g, 5.52 mmol) dissolved in THF (7 mL) was added via a cannula at −78° C. The reaction mixture was allowed to warm to room temperature over 16 h. The reaction was then quenched with 65 mL of saturated aqueous NH₄Cl solution. The mixture was extracted (2×100 mL) with EtOAc. The combined organic layers were then dried over MgSO₄ and filtered. The filtrate was concentrated and purified by silica gel chromatography (20% EtOAc/hexanes) to give the intermediate title compound as a yellow foam (0.590 g, 26%). IR (CHCl₃) 3474, 3350 (br) cm⁻¹. IR (CHCl₃) 3350 (br), 1680 cm⁻¹. Ion Spray MS 408 (M+H)⁺; 390 (M−H₂0)⁺; 334 (M−74)⁺ (base peak); 466(M+CH₃COO⁻)⁻. ¹HNMR (CDCl₃) 7.17 (s, 1H), 6.83 (d, J=2.0 Hz, 1H), 6.36 (d, J=2.0 Hz, 1H), 4.43 (br m, 1H), 3.97–4.00 (br m, 1H), 3.87 (s, 3H), 3.82 (s, 3H), 3.33 (br t, 1H), 2.15 (dd, J=14.7, 6.8 Hz, 1H), 1.89–2.05 (m, 3H), 1.47 (s, 1H), 1.46 (s, 9H), 1.37 (d, J=7.3 Hz, 3H).

Preparation of (±)-cis-4-(4,6-Dimethoxybenzo[b]thiophen-2-yl)-2-methylpiperidine.

Scheme IA, Steps B and C: To a solution of N-t-butoxycarbonyl-4-(4,6-dimethoxybenzo[b]thiophen-2-yl)-2-methyl-4-piperidinol (1.23 g, 3.03 mmol) in dry CH₂Cl₂ (10.5 mL) at 0° C. was added 4.5 mL of trifluoroacetic acid. The solution was stirred at 0° C. for 1 h 30 min. The reaction was then quenched at room temperature with saturated aqueous NaHCO₃ solution (60 mL). The mixture was extracted (2×125 mL) with CH₂Cl₂. The combined organic layers were dried over MgSO₄ and concentrated to yield 1.02 g of crude regioisomeric olefins. To a solution of the crude olefins (1.02 g) in a 3:1 mixture of ethanol (23 mL) and 2,2,2-trifluoroethanol (8 mL) was added 10% Pd/C (1.10 g). The black slurry was stirred vigorously at room temperature under hydrogen (balloon pressure) for 2.5 days. The black slurry was then filtered over a pad of diatomaceous earth and washed with ethanol. The filtrate was concentrated, and the residue was purified by silica gel chromatography (4–5% (2.0 M NH₃ in MeOH)/CH₂Cl₂] to give the intermediate title compound as a yellow semi-solid (0.276 g, 31%). Ion Spray MS 292 (M+H)⁺.

Preparation of (±)-trans-4-(4,6-Dimethoxybenzo[b]thiophen-2-yl)-2-methylpiperidine.

Scheme IA, Steps B and C: To a solution of N-t-butoxycarbonyl-4-(4,6-dimethoxybenzo[b]thiophen-2-yl)-2-methyl-4-piperidinol (1.23 g, 3.03 mmol) in dry CH₂Cl₂ (10.5 mL) at 0° C. was added 4.5 mL of trifluoroacetic acid. The solution was stirred at 0° C. for 1 h 30 min. The reaction was then quenched at room temperature with saturated aqueous NaHCO₃ solution (60 mL). The mixture was extracted (2×125 mL) with CH₂Cl₂. The combined organic layers were dried over MgSO₄ and concentrated to yield 1.02 g of crude regioisomeric olefins. To a solution of the crude olefins (1.02 g) in a 3:1 mixture of ethanol (23 mL) and 2,2,2-trifluoroethanol (8 mL) was added 10% Pd/C (1.10 g). The black slurry was stirred vigorously at room temperature under hydrogen (balloon pressure) for 2.5 days. The black slurry was then filtered over a pad of diatomaceous earth and washed with ethanol. The filtrate was concentrated, and the residue was purified by silica gel chromatography (4–5% (2.0 M NH₃ in MeOH)/CH₂Cl₂] to give the intermediate title compound as a yellow semi-solid (0.102 g, 12%). Ion Spray MS 292 (M+H)⁺.

Preparation of Final Title Compound.

Scheme IV, Step B: A solution of (±)-cis-4-(4,6-dimethoxybenzo[b]thiophen-2-yl)-2-methylpiperidine (0.203 g, 0.697 mmol) and (2S)-4-glycidyloxy-2-methylindole (0.142 g, 0.697 mmol) in MeOH (10 mL) was heated at reflux for 18 h and then cooled and evaporated. The residue was purified using silica gel chromatography [1.5% (2.0 M NH₃ in MeOH)/CH₂Cl₂] to give the free base of the final title compound as a white foam (0.117 g, 34%). The oxalate salt was prepared with 1 equiv. of oxalic acid in EtOAc. mp (oxalate) 117–121° C. (dec.). IR (CHCl₃) 3474, 3350 (br) cm⁻¹. Ion Spray MS 495 (M+H)⁺; 493 (M−H)⁻. $[\alpha]_D$=−3.51 (c 0.57, MeOH). $C_{28}H_{34}N_2O_4S \cdot 0.1CH_2Cl_2$

| analysis: | calculated | found |
| --- | --- | --- |
| C | 67.08 | 66.73 |
| H | 6.85 | 6.84 |
| N | 5.57 | 5.48 |

EXAMPLE 72

Preparation of (2S)-(+)-3-[(2S, 4S)-4-(4,6-Dimethoxybenzo[b]thiophen-2-yl)-2-methylpiperidinyl]-1-(1H-2-methylindol-4-yl)oxy-2-propanol oxalate

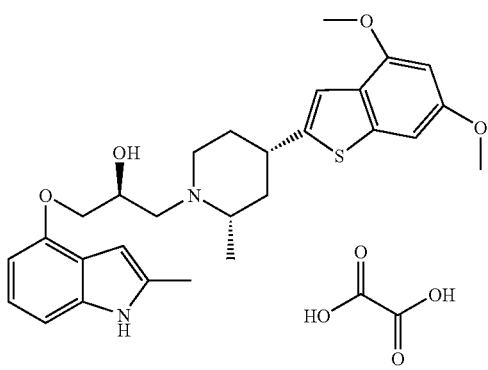

Scheme IV, Step B: A solution of (±)-cis-4-(4,6-dimethoxybenzo[b]-thiophen-2-yl)-2-methylpiperidine (0.203 g, 0.697 mmol, prepared in example 71) and (2S)-4-glycidyloxy-2-methylindole (0.142 g, 0.697 mmol) in MeOH (10 mL) was heated at reflux for 18 h and then cooled and evaporated. The residue was purified using silica gel chromatography [1.5% (2.0 M $NH_3$ in MeOH)/$CH_2Cl_2$] to give the free base of the final title compound as a white foam (0.127 g, 37%). The oxalate salt was prepared with 1 equiv. of oxalic acid in EtOAc. mp (oxalate) 142–145° C. (dec.). IR ($CHCl_3$) 3474, 3350 (br) $cm^{-1}$. Ion Spray MS 495 $(M+H)^+$; 493 $(M-H)^-$. $[\alpha]_D$=21.99 (c 0.45, MeOH). $C_{28}H_{34}N_2O_4S$

| analysis: | calculated | found |
| --- | --- | --- |
| C | 67.99 | 67.99 |
| H | 6.93 | 7.17 |
| N | 5.66 | 5.57 |

EXAMPLE 73

Preparation of (2S,)-3-[(2S 4R)-4-(4,6-Dimethoxy-benzo[b]thiophen-2-yl)-2-methylpiperidinyl]-1-(1H-2-methylindol-4-yl)oxy-2-propanol oxalate

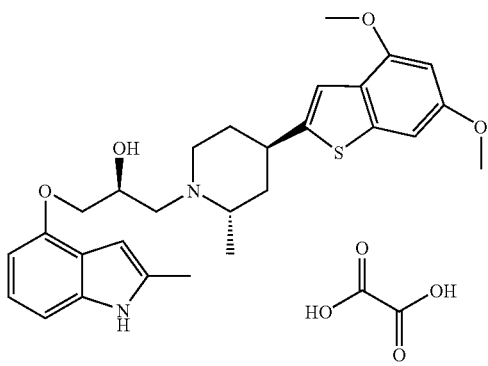

Scheme IV, Step B: A solution of (±)-trans-4-(4,6-dimethoxybenzo[b]thiophen-2-yl)-2-methylpiperidine (0.091 g, 0.313 mmol, prepared in example 71) and (2S)-4-glycidyloxy-2-methylindole (0.064 g, 0.313 mmol) in MeOH (5 mL) was heated at reflux for 24 h and then cooled and evaporated. The residue was purified using silica gel chromatography [1.5% (2.0 M $NH_3$ in MeOH)/$CH_2Cl_2$] to give the free base of the title compound as a white foam (0.056 g, 36%). The oxalate salt was prepared with 1 equiv. of oxalic acid in EtOAc. Ion Spray MS 495 $(M+H)^+$; 493 $(M-H)^-$. $C_{28}H_{34}N_2O_4S \cdot 0.2CH_2Cl_2$

| analysis: | calculated | found |
| --- | --- | --- |
| C | 66.20 | 66.28 |
| H | 6.78 | 6.83 |
| N | 5.48 | 5.60 |

EXAMPLE 74

Preparation of (2S)-(+)-3-[(2R,4S)-4-(4,6-Dimethoxybenzo[b]thiophen-2-yl)-2-methylpiperidinyl]-1-(1H-2-methylindol-4-yl)oxy-2-propanol oxalate

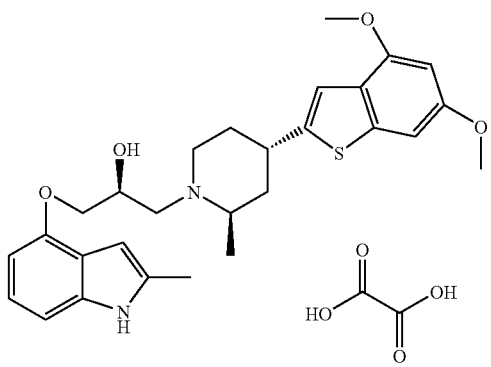

Scheme IV, Step B: A solution of (±)-trans-4-(4,6-dimethoxybenzo[b]thiophen-2-yl)-2-methylpiperidine (0.091 g, 0.313 mmol, prepared in example 71) and (2S)-4-glycidyloxy-2-methylindole (0.064 g, 0.313 mmol) in MeOH (5 mL) was heated at reflux for 24 h and then cooled and evaporated. The residue was purified using silica gel chromatography [1.5% (2.0 M $NH_3$ in MeOH)/$CH_2Cl_2$] to give the free base of the title compound as a white foam (0.077 g, 49%). The oxalate salt was prepared with 1 equiv. of oxalic acid in EtOAc. IR ($CHCl_3$) 3474, 3350 (br) $cm^{-1}$. Ion Spray MS 495 $(M+H)^+$; 493 $(M-H)^-$. $[\alpha]_D$=11.01 (c 0.36, MeOH). $C_{28}H_{34}N_2O_4S \cdot 0.2CH_2Cl_2$

| analysis: | calculated | found |
| --- | --- | --- |
| C | 66.20 | 66.25 |
| H | 6.78 | 6.88 |
| N | 5.48 | 5.48 |

EXAMPLE 75

Preparation of (2S)-3-[4-(5-Fluorobenzo[b]thiophen-2-yl)piperidinyl]-1-(1H-2-methylindol-4-yl)oxy-2-propanol oxalate

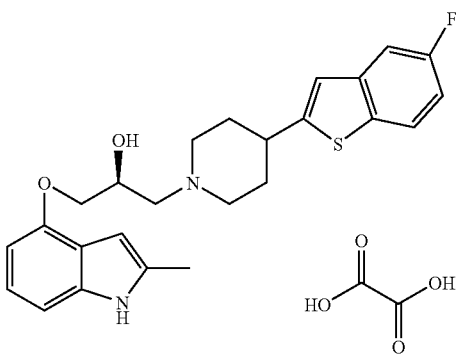

Preparation of 4-Fluorobenzenethioacetaldehyde diethyl acetal.

The intermediate title compound was prepared in 95% crude yield from 4-flourobenzenethiol in a manner analogous to the procedure described by Graham, S. L., et. al. *J. Med. Chem.* 1989,32, 2548–2554.

Preparation of 5-Fluorobenzo[b]thiophene.

A slurry of amberlyst-15 (19.0 g) in 1,1,2-trichloroethane (285 mL) was heated at reflux. Approximately 30 mL of wet distillate was removed (cloudy in appearance) via a Dean-Stark trap. 4-Fluorobenzenethioacetaldehyde diethyl acetal (19.0 g, 77.8 mmol) was dissolved in 1,1,2-trichloroethane (95 mL) and added dropwise to the slurry at reflux over a period of 1 h 15 min. Distillate was removed at an approximate rate of 0.5 mL/min. The reaction mixture was cooled to room temperature and filtered with $CH_2Cl_2$ rinse. The filtrate and washing were concentrated, and the residue was purified by medium pressure chromatography (silica gel, 100% hexanes) to give the intermediate title compound as a colorless oil (2.81 g, 24%). Ion Spray MS 211 $(M+CH_3COO)^-$. $^1$HNMR ($CDCl_3$) 7.78 (dd, J=8.8, 4.9 Hz, 1H), 7.51 (d, J=5.4 Hz, 1H), 7.46 (dd, J=9.3, 2.4 Hz, 1H), 7.27 (d, J=5.4 Hz, 1H), 7.09 (dt, J=8.8, 2.4 Hz, 1H).

Preparation of 4-(5-Fluorobenzo[b]thiophen-2-yl)-1,2,5,6-tetrahydropyridine.

Scheme IA, Steps A and B: To a solution of 5-fluorobenzo[b]thiophene (0.500 g, 3.29 mmol) in dry THF (15 mL) at −78° C. was added 1.6 M n-BuLi in hexanes (2.26 mL, 3.61 mmol). The solution was stirred at −78° C. for 45 min. N-t-Butoxycarbonyl-4-piperidone (0.786 g, 3.94 mmol) dissolved in THF (7 mL) was added via a cannula at −78° C. The reaction mixture was allowed to warm slowly to −30° C. over 2 h. The reaction was quenched with saturated aqueous $NH_4Cl$ solution (50 mL). The mixture was extracted (3×100 mL) with EtOAc. The combined organic layers were dried over $MgSO_4$ and filtered. The filtrate was concentrated to give a crude tertiary alcohol intermediate (1.29 g). To a solution of the crude tertiary alcohol intermediate (1.29 g, 3.67 mmol) in dry $CH_2Cl_2$ (11 mL) at 0° C. was added 5 mL of trifluoroacetic acid. The resulting solution was stirred at 0° C. for 2.5 h. The reaction was then quenched at 0° C. with saturated aqueous $NaHCO_3$ solution (65 mL). The mixture was extracted (2×125 mL) with $CH_2Cl_2$. The combined organic layers were dried over $MgSO_4$ and concentrated to give the intermediate title compound as an off-white solid (0.450 g, 59%). IR ($CHCl_3$) 1445 $cm^{-1}$. Ion Spray MS 234 $(M+H)^+$.

Preparation of 4-(5-Fluorobenzo[b]thiophen-2-yl)piperidine.

Scheme IA, Step C: To a solution of 4-(5-fluorobenzo[b]thiophen-2-yl)-1,2,5,6-tetrahydropyridine (0.440 g, 1.89 mmol) in a 3:1 mixture of ethanol (15 mL) and 2,2,2-trifluoroethanol (5 mL) was added 10% Pd/C (0.450 g). The black slurry was stirred vigorously at room temperature under hydrogen (balloon pressure) for 20 h. The black slurry was then filtered over a pad of diatomaceous earth and washed with ethanol. The filtrate was concentrated, and the residue was purified by silica gel chromatography [6% (2.0 M $NH_3$ in MeOH)/$CH_2Cl_2$] to give the intermediate title compound as a white solid (0.270 g, 61%). IR ($CHCl_3$) 1446 $cm^{-1}$. Ion Spray MS 236 $(M+H)^+$.

Preparation of Final Title Compound.

Scheme IV, Step B: A solution of 4-(5-fluorobenzo[b]thiophen-2-yl)piperidine (0.100 g, 0.425 mmol) and (2S)-4-glycidyloxy-2-methylindole (0.086 g, 0.425 mmol) in MeOH (5 mL) was heated at reflux for 18 h and then cooled and evaporated. The residue was purified using silica gel chromatography [1% (2.0 M $NH_3$ in MeOH)/$CH_2Cl_2$] to give the free base of the final title compound as a white foam (0.145 g, 79%). The oxalate salt was prepared with 1 equiv. of oxalic acid in EtOAc. IR ($CHCl_3$) 3474, 3350 (br), 1247 $cm^{-1}$. Ion Spray MS 439 $(M+H)^+$; 437 $(M-H)^-$. $[\alpha]_D$=0 (c 0.40, MeOH). $C_{25}H_{27}FN_2O_2S$

| analysis: | calculated | found |
|---|---|---|
| C | 68.47 | 68.64 |
| H | 6.21 | 6.35 |
| N | 6.39 | 6.39 |

EXAMPLE 76

Preparation of (2S)-(−)-3-[(2R,4R)-4-(5-Fluorobenzo[b]thiophen-2-yl)-2-methylpiperidinyl]-1-(1H-2-methylindol-4-yl)oxy-2-propanol oxalate

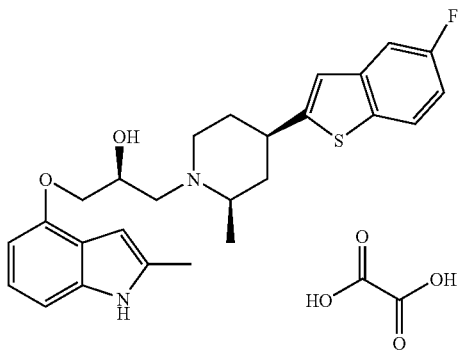

Preparation of N-t-Butoxycarbonyl-4-(5-fluorobenzo[b]thiophen-2-yl)-2-methyl-4-piperidinol.

Scheme IA, Step A: To a solution of 5-fluorobenzo[b]thiophene (2.25 g, 14.8 mmol, prepared in example 75) in dry THF (65 mL) at −78° C. was added 1.6 M n-BuLi in hexanes (10.1 mL, 16.2 mmol). The solution was stirred at −78° C., for 45 min. N-t-butoxycarbonyl-2-methyl-4-piperidone (3.15 g, 14.8 mmol) dissolved in THF (15 mL) was added via a cannula at −78° C. The reaction mixture was warmed slowly to −50° C. over 19 h. The reaction was then quenched with 130 mL of saturated aqueous NH$_4$Cl solution. The mixture was extracted (2×300 mL) with EtOAc. The combined organic layers were dried over MgSO$_4$ and filtered. The filtrate was concentrated and purified by medium pressure chromatography (silica gel, 25–30% EtOAc/hexanes) to give the intermediate title compound as a white solid (2.64 g, 49%). IR (CHCl$_3$) 1680, 1418,1161 cm$^{-1}$. Ion Spray MS 366 (M+H)$^+$; 424 (M+CH$_3$COO$^-$)$^-$.

Preparation of (±)-cis-4-(5-Fluorobenzo[b]thiophen-2-yl)-2-methylpiperidine.

Scheme IA, Steps B and C: To a solution of N-t-butoxycarbonyl-4-(5-fluorobenzo[b]thiophen-2-yl)-2-methyl-4-piperidinol (2.63 g, 7.19 mmol) in dry CH$_2$Cl$_2$ (22 mL) at 0° C. was added 10 mL of trifluoroacetic acid. The solution was stirred at 0° C. for 1 h 30 min. The reaction was then quenched at room temperature with saturated aqueous NaHCO$_3$ solution (130 mL). The mixture was extracted (2×250 mL) with CH$_2$Cl$_2$. The combined organic layers were dried over MgSO$_4$ and concentrated to yield 1.82 g of crude regioisomeric olefins. To a solution of the crude olefins (1.82 g) in a 3:1 mixture of ethanol (54 mL) and 2,2,2-trifluoroethanol (18 mL) was added 10% Pd/C (1.85 g). The black slurry was stirred vigorously at room temperature under hydrogen (balloon pressure) for 16 h. The black slurry was then filtered over a pad of diatomaceous earth and washed with ethanol. The filtrate was then concentrated, and the residue was purified by silica gel chromatography [5.5% (2.0 M NH$_3$ in MeOH)/CH$_2$Cl$_2$] to the intermediate title compound as a white solid (0.692 g, 39%). IR (CHCl$_3$) 1446 cm$^{-1}$. Ion Spray MS 250 (M+H)$^+$.

Preparation of (±)-trans4-(5-Fluorobenzo[b]thiophen-2-yl)-2-methylpiperidine.

Scheme IA, Steps B and C: To a solution of N-t-butoxycarbonyl-4-(5-fluorobenzo[b]thiophen-2-yl)-2-methyl-4-piperidinol (2.63 g, 7.19 mmol) in dry CH$_2$Cl$_2$ (22 mL) at 0° C. was added 10 mL of trifluoroacetic acid. The solution was stirred at 0° C. for 1 h 30 min. The reaction was then quenched at room temperature with saturated aqueous NaHCO$_3$ solution (130 mL). The mixture was extracted (2×250 mL) with CH$_2$Cl$_2$. The combined organic layers were dried over MgSO$_4$ and concentrated to yield 1.82 g of crude regioisomeric olefins. To a solution of the crude olefins (1.82 g) in a 3:1 mixture of ethanol (54 mL) and 2,2,2-trifluoroethanol (18 mL) was added 10% Pd/C (1.85 g). The black slurry was stirred vigorously at room temperature under hydrogen (balloon pressure) for 16 h. The black slurry was then filtered over a pad of diatomaceous earth and washed with ethanol. The filtrate was then concentrated, and the residue was purified by silica gel chromatography [5.5% (2.0 M NH$_3$ in MeOH)/CH$_2$Cl$_2$] to give the intermediate title compound as a white solid (0.438 g, 24%). IR (CHCl$_3$) 1445 cm$^{-1}$. Ion Spray MS 250 (M+H)$^+$.

Preparation of Final Title Compound.

Scheme IV, Step B: A solution of (±)-cis-4-(5-fluorobenzo[b]thiophen-2-yl)-2-methylpiperidine (0.200 g, 0.802 mmol) and (2S)-4-glycidyloxy-2-methylindole (0.163 g, 0.802 mmol) in MeOH (10 mL) was heated at reflux for 20 h and then cooled and evaporated. The residue was purified using silica gel chromatography [1–1.5% (2.0 M NH$_3$ in MeOH)/CH$_2$Cl$_2$] to give the free base of the final title compound as a white foam (0.156 g, 43%). The oxalate salt was prepared with 1 equiv. of oxalic acid in EtOAc. IR (CHCl$_3$) 3474, 3350 (br), 1246 cm$^{-1}$. Ion Spray MS 453 (M+H)$^+$; 451 (M−H)$^-$. [α]$_D$=−8.61 (c 0.47, MeOH). C$_{26}$H$_{29}$FN$_2$O$_2$S

| analysis: | calculated | found |
|---|---|---|
| C | 69.00 | 69.30 |
| H | 6.46 | 6.53 |
| N | 6.19 | 6.25 |

EXAMPLE 77

Preparation of (2S)-(+)-3-[(2S,4S)-4-(5-Fluorobenzo[b]thiophen-2-yl)-2-methylpiperidinyl]-1-(1H-2-methylindol-4-yl)oxy-2-propanol oxalate

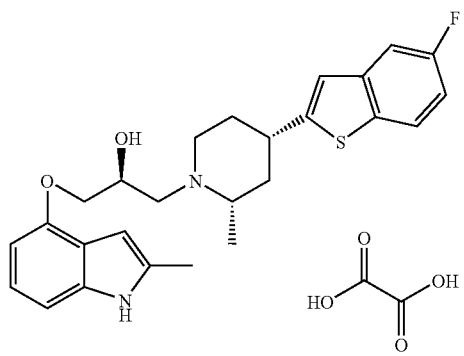

Scheme IV, Step B: A solution of (±)-cis-4-(5-fluorobenzo[b]thiophen-2-yl)-2-methylpiperidine (0.200 g, 0.802 mmol, prepared in example 76) and (2S)-4-glycidyloxy-2-methylindole (0.163 g, 0.802 mmol) in MeOH (10 mL) was heated at reflux for 20 h and then cooled and evaporated. The residue was purified using silica gel chromatography [1–1.5% (2.0 M NH$_3$ in MeOH)/CH$_2$Cl$_2$] to give the free base of the title compound as a white foam (0.165 g, 45%). The oxalate salt was prepared with 1 equiv. of oxalic acid in EtOAc. IR (CHCl$_3$) 3474, 3350 (br), 1246 cm$^{-1}$. Ion Spray MS 453 (M+H)$^+$; 451 (M−H)$^-$. [α]$_D$=30.27 (c 0.46, MeOH). C$_{26}$H$_{29}$FN$_2$O$_2$S

| analysis: | calculated | found |
|---|---|---|
| C | 69.00 | 69.27 |
| H | 6.46 | 6.70 |
| N | 6.19 | 6.35 |

EXAMPLE 78

Preparation of (2S)-3-[(2S,4R)-4-(5-Fluorobenzo[b]thiophen-2-yl)-2-methylpiperidinyl]-1-(1H-2-methylindol-4-yl)oxy-2-propanol oxalate

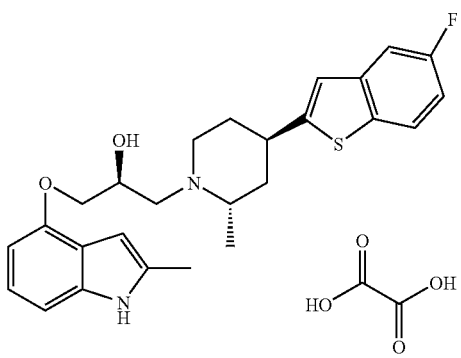

Scheme IV, Step B: A solution of (±)-trans-4-(5-fluorobenzo[b]thiophen-2-yl)-2-methylpiperidine (0.200 g, 0.802 mmol, prepared in example 76) and (2S)-4-glycidyloxy-2-methylindole (0.163 g, 0.802 mmol) in MeOH (10 mL) was heated at reflux for 22 h and then cooled and evaporated. The residue was purified using silica gel chromatography [1–1.5% (2.0 M $NH_3$ in MeOH)/$CH_2Cl_2$] to give the free base of the title compound as a white foam (0.159 g, 44%). The oxalate salt was prepared with 1 equiv. of oxalic acid in EtOAc. IR ($CHCl_3$) 3474, 3350 (br), 1246 cm$^{-1}$. Ion Spray MS 453 (M+H)$^+$; 451 (M–H)$^-$. $[\alpha]_D$=0 (c 0.42, MeOH). $C_{26}H_{29}FN_2O_2S$

| analysis: | calculated | found |
|---|---|---|
| C | 69.00 | 69.30 |
| H | 6.46 | 6.51 |
| N | 6.19 | 6.42 |

EXAMPLE 79

Preparation of (2S)-(+)-3-[(2R,4S)-4-(5-Fluorobenzo[b]thiophen-2-yl)-2-methylpiperidinyl]-1-(1H-2-methylindol-4-yl)oxy-2-propanol

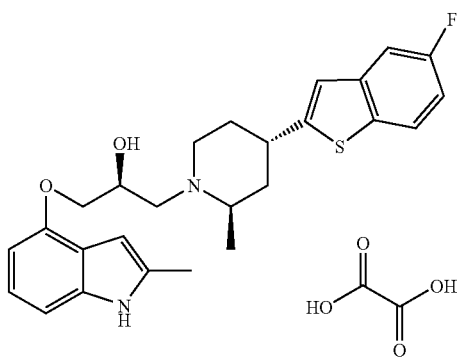

Scheme IV, Step B: A solution of (±)-trans-4-(5-fluorobenzo[b]thiophen-2-yl)-2-methylpiperidine (0.200 g, 0.802 mmol, prepared in example 76) and (2S)-4-glycidyloxy-2-methylindole (0.163 g, 0.802 mmol) in MeOH (10 mL) was heated at reflux for 22 h and then cooled and evaporated. The residue was purified using silica gel chromatography [1–1.5% (2.0 M $NH_3$ in MeOH)/$CH_2Cl_2$] to give the free base of the title compound as a white foam (0.163 g, 45%). The oxalate salt was prepared with 1 equiv. of oxalic acid in EtOAc. IR ($CHCl_3$) 3474, 3350 (br), 1246 cm$^{-1}$. Ion Spray MS 453 (M+H)$^+$; 451 (M–H)$^-$. $[\alpha]_D$=13.84 (c 0.58, MeOH). $C_{25}H_{27}FN_2O_2S \cdot 0.2H_2O$

| analysis: | calculated | found |
|---|---|---|
| C | 68.45 | 68.45 |
| H | 6.50 | 6.88 |
| N | 6.14 | 6.12 |

EXAMPLE 80

Preparation of (2S)-(–)-3-[(2R,4R)-4-(5-Fluorobenzo[b]thiophen-2-yl)-2-methylpiperidinyl]-1-(1H-indol-4-yl)oxy-2-propanol oxalate

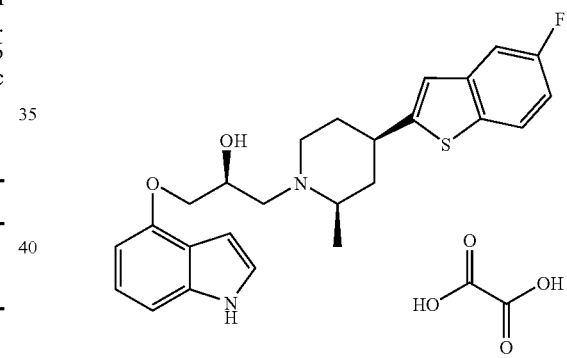

Scheme IV, Step B: A solution of (±)-cis-4-(5-fluorobenzo[b]thiophen-2-yl)-2-methylpiperidine (0.200 g, 0.802 mmol, prepared in example 76) and (S)-4-(oxiranylmethoxy)indole (0.152 g, 0.802 mmol) in MeOH (10 mL) was heated at reflux for 24 h and then cooled and evaporated. The residue was purified using silica gel chromatography [1–1.5% (2.0 M $NH_3$ in MeOH)/$CH_2Cl_2$] to give the free base of the title compound as a white foam (0.123 g, 35%). The oxalate salt was prepared with 1 equiv. of oxalic acid in EtOAc. IR ($CHCl_3$) 3482, 3350 (br), 1244 cm$^{-1}$. Ion Spray MS 439 (M+H)$^+$; 437 (M–H)$^-$. $[\alpha]_D$=–19.35 (c 0.31, MeOH). $C_{25}H_{27}FN_2O_2S \cdot C_2H_2O_4$

| analysis: | calculated | found |
|---|---|---|
| C | 61.35 | 61.06 |
| H | 5.53 | 5.46 |
| N | 5.30 | 5.35 |

EXAMPLE 81

Preparation of (2S)-(+)-3-[(2S,4S)-4-(5-Fluorobenzo[b]thiophen-2-yl)-2-methylpiperidinyl]-1-(1H-indol-4-yl)oxy-2-propanol oxalate

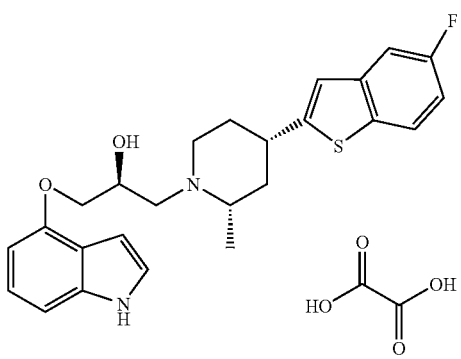

Scheme IV, Step B: A solution of (±)-cis-4-(5-fluorobenzo[b]thiophen-2-yl)-2-methylpiperidine (0.200 g, 0.802 mmol, prepared in example 76) and (S)-4-(oxiranylmethoxy)indole (0.152 g, 0.802 mmol) in MeOH (10 mL) was heated at reflux for 24 h and then cooled and evaporated. The residue was purified using silica gel chromatography [1–1.5% (2.0 M $NH_3$ in MeOH)/$CH_2Cl_2$] to give the free base of the title compound as a white foam (0.098 g, 28%). The oxalate salt was prepared with 1 equiv. of oxalic acid in EtOAc. IR ($CHCl_3$) 3482, 3350 (br), 1243 $cm^{-1}$. Ion Spray MS 439 $(M+H)^+$; 437 $(M-H)^-$. $[\alpha]_D$=38.30 (c 0.47, MeOH). $C_{25}H_{27}FN_2O_2S.C_2H_2O_4.0.2H_2O.0.3C_4H_8O_2$

| analysis: | calculated | found |
|---|---|---|
| C | 60.63 | 60.30 |
| H | 5.74 | 5.78 |
| N | 5.01 | 5.18 |

EXAMPLE 82

Preparation of (2S)-3-[(2S,4R)-4-(5-Fluorobenzo[b]thiophen-2-yl)-2-methylpiperidinyl]-1-(1H-indol-4-yl)oxy-2-propanol oxalate

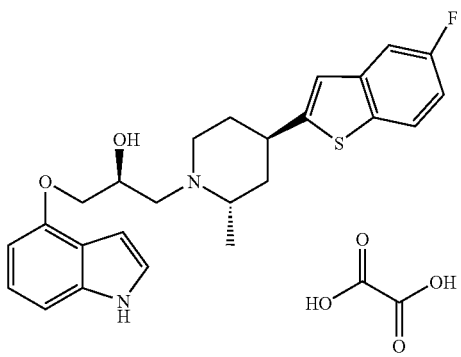

Scheme IV, Step B: A solution of (±)-trans-4-(5-fluorobenzo[b]thiophen-2-yl)-2-methylpiperidine (0.200 g, 0.802 mmol, prepared in example 76) and (S)-4-(oxiranylmethoxy)indole (0.152 g, 0.802 mmol) in MeOH (10 mL) was heated at reflux for 16 h and then cooled and evaporated. The residue was purified using silica gel chromatography [1–1.5% (2.0 M $NH_3$ in MeOH)/$CH_2Cl_2$] to give the free base of the title compound as a white foam (0.118 g, 34%). The oxalate salt was prepared with 1 equiv. of oxalic acid in EtOAc. IR ($CHCl_3$) 3482, 3350 (br) $cm^{-1}$. Ion Spray MS 439 $(M+H)^+$; 437 $(M-H)^-$. $[\alpha]_D$ (oxalate)=0 (c 0.45, DMSO). $C_{25}H_{27}FN_2O_2S.C_2H_2O_4$

| analysis: | calculated | found |
|---|---|---|
| C | 61.35 | 61.73 |
| H | 5.53 | 5.52 |
| N | 5.30 | 5.46 |

EXAMPLE 83

Preparation of (2S)-(+)-3-[(2R,4S)-4-(5-Fluorobenzo[b]thiophen-2-yl)-2-methylpiperidinyl]-1-(1H-indol-4-yl)oxy-2-propanol oxalate

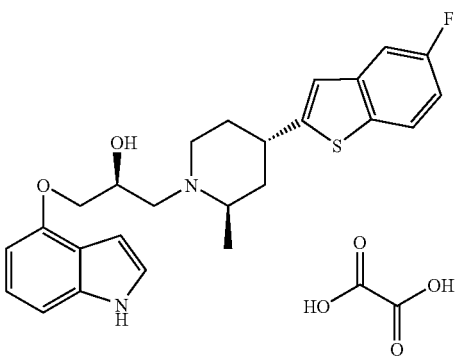

Scheme IV, Step B: A solution of (±)-trans-4-(5-fluorobenzo[b]thiophen-2-yl)-2-methylpiperidine (0.200 g, 0.802 mmol, prepared in 102) and (S)-4-(oxiranylmethoxy)indole (0.152 g, 0.802 mmol) in MeOH (10 mL) was heated at reflux for 16 h and then cooled and evaporated. The residue was purified using silica gel chromatography [1–1.5% (2.0 M $NH_3$ in MeOH)/$CH_2Cl_2$] to give the free base of the title compound as a white foam (0.112 g, 32%). The oxalate salt was prepared with 1 equiv. of oxalic acid in EtOAc. IR ($CHCl_3$) 3482, 3350 (br) $cm^{-1}$. Ion Spray MS 439 $(M+H)^+$; 437 $(M-H)^-$. [ $]_D$=11.32 (c 0.53, MeOH). $C_{25}H_{27}FN_2O_2S.0.6CH_2Cl_2$

| analysis: | calculated | found |
|---|---|---|
| C | 62.81 | 62.62 |
| H | 5.81 | 5.68 |
| N | 5.72 | 5.89 |

EXAMPLE 84

Preparation of (2S)-3-[4-(8-Methoxynaphth-2-yl)piperidinyl]-1-(1H-2-methylindol-4-yl)oxy-2-propanol oxalate

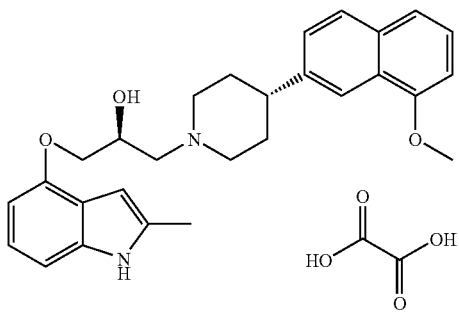

Preparation of 7-Bromo-1-tetralone.

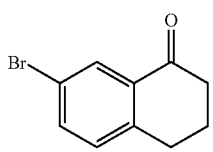

1-tetralone (27.1 mL, 200 mmol) was added dropwise to aluminum chloride (66.7 g, 500 mmol) while stirred with the aid of a mechanical stirrer over a period of 7 min. To the tarry mixture was added bromine (12.4 mL, 240 mmol) over a 20 min period. The mixture was then heated to 80° C. for 5 min. The hot mixture was then poured in a bath containing ice (600 g) and conc. HCl (80 mL). This mixture was extracted (2×500 mL) with $CH_2Cl_2$. The combined organic layers were then dried over $MgSO_4$, concentrated, and the residue was purified using medium pressure chromatography (silica gel, 10% tert-butyl methyl ether/heptane) to give the intermediate title compound as an orange solid (16.50 g, 37%). IR ($CHCl_3$) 1685 cm$^{-1}$. Ion Spray MS 225 (M+H)

Preparation of 7-Bromo-1-naphthol.

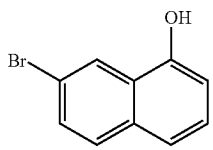

HCl gas was bubbled into a solution of 7-bromo-1-tetralone (16.5 g, 73.3 mmol) in 750 mL of $Et_2O$ cooled to −7° C. for 2 min. Bromine (3.78 mL, 73.3 mmol) diluted with 33 mL of a mixture of 10:1 $CH_2Cl_2/Et_2O$ was then added dropwise over a period of 3 h. The reaction was quenched with $H_2O$ (200 mL). The layers were separated, and the organic layer was dried over $MgSO_4$ and concentrated to yield 22.0 g (72.4 mmol) of the dibromo tetralone intermediate. To the intermediate dissolved in DMF (150 mL). was added lithium chloride (6.14 g, 145 mmol), and the solution was heated at reflux for 2 h. The reaction was cooled to room temperature and quenched with 1.0 N HCl (250 mL). The mixture was extracted with (1×150, 1×75, 1×50 mL) with $Et_2O$. Combined organic layers were washed with (1×100 mL) with 10% lithium chloride solution and then stirred vigorously with decolorizing carbon (8.00 g). The slurry was filtered over a pad of diatomaceous earth and washed with $Et_2O$. The filtrate was concentrated, and the residue was partitioned between 3.0 N NaOH (40 mL) and heptane (80 mL). The layers were separated. The aqueous layer was acidified to a pH=1 with conc. HCl in the presence of $CH_2Cl_2$ (80 mL). The layers were partitioned, and to the organic layer was added heptane (80 mL). The solution was then concentrated at 30° C. to a volume of 80 mL. Heptane was added to increase the volume to 160 mL. This was repeated twice. A slurry was then formed and kept in the refrigerator overnight. The slurry was then filtered, and the precipitate was washed with cold heptane. The precipitate was dried in a vacuum oven at 45° C. over $P_2O_5$ for 2 h to give the intermediate title compound as a brown solid (8.89 g, 55%). IR ($CHCl_3$) 3595, 3275 (br) cm$^{-1}$. Ion Spray MS 221 (M−H)$^{-1}$.

Preparation of 7-Bromo-1-methoxynaphthalene.

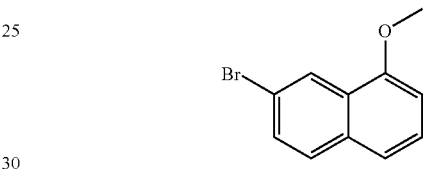

A slurry of 7-bromo-1-naphthol (8.89 g, 39.9 mmol), potassium carbonate (8.26 g, 59.8 mmol), dimethyl sulfate (5.66 mL, 59.8 mmol) and tetrabutylammonium bromide (0.085 g, 0.264 mmol) in acetonitrile (160 mL) was heated at reflux for 2 h 45 min. The reaction was cooled to room temperature, and water was added (200 mL). The mixture was then extracted (1×100, 1×40 mL) with $CH_2Cl_2$. The combined organic layers were washed (1×40 mL) with saturated aqueous $NaHCO_3$ solution, dried over $MgSO_4$, and concentrated. The residue was purified by medium pressure chromatography (100% hexanes) to give the intermediate title compound as a yellow oil (8.42 g, 89%). FDMS m/e=236 M$^+$.

Preparation of N-t-Butoxycarbonyl-4-(8-methoxynaphth-2-yl)-4-piperidinol.

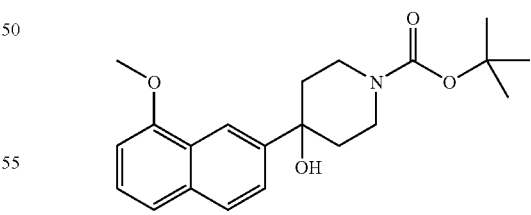

Scheme I, Step A: To a solution of 7-bromo-1-methoxynaphthalene (1.50 g, 6.33 mmol) in dry THF (30 mL) at −78° C. was added 1.6 M n-BuLi in hexanes (4.35 mL, 6.96 mmol). The solution was stirred at −78° C. for 15 min. N-t-Butoxycarbonyl-4-piperidone (1.51 g, 7.59 mmol) dissolved in THF (10 mL) was added via a cannula at −78° C. The reaction mixture was stirred at −78° C. for 2.5 h. The reaction was then quenched with 30 mL of saturated aqueous $NH_4Cl$ solution. The mixture was extracted (2×150 mL)

with EtOAc. The combined organic layers were then dried over MgSO$_4$ and filtered. The filtrate was concentrated and purified by silica gel chromatography (25% EtOAc/hexanes) to give the intermediate title compound as a white foam (1.42 g, 63%). IR (CHCl$_3$) 3350 (br), 1681 cm$^{-1}$. Ion Spray MS 358 (M+H)$^+$; 240 (M−117(−(Boc+H$_2$0)))$^+$; 430 (M+CH$_3$COO$^-$)$^-$. $^1$HNMR (CDCl$_3$) 8.31 (d, J=2.0 Hz, 1H), 7.79 (d, J=8.3 Hz, 1H), 7.60 (dd, J=8.8, 2.0 Hz, 1H), 7.34–7.40 (m, 2H), 6.81 (dd, J=7.1, 2.0 Hz, 1H), 4.03–4.06 (br m, 2H), 3.99 (s, 3H), 3.29 (br dt, J=13.0, 2.4 Hz, 2H), 2.12 (dt, J=13.0, 4.9 Hz, 2H), 1.79–1.83 (br m, 2H), 1.61 (br s, 1H), 1.48 (s, 9H).

Preparation of 4-(8-Methoxynaphth-2-yl)piperidine.

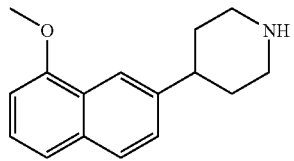

Scheme I, Steps B and C: To a solution of N-t-butoxycarbonyl-4-(8-methoxynaphth-2-yl)-4-piperidinol (1.42 g, 3.97 mmol) in dry CH$_2$Cl$_2$ (12 mL) at 0° C. was added 5 mL of trifluoroacetic acid. The solution was stirred at 0° C. for 2 h. The reaction was then quenched at room temperature with saturated aqueous NaHCO$_3$ solution (70 mL). The mixture was extracted (2×150 mL) with CH$_2$Cl$_2$. The combined organic layers were dried over MgSO$_4$ and concentrated to yield 0.980 g of crude regioisomeric olefins. To a solution of the crude olefins (0.980 g) in a 3:1 mixture of ethanol (30 mL) and 2,2,2-trifluoroethanol (10 mL) was added 10% Pd/C (0.250 g). The black slurry was stirred vigorously at room temperature under hydrogen (balloon pressure) for 16 h. The black slurry was then filtered over a pad of diatomaceous earth and washed with ethanol. The filtrate was concentrated, and the residue was purified by silica gel chromatography [6% (2.0 M NH$_3$ in MeOH)/CH$_2$Cl$_2$] to give the intermediate title compound as a white solid (0.508 g, 53%). Ion Spray MS 242 (M+H)$^+$.

Scheme IV, Step B: A solution of 4-(8-methoxynaphth-2-yl)piperidine (0.100 g, 0.414 mmol, prepared above) and (2S)-4-glycidyloxy-2-methylindole (0.084 g, 0.414 mmol) in MeOH ( 5 mL) was heated at reflux for 16 h and then cooled and evaporated. The residue was purified using silica gel chromatography [1% (2.0 M NH$_3$ in MeOH)/CH$_2$Cl$_2$] to give the free base of the title compound as a white foam (0.130 g, 71%). The oxalate salt was prepared with 1 equiv. of oxalic acid in EtOAc. IR (CHCl$_3$) 3474, 3350 (br) cm$^{-1}$. Ion Spray MS 445 (M+H)$^+$; 443 (M−H)$^-$. [α]$_D$=0 (c 0.48, MeOH). C$_{28}$H$_{32}$N$_2$O$_3$.0.8C$_2$H$_2$O$_4$.0.2H$_2$O

| analysis: | calculated | found |
|---|---|---|
| C | 68.58 | 68.53 |
| H | 6.60 | 6.49 |
| N | 5.33 | 5.33 |

EXAMPLE 85

Preparation of (2S)-3-[(2R,4R)-4-(8-Methoxynaphth-2-yl)-2-methylpiperidinyl]-1-(1H-2-methylindol-4-yl)oxy-2-propanol oxalate

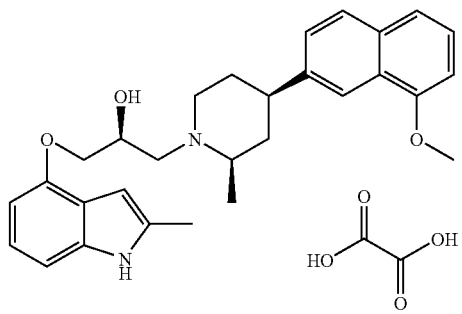

Preparation of N-t-Butoxycarbonyl-4-(8-methoxynaphth-2-yl)-2-methyl-4-piperidinol.

Scheme I, Step A: To a solution of 7-bromo-1-methoxynaphthalene (6.50 g, 27.4 mmol, prepared in example 84) in dry THF (140 mL) at −78° C. was added 1.6 M n-BuLi in hexanes (17.1 mL, 27.4 mmol). The solution was stirred at −78° C. for 45 min. N-t-Butoxycarbonyl-2-methyl-4-piperidone (5.85 g, 27.4 mmol) dissolved in THF (25 mL) was added via a cannula at −78° C. The reaction mixture was stirred at −78° C. for 5 h. The reaction was then quenched with 140 mL of saturated aqueous NH$_4$Cl solution. The mixture was extracted (2×250 mL) with EtOAc. The combined organic layers were then dried over MgSO$_4$ and filtered. The filtrate was concentrated and purified by medium pressure chromatography (silica gel, 25% EtOAc/hexanes) to give the intermediate title compound as a white foam (6.06 g, 60%). IR (CHCl$_3$) 3350 (br), 1680 cm$^{-1}$. Ion Spray MS 371 (M+H)$^+$; 254 (M−117(−(Boc+H$_2$0)))$^+$ (base peak); 430 (M+CH$_3$COO$^-$)$^-$.

Preparation of (±)-cis-4-(8-Methoxynaphth-2-yl)-2-methylpiperidine.

Scheme I, Steps B and C: To a solution of N-t-butoxycarbonyl-4-(8-methoxynaphth-2-yl)-2-methyl-4-piperidinol (6.06 g, 16.3 mmol) in dry CH$_2$Cl$_2$ (49 mL) at 0° C. was added 21 mL of trifluoroacetic acid. The solution was stirred at 0° C. for 1.5 h. The reaction was then quenched at room temperature with saturated aqueous NaHCO$_3$ solution (280 mL). The mixture was extracted (2×300 mL) with CH$_2$Cl$_2$. The combined organic layers were dried over MgSO$_4$ and concentrated to yield 4.02 g of crude regioisomeric olefins. To a solution of the crude olefins (4.02 g) in a 3:1 mixture of ethanol (120 mL) and 2,2,2-trifluoroethanol (40 mL) was added 10% Pd/C (1.50 g). The black slurry was stirred vigorously at room temperature under hydrogen (balloon pressure) for 16 h. The black slurry was then filtered over a pad of diatomaceous earth and washed with ethanol. The filtrate was concentrated, and the residue was purified by medium pressure chromatography [silica gel, 4–6% (2.0 M NH$_3$ in MeOH)/CH$_2$Cl$_2$] to give cis-(±)-4-(8-methoxynaphth-2-yl)-2-methylpiperidine as a brown oil (1.86 g, 45%). Ion Spray MS 256 (M+H)$^+$.

Preparation of (±)-trans-4-(8-Methoxynaphth-2-yl)-2-methylpiperidine.

Scheme I, Steps B and C: To a solution of N-t-butoxycarbonyl-4-(8-methoxynaphth-2-yl)-2-methyl-4-piperidinol (6.06 g, 16.3 mmol) in dry CH$_2$Cl$_2$ (49 mL) at 0° C. was added 21 mL of trifluoroacetic acid. The solution was stirred at 0° C. for 1.5 h. The reaction was then quenched at room temperature with saturated aqueous NaHCO$_3$ solution (280 mL). The mixture was extracted (2×300 mL) with CH$_2$Cl$_2$. The combined organic layers were dried over MgSO$_4$ and concentrated to yield 4.02 g of crude regioisomeric olefins. To a solution of the crude olefins (4.02 g) in a 3:1 mixture of ethanol (120 mL) and 2,2,2-trifluoroethanol (40 mL) was added 10% Pd/C (1.50 g). The black slurry was stirred vigorously at room temperature under hydrogen (balloon pressure) for 16 h. The black slurry was then filtered over a pad of diatomaceous earth and washed with ethanol. The filtrate was concentrated, and the residue was purified by medium pressure chromatography [silica gel, 4–6% (2.0 M NH$_3$ in MeOH)/CH$_2$Cl$_2$] to give the intermediate title compound as a brown solid (0.984 g, 24%). Ion Spray MS 256 (M+H)$^+$.

Preparation of Final Title Compound.

Scheme IV, Step B: A solution of (±)-cis-4-(8-methoxynaphth-2-yl)-2-methylpiperidine (1.30 g, 5.09 mmol) and (2S)-4-glycidyloxy-2-methylindole (1.030 g, 5.09 mmol) in MeOH (65 mL) was heated at reflux for 20 h and then cooled and evaporated. The residue was purified using silica gel chromatography [1.5% (2.0 M NH$_3$ in MeOH)/CH$_2$Cl$_2$] to give the free base of the final title compound as an off-white foam (0.829 g, 36%). The oxalate salt was prepared with 1 equiv. of oxalic acid in EtOAc. IR (KBr) 3399, 3350 (br) cm$^{-1}$. Ion Spray MS 459 (M+H)$^+$; 457 (M−H)$^-$. [α]$_D$=0 (c 0.35, MeOH). C$_{29}$H$_{34}$N$_2$O$_3$

| analysis: | calculated | found |
|---|---|---|
| C | 75.95 | 76.19 |
| H | 7.47 | 7.37 |
| N | 6.11 | 6.27 |

EXAMPLE 86

Preparation of (2S)-(+)-3-[(2S,4S)-4-(8-Methoxynaphth-2-yl)-2-methylpiperidinyl]-1-(1H-2-methylindol-4-yl)oxy-2-propanol oxalate

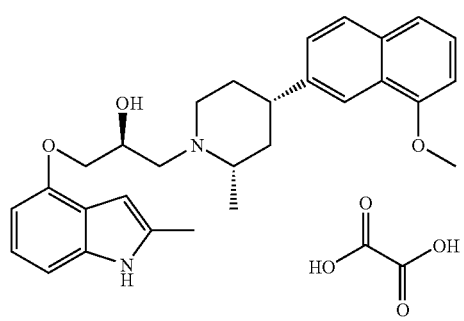

Scheme IV, Step B: A solution of (±)-cis-4-(8-methoxynaphth-2-yl)-2-methylpiperidine (0.120 g, 0.468 mmol, prepared in example 85) and (2S)-4-glycidyloxy-2-methylindole (0.095 g, 0.468 mmol) in MeOH (6 mL) was heated at reflux for 16 h and then cooled and evaporated. The residue was purified using silica gel chromatography [1.5% (2.0 M NH$_3$ in MeOH)/CH$_2$Cl$_2$] to give the free base of the final title compound as an off-white foam (0.076 g, 35%). The oxalate salt was prepared with 1 equiv. of oxalic acid in EtOAc. mp (oxalate) 144–147° C. (dec.). IR (KBr) 3402, 3350 (br) cm$^{-1}$. Ion Spray MS 459 (M+H)$^+$; 457 (M−H)$^-$. [α]$_D$=25.48 (c 0.47, MeOH). C$_{29}$H$_{34}$N$_2$O$_3$·C$_2$H$_2$O$_4$·0.2C$_4$H$_8$O$_2$

| analysis: | calculated | found |
|---|---|---|
| C | 67.45 | 67.25 |
| H | 6.69 | 6.88 |
| N | 4.95 | 4.97 |

EXAMPLE 87

Preparation of (2S)-(−)-3-[(2S,4R)-4-(8-Methoxynaphth-2-yl)-2-methylpiperidinyl]-1-(1H-2-methylindol-4-yl)oxy-2-propanol oxalate

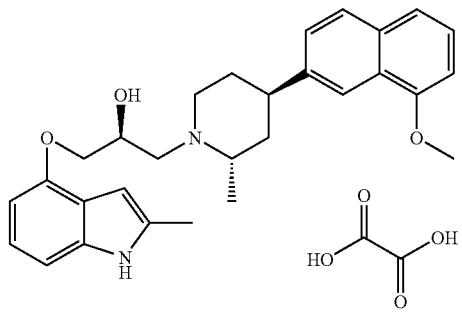

Scheme IV, Step B: A solution of (±)-trans-4-(8-methoxynaphth-2-yl)-2-methylpiperidine (0.700 g, 2.74 mmol, example 85) and (2S)-4-glycidyloxy-2-methylindole (0.557 g, 2.74 mmol) in MeOH (35 mL) was heated at reflux for 24 h and then cooled and evaporated. The residue was purified using silica gel chromatography [1.5% (2.0 M NH$_3$ in MeOH)/CH$_2$Cl$_2$] to give the free base of the final title compound as a light green foam (0.414 g, 33%). The oxalate salt was prepared with 1 equiv. of oxalic acid in EtOAc. IR (CHCl$_3$) 3474, 3350 (br) cm$^{-1}$. Ion Spray MS 459 (M+H)$^+$; 457 (M−H)$^-$ [α]$_D$=−4.13 (c 0.48, MeOH). C$_{29}$H$_{34}$N$_2$O$_3$·0.3CH$_2$Cl$_2$

| analysis: | calculated | found |
|---|---|---|
| C | 72.70 | 72.81 |
| H | 7.20 | 7.33 |
| N | 5.79 | 6.11 |

EXAMPLE 88

Preparation of (2S)-(+)-3-[(2R, 4S)-4-(8-Methoxynaphth-2-yl)-2-methylpiperidinyl]-1-(1H-2-methylindol-4-yl)oxy-2-propanol oxalate

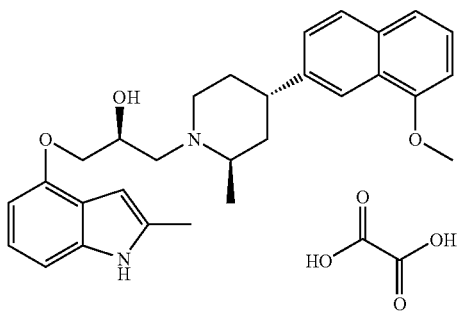

Scheme IV, Step B: A solution of (±)-trans-4-(8-methoxynaphth-2-yl)-2-methylpiperidine (0.700 g, 2.74 mmol, prepared in example 85) and (2S)-4-1.5 glycidyloxy-2-methylindole (0.557 g, 2.74 mmol) in MeOH (35 mL) was heated at reflux for 24 h and then cooled and evaporated. The residue was purified using silica gel chromatography [1.5% (2.0 M $NH_3$ in MeOH)/$CH_2Cl_2$] to give the free base of the title compound as a light green foam (0.579 g, 46%). The oxalate salt was prepared with 1 equiv. of oxalic acid in EtOAc. IR ($CHCl_3$) 3474, 3350 (br) $cm^{-1}$. Ion Spray MS 459 $(M+H)^+$; 457 $(M-H)^-$. $[\alpha]_D = 12.00$ (c 0.50, MeOH). $C_{29}H_{34}N_2O_3 \cdot C_2H_2O_4$

| analysis: | calculated | found |
|---|---|---|
| C | 67.87 | 68.13 |
| H | 6.61 | 6.87 |
| N | 5.11 | 4.97 |

EXAMPLE 89

Preparation of (2S)-(+)-1-(1H-2-Carboxamidoindol-4-yl)oxy-3-[4-(6-fluorobenzo[b]thiophen-2-yl)piperidinyl]-2-propanol oxalate

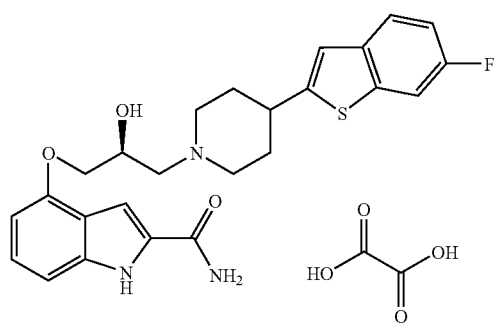

Preparation of N-t-Butoxycarbonyl4-(6-fluorobenzo[b]thiophen-2-yl))-4-piperidinol.

Scheme IA, Step A: To a solution of 4- and 6-fluorobenzo[b]thiophene (1.70 g, 11.2 mmol) in dry THF (50 mL) at −78° C. was added 1.6 M n-BuLi in hexanes (9.08 mL, 14.5 mmol). The solution was stirred at −78° C. for 35 min. N-t-Butoxycarbonyl-4-piperidone (2.67 g, 15.6 mmol) dissolved in THF (10 mL) was added via a cannula at −78° C. The reaction mixture was kept at −78° C. for 1.5 h then allowed to warm to room temperature. The reaction was then quenched with 150 mL of saturated aqueous $NH_4Cl$ solution. The mixture was extracted (3×300 mL) with EtOAc. The combined organic layers were dried over $MgSO_4$ and filtered. The filtrate was concentrated and purified by medium pressure chromatography (silica gel, 20% EtOAc/hexanes) to give the intermediate title compound as a white foam (2.24 g, 57%). mp 48–51° C. IR ($CHCl_3$) 3350 (br), 1682,1250 $cm^{-1}$. Ion Spray MS 352 $(M+H)^+$; 234 $(M-(BOC+H_2O)^+$; 278 $(M-73)^+$ (base peak); 410 $(M+CH_3COO^-)^-$.

Preparation of 4-(6-Fluorobenzo[b]thiophen-2-yl)-1,2,5,6-tetrahydropyridine.

Scheme IA, Step B: To a solution of N-t-butoxycarbonyl4-(6-fluorobenzo[b]thiophen-2-yl))-4-piperidinol (2.14 g, 6.10 mmol) in dry $CH_2Cl_2$ (21 mL) at 0° C. was added 9 mL of trifluoroacetic acid. The solution was stirred at 0° C. for 1.5 h. The reaction was then quenched at room temperature with saturated aqueous $NaHCO_3$ solution (100 mL). The mixture was extracted (3×200 mL) with 10% MeOH in $CH_2Cl_2$. The combined organic layers were dried over $MgSO_4$ and concentrated to give the intermediate title compound as an off-white solid (1.25 g, 88%). mp 155–157° C. IR (KBr) 3450 (br), 1248 $cm^{-1}$. Ion Spray MS 234 $(M+H)^+$.

Preparation of 4-(6-Fluorobenzo[b]thiophen-2-yl)piperidine.

Scheme IA, Step C: To a solution of 4-(6-fluorobenzo[b]thiophen-2-yl)-1,2,5,6-tetrahydropyridine (0.850 g, 3.64 mmol) in a 3:1 mixture of ethanol (30 mL) and 2,2,2-trifluoroethanol (10 mL) was added 10% Pd/C (0.900 g). The black slurry was stirred vigorously at room temperature under hydrogen (balloon pressure) for 1 day. The black slurry was then filtered over a pad of diatomaceous earth and washed with ethanol. The filtrate was concentrated to provide the intermediate title compound as a white solid (0.735 g, 86%). mp 115–120° C. IR (KBr) 3350 (br), 1247 $cm^{-1}$. Ion Spray MS 236 $(M+H)^+$.

Preparation of Final Title Compound.

Scheme IV, Step B: A solution of 4-(6-fluorobenzo[b]thiophen-2-yl)piperidine (0.100 g, 0.425 mmol, prepared above) and (S)-4-(oxiranylmethoxy)indole-2-carboxamide (0.099 g, 0.425 mmol) in MeOH (5 mL) was heated at reflux for 9 h and then cooled and evaporated. The residue was purified using silica gel chromatography [5% (2.0 M $NH_3$ in MeOH)/$CH_2Cl_2$] to give the free base of the title compound as a white solid (0.156 g, 79%). The oxalate salt was prepared with 1 equiv. of oxalic acid in EtOAc. mp (oxalate) 138–141° C (dec.). IR (KBr) 3300 (br), 1657 $cm^{-1}$. Ion Spray MS 468 $(M+H)^+$; 466 $(M-H)^-$. $[\alpha]_D = 5.73$ (c 0.35, MeOH). $C_{25}H_{26}FN_3O_3S$

| analysis: | calculated | found |
|---|---|---|
| C | 64.22 | 64.04 |
| H | 5.61 | 5.67 |
| N | 8.99 | 8.84 |

EXAMPLE 90

Preparation of (2S)-(−)-3-[(2R,4R)-4-(6-Fluorobenzo[b]thiophen-2-yl)-2-methylpiperidinyl]-1-(1-H-indol-4-yl)oxy-2-propanol oxalate

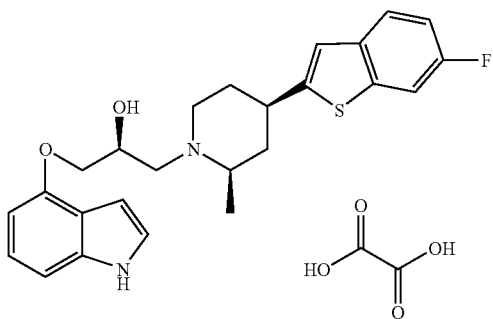

Preparation of N-t-Butoxycarbonyl-4-(6-fluorobenzo[b]thiophen-2-yl)-2-methyl-4-piperidinol.

Scheme IA, Step A: To a solution of 4- and 6-fluorobenzo[b]thiophene (12.4 g, 81.7 mmol) in dry THF (415 mL) at −78° C. was added 1.6 M n-BuLi in hexanes (56.4 mL, 90.2 mmol). The solution was stirred at −78° C. for 1.5 h. N-t-Butoxycarbonyl-2-methyl-4-piperidone (15.7 g, 73.5 mmol) dissolved in THF (40 mL) was added via a cannula at −78° C. The reaction mixture was stirred at −78° C. for 4 h. The reaction was then quenched with 300 mL of saturated aqueous $NH_4Cl$ solution. The mixture was extracted (2×500 mL) with EtOAc. The combined organic layers were then dried over $MgSO_4$ and filtered. The filtrate was concentrated and purified by medium pressure chromatography (15% EtOAc/hexanes) to give the intermediate title compound as a white foam (19.12 g, 71%). $^1$HNMR (CDCl$_3$) 7.61 (dd, J=8.8, 4.9 Hz, 1H), 7.46 (dd, J=8.8, 2.4 Hz, 1H), 7.08 (s, 1H), 7.06 (dt, J=8.8, 2.4 Hz, 1H), 4.44 (br m, 1H), 3.99–4.03 m, 1H), 3.30–3.38 (br m, 1H), 2.16 (dd, J=14.2, 6.8 Hz, 1H), 1.89–2.05 (m, 3H), 1.60 (br s, 1H), 1.46 (s, 9H), 1.38 (d, J=7.3 Hz, 3H).

Preparation of (±)-cis-4-(6-Fluorobenzo[b]thiophen-2-yl)-2-methylpiperidine.

Scheme IA, Steps B and C: To a solution of N-t-butoxycarbonyl4-(6-fluorobenzo[b]thiophen-2-yl)-2-methyl-4-piperidinol (7.14 g, 19.5 mmol) in dry $CH_2Cl_2$ (63 mL) at 0° C. was added 27 mL of trifluoroacetic acid. The solution was stirred at 0° C. for 2 h. The reaction was then quenched at room temperature with saturated aqueous $NaHCO_3$ solution (350 mL). The mixture was extracted (2×500 mL) with $CH_2Cl_2$. The combined organic layers were dried over $MgSO_4$ and concentrated to yield 4.48 g of crude regioisomeric olefins. To a solution of the crude olefins (4.48 g) in a 3:1 mixture of ethanol (150 mL) and 2,2,2-trifluoroethanol (50 mL) was added 10% Pd/C (4.50 g). The black slurry was stirred vigorously at room temperature under hydrogen (balloon pressure) for 15 h. The black slurry was then filtered over a pad of diatomaceous earth and washed with ethanol. The filtrate was concentrated, and the residue was purified by medium pressure chromatography [silica gel, 5% (2.0 M $NH_3$ in MeOH)/$CH_2Cl_2$] to give the intermediate title compound as a brown solid (1.87 g, 38%). mp 34–37° C. IR (KBr) 3400 (br), 3235, 1237 cm$^{−1}$. Ion Spray MS 250 (M+H)$^+$.

Preparation of (±)-trans-4-(6-Fluorobenzo[b]thiophen-2-yl)-2-methylpiperidine.

Scheme IA, Steps B and C: To a solution of N-t-butoxycarbonyl-4-(6-fluorobenzo[b]thiophen-2-yl)-2-methyl-4-piperidinol (7.14 g, 19.5 mmol) in dry $CH_2Cl_2$ (63 mL) at 0° C. was added 27 mL of trifluoroacetic acid. The solution was stirred at 0° C. for 2 h. The reaction was then quenched at room temperature with saturated aqueous $NaHCO_3$ solution (350 mL). The mixture was extracted (2×500 mL) with $CH_2Cl_2$. The combined organic layers were dried over $MgSO_4$ and concentrated to yield 4.48 g of crude regioisomeric olefins. To a solution of the crude olefins (4.48 g) in a 3:1 mixture of ethanol (150 mL) and 2,2,2-trifluoroethanol (50 mL) was added 10% Pd/C (4.50 g). The black slurry was stirred vigorously at room temperature under hydrogen (balloon pressure) for 15 h. The black slurry was then filtered over a pad of diatomaceous earth and washed with ethanol. The filtrate was concentrated, and the residue was purified by medium pressure chromatography [silica gel, 5% (2.0 M $NH_3$ in MeOH)/$CH_2Cl_2$] to the intermediate title compound as a brown solid (1.20 g, 25%). IR (CHCl$_3$) 1251 cm$^{−1}$. Ion Spray MS 250 (M+H)$^+$.

Preparation of Final Title Compound.

Scheme IV, Step B: A solution of (±)-cis-4-(6-fluorobenzo[b]-thiophen-2-yl)-2-methylpiperidine (0.200 g, 0.802 mmol) and (S)-4-(oxiranylmethoxy)indole (0.152 g, 0.802 mmol) in MeOH (10 mL) was heated at reflux for 23 h and then cooled and evaporated. The residue was purified using silica gel chromatography [1% (2.0 M $NH_3$ in MeOH)/$CH_2Cl_2$] to give the free base of the final title compound as a white foam (0.166 g, 47%). The oxalate salt was prepared with 1 equiv. of oxalic acid in EtOAc. IR (KBr) 3407, 3300 (br), 1246 cm$^{−1}$. Ion Spray MS 439 (M+H)$^+$; 437 (M−H)$^−$; 497 (M+CH$_3$COO$^−$)$^−$. [α]$_D$=−11.49 (c 0.52, MeOH). $C_{25}H_{27}FN_2O_2S \cdot C_2H_2O_4$

| analysis: | calculated | found |
|---|---|---|
| C | 61.35 | 61.49 |
| H | 5.53 | 5.51 |
| N | 5.30 | 5.36 |

EXAMPLE 91

Preparation of (2S)-(+)-3-[(2S,4S)-4-(6-Fluorobenzo[b]thiophen-2-yl)-2-methylpiperidinyl]-1-(1H-indol-4-yl)oxy-2-propanol oxalate

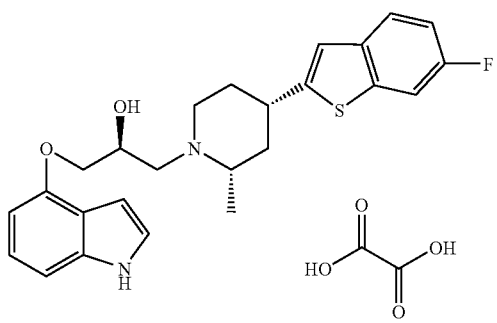

Scheme IV, Step B: A solution of (±)-cis-4-(6-fluorobenzo[b]thiophen-2-yl)-2-methylpiperidine (0.200 g, 0.802 mmol, prepared in example 90) and (S)-4-(oxiranylmethoxy)indole (0.152 g, 0.802 mmol) in MeOH (10 mL) was heated at reflux for 23 h and then cooled and evaporated. The residue was purified using silica gel chromatography [1% (2.0 M NH$_3$ in MeOH)/CH$_2$Cl$_2$] to give the free base of the title compound as a white foam (0.123 g, 35%). The oxalate salt was prepared with 1 equiv. of oxalic acid in EtOAc. IR (KBr) 3405, 3300 (br), 1246 cm$^{-1}$. Ion Spray MS 439 (M+H)$^+$; 437 (M−H)$^-$; 497 (M+CH$_3$COO$^-$)$^-$. [α]$_D$=27.71 (c 0.43, MeOH). C$_{25}$H$_{27}$FN$_2$O$_2$S.C$_2$H$_2$O$_4$

| analysis: | calculated | found |
|---|---|---|
| C | 61.35 | 61.47 |
| H | 5.53 | 5.75 |
| N | 5.30 | 5.17 |

EXAMPLE 92

Preparation of (2S)-3-[(2S,4R)-4-(6-Fluorobenzo[b]thiophen-2-yl)-2-methylpiperidinyl]-1-(1H-indol-4-yl)oxy-2-propanol oxalate

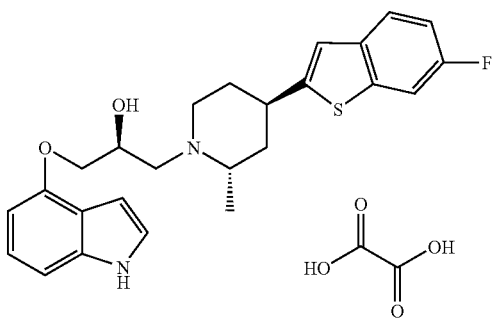

Scheme IV, Step B: A solution of (±)-trans-4-(6-fluorobenzo[b]thiophen-2-yl)-2-methylpiperidine (0.194 g, 0.779 mmol, prepared in example 90) and (S)-4-(oxiranylmethoxy)indole (0.147 g, 0.779 mmol) in MeOH (10 mL) was heated at reflux for 20 h and then cooled and evaporated. The residue was purified using silica gel chromatography [1% (2.0 M NH$_3$ in MeOH)/CH$_2$Cl$_2$] to give the free base of the title compound as a white foam (0.142 g, 41%). The oxalate salt was prepared with 1 equiv. of oxalic acid in EtOAc. mp (oxalate) 113–116° C. IR (KBr) 3405, 3300 (br), 1246 cm$^{-1}$. Ion Spray MS 439 (M+H)$^+$; 437 (M−H)$^-$. [α]$_D$=0 (c 0.56, MeOH). C$_{25}$H$_{27}$FN$_2$O$_2$S.C$_2$H$_2$O$_4$

| analysis: | calculated | found |
|---|---|---|
| C | 61.35 | 61.07 |
| H | 5.53 | 5.27 |
| N | 5.30 | 5.22 |

EXAMPLE 93

Preparation of (2S)-(+)-3-[(2R,4S)-4-(6-Fluorobenzo[b]thiophen-2-yl)-2-methylpiperidinyl]-1-(1H-indol-4-yl)oxy-2-propanol oxalate

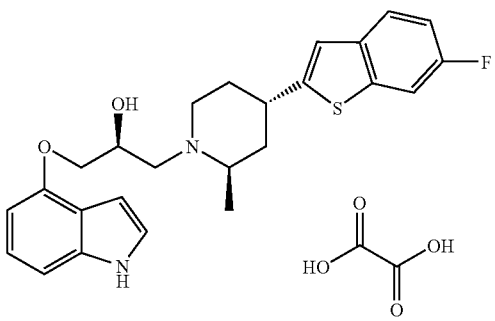

Scheme IV, Step B: A solution of (±)-trans-4-(6-fluorobenzo[b]thiophen-2-yl)-2-methylpiperidine (0.194 g, 0.779 mmol, prepared in example 90) and (S)-4-(oxiranylmethoxy)indole (0.147 g, 0.779 mmol) in MeOH (10 mL) was heated at reflux for 20 h and then cooled and evaporated. The residue was purified using silica gel chromatography [1% (2.0 M NH$_3$ in MeOH)/CH$_2$Cl$_2$] to give the free base of the title compound as a white foam (0.150 g, 44%). The oxalate salt was prepared with 1 equiv. of oxalic acid in EtOAc. mp (oxalate) 107–110° C. IR (KBr) 3408, 3300 (br), 1246 cm$^{-1}$. Ion Spray MS 439 (M+H)$^+$; 437 (M−H)$^-$; 497 (M+CH$_3$COO$^-$)$^-$. [α]$_D$=14.79 (c 0.54, MeOH). C$_{25}$H$_{27}$FN$_2$O$_2$S.C$_2$H$_2$O$_4$

| analysis: | calculated | found |
|---|---|---|
| C | 61.35 | 61.30 |
| H | 5.53 | 5.58 |
| N | 5.30 | 5.18 |

EXAMPLE 94

Preparation of (2S)-(+)-3-[4-(6-Fluorobenzo[b]thiophen-2-yl)piperidinyl]-1-(1H-2-methylindol-4-yl)oxy-2-propanol oxalate

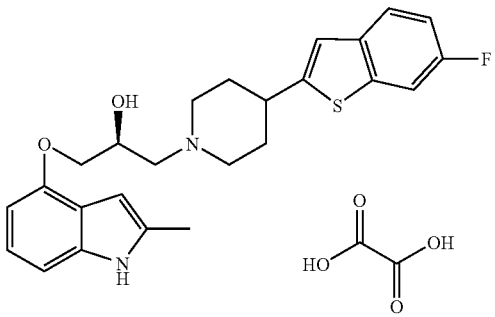

Scheme IV, Step B: A solution of 4-(6-fluorobenzo[b]thiophen-2-yl)piperidine (0.100 g, 0.425 mmol, prepared in example 89) and (2S)-4-glycidyloxy-2-methylindole (0.086 g, 0.425 mmol) in MeOH (5 mL) was heated at reflux for 9 h and then cooled and evaporated. The residue was purified using silica gel chromatography [1% (10% conc. NH$_4$OH in MeOH)/CH$_2$Cl$_2$] to give the free base of the title compound as a green foam (0.159 g, 85%). The oxalate salt was prepared with 1 equiv. of oxalic acid in EtOAc. IR (CHCl$_3$) 3474, 3350 (br), 1249 cm$^{-1}$. Ion Spray MS 439 (M+H)$^+$; 437 (M−H)$^-$; 497 (M+CH$_3$COO$^-$)$^-$. [α]$_D$=7.80 (c 0.51, MeOH). C$_{25}$H$_{27}$FN$_2$O$_2$S.C$_2$H$_2$O$_4$

| analysis: | calculated | found |
|---|---|---|
| C | 61.35 | 61.10 |
| H | 5.53 | 5.72 |
| N | 5.30 | 5.08 |

EXAMPLE 95

Preparation of (2S)-(−)-3-[(2R,4R)-4-(6-Fluorobenzo[b]thiophen-2-yl)-2-methylpiperidinyl]-1-(1H-2-methylindol-4-yl)oxy-2-propanol oxalate

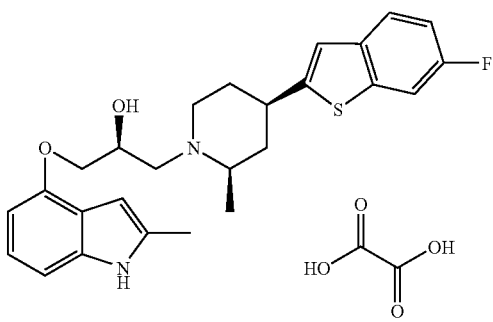

Scheme IV, Step B: A solution of (±)-cis-4-(6-fluorobenzo[b]thiophen-2-yl)-2-methylpiperidine (0.200 g, 0.802 mmol, prepared in example 90) and (2S)-4-glycidyloxy-2-methylindole (0.163 g, 0.802 mmol) in MeOH (10 mL) was heated at reflux for 21 h and then cooled and evaporated. The residue was purified using silica gel chromatography [2% (2.0 M NH$_3$ in MeOH)/CH$_2$Cl$_2$] to give the free base of the title compound as an off-white foam (0.154 g, 42%). The oxalate salt was prepared with 1 equiv. of oxalic acid in EtOAc. IR (CHCl$_3$) 3474, 3350 (br), 1249 cm$^{-1}$. Ion Spray MS 453 (M+H)$^+$; 451 (M−H)$^-$ 511 (M+CH$_3$COO$^-$)$^-$. [α]$_D$=−7.45 (c 0.54, MeOH). C$_{26}$H$_{29}$FN$_2$O$_2$S.C$_2$H$_2$O$_4$

| analysis: | calculated | found |
|---|---|---|
| C | 61.98 | 62.05 |
| H | 5.76 | 5.69 |
| N | 5.16 | 5.45 |

EXAMPLE 96

Preparation of (2S)-(+)-3-[(2S,4S)-4-(6-Fluorobenzo[b]thiophen-2-yl)-2-methylpiperidinyl]-1-(1H-2-methylindol-4-yl)oxy-2-propanol oxalate

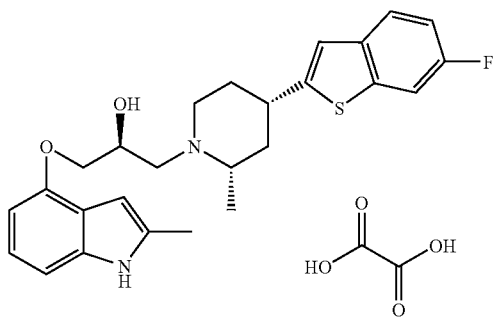

Scheme IV, Step B: A solution of (±)-cis-4-(6-fluorobenzo[b]thiophen-2-yl)-2-methylpiperidine (0.200 g, 0.802 mmol, prepared in example 90) and (2S)-4-glycidyloxy-2-methylindole (0.163 g, 0.802 mmol) in MeOH (10 mL) was heated at reflux for 21 h and then cooled and evaporated. The residue was purified using silica gel chromatography [2% (2.0 M NH$_3$ in MeOH)/CH$_2$Cl$_2$] to give the free base of the title compound as an off-white foam (0.141 g, 39%). The oxalate salt was prepared with 1 equiv. of oxalic acid in EtOAc. mp (oxalate) 105–108° C. (dec.). IR (CHCl$_3$) 3474, 3350 (br), 1250 cm$^{-1}$. Ion Spray MS 453 (M+H)$^+$; 451 (M−H)$^-$ 511 (M+CH$_3$COO$^-$)$^-$. [α]$_D$=27.86 (c 0.36, MeOH). C$_{26}$H$_{29}$FN$_2$O$_2$S

| analysis: | calculated | found |
|---|---|---|
| C | 69.00 | 69.23 |
| H | 6.46 | 6.63 |
| N | 6.19 | 6.14 |

EXAMPLE 97

Preparation of (2S)-3-[(2S, 4R)-4-(6-Fluorobenzo[b]thiophen-2-yl)-2-methylpiperidinyl]-1-(1H-2-methylindol-4-yl)oxy-2-propanol oxalate

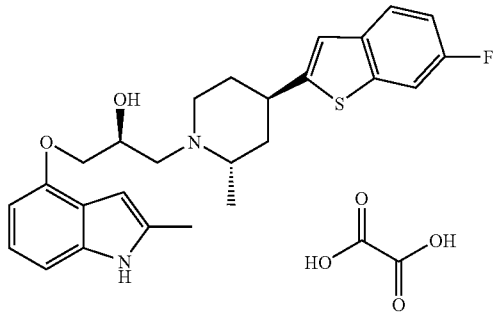

Scheme IV, Step B: A solution of (±)-trans-4-(6-fluorobenzo[b]thiophen-2-yl)-2-methylpiperidine (0.200 g, 0.802 mmol, prepared in example 90) and (2S)-4-glycidyloxy-2-methylindole (0.163 g, 0.802 mmol) in MeOH (10 mL) was heated at reflux for 20 h and then cooled and evaporated. The residue was purified using silica gel chromatography [1% (2.0 M $NH_3$ in MeOH)/$CH_2Cl_2$] to give the free base of the title compound as a white foam (0.174 g, 48%). The oxalate salt was prepared with 1 equiv. of oxalic acid in EtOAc. IR ($CHCl_3$) 3474, 3350 (br), 1249 $cm^{-1}$. Ion Spray MS 453 $(M+H)^+$; 451 $(M-H)^-$. $[\alpha]_D=0$ (c 0.48, MeOH). $C_{26}H_{29}FN_2O_2S \cdot 0.1CH_2Cl_2$

| analysis: | calculated | found |
|---|---|---|
| C | 67.99 | 68.09 |
| H | 6.38 | 6.57 |
| N | 6.08 | 5.84 |

EXAMPLE 98

Preparation of (2S)-(+)-3-[(2R,4S)-4-(6-Fluorobenzo[b]thiophen-2-yl)-2-methylpiperidinyl]-1-(1H-2-methylindol4-yl)oxy-2-propanol oxalate

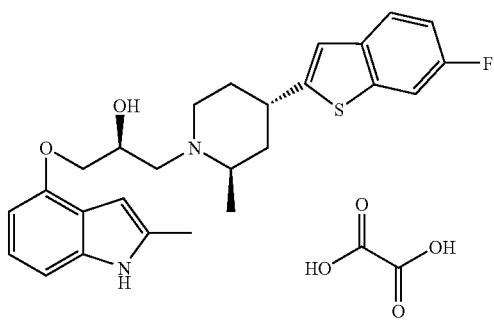

Scheme IV, Step B: A solution of (±)-trans-4-(6-fluorobenzo[b]thiophen-2-yl)-2-methylpiperidine (0.200 g, 0.802 mmol, prepared in example 90) and (2S)-4-glycidyloxy-2-methylindole (0.163 g, 0.802 mmol) in MeOH (10 mL) was heated at reflux for 20 h and then cooled and evaporated. The residue was purified using silica gel chromatography [1% (2.0 M $NH_3$ in MeOH)/$CH_2Cl_2$] to give the free base of the title compound as a white foam (0.158 g, 43%). The oxalate salt was prepared with 1 equiv. of oxalic acid in EtOAc. IR ($CHCl_3$) 3474, 3350 (br), 1250 $cm^{-1}$. Ion Spray MS 453 $(M+H)^+$; 451 $(M-H)^-$. $[\alpha]_D=11.95$ (c 0.50, MeOH). $C_{26}H_{29}FN_2O_2S \cdot 0.1CH_2Cl_2$

| analysis: | calculated | found |
|---|---|---|
| C | 67.99 | 68.27 |
| H | 6.38 | 6.41 |
| N | 6.08 | 6.14 |

EXAMPLE 99

Preparation of (2S)-1-(1H-2-Carboxamidoindol-4-yl)oxy-3-[(2R,4R)-4-(4-methoxybenzo[b]thiophen-2-yl)-2-methylpiperidinyl]-2-propanol oxalate

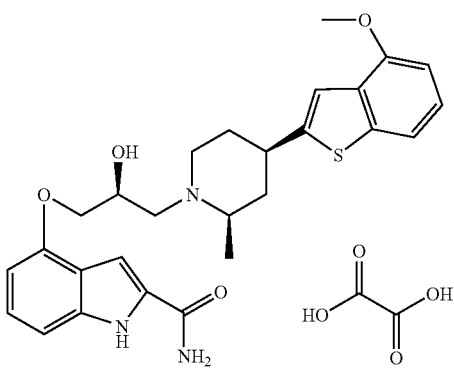

Preparation of N-t-Butoxycarbonyl-4-(4-methoxybenzo[b]thiophen-2-yl)-2-methyl-4-piperidinol.

Scheme IA, Step A: To a solution of 4-methoxybenzo[b]thiophene (7.70 g, 46.9 mmol) in dry THF (230 mL) at −78° C. was added 1.6 M n-BuLi in hexanes (32.2 mL, 51.6 mmol). The solution was stirred at −78° C. for 45 min. N-t-Butoxycarbonyl-2-methyl-4-piperidone (6.00 g, 28.1 mmol) dissolved in THF (40 mL) was added via a cannula at −78° C. The reaction mixture was slowly warmed to room temperature and stirred for 16 h. The reaction was then quenched with 600 mL of saturated aqueous $NH_4Cl$ solution. The mixture was extracted (1×1 L) with EtOAc. The combined organic layers were then dried over $MgSO_4$ and filtered. The filtrate was concentrated and purified by medium pressure chromatography (silica gel, 25% $Et_2O$/hexanes) to give the intermediate title compound as a white foam (5.06 g, 48%). mp 73–76° C. IR ($CHCl_3$) 3474, 3350 (br) $cm^{-1}$. IR ($CHCl_3$) 3350 (br), 1680 $cm^{-1}$. Ion Spray MS 378 $(M+H)^+$; 260 $(M-(Boc+H_2O))^+$; 304 $(M-74)^+$ (base peak); 436 $(M+CH_3COO^-)^-$.

Preparation of (±)-cis-4-(4-Methoxybenzo[b]thiophen-2-yl)-2-methylpiperidine.

Scheme IA, Steps B and C: To a solution of N-t-butoxycarbonyl4-(4-methoxybenzo[b]thiophen-2-yl)-2-methyl-4-piperidinol (5.00 g, 13.2 mmol) in dry $CH_2Cl_2$ (92 mL) at 0° C. was added 18 mL of trifluoroacetic acid. The resulting purple solution was stirred at 0° C. for 1 h 20 min. The reaction was then quenched at room temperature with saturated aqueous $NaHCO_3$ solution (220 mL). The mixture was extracted (2×500 mL) with $CH_2Cl_2$. The combined organic layers were washed (1×100 mL) with brine, dried over $MgSO_4$, and concentrated to yield 3.67 g of crude regioisomeric olefins. To a solution of the crude olefins (3.67 g) in a 3:1 mixture of ethanol (99 mL) and 2,2,2-trifluoroethanol (33 mL) was added 10% Pd/C (3.50 g). The black slurry was stirred vigorously at room temperature under hydrogen (balloon pressure) for 24 h. The black slurry was then filtered over a pad of diatomaceous earth and washed with ethanol. The filtrate was concentrated, and the residue was purified by medium pressure chromatography [silica gel, 5% (2.0 M $NH_3$ in MeOH)/$CH_2Cl_2$] to give the intermediate title compound as an orange solid (1.87 g, 54%). mp 70–73° C. IR (KBr) 3436 (br), 3246 $cm^{-1}$. Ion Spray MS 262 $(M+H)^+$.

Preparation of (±)-trans-4-(4-Methoxybenzo[b]thiophen-2-yl)-2-methylpiperidine.

Scheme IA, Steps B and C: To a solution of N-t-butoxycarbonyl-4-(4-methoxybenzo[b]thiophen-2-yl)-2-methyl-4- piperidinol (5.00 g, 13.2 mmol) in dry CH$_2$Cl$_2$ (92 mL) at 0° C. was added 18 mL of trifluoroacetic acid. The resulting purple solution was stirred at 0° C. for 1 h 20 min. The reaction was then quenched at room temperature with saturated aqueous NaHCO$_3$ solution (220 mL). The mixture was extracted (2×500 mL) with CH$_2$Cl$_2$. The combined organic layers were washed (1×100 mL) with brine, dried over MgSO$_4$, and concentrated to yield 3.67 g of crude regioisomeric olefins. To a solution of the crude olefins (3.67 g) in a 3:1 mixture of ethanol (99 mL) and 2,2,2-trifluoroethanol (33 mL) was added 10% Pd/C (3.50 g). The black slurry was stirred vigorously at room temperature under hydrogen (balloon pressure) for 24 h. The black slurry was then filtered over a pad of diatomaceous earth and washed with ethanol. The filtrate was concentrated, and the residue was purified by medium pressure chromatography [silica gel, 5% (2.0 M NH$_3$ in MeOH)/CH$_2$Cl$_2$] to give the intermediate title compound as an orange solid (0.580 g, 17%). mp 76–78° C. IR (KBr) 3400 (br), 3223 cm$^{-1}$. Ion Spray MS 262 (M+H)$^+$.

Preparation of Final Title Compound.

Scheme IV, Step B: A solution of (±)-cis-4-(4-methoxy-benzo[b]thiophen-2-yl)-2-methylpiperidine (0.134 g, 0.527 mmol) and (S)-4-(oxiranylmethoxy)indole-2-carboxamide (0.122 g, 0.527 mmol) in MeOH (7 mL) was heated at reflux for 8 h and then cooled and evaporated. The residue was purified using silica gel chromatography [4.5% (2.0 M NH$_3$ in MeOH)/CH$_2$Cl$_2$] to give the free base of the title compound as an off-white foam (0.119 g, 46%). The oxalate salt was prepared with 1 equiv. of oxalic acid in EtOAc. mp (oxalate) 172° C. (dec.). IR (KBr) 3300 (br), 1653 cm$^{-1}$. Ion Spray MS 494 (M+H)$^+$; 492 (M−H)$^−$. [α]$_D$ (oxalate)=0 (c 0.34, DMSO). C$_{27}$H$_{31}$N$_3$O$_4$S.C$_2$H$_2$O$_4$.0.3C$_4$H$_8$O$_2$

| analysis: | calculated | found |
|---|---|---|
| C | 59.45 | 59.06 |
| H | 5.85 | 5.73 |
| N | 6.89 | 6.73 |

EXAMPLE 100

Preparation of (2S)-(+)-1-(1H-2-Carboxamidoindol-4-yl)oxy-3-[(2S,4S)-4-(4-methoxybenzo[b]thiophen-2-yl)-2-methylpiperidinyl]-2-propanol oxalate

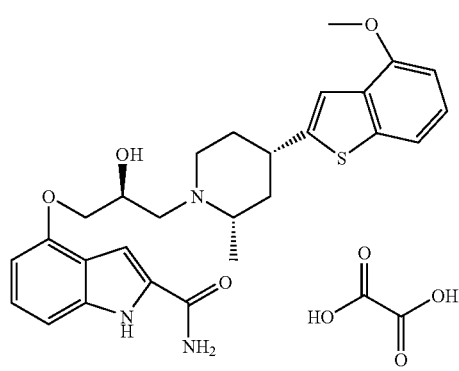

Scheme IV, Step B: A solution of (±)-cis-4-(4-methoxy-benzo[b]thiophen-2-yl)-2-methylpiperidine (0.134 g, 0.527 mmol, prepared in example 99) and (S)-4-(oxiranyl-methoxy)indole-2-carboxamide (0.122 g, 0.527 mmol) in MeOH (7 mL) was heated at reflux for 8 h and then cooled and evaporated. The residue was purified using silica gel chromatography [4.5% (2.0 M NH$_3$ in MeOH)/CH$_2$Cl$_2$] to give the free base of the title compound as an off-white foam (0.102 g, 39%). The oxalate salt was prepared with 1 equiv. of oxalic acid in EtOAc. mp (oxalate) 162 (dec.). IR (KBr) 3300 (br), 1653 cm$^{-1}$. Ion Spray MS 494 (M+H)$^+$; 492 (M−H)$^−$. [α]$_D$ (oxalate)=5.26 (c 0.38, DMSO). C$_{27}$H$_{31}$N$_3$O$_4$S.C$_2$H$_2$O$_4$.0.3C$_4$H$_8$O$_2$

| analysis: | calculated | found |
|---|---|---|
| C | 59.45 | 59.08 |
| H | 5.85 | 5.67 |
| N | 6.89 | 6.84 |

EXAMPLE 101

Preparation of (2S)-1-(1H-2-Carboxamidoindol-4-yl)oxy-3-[(2S,4R)-4-(4-5methoxybenzo[b]thiophen-2-yl)-2-methylpiperidinyl]-2-propanol oxalate

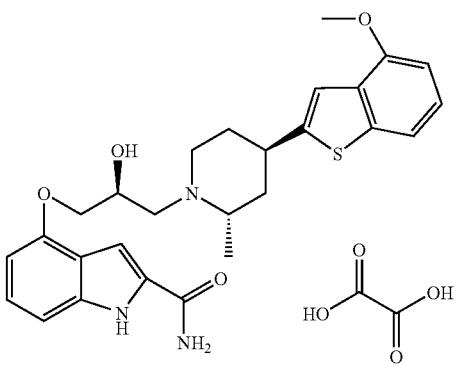

Scheme IV, Step B: A solution of (±)-trans-4-(4-methoxy-benzo[b]thiophen-2-yl)-2-methylpiperidine (0.063 g, 0.239 mmol, prepared in example 99) and (S)-4-(oxiranyl-methoxy)indole-2-carboxamide (0.056 g, 0.239 mmol) in MeOH (3 mL) was heated at reflux for 8 h and then cooled and evaporated. The residue was purified using silica gel chromatography [6% (2.0 M NH$_3$ in MeOH)/CH$_2$Cl$_2$] to give the free base of the title compound as an off-white foam (0.041 g, 35%). The oxalate salt was prepared with 1 equiv. of oxalic acid in EtOAc. mp (oxalate) 170° C. (dec.). IR (KBr) 3300 (br), 1658 cm$^{-1}$. Ion Spray MS 494 (M+H)$^+$; 492 (M−H)$^−$. C$_{27}$H$_{31}$N$_3$O$_4$S.C$_2$H$_2$O$_4$

| analysis: | calculated | found |
|---|---|---|
| C | 59.68 | 59.47 |
| H | 5.70 | 5.51 |
| N | 7.20 | 7.08 |

EXAMPLE 102

Preparation of (2S)-1-(1H-2-Carboxamidoindol-4-yl)oxy-3-[(2R,4S)-4-(4-methoxybenzo[b]thiophen-2-yl)-2-methylperidinyl]-2-propanol oxalate

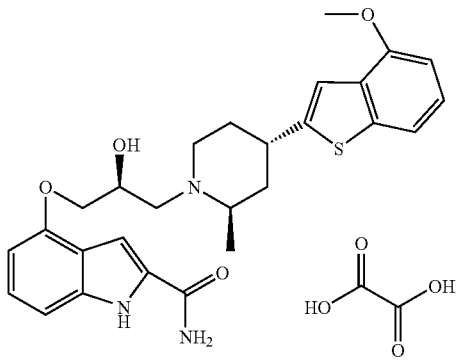

Scheme IV, Step B: A solution of (±)-trans-4-(4-methoxybenzo[b]thiophen-2-yl)-2-methylpiperidine (0.063 g, 0.239 mmol, prepared in example 99) and (S)-4-(oxiranylmethoxy)indole-2-carboxamide (0.056 g, 0.239 mmol) in MeOH (3 mL) was heated at reflux for 8 h and then cooled and evaporated. The residue was purified using silica gel chromatography [6% (2.0 M $NH_3$ in MeOH)/$CH_2Cl_2$] to give the free base of the title compound as an off-white foam (0.044 g, 37%). The oxalate salt was prepared with 1 equiv. of oxalic acid in EtOAc. mp 158–161° C. IR (KBr) 3300 (br), 1658 $cm^{-1}$. Ion Spray MS 494 (M+H)$^+$; 492 (M−H)$^-$. $C_{27}H_{31}N_3O_4S.0.1CH_2Cl_2$

| analysis: | calculated | found |
|---|---|---|
| C | 64.82 | 64.68 |
| H | 6.26 | 6.41 |
| N | 8.37 | 8.52 |

EXAMPLE 103

Preparation of (2S)-(−)-1-(1H-Indol-4-yl)oxy-3-[(2R,4R)-4-(4-methoxybenzo[b]thiophen-2-yl)-2-methylpiperidinyl]-2-propanol oxalate

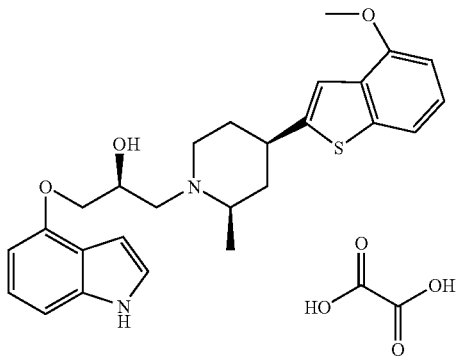

Scheme IV, Step B: A solution of (±)-cis-4-(4-methoxybenzo[b]thiophen-2-yl)-2-methylpiperidine (0.200 g, 0.765 mmol, prepared in example 99) and (S)-4-(oxiranylmethoxy)indole (0.145 g, 0.765 mmol) in MeOH (10 mL) was heated at reflux for 10 h and then cooled and evaporated. The residue was purified using silica gel chromatography [1% (2.0 M $NH_3$ in MeOH)/$CH_2Cl_2$] to give the free base of the title compound as a white foam (0.137 g, 40%). The oxalate salt was prepared with 1 equiv. of oxalic acid in EtOAc. mp (oxalate) 136–139° C. IR (KBr) 3409, 3350 (br) $cm^{-1}$. Ion Spray MS 451 (M+H)$^+$; 449 (M−H)$^-$; 509 (M+$CH_3COO^-$)$^-$. $[\alpha]_D=-7.37$ (c 0.54, MeOH. $C_{26}H_{30}N_2O_3S.C_2H_2O_4$

| analysis: | calculated | found |
|---|---|---|
| C | 62.21 | 62.07 |
| H | 5.97 | 6.10 |
| N | 5.18 | 5.03 |

EXAMPLE 104

Preparation of (2S)-(+)-1-(1H-Indol-4-yl)oxy-3-[(2S,4S)-4-(4-methoxybenzo[b]thiophen-2-yl)-2-methylpiperidinyl]-2-propanol oxalate

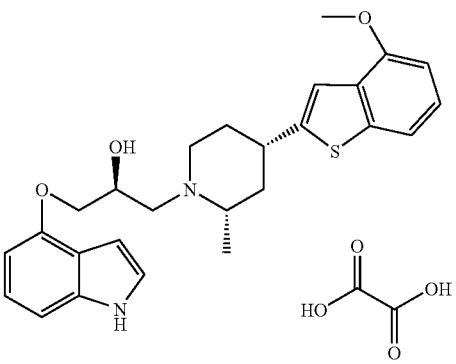

Scheme IV, Step B: A solution of (±)-cis-4-(4-methoxybenzo[b]thiophen-2-yl)-2-methylpiperidine (0.200 g, 0.765 mmol, prepared in example 99) and (S)-4-(oxiranylmethoxy)indole (0.145 g, 0.765 mmol) in MeOH (10 mL) was heated at reflux for 10 h and then cooled and evaporated. The residue was purified using silica gel chromatography [1% (2.0 M $NH_3$ in MeOH)/$CH_2Cl_2$] to give the free base of the title compound as a white foam (0.143 g, 42%). The oxalate salt was prepared with 1 equiv. of oxalic acid in EtOAc. mp (oxalate) 134–137° C. IR (KBr) 3412, 3350 (br) $cm^{-1}$. Ion Spray MS 451 (M+H)$^+$; 449 (M−H)$^-$. $[\alpha]_D=4.37$ (c 0.46, MeOH). $C_{26}H_{30}N_2O_3S.C_2H_2O_4$

| analysis: | calculated | found |
|---|---|---|
| C | 62.21 | 62.13 |
| H | 5.97 | 6.07 |
| N | 5.18 | 5.14 |

EXAMPLE 105

Preparation of (2S)-1-(1H-Indol-4-yl)oxy-3-[(2S,4R)-4-(4-methoxybenzo[b]thiophen-2-yl)-2-methylpiperidinyl]-2-propanol oxalate

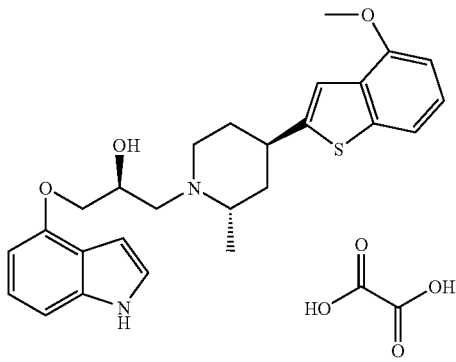

Scheme IV, Step B: A solution of (±)-trans-4-(4-methoxybenzo[b]thiophen-2-yl)-2-methylpiperidine (0.192 g, 0.734 mmol, prepared in example 99) and (S)-4-(oxiranylmethoxy)indole (0.139 g, 0.734 mmol) in MeOH (10 mL) was heated at reflux for 10 h and then cooled and evaporated. The residue was purified using silica gel chromatography [1% (2.0 M NH$_3$ in MeOH)/CH$_2$Cl$_2$] to give the free base of the title compound as a white foam (0.146 g, 44%). The oxalate salt was prepared with 1 equiv. of oxalic acid. mp (oxalate) 112–115° C. IR (CHCl$_3$) 3409, 3350 (br) cm$^{-1}$. Ion Spray MS 451 (M+H)$^+$; 449 (M–H)$^-$. [α]$_D$=0 (c 0.53, MeOH). C$_{26}$H$_{30}$N$_2$O$_3$S

| analysis: | calculated | found |
|---|---|---|
| C | 69.30 | 69.55 |
| H | 6.71 | 6.63 |
| N | 6.22 | 6.16 |

In addition, the corresponding hydrochloride salt and corresponding succinate salts were prepared from 1 equivalent of hydrochloric acid and 1 equivalent of succinic acid respectively.

EXAMPLE 106

Preparation of (2S)-(+)-1-(1H-Indol-4-yl)oxy-3-[(2R,4S)-4-(4-methoxybenzo[b]thiophen-2-yl)-2-methylpiperidinyl]-2-propanol oxalate

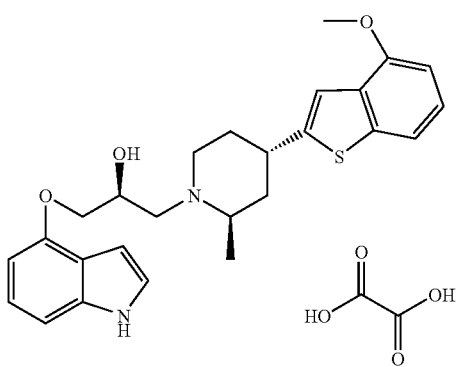

Scheme IV, Step B: A solution of (±)-trans-4-(4-methoxybenzo[b]thiophen-2-yl)-2-methylpiperidine (0.192 g, 0.734 mmol, prepared in example 99) and (S)4-(oxiranylmethoxy)indole (0.139 g, 0.734 mmol) in MeOH (10 mL) was heated at reflux for 10 h and then cooled and evaporated. The residue was purified using silica gel chromatography [1% (2.0 M NH$_3$ in MeOH)/CH$_2$Cl$_2$] to give the free base of the title compound as a white foam (0.149 g, 45%). The oxalate salt was prepared with 1 equiv. of oxalic acid in EtOAc. mp (oxalate) 120–123° C. IR (CHCl$_3$) 3410, 3350 (br) cm$^{-1}$. Ion Spray MS 453 (M+H)$^+$; 451 (M–H)$^-$. [α]$_D$=11.17 (c 0.54, MeOH). C$_{26}$H$_{30}$N$_2$O$_3$S.1.2C$_2$H$_2$O$_4$.0.1 C$_4$H$_8$O$_2$

| analysis: | calculated | found |
|---|---|---|
| C | 60.96 | 60.61 |
| H | 5.90 | 5.57 |
| N | 4.94 | 5.03 |

EXAMPLE 107

Preparation of cis-(2S)-(–)-1-(4-Indolyioxy)-3-(4-(4-fluorobenzothiazol-2-yl)-2-methylpiperidin-1-yl)-2-propanol Oxalate.

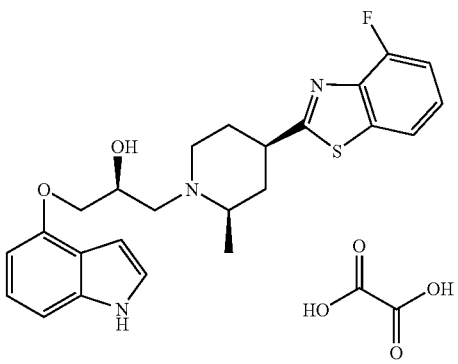

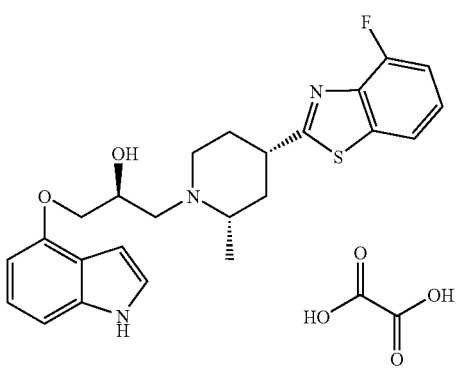

Preparation of 4-(4-Fluorobenzothiazol-2-yl)-1-(t-butyloxycarbonyl)-2-methyl-1,2,3,6-tetrahydropyridine

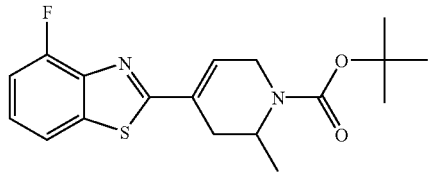

Scheme IA, Step A: To a mixture of 2-chloro-4-fluorobenzothiazole (1.012 g, 5.39 mmol) in 1,4-dioxane (60 mL) was added 2-methyl-4-trifluoromethylsulfonyl-1-(t-butyloxycarbonyl)-1,2,3,6-tetrahydropyridine (1.956 g, 5.66 mmol), hexamethylditin (1.767 g, 5.39 mmol), tetrakis(triphenylphosphine)-palladium (0.312 g, 0.269 mmol) and lithium chloride (0.686 g, 16.2 mmol). The mixture was heated at reflux for 20 hours, then cooled to 20° C. and diluted with saturated potassium fluoride and ethyl acetate. The mixture was stirred for 2 hours then partitioned and the organic layer was washed with brine, dried over sodium sulfate and evaporated. The residue was chromatographed over silica gel (hexanes/50% ethyl acetate in hexanes gradient elution) to give the intermediate title compound as a yellow amorphous solid (1.227 g, 72%). FDMS m/e=349 (M$^+$+1).

Preparation of 4-(4-Fluorobenzothiazol-2-yl)-2-methyl-1,2,3,6-tetrahydropyridine.

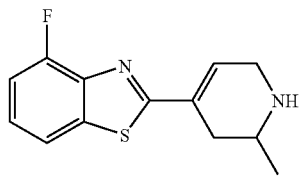

Scheme IIA, Step B: To a mixture of 4-(4-fluorobenzothiazol-2-yl))-1-(t-butyloxycarbonyl)-2-methyl-1,2,3,6-tetrahydropyridine (1.207 g, 3.81 mmol) in dichloromethane (10 mL) at 0° C. was added trifluoroacetic acid (10 mL). The mixture was stirred at 0° C. for 30 minutes, then at 20° C. for 30 minutes. The mixture was diluted with 2 N sodium hydroxide and extracted 3 times with ethyl acetate. The combined organic layers were dried over sodium sulfate, then filtered and evaporated. The residue was chromatographed over silica gel (dichloromethane/10% methanol 1% ammonium hydroxide in dichloromethane gradient elution) to give the intermediate title compound as a yellow oil (0.794 g, 84%). FDMS m/e=249 (M$^+$+1).

Preparation of Cis- and Trans-4-(4-Fluorobenzothiazol-2-yl)-2-methylpiperidine.

Cis

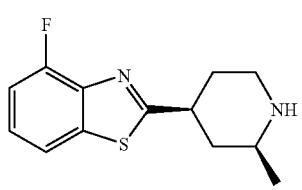

Trans

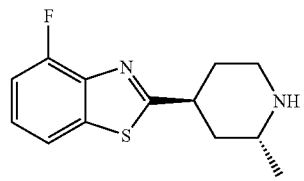

Scheme IIA, Step C: To a mixture of 4-(4-fluorobenzothiazol-2-yl))-2-methyl-1,2,3,6-tetrahydropyridine (0.691 g, 3.04 mmol) in ethanol (20 mL) was added platinum oxide (0.03 g). The mixture was hydrogenated at one atmosphere for 20 hours. The mixture was carefully filtered and evaporated to give the title compounds as a pair of yellow oils.

Cis: 0.267 g, 34%. FDMS m/e=251 (M$^+$+1).

Trans: 0.243 g, 31%. FDMS m/e=251 (M$^+$+1).

Preparation of Final Title Compound.

Scheme IV, Step B: A solution cis-4-(4-fluorobenzothiazol-2-yl))-2-methylpiperidine (0.130 g, 0.519 mmol, isomer 1) and (S)-(+)-4-(oxiranylmethoxy)-1H-indole (0.098 g, 0.519 mmol) in methanol (5 mL) was heated at reflux for 18 hours and then cooled and evaporated. The residue was purified by silica gel chromatography (dichloromethane/2% methanol 0.2% anhydrous ammonia in dichloromethane gradient elution) to give cis-(2S)-1-(4-indolyloxy)-3-(4-(4-fluorobenzothiazol-2-yl)-2-methylpiperidin-1-yl)-2-propanol as two white amorphous solids. The oxalate salts were prepared to give the title compounds.

Isomer 1 (0.114 g, 50%, free base). FDMS m/e=440 (M$^+$+1 of free base). $[\alpha]_D$=−9.13 (c 0.438, methanol). $C_{24}H_{26}FN_3O_2S \cdot 0.9C_2H_2O_4 \cdot 0.1H_2O$

| analysis: | calculated | found |
|---|---|---|
| C | 59.32 | 59.56 |
| H | 5.40 | 5.80 |
| N | 8.04 | 7.75 |

Isomer 2 (0.110 g, 48%, free base). FDMS m/e=440 (M$^+$+1 of free base). $[\alpha]_D$=−3.93 (c 0.509, methanol). $C_{24}H_{26}FN_3O_2S \cdot 0.9C_2H_2O_4 \cdot 0.1H_2O$

| analysis: | calculated | found |
|---|---|---|
| C | 59.32 | 59.71 |
| H | 5.40 | 5.31 |
| N | 8.04 | 8.10 |

EXAMPLE 108

Preparation of trans-(2S)-(−)-1-(4-Indolyloxy)-3-(4-(4-fluorobenzothiazol-2-yl)-2-methylpiperidin-1-yl)-2-pronpanol Oxalate.

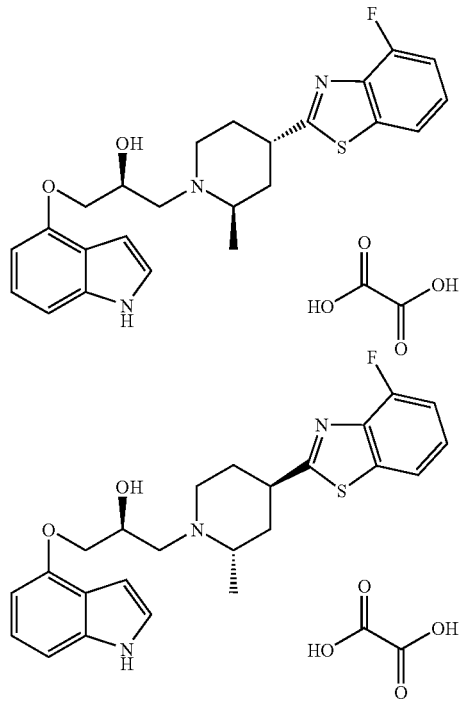

Scheme IV, Step B: A solution of trans-4-(4-fluorobenzothiazol-2-yl))-2-methylpiperidine (0.121 g, 0.483 mmol, isomer 1) and (S)-(+)-4-(oxiranylmethoxy)-1H-indole (0.091 g, 0.483 mmol) in methanol (5 mL) was heated at reflux for 18 hours and then cooled and evaporated. The residue was purified by silica gel chromatography (dichloromethane/2% methanol 0.2% anhydrous ammonia in dichloromethane gradient elution) to give the free base of the title compounds as two white amorphous solids. The oxalate salts were prepared to give the title compounds.

Isomer 1 (0.081 g, 38%, free base). FDMS m/e=440 (M$^+$+1 of free base). [α]$_D$=−7.98 (c 0.501, methanol). $C_{24}H_{26}FN_3O_2S \cdot 2.0 C_2H_2O_4 \cdot 0.7 H_2O$

| analysis: | calculated | found |
|---|---|---|
| C | 53.19 | 52.82 |
| H | 5.01 | 4.61 |
| N | 6.65 | 6.89 |

Isomer 2 (0.92 g, 44%, free base). FDMS m/e=440 (M$^+$+1 of free base). [α]$_D$=−7.86 (c 0.509, methanol). $C_{24}H_{26}FN_3O_2S \cdot C_2H_2O_4$.

| analysis: | calculated | found |
|---|---|---|
| C | 58.97 | 59.13 |
| H | 5.33 | 5.27 |
| N | 7.93 | 7.85 |

EXAMPLE 109

Preparation of cis-(2S)-1-(4-Indolyloxy)-3-(4-(4-methylbenzothiazol-2-yl)-2-methylpiperidin-1-yl)-2-propanol Oxalate.

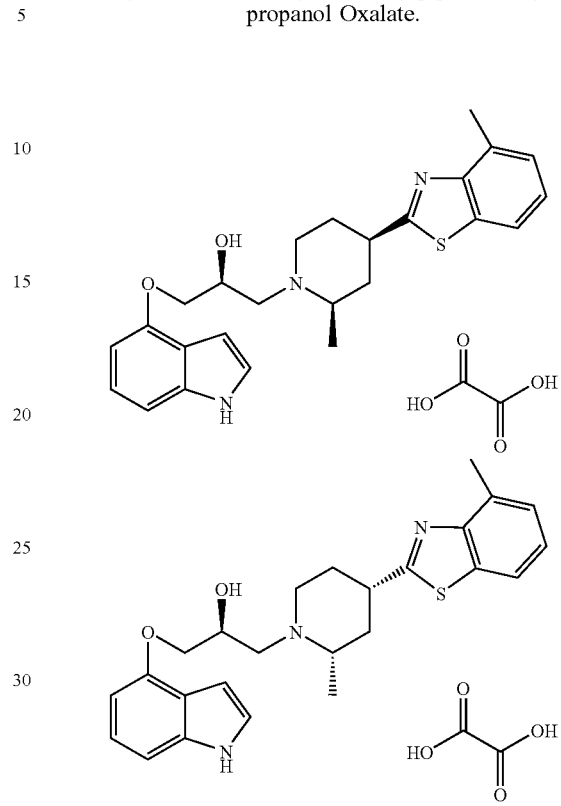

Preparation of 4-(4-Methylbenzothiazol-2-yl)-1-(t-butyloxycarbonyl)-2-methyl-1,2,3,6-tetrahydropyridine.

Scheme IIA, Step A: To a mixture of 2-chloro-4-methylbenzothiazole (1.052 g, 5.73 mmol) in 1,4-dioxane (60 mL) was added 2-methyl-4-trifluoromethylsuffonyl-1-(t-butyloxycarbonyl)-1,2,3,6-tetrahydropyridine (2.077 g, 6.01 mmol), bis(trimethyltin) (1.876 g, 5.73 mmol), tetrakis(triphenylphosphine)-palladium (0.331 g, 0.286 mmol) and lithium chloride (0.729 g, 17.2 mmol). The mixture was heated at reflux for 20 hours then cooled to 20° C. and diluted with saturated potassium fluoride and ethyl acetate. The mixture was stirred for 2 hours, then partitioned and the organic layer was washed with brine, dried over sodium sulfate and evaporated. The residue was chromatographed over silica gel (hexanes/50% ethyl acetate in hexanes gradient elution) to give the intermediate title compound as a yellow amorphous solid (1.3 g, 66%). FDMS m/e=345 (M$^+$+1).

Preparation of 4-(4-Methylbenzothiazol-2-yl)-2-methyl-1,2,3,6-tetrahydropyridine.

Scheme IIA, Step B: To a mixture of 4-(4-methylbenzothiazol-2-yl)-1-(t-butyloxycarbonyl)-2-methyl-1,2,3,6-tetrahydropyridine (1.297 g, 3.77 mmol) in dichloromethane (12 mL) at 0° C. was added trifluoroacetic acid (12 mL). The mixture was stirred at 0° C. for 30 minutes, then at 20° C. for 30 minutes. The mixture was diluted with 2 N sodium hydroxide and extracted 3 times with ethyl acetate. The combined organic layers were dried over sodium sulfate, then filtered and evaporated. The residue was chromatographed over silica gel (dichloromethane/10% methanol 1% ammonium hydroxide in dichloromethane gradient elution) to give the intermediate title compound as a yellow oil (0.738 g, 85%). FDMS m/e=245 (M$^+$+1).

Preparation of cis- and trans-4-(4-Methylbenzothiazol-2-yl)-2-methylpiperidine.

Scheme IIA, Step C: To a mixture of 4-(4-methylbenzothiazol-2-yl)-2-methyl-1,2,3,6-tetrahydropyridine (0.717 g, 2.93 mmol) in methanol (25 mL) was added platinum oxide (0.7 g). The mixture was hydrogenated at one atmosphere for 20 hours. The mixture was carefully filtered and evaporated to give the intermediate title compounds as a pair of yellow oils.

Cis: 0.194 g, 27%. FDMS m/e=246 (M$^+$). $C_{14}H_{18}N_2S$.

| analysis: | calculated | found |
|---|---|---|
| C | 68.25 | 68.45 |
| H | 7.36 | 7.60 |
| N | 11.37 | 11.48 |

Trans: 0.132 g, 18%. FDMS m/e=247 (M$^+$+1). $C_{14}H_{18}N_2S$.

| analysis: | calculated | found |
|---|---|---|
| C | 68.25 | 68.26 |
| H | 7.36 | 7.57 |
| N | 11.37 | 11.45 |

Preparation of Final Title Compounds.

Scheme IV, Step B: A solution cis-4-(4-methylbenzothiazol-2-yl)-2-methylpiperidine (0.098 g, 0.398 mmol) and (S)-(+)-4-(oxiranylmethoxy)-1H-indole (0.075 g, 0.398 mmol) in methanol (4 mL) was heated at reflux for 18 hours and then cooled and evaporated. The residue was purified by silica gel chromatography (dichloromethane/5% methanol 0.5% ammonium hydroxide in dichloromethane gradient elution) to give the free base of the final title compounds as two white amorphous solids. The oxalate salts were prepared to give the title compounds.

Isomer 1 (0.089 g, 50%, free base). FDMS m/e=436 (M$^+$+1 of free base). $[\alpha]_D$=−14.73 (c 0.543, methanol). $C_{25}H_{29}N_3O_2S \cdot C_2H_2O_4$.

| analysis: | calculated | found |
|---|---|---|
| C | 61.70 | 61.52 |
| H | 5.94 | 5.85 |
| N | 7.99 | 7.74 |

Isomer 2 (0.076 g, 44%). Data for free base. FDMS m/e=436 (M$^+$+1). $C_{25}H_{29}N_3O_2S$.

| analysis: | calculated | found |
|---|---|---|
| C | 68.94 | 69.14 |
| H | 6.71 | 6.91 |
| N | 9.65 | 9.60 |

EXAMPLE 110

Preparation of trans-(2S)-1-(4-Indolyloxy)-3-(4-(4-methyl)benzothiazol-2-yl)-2-methylpiperidin-1-yl)-2-propanol Oxalate

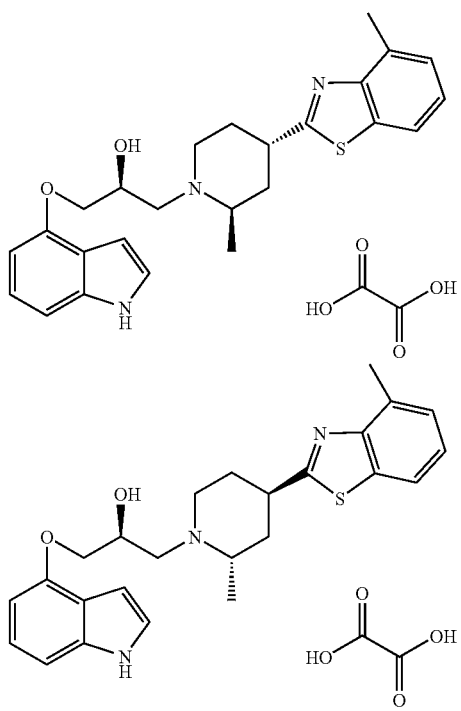

Scheme IV, Step B: A solution trans-4-(4-methylbenzothiazol-2-yl)-2-methylpiperidine (0.062 g, 0.252 mmol, prepared in example 109) and (S)-(+)-4-(oxiranylmethoxy)-1H-indole (0.048 g, 0.252 mmol) in methanol (3 mL) was heated at reflux for 18 hours and then cooled and evaporated. The residue was purified by silica gel chromatography (dichloromethane/5% methanol 0.5% ammonium hydroxide in dichloromethane gradient elution) to give the free base of title compounds as two white amorphous solids. The oxalate salts were prepared to give the title compounds.

Isomer 1 (0.050 g, 45%). Data for free base. FDMS m/e=436 (M$^+$+1). $C_{25}H_{29}N_3O_2S$

| analysis: | calculated | found |
|---|---|---|
| C | 68.94 | 69.15 |
| H | 6.71 | 6.52 |
| N | 9.65 | 9.46 |

Isomer 2 (0.52 g, 47%, free base). FDMS m/e=436 (M$^+$+1 of free base). $[\alpha]_D$=−5.6 (c 0.357, methanol). $C_{25}H_{29}N_3O_2S \cdot 0.9C_2H_2O_4 \cdot 0.2H_2O$.

| analysis: | calculated | found |
|---|---|---|
| C | 61.87 | 62.23 |
| H | 6.05 | 6.33 |
| N | 8.08 | 7.98 |

EXAMPLE 111

Preparation of cis-(2S)-(−)-1-(4-Indolyloxy)-3-((2-methyl-4-naphth-2-yl)piperidin-1-yl)-2-propanol maleate.

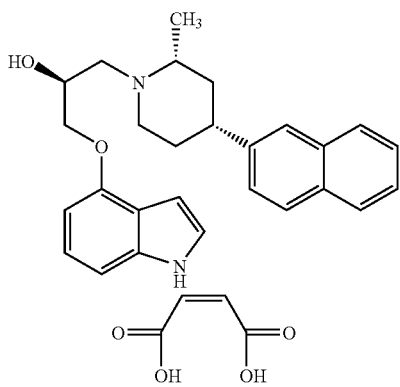

Preparation of 1,2-Dimethyl-4-hydroxy-4-(naphth-2-yl)piperidine.

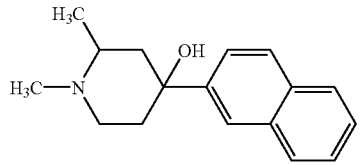

Scheme I, Step A: t-Butyllithium (11 mL of a 1.7 M solution in tetrahydrofuran, 18.8 mmol) was added to a solution of 2-bromonaphthalene (1.77 g, 8.5 mmol) in tetrahydrofuran (60 mL) at −78° C. The reaction mixture was stirred at that temperature for 1.5 hours and to it was then added dropwise a solution of 1,2-dimethyl-4-piperidone (1.14 g, 8.9 mmol, prepared by methods well known to one of ordinary skill in the art) in tetrahydrofuran (10 mL). The reaction mixture was allowed to warm to room temperature. The mixture was then partitioned between ethyl acetate and water. The phases were separated and the aqueous phase was extracted well with ethyl acetate. The combined organic phases were washed with brine, dried over sodium sulfate, and concentrated under reduced pressure to provide 1,2-dimethyl-4-hydroxy4-(naphth-2-yl)piperidine (2.13 g, 98%) as a clear viscous oil. The crude product was taken on, to the next step without further purification.

Preparation of 1,2-dimethyl-4-(naphth-2-yl)-1,2,3,6-tetrahydropyridine.

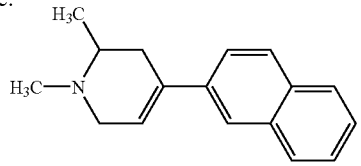

Scheme I, Step B: A mixture of 1,2-dimethyl-4-hydroxy-4-(naphth-2-yl)piperidine (2.13 g, 8.3 mmol) and p-toluenesulfonic acid monohydrate (3.17 g, 16.7 mmol) in toluene (45 mL) was stirred for 12 hours at reflux. The reaction mixture was cooled to room temperature and partitioned between ethyl acetate and 2 N sodium hydroxide. The combined organic phases were washed with brine, dried over sodium sulfate, and concentrated under reduced pressure. The crude residue was purified by flash chromatography (4% methanol in dichloromethane, silica gel). Fractions containing product were combined and concentrated under reduced pressure to provide 1,2-dimethyl-4-(naphth-2-yl)-1,2,3,6-tetrahydropyridine (0.983 g, 50% pure) as an off-white, waxy solid.

Preparation of 1,2-dimethyl-4-(naphth-2-yl)piperidine.

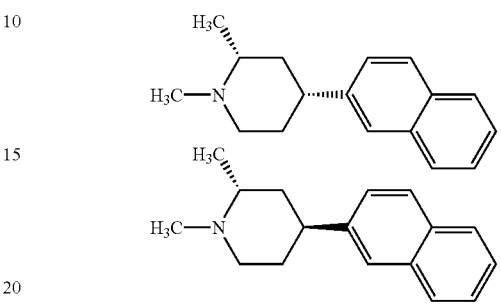

Scheme I, Step C: A mixture of 1,2-dimethyl-4-(naphth-2-yl)-1,2,3,6-tetrahydropyridine (0.983 g, 4.1 mmol) and 0.1 g of 5% palladium on carbon in methanol (20 mL) was stirred under a hydrogen atmosphere for 12 hours at room temperature. The mixture was then filtered through a bed of Celite and the filtrate concentrated under reduced pressure to provide 1,2-dimethyl-4-(naphth-2-yl)piperidine (0.890 g, 90% pure) as a clear oil.

Preparation of 2-methyl-4-(naphth-2-yl)piperidine.

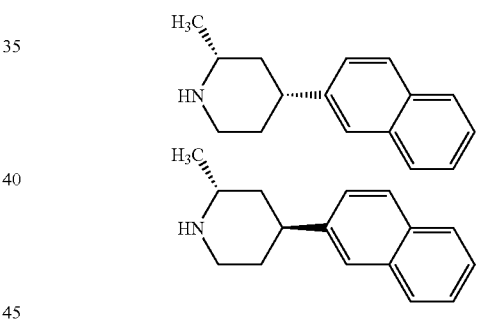

Scheme I, Step D: To a solution of 1,2-dimethyl-4-(naphth-2-yl)piperidine (0.89 g, 3.7 mmol) in 1,2-dichloroethane (15 mL) was slowly added 1-chloroethyl chloroformate (1.2 mL, 11.2 mmol) at 0° C. The reaction mixture was allowed to warm to room temperature and was subsequently heated at reflux for 12 hours. The solvent was evaporated under reduced pressure and the residue was dissolved in 15 mL methanol. After stirring at reflux for 4 hours the reaction mixture was concentrated under reduced pressure and partitioned between ethyl acetate and 2 N sodium hydroxide. The phases were separated and the aqueous phase was extracted well with ethyl acetate. The combined organic phases were washed with brine, dried over sodium sulfate, and concentrated under reduced pressure. The crude residue was purified by radial chromatography (8% methanol in dichloromethane, 2 mm silica gel plate) to provide 0.189 g (31%, based on the recovered starting material) of cis-Isomer 1 ($R_f$ 0.26) as a tan oil and 0.159 g (26%, based on recovered starting material) of trans-Isomer ($R_f$ 0.17) as a tan oil.

Alternative Preparation of 2-Methyl-4-(naphth-2-yl)piperidine.

Preparation of 2-methyl-4-(naphth-2-yl)-1-phenoxycarbonyl-1,2,3,6-tetrahydropyridine.

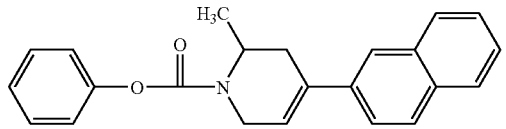

Scheme II, Step A: n-Butyllithium (47.4 mL of a 1.6 M in tetrahydrofuran, 75.9 mmol) was added to a solution of 2-bromonaphthalene (15.0 g, 63.3 mmol) in tetrahydrofuran (350 mL) at −78° C. The reaction mixture was stirred at that temperature for 1.5 hours and to it was then added dropwise a solution of triisopropylborate (19.0 mL, 82.2 mmol). The reaction mixture was allowed to warm to room temperature and stir for 12 hours. The mixture was then partitioned between ethyl acetate and saturated aqueous sodium chloride. The phases were separated and the aqueous phase was extracted well with ethyl acetate. The combined organic phases were washed with brine, dried over sodium sulfate, and concentrated under reduced pressure. The residue was sonicated in a mixture of hexanes:ethyl acetate. The resulting suspension was filtered to provide 2-naphthylboronic acid (8.28 g, 76%) as a white solid.

A mixture of the 2-naphthylboronic acid (3.71 g, 21.6 mmol), 2-methyl-1-phenoxycarbonyl-4-trifluoromethanesulfonyloxy-1,2,3,6-tetrahydropyridine (5.60 g, 15.6 mmol, this reagent may be prepared by methods well known to one of ordinary skill in the art), lithium chloride (1.96 g, 46.2 mmol), tetrakis(triphenylphosphine)palladium(0) (0.712 g, 0.62 mmol), and 4 mL of 2 M aqueous sodium carbonate in tetrahydrofuran (40 mL) was stirred at reflux for 12 hours. The reaction mixture was cooled to room temperature and then partitioned between ethyl acetate and 2 N sodium hydroxide. The phases were separated and the aqueous phase was extracted well with ethyl acetate. The combined organic phases were washed with brine, dried over sodium sulfate, and concentrated under reduced pressure. The residue was purified by flash silica gel chromatography, eluting with 10:1 hexanes:ethyl acetate. Fractions containing product were combined and concentrated under reduced pressure to provide 2-methyl-4-(naphth-2-yl)-1-phenoxycarbonyl-1,2,3,6-tetrahydropyridine (4.26 g, 81%) as a waxy, white solid.

Preparation of 2-methyl-4-(naphth-2-yl)-1-(phenoxycarbonyl)piperidine.

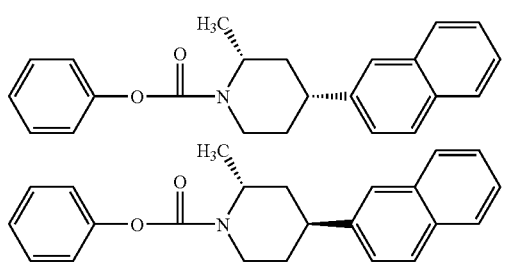

Scheme II, Step B: A mixture of 2-methyl-4-(naphth-2-yl)-1-phenoxycarbonyl-1,2,3,6-tetrahydropyridine (3.87 g, 11.3 mmol) and 5% palladium on carbon (0.2 g) in 50 mL of methanol was stirred under a hydrogen atmosphere for 12 hours at room temperature. The mixture was then filtered through a bed of Celite and the filtrate was concentrated under reduced pressure to provide 2-methyl-4-(naphth-2-yl)-1-(phenoxycarbonyl)piperidine. (3.42 g, 88%) as a clear oil.

Preparation of 2-methyl-4-(naphth-2-yl)piperidine.

Scheme II, Step C: A mixture of 2-methyl-4-(naphth-2-yl)-1-phenoxycarbonylpiperidine (3.42 g, 9.9 mmol) and potassium hydroxide (59 g, 1.05 mol) in 150 mL of 50% water in isopropyl alcohol was stirred at reflux for about 72 hours. The reaction mixture was cooled to room temperature and partitioned between ethyl acetate and 2 N sodium hydroxide. The phases were separated and the aqueous phase was extracted well with ethyl acetate. The combined organic phases were washed with brine, dried over sodium sulfate, and concentrated under reduced pressure. The crude residue was purified by flash chromatography (8% methanol in dichloromethane, silica gel) to provide 0.872 g (39%) of cis-Isomer(Rf 0.26) as a tan oil and 0.368 g (16%) of trans-Isomer (Rf 0.17) as a tan oil.

Preparation of Final Title Compound.

Scheme IV, Step B: A solution of (S)-(+)-4-(oxiranylmethoxy)-1H-indole (0.149 g, 0.79 mmol) and 2-methyl-4-(naphth-2-yl)piperidine (0.177 g, 0.79 mmol, cis-isomer) in methanol was stirred at reflux for 12 h. The mixture was cooled to room temperature and the solvent was evaporated. The crude residue was purified by radial chromatography (2% methanol in dichloromethane, 2 mm silica gel plate) providing 0.130 g (40%) of a free base of the title compound (Rf 0.65) as a white foam. The maleate salt was prepared to provide the title compound.

$[\alpha]_D = -15.02$ (c 0.53, methanol).

FDMS m/e=414 (M$^+$ of free base). $C_{27}H_{30}N_2O_2 \cdot C_4H_4O_4$

| analysis: | calculated | found |
|---|---|---|
| C | 70.31 | 70.05 |
| H | 6.28 | 6.47 |
| N | 5.29 | 5.26 |

EXAMPLE 112

Preparation of cis-(2S)-(−)-1-(4-Indolyloxy)-3-((2-methyl-4-naphth-2-yl)piperidin-1-yl)-2-propanol maleate

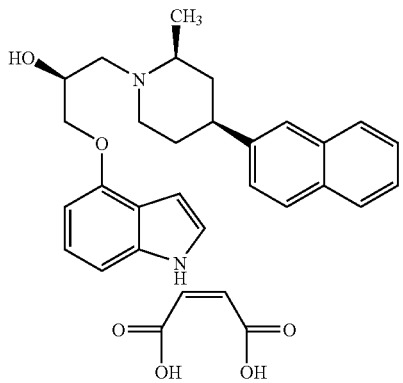

Scheme IV, Step B: A solution of (S)-(+)-4-(oxiranylmethoxy)-1H-indole (0.149 g, 0.79 mmol) and 2-methyl-4-(naphth-2-yl) piperidine (0.177 g, 0.79 mmol, cis-Isomer, prepared in example 111 ) in methanol was stirred at reflux for 12 h. The mixture was cooled to room temperature and the solvent was evaporated. The crude residue was purified by radial chromatography (2% methanol in dichloromethane, 2 mm silica gel plate) to provide 0.134 g (41%) of a free base of the title compound ($R_f$ 0.61) as a white foam. The maleate salt was prepared to provide the title compound.

$[\alpha]_D = -3.99$ (c 0.40, methanol).

FDMS m/e=414 (M⁺ of free base). $C_{27}H_{30}N_2O_2 \cdot C_4H_4O_4$

| analysis: | calculated | found |
|---|---|---|
| C | 70.31 | 70.10 |
| H | 6.28 | 6.34 |
| N | 5.29 | 5.19 |

EXAMPLE 113

Preparation of trans-(2S)-(−)-1-(4-Indolyioxy)-3-((2-methyl-4-naphth-2-yl)piperidin-1-yl)-2-propanol maleate.

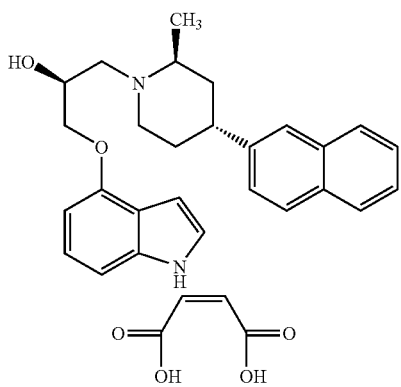

Scheme IV, Step B: A solution of (S)-(+)4-(oxiranylmethoxyy-1H-indole (0.118 g, 0.62 mmol) and 2-methyl-4-(naphth-2-yl) piperidine (0.141 g, 0.61 mmol, trans-Isomer, prepared in example 111) in methanol was stirred at reflux for 12 h. The mixture was cooled to room temperature and the solvent was evaporated. The crude residue was purified by radial chromatography (2% methanol in dichloromethane, 2 mm silica gel plate) to provide 0.102 g (39%) of a free base of the title compound ($R_f$ 0.67) as a white foam. The maleate salt was prepared to provide the title compound.

$[\alpha]_D = -9.75$ (c 0.41, methanol).

FDMS m/e=414 (M⁺ of free base).
$C_{27}H_{30}N_2O_2 \cdot C_4H_4O_4 \cdot 3/2H_2O$

| analysis: | calculated | found |
|---|---|---|
| C | 67.13 | 66.85 |
| H | 6.17 | 6.20 |
| N | 5.05 | 5.03 |

EXAMPLE 114

Preparation of trans-(2S)-(−)-1-(4-Indolyloxy)-3-((2-methyl-4-naphth-2-yl)piperidin-1-yl)-2-propanol maleate.

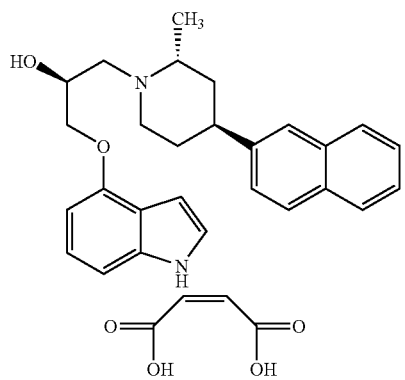

Scheme IV, Step B: A solution of (S)-(+)-4-(oxiranylmethoxy)-1H-indole (0.118 g, 0.62 mmol) and 2-methyl-4-(naphth-2-yl) piperidine (0.141 g, 0.61 mmol, trans-isomer, prepared in example 111) in methanol was stirred at reflux for 12 h. The mixture was cooled to room temperature and the solvent was evaporated. The crude residue was purified by radial chromatography (2% methanol in dichloromethane, 2 mm silica gel plate) to provide 0.101 g (39%) of the free base of the title compound ($R_f$ 0.62) as a white foam. The maleate salt is was prepared to provide the title compound.

$[\alpha]_D = -8.59$ (c 0.46, methanol).

FDMS m/e=414 (M⁺ of free base).
$C_{27}H_{30}N_2O_2 \cdot C_4H_4O_4 \cdot 3/4H_2O$

| analysis: | calculated | found |
|---|---|---|
| C | 68.43 | 68.46 |
| H | 6.58 | 6.49 |
| N | 5.15 | 5.18 |

EXAMPLE 115

Preparation of 3-(2,2-Dimethyl-4-naphth-2-yl)piperidin-1-yl-4-indolyloxy-2-propanol

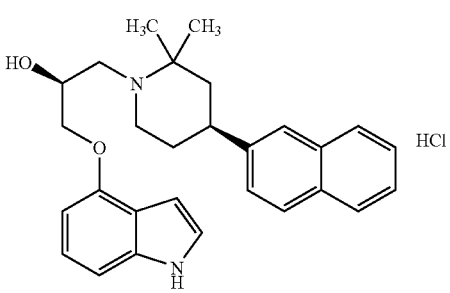

Preparation of 2,2-dimethyl-4-hydroxy-4-(naphth-2-yl)-1-(t-butoxycarbonyl)-piperidine.

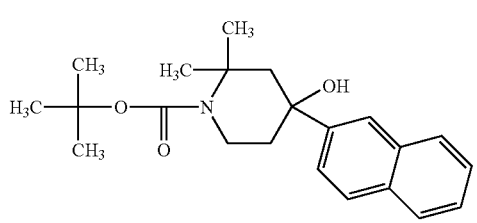

Scheme I, Step A: 2-bromonaphthalene (1.035 g, 5 mmol) was dissolved in tetrahydrofuran (20 mL) and cooled to below −65° C. The cooled solution was then treated slowly with s-butyllithium (5.9 mL of a 0.84 M solution in THF, 5 mmol) and the reaction mixture was stirred for 1.5 hours. Then N—BOC-2,2-dimethyl-4-piperidone (0.745 g, 3.28 mmol, prepared following the general procedure described in *J. Org. Chem.*, 56, 2154–2161 (1991)) was dissolved in THF and added slowly to the reaction mixture, while maintaining the temperature below −65° C. After addition was complete, the dry ice/acetone cooling bath was left in place and the reaction was allowed to slowly warm to room temperature overnight with stirring. The reaction mixture was then diluted with ethyl acetate and washed with 1 N sodium hydroxide, then 1 N HCl, followed by saturated sodium chloride, dried over anhydrous sodium sulfate, filtered and concentrated under vacuum to provide a crude material (1.48 g). The crude material was purified by column chromatography (chloroform to 0.5% methanol/chloroform gradient, silica gel) to provide the title compound (0.85 g, 73%).

Preparation of 2,2-dimethyl-4-(naphth-2-yl)-1,2,5,6-tetrahydropyridine and 2,2-dimethyl-4-(naphth-2-yl)-1,2,3,6-tetrahydropyridine.

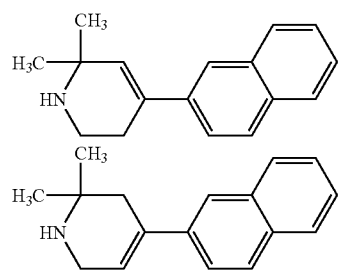

Scheme I, Step B: 2,2-Dimethyl-4-hydroxy-4-(naphth-2-yl)-1-(t-butoxycarbonyl)piperidine (200 mg, prepared above) was dissolved in methylene chloride (9 mL) and treated with trifluoroacetic acid (1 mL). The mixture was stirred for 1.5 hours at room temperature and then poured into saturated aqueous sodium bicarbonate solution. The mixture was then extracted with chloroform (3 times). The organic extracts were combined, washed with saturated sodium chloride, dried over anhydrous sodium sulfate, filtered and concentrated under vacuum to provide the crude mixture of the title compounds (131 mg, 99%) which were carried onto the next step without separation.

Preparation of 2,2-dimethyl-4-(naphth-2-yl)piperidine.

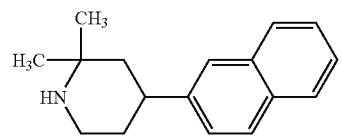

Scheme I, Step C: 2,2-Dimethyl-4-(naphth-2-yl)-1-(t-butoxycarbonyl)-1,2,5,6-tetrahydropyridine and 2,2-dimethyl-4-(naphth-2-yl)-1-(t-butoxycarbonyl)-1,2,3,6-tetrahydropyridine (127 mg, 0.54 mmol) were dissolved in methanol/THF (1/1) and 5% Palladium on carbon (156 mg) was added to the solution. The reaction mixture was placed on a Parr hydrogenation apparatus at 35 psi of hydrogen. After 2 hours of hydrogenation, an additional amount of 5% palladium on carbon (188 mg) was added and hydrogenation continued for an additional 4 hours. The reaction mixture was then filtered through Celite and the filtrate was concentrated under vacuum to provide the title compound. The crude material was then carried on to the next step without further purification.

Preparation of Final Title Compound.

Scheme IV, Step B: 2,2-dimethyl-4-(naphth-2-yl)piperidine (129 mg, 0.54 mmol) and (S)-(+)-4-(oxiranylmethoxy)-1H-indole (102 mg, 0.54 mmol) were dissolved in methanol (20 mL) and heated at reflux overnight. The reaction mixture was then evaporated to dryness and the crude residue was purified by column chromatography (methylene chloride to 1% methanol/methylene chloride gradient, silica gel) to provide the free base of the final title compound (92 mg). This material was converted to the HCl salt by precipitation with one equivalent of saturated HCl in diethyl ether, and then further purified by reverse phase preparative high performance liquid chromatography (silica gel, 10% ethyl is acetate/hexanes) to provide the final title compound (30 mg).

EXAMPLE 116

Preparation of 1-(t-Butyloxycarbonyl)-2-methyl-4-(3-methylbenzo[b]thiophen-5-yl)-piperidin-4-ol.

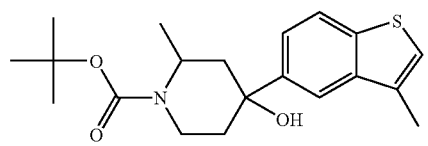

Scheme IA, step A: To a solution of 5-bromo-3-methylbenzo[b]thiophene (3.621 g, 15.9 mmol, from preparation 8) in diethyl ether (100 mL) was added magnesium (0.775 g, 31.9 mmol) and 1,2-dibromoethane (1.37 mL, 15.9 mmol). The mixture was heated at reflux for 4 hours then cooled to 20° C. for 18 hours. A solution of 1-(t-butyloxycarbonyl)-2-methyl-4-piperidone (3.74 g, 17.5 mmol) in tetrahydrofuran (15 mL) was added dropwise to the mixture. The mixture was stirred for 24 hours, then diluted with saturated ammonium chloride and extracted with ethyl acetate three times. The residue was purified by silica gel chromatography (dichloromethane/5% methanol in dichloromethane gradient eluent) to give 4.36 g (76%) of the intermediate title compound as a yellow amorphous solid. FDMS m/e=362 (M$^+$+1).

Preparation of 2-Methyl-4-(3-methylbenzo[b]thiophen-5-yl)-1,2,3,6-tetrahydropyridine.

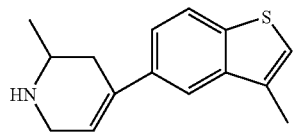

Scheme IA, step B: 1-(t-Butyloxycarbonyl)-2-methyl-4-(3-methylbenzo[b]thiophen-5-yl)-piperidin-4-ol (26.08 g, 72.1 mmol) was suspended in toluene (700 mL) and p-toluenesulphonic acid hydrate (41.17 g, 0.216 mol) was added. The mixture was heated at reflux for 3 hours, then cooled to room temperature. The mixture was evaporated and the residue was diluted with 2 N sodium hydroxide then extracted 3 times with ethyl acetate. The combined organic layers were dried over sodium sulfate, filtered and evaporated to give the title compound as a yellow oil (14.3 g, 81%). FDMS m/e=244 (M$^+$+1).

Preparation of 2-Methyl-4-(3-methylbenzo[b]thiophen-5-yl)piperidine.

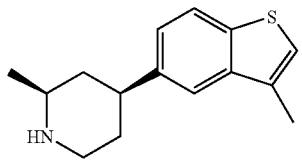

Cis

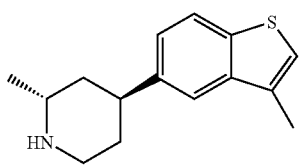

Trans

Scheme IA, step C: To a solution 2-Methyl-4-(3-methylbenzo[b]thiophen-5-yl)-1,2,3,6-tetrahydropyridine (4.422 g, 18.2 mmol) in methanol (30 mL) was added 3% palladium on polyethylenimine/SiO$_2$ (4.9 g). The mixture was hydrogenated on a PARR shaker at 50° C. and 45 psi for 24 hours. At this time another 6 g of 3% palladium on polyethylenimine/SiO$_2$ was added and the mixture was hydrogenated for 48 hours at 50° C. and 45 psi. The mixture was cooled and then filtered and the catalyst was washed with boiling methanol. The combined organic layers were evaporated and the residue was purified by silica gel chromatography (dichloromethane/5% methanol, 0.35 M ammonia in dichloromethane gradient elution) to give the title compounds as two yellow oils.

Isomer 1 (cis isomer, 1.9 g, 43%). FDMS m/e=246 (M$^+$+1). C$_{15}$H$_{19}$NS.0.3H$_2$O.

| analysis: | calculated | found |
|---|---|---|
| C | 71.84 | 72.08 |
| H | 7.88 | 7.90 |
| N | 5.59 | 5.71 |

Isomer 2 (trans isomer, 1.5 g, 34%). FDMS m/e=246 (M$^+$+1). C$_{15}$H$_{19}$NS.0.2H$_2$O

| analysis: | calculated | found |
|---|---|---|
| C | 72.36 | 72.35 |
| H | 7.85 | 7.92 |
| N | 5.63 | 5.83 |

Preparation of cis-(2S)-(−)-3-(2-Methyl-4-(3-methylbenzo[b]thiophen-5-yl)piperidin-1-yl)-1-(2-methylindol-4-yl)oxy-2-propanol Succinate.

Isomer 1
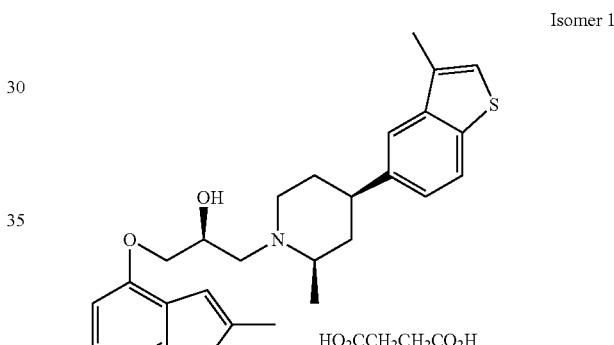

Isomer 2
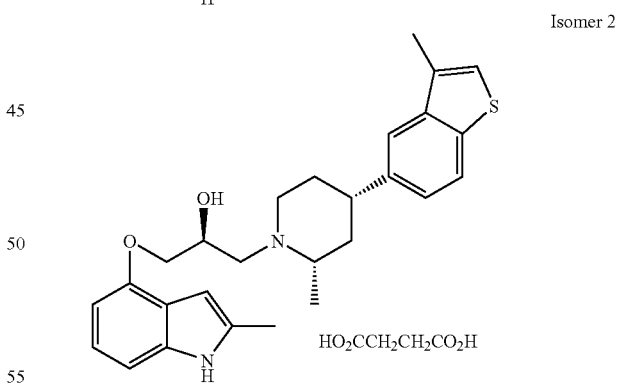

Scheme IV, step B: A solution of cis-2-methyl-4-(3-methylbenzo[b]thiophen-5-yl)piperidine (1.869 g, 7.62 mmol, isomer 1) and (2S)-4-glycidyloxy-2-methylindole (1.548 g, 7.62 mmol) in methanol (30 mL) was heated at reflux for 18 hours and then cooled and evaporated. The residue was purified by silica gel chromatography (dichloromethane/5% methanol, 0.35 M ammonia in dichloromethane gradient elution) to give the free bases of the title compounds as two yellow amorphous solids. The succinate salts were prepared to give the title compounds.

Isomer 1 (0.825 g, 24%, free base). FDMS m/e=449 (M$^+$+1 of free base). [α]$_D$=−14.06 (c 0.569, methanol). C$_{27}$H$_{32}$N$_2$O$_2$S.C$_4$H$_6$O$_4$.

| analysis: | calculated | found |
|---|---|---|
| C | 65.70 | 65.48 |
| H | 6.76 | 6.76 |
| N | 4.94 | 4.94 |

Isomer 2 (0.632 g, 18%, free base). FDMS m/e=449 (M$^+$+1 of free base). [α]$_D$=−7.27 (c 0.55, methanol). C$_{27}$H$_{32}$N$_2$O$_2$S.C$_4$H$_6$O$_4$.

| analysis: | calculated | found |
|---|---|---|
| C | 65.70 | 65.30 |
| H | 6.76 | 6.77 |
| N | 4.94 | 4.88 |

Preparation of trans-(2S)-(−)-3-(2-Methyl-4-(3-methylbenzo[b]thiophen-5-yl)piperidin-1-yl)-1-(2-methylindol-4-yl)oxy-2-propanol Succinate (Isomers 3 and 4)

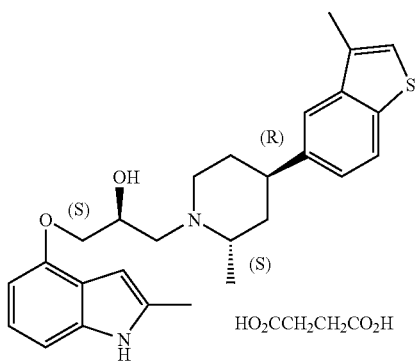

Isomer 3

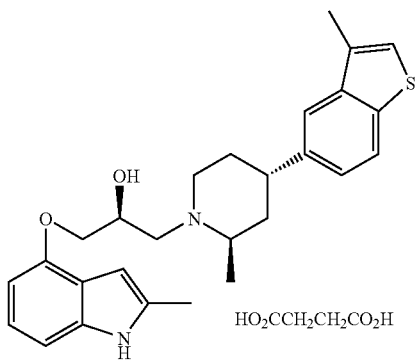

Isomer 4

Scheme IV, step B: A solution of trans-2-methyl-4-(3-methylbenzo[b]-thiophen-5-yl)piperidine (3.406 g, 13.9 mmol, isomer 2) and (2S)-4-glycidyloxy-2-methylindole (2.821 g, 13.9 mmol) in methanol (80 mL) was heated at reflux for 18 hours and then cooled and evaporated. The residue was purified by silica gel chromatography (dichloromethane/5% methanol, 0.35 M ammonia in dichloromethane gradient elution) to give the free bases of the title compounds as two yellow amorphous solids. The succinate salts were prepared to give the title compounds.

Isomer 3 (1.918 g, 31%, free base). FDMS m/e=449 (M$^+$+1 of free base). [α]$_D$=−4.02 (c 0.498, methanol). C$_{27}$H$_{32}$N$_2$O$_2$S.C$_4$H$_6$O$_4$.

| analysis: | calculated | found |
|---|---|---|
| C | 65.70 | 65.66 |
| H | 6.76 | 6.74 |
| N | 4.94 | 5.00 |

Isomer 4 (1.248 g, 20%, free base). FDMS m/e=449 (M$^+$+1 of free base). [α]$_D$=−12.2 (c 0.492, methanol). C$_{27}$H$_{32}$N$_2$O$_2$S.C$_4$H$_6$O$_4$.

| analysis: | calculated | found |
|---|---|---|
| C | 65.70 | 66.01 |
| H | 6.76 | 6.81 |
| N | 4.94 | 4.97 |

Alternative synthesis of trans-(2S)-(−)-3-(2-Methyl-4-(3-methylbenzo[b]thiophen-5-yl)piperidin-1-yl)-1-(2-methylindol-4-yl)oxy-2-propanol, Isomer 3.

Preparation of 5-Bromo-3-methyl-1-trimethylsilylbenzo[b]thiophene.

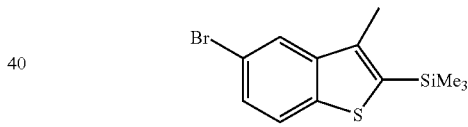

A solution of 5-bromo-3-methylbenzo[b]thiophene (149.1 g, 0.66 mole, prepared in preparation 8) in THF (1.4 L) under nitrogen was cooled to −78° C. and trimethylsilyl chloride (163 mL, 1.3 mole, 2 eq) was added dropwise. Lithium diisopropylamide (625 mL, 1.2 mole, 2 eq, 2.0 M solution in THF, heptane, ethylbenzene) was added and the mixture was stirred for 4 h. The solution was poured into a mixture of methyl tert-butylether and H$_2$O (3 L each). The layers were separated and the organic layer was extracted with 1 N HCl (2 L), then H$_2$O (2 L) and dried (Na$_2$SO$_4$). The solvent was removed by rotary evaporation to afford 237.3 g of crude product. The crude material was slurried in EtOH (400 mL) to afford 5-bromo-3-methyl-1-trimethylsilylbenzo[b]thiophene as a white granular solid (152.7 g, 78%, 3 crops). mp 64–67° C. IR (KBr) 1252, 1245, 841 cm$^{-1}$; $^1$H NMR (300 MHz, CDCl$_3$) δ 7.851 (d, 1, J=1.8 Hz), 7.69 (d, 1, J=8.5 Hz), 7.41 (dd, 1, J=8.5, 1.8 Hz), 2.48 (s, 3,), 0.42 (d, 9, J=3.4 Hz). $^{13}$C NMR (75 MHz, CDCl$_3$) δ 143.6, 141.3, 137.9, 132.2, 126.9, 124.4, 123.4, 117.8, 14.4, 0.14. MS (FD) m/z 298 (M+). Anal. Calcd for C$_{10}$H$_{15}$BrSSi: C, 48.16; H, 5.05. Found: C, 48.19; H,4.98.

Preparation of 1-(t-Butyloxycarbonyl)-4-(3-methylbenzo[b]thiophen-5-yl)-piperidin-4-ol.

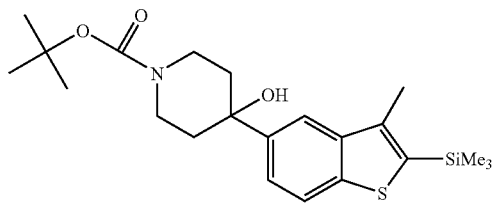

To a solution of 5-bromo-3-methyl-1-trimethylsilylbenzo[b]thiophene (211.7 g, 707 mmol) in THF (1 L) cooled to −78° C. under nitrogen was added n-BuLi (311 mL, 2.5 M solution in hexanes, 778 mmol) dropwise. After 30 min, N-Boc-piperidone (155.1 g, 778 mmol) in THF (816 mL) was added. After 2 hr, the mixture was poured into $H_2O$ and methyl tert-butylether (2 L each). The layers were separated and the organic layer was washed with 1 N HCl (2.1 L), then $H_2O$ (2.1 L) and dried ($Na_2SO_4$). The solvent was removed with a rotary evaporator to afford 348 g of crude 1-(t-butyloxycarbonyl)-4-(3-methyl-1-trimethylsilylbenzo[b]thiophen-5-yl)-piperidin-4-ol. Hexane (700 mL) was added to the crude product. After stirring overnight, the precipitate was filtered, washed with hexane, and dried in a vacuum oven for 2 hr to give 246.3 g (83%) of 1-(t-butyloxycarbonyl)-4-(3-methyl-1-trimethylsilylbenzo[b]thiophen-5-yl)-piperidin-4-ol as a white powder. mp 141–145° C. IR ($CHCl_3$) 3595,1680 $cm^{-1}$.
$^1$H NMR (300 MHz, $CDCl_3$) δ 7.83 (d, 1, J=8.0 Hz), 7.81 (s, 1), 7.43 (dd, 1, J=8.2, 1.8 Hz), 4.06 (br s, 2), 3.28 (t, 2, J=12.2 Hz), 2.51 (s, 3), 2.09 (br s, 2), 1.79 (d, 2, J=12.2 Hz), 1.70 (s, 1), 1.49 (s, 9), 0.40 (s, 9). $^{13}$C NMR (75 MHz, DMSO) δ 154.2, 145.9, 141.5, 140.3, 139.1, 134.1, 122.2, 121.8, 117.7, 78.6, 70.2, 38.0, 28.3, 14.4, 0.00. MS (FD) m/z 418 (M−1). Anal. Calcd for $C_{22}H_{33}NO_3SSi$: C, 62.97; H, 7.93; N, 3.34. Found: C, 63.28; H, 8.04; N, 3.44.

Preparation of 4-(3-Methylbenzo[b]thiophen-5-yl)-piperidine hydrochloride.

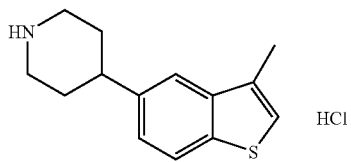

To a solution of 1-(t-butyloxycarbonyl)-4-(3-methyl-1-trimethylsilylbenzo[b]thiophen-5-yl)-piperidin-4-ol (458 g, 1.09 mol) in $CH_2Cl_2$ (4.6 L) was added 871 mL (5.46 mol, 5.0 equiv) of triethylsilane. The mixture was cooled to −30° C. and 420 mL of trifluoracetic acid (5.45 mol. 5.0 equiv) was added dropwise to the solution over 35 minutes. The mixture was stirred for 2.5 hours while gradually warming to 13° C. An additional 420 mL of trifluoroacetic acid was added over 15 minutes. After warming to room temperature over 3.5 hours, ice (6 L), water (5 L), and concentrated aqueous NaOH (628 mL, 12.0 mol, 11.0 eq) were added. The layers were separated and the aqueous layer was extracted with two 1.5 L portions of $CH_2Cl_2$. The organic layers were combined, dried ($Na_2SO_4$), and concentrated under vacuum to give a clear, colorless oil, which was redissolved in 4 L of ether. The hydrochloride salt was formed by dropwise addition of a solution of HCl in EtOAc (245 mL) until the slurry pH measured 2–3. The resulting slurry was stirred for 2 hours, filtered, rinsed with ether, and dried overnight in a vacuum oven at 45° C. to give 271 g of white crystalline 4-(3-methylbenzo[b]thiophen-5-yl)-piperidine hydrochloride (92.8% yield).
$^1$H NMR (500 MHz, DMSO) δ 2.10–2.20 (m, 2), 2.30 (q, 2), 2.42 (s, 3), 2.93 (m, 1), 3.0–3.10 (m, 2), 7.09 (s, 1), 7.25 (d, 1), 7.57 (s, 1), 7.80 (d, 1); $^{13}$C NMR (75 MHz, DMSO) δ 13.5, 29.6, 38.9, 43.4, 119.3, 122.7, 122.9, 123.2, 131.5, 137.7, 139.6, 140.9. Anal. Calcd for $C_{14}H_{18}ClNS$: C, 62.79; H, 6.77; N, 5.23. Found: C, 62.66; H, 6.65; N, 5.24.

Preparation of N-Chloro-4-(3-methylbenzo[b]thiophen-5-yl)-piperidine.

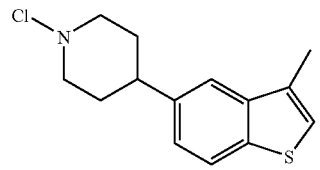

To 10 g (37 mmol) of 4-(3-methylbenzo[b]thiophen-5-yl)-piperidine hydrochloride was added 160 mL of ether, 34 mL of $H_2O$ and 41 mL (41 mmol, 1.1 equiv) of 1 M NaOH. The mixture was stirred until the solid dissolved and the layers were separated using a separatory funnel. The aqueous layer was extracted with 100 mL of ether and the combined organic layers were dried ($Na_2SO_4$) and evaporated to afford 8.73 g of 4-(3-methylbenzo[b]thiophen-5-yl)-piperidine. 4-(3-methylbenzo[b]thiophen-5-yl)-piperidine was dissolved in 83 mL of ether and 83 mL of THF, and 4.99 g (37 mmol, 1 equiv) of N-chlorosuccinimide was added. After stirring overnight, 100 mL of saturated aqueous $NaHCO_3$ was added and the mixture was transferred to a separatory funnel containing 100 mL of $H_2O$ and 60 mL of ether. The layers were separated and the aqueous layer was washed with 10 mL of ether. The combined organic layers were dried ($Na_2SO_4$) and evaporated to afford 10.1 g (100% yield) of N-chloro4-(3-methylbenzo[b]thiophen-5-yl)-piperidine; mp57–61.5° C. IR ($CHCl_3$) 3009, 1602, 1471, 1448$cm^{-1}$.
$^1$H NMR (300 MHZ, $CDCl_3$) δ 7.78 (d, 1, J=8.2 Hz), 7.53 (d, 1, J=1.5 Hz), 7.21 (dd, 1, J=8, 2 Hz), 7.07 (d, 1, J=0.9 Hz), 3.6 (d, 2, J=11 Hz) 3.05 (t, J=12), Hz), 2.85–2.70 (m, 1), 2.43 (d, 3, J=1.2 Hz), 2.20–2.00 (m, 2, $CH_2$), 1.9 (br d, 2). $^{13}$C NMR (75 MHz, $CDCl_3$) δ 141.0, 139.6, 137.5, 131.5, 123.4, 122.9, 122.7, 119.3, 43.6, 40.1, 29.7, 13.5. MS (FD) m/z 266 (M+). Anal. Calcd for $C_{14}H_{16}ClNS$: C, 63.26; H, 6.07; N, 5.27. Found: C, 63.34; H, 6.06; N, 5.30.

Preparation of trans-2-Methyl-4-(3-methylbenzo[b]-thiophen-5-yl)piperidine.

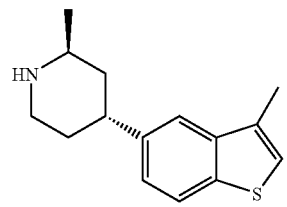

To 13.9 g (51.9 mmol) of N-chloro-4-(3-methylbenzo[b]thiophen-5-yl)-piperidine was added 207 mL of THF, 1.0 g (3.8 mmol, 0.073 equiv) of 18-crown-6 and a slurry of 10.16 g (assume 85% KOH and 15% H₂O, 156 mmol, 3 equiv) of potassium hydroxide in 4 mL of H₂O. After stirring for 16 h, the resulting solution of imine was dried over Na₂SO₄, filtered and the cake rinsed with 20 mL of THF. A solution of methyllithium in ether (185 mL, 1.5 M, 260 mmol, 5 equiv) was cooled to −10° C. and the precooled (5° C.) imine solution was added over 1 min. After 20 min, the cooling bath was removed and the mixture was allowed to stir at ambient temperature. After 2 h, 200 mL of H₂O was added, the layers were separated and the aqueous layer was extracted with ether (200 mL). The combined organic layers were washed with water (300 mL) and dried (Na₂SO₄). The solvent was evaporated to afford 13.6 g of a viscous oil. The crude product was dissolved in 80 mL of methanol and 25 mL of THF and 0.55 g (12 mmol) of NaBH₄ was added. After 2 h, pivalic anyhydride (2.8 g, 12 mmol), was added. After 2 h, the methanol was removed by evaporation and the mixture was partitioned between 200 mL of 1 N HCl and 100 mL of ether. The layers were separated and the aqueous layer was washed with ether. The aqueous layer was made basic with 5 N NaOH and extracted with ether (2×150 mL). The organic layers were dried and evaporated to afford 8.9 g (63% yield) of trans-2-methyl-4-(3-methylbenzo[b]-thiophen-5-yl)piperidine as a viscous oil.

Preparation of trans-(2S,4R)-2-Methyl-4-(3-methylbenzo[b]-thiophen-5-yl)piperidine D-(−)-tartrate.

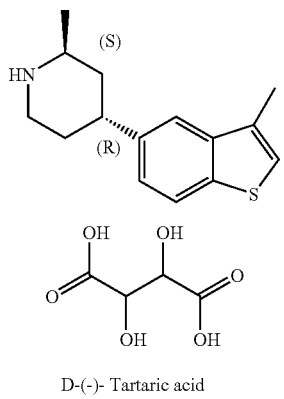

D-(-)- Tartaric acid

To a solution of racemic trans-2-methyl-4-(3-methyl-benzo[b]-thiophen-5-yl)piperidine (32.7 g, 0.13 mol), which had been purifed by filtration through silica gel (2 g silica gel per g) in 92% recovery, in 3A EtOH (650 mL) at 72° C. was added a solution of D(−)-tartaric acid (20.0 g, 0.13 mol, 1.0 equiv) in 3A EtOH (450 mL) over 1 hour. The resulting slurry was stirred at 72° C. for 2 hours and then allowed to cool to room temperature over 16 hours. The solid was collected by filtration, rinsed with 3A EtOH and dried briefly under vacuum at 45° C. The wet cake was slurried in a fresh portion of 3A EtOH (1.6 L) at 72° C. for 0.5 hour, cooled to room temperature, filtered and rinsed with 3A EtOH. This reslurry was repeated 2 more times and the resulting final salt dried overnight under vacuum at 45° C. to give the resolved tartrate salt of trans-2-methyl-4-(3-methylbenzo[b]-thiophen-5-yl)piperidine (13.1 g, 80% yield of desired isomer, 92% ee).

¹H NMR (300 MHz, DMSO) δ 1.37 (d, 3), 1.73–1.85 (m, 1), 1.85–2.04 (m, 2), 2.04–2.2 (m, 1), 2.38 (s, 3), 2.50 (s, 1H, 3.06–3.30 (m, 3), 4.00 (s, 2), 7.25 (d, 1), 7.34 (s, 1), 7.60 (s, 1), 7.87 (s, 1). Anal. Calcd for C₁₉H₂₅NO₆S: C, 57.71; H, 6.37; N, 3.54. Found: C, 57.56; H. 6.47; N, 3.56.

Preparation of trans-(2S)-(−)-3-(2-Methyl-4-(3-methyl-benzo[b]thiophen-5-yl)piperidin-1-yl)-1-(2-methylindol-4-yl)oxy-2-propanol p-toluenesulfonate.

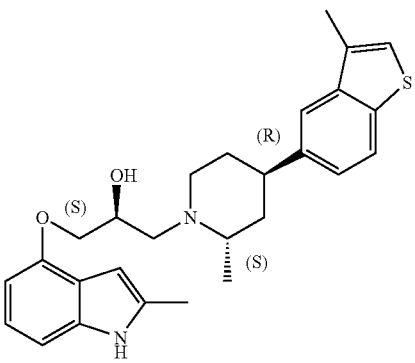

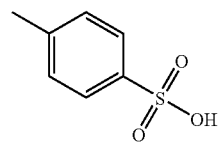

The trans-(2S,4R)-2-methyl-4-(3-methylbenzo[b]-thiophen-5-yl)piperidine tartrate (0.50 g, 1.26 mmol, 1.0 equiv, prepared directly above) was free based by addition of EtOAc (10 mL), water (10 mL), and 5N NaOH (1.0 mL). The layers were separated and the aqueous layer extracted with EtOAc (10 mL). The combined organic layers were dried (Na₂SO₄) and concentrated under vacuum to give an oil (0.30 g). This oil was dissolved in isopropyl alcohol (4.0 mL), (2S)-4-glycidyloxy-2-methylindole (0.2 g, 1.25 mmol, prepared in example 1) was added, and the mixture heated at 80° C. for 2 hours. The mixture was added to a separatory funnel containing EtOAc (25 mL), water (25 mL), and 1 N NaOH (1 mL). The layers were separated and the aqueous layer was washed with EtOAc (25 mL). The combined organic layers were dried (Na₂SO₄) and 0.24 g of p-toluenesulfonic acid (1.0 equiv) was added. The solution was concentrated, seeded, and heated to generate a crystalline slurry. The slurry was stirred at room temperature for 1 hour. The solid was collected by filtration, rinsed with EtOAc, and dried overnight at 45° C. under vacuum to afford the title compound (0.64 g, 82% yield). ¹H NMR (500 MHz, CDCl₃) δ 1.50 (d, 3), 1.90 (d, 1), 2.08 (d, 1), 2.27 (s, 3), 2.40 (s, 3), 2.43 (s, 3), 2.59–2.66 (m, 1), 2.85 (dt, 1), 3.02–3.17 (m, 2), 3.25–3.3.38 (m, 2), 3.67 (d, 1), 4.0–4.15 (m, 2), 4.30 (m, 1), 4.70 (m, 1), 6.20 (s, 1), 6.50 (d, 1), 6.93–7.02 (m, 2), 7.15–7.28 (m, 4), 7.60 (s, 1), 7.75 (d, 1), 7.83 (d, 1), 8.0 (s, 1), 10.30 (s, 1). ¹³C NMR (75 MHz, DMSO) δ 10.96, 13.28, 13.50, 13.56, 15.83, 20.72, 25.95, 30.35, 30.93, 32.92, 33.26, 35.98, 45.75, 46.85, 53.71, 54.07, 55.99, 56.49, 64.25, 64.57, 69.83, 69.97, 96.45, 100.48, 104.61, 119.06, 119.56, 119.83, 120.58, 122.59, 122.72, 122.89, 123.36, 123.67, 125.47, 128.06, 131.48, 131.60, 133.75, 137.53, 137.72, 137.81, 139.61, 140.13, 140.34, 145.48, 150.75. Anal. Calcd for C₃₄H₄₀NO₅S₂: C, 65.78; H, 6.49; N, 4.51. Found: C, 65.04; H, 6.29; N, 4.36.

Additional Preparation of trans-(2S)-(−)-3-(2-Methyl-4-(3-methylbenzo[b]thiophen-5-yl)piperidin-1-yl)-1-(2-methylindol-4-yl)oxy-2-propanol Salts from Example 116, Isomer 3 Free Base.

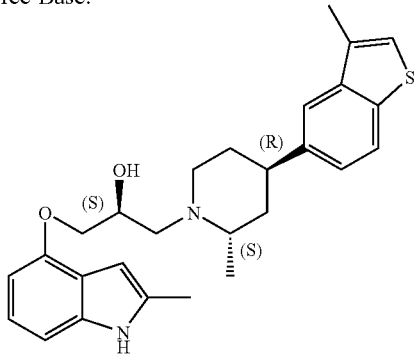

Crude trans-(2S)-(−)-3-(2-methyl-4-(3-methylbenzo[b]thiophen-5-yl)piperidin-1-yl)-1-(2-methylindol-4-yl)oxy-2-propanol (isomer 3, foam) (2.80 g, 6.3 mmol) was dissolved in isopropyl alcohol (20 mL) at room temperature. The solution was divided into three equal portions, and different acids were added to each portion: 1) p-TsOH (0.40 g, 1.0 equiv) was added directly to the solution; 2) benzenesulfonic acid (0.33 g, 1.0 equiv) was dissolved in 2 mL of EtOAc and added to the solution; 3) methanesulfonic acid (0.135 mL, 1.0 equiv) was mixed with 2 mL of EtOAc and added to the solution. These mixtures were briefly heated, scraped and stirred overnight at room temperature. Each slurry was filtered, rinsed with EtOAc, and dried overnight at 45° C. under vacuum to give the following corresponding solids:

trans-(2S)-(−)-3-(2-methyl-4-(3-methylbenzo[b]thiophen-5-yl)piperidin-1-yl)-1-(2-methylindol-4-yl)oxy-2-propanol p-toluenesulfonate:
1.17 g, 89% yield, mp 207° C.;

trans-(2S)-(−)-3-(2-methyl-4-(3-methylbenzo[b]thiophen-5-yl)piperidin-1-yl)-1-(2-methylindol-4-yl)oxy-2-propanol benzenesulfonate:
1.04 g, 81.1% yield, mp 185° C.;

trans-(2S)-(−)-3-(2-methyl-4-(3-methylbenzo[b]thiophen-5-yl)piperidin-1-yl)-1-(2-methylindol-4-yl)oxy-2-propanol methanesulfonate:
0.75 g, 66.7% yield, mp 124° C.

EXAMPLE 117

Preparation of cis-(2S)-1-(4-Indolyloxy)-3-(2-methyl-4-(3-methylbenzo[b]-thiophen-5-yl)piperidin-1-yl)-2-propanol oxalate isomers 1 and 2

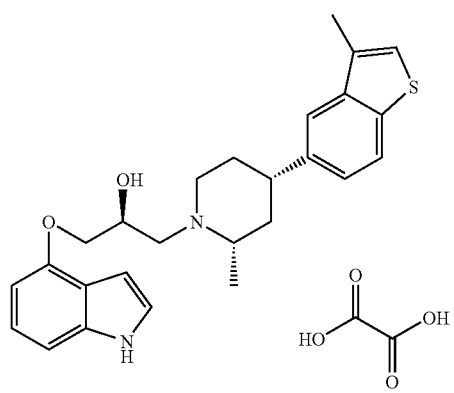

-continued

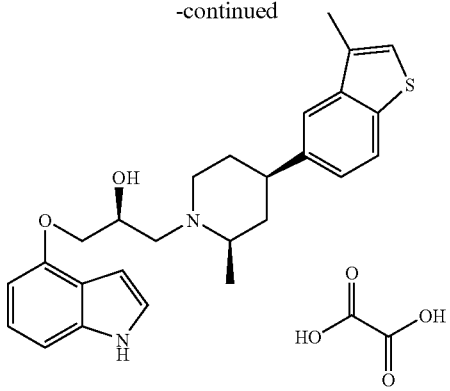

Scheme IV, step B: A solution of cis-2-methyl-4-(3-methylbenzo[b]thiphen-5-yl)piperidine (0.110 g, 0.448 mmol, isomer 1) and (2S)-4-glycidyloxy-2-methylindole (0.085 g, 0.448 mmol) in methanol (5 mL) was heated at reflux for 18 hours and then cooled and evaporated. The residue was purified by silica gel chromatography (dichloromethane/2% methanol, 0.15 M is ammonia in dichloromethane gradient elution) to give the free bases of the title compounds as two yellow oils. The oxalate salts were prepared to give the title compounds.

Isomer 1 (0.058 g, 30%, free base). FDMS m/e=435 (M$^+$+1 of free base).

Isomer 2 (0.086 g, 44%, free base). FDMS m/e=435 (M$^+$+1 of free base).

Preparation of trans-(2S)-1-(4-Indolyloxy)-3-(2-methyl-4-(3-methylbenzo[b]-thiophen-5-yl)piperidin-1-yl)-2-propanol oxalate isomers 3 and 4

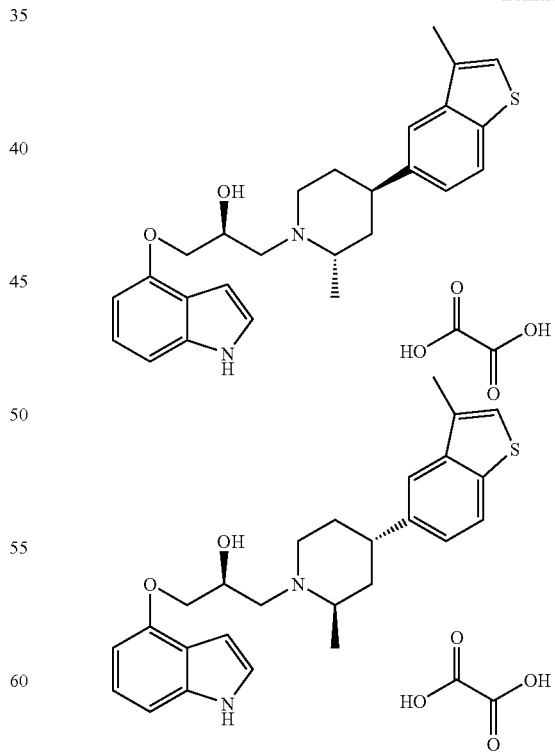

Scheme IV, step B: A solution of trans-2-methyl-4-(3-methylbenzo[b]-thiophen-5-yl)piperidine (0.104 g, 0.424 mmol, isomer 2) and (S)-(+)-4-(oxiranylmethoxy)-1H-indole (0.080 g, 0.424 mmol) in methanol (5 mL) was heated at reflux for 18 hours and then cooled and evaporated. The residue was purified by silica gel chromatography (dichloromethane/5% methanol, 0.35 M ammonia in dichloromethane gradient elution) to give the free bases of the title compounds as two yellow oils. The oxalate salts were prepared to give the title compounds.

Isomer 3 (0.048 g, 26%, free base). FDMS m/e=435 ($M^++1$ of free base).

Isomer 4 (0.070 g, 38%, free base). FDMS m/e=435 ($M^++1$ of free base).

EXAMPLE 118

Preparation of 1-(t-Butyloxycarbonyl)-4-(6-methoxynaphth-2-yl)-2-methylpiperidin-4-ol.

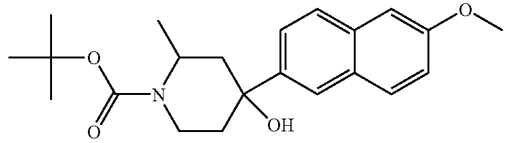

Scheme I, step A: To a solution of 2-bromo-6-methoxynaphthalene (13.009 g, 54.9 mmol) in tetrahydrofuran (400 mL) at −78° C. was added dropwise t-butyllithium (71.0 mL, 0.121 mol). After 30 minutes at −78° C., a solution of 1-(t-butyloxycarbonyl)-2-methyl-4-piperidone (12.87 g, 60.4 mmol) in tetrahydrofuran (50 mL) was added dropwise. The mixture was stirred at −78° C. for 4 hours and then diluted with saturated ammonium chloride and extracted 3 times with ethyl acetate. The combined organic layers were dried over sodium sulfate, filtered and evaporated. The residue was purified by silica gel chromatography (dichloromethane/2% methanol in dichloromethane gradient eluent) to give 5.81 g (29%) of the title compound as a yellow oil. FDMS m/e=362 ($M^++1$).

Preparation of 4-(6-Methoxynaphth-2-yl)-2-methyl-1,2,3,6-tetrahydropyridine.

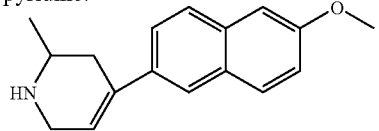

Scheme I, step B: 1-(t-Butyloxycarbonyl)-4-(6-methoxynaphth-2-yl)-2-methylpiperidin-4-ol (5.795 g, 8.79 mmol) was suspended in toluene (100 mL) and p-toluenesulphonic acid hydrate (5.016 g, 26.4 mmol) was added. The mixture was heated at reflux for 2 hours, then cooled to room temperature. The mixture was evaporated and the residue was diluted with 2 N sodium hydroxide, then extracted 3 times with ethyl acetate. The combined organic layers were dried over sodium sulfate, filtered and evaporated to give the title compound as a yellow oil (3.95 g, 100%). FDMS m/e=254 ($M^++1$).

Preparation of 4-(6-Methoxynaphth-2-yl)-2-methylpiperidine.

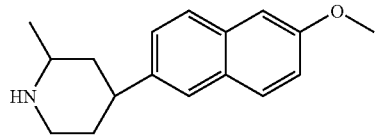

Scheme I, step C: To a solution 4-(6-Methoxynaphth-2-yl)-2-methyl-1,2,3,6-tetrahydropyridine (3.9 g, 15.4 mmol) in ethanol (200 mL) and 2,2,2-trifluoroethanol (70 mL) was added 10% palladium on carbon (400 mg). The mixture was stirred under one atmosphere of hydrogen for 19 hours. The mixture was filtered and the catalyst was washed with boiling methanol. The combined organic layers were evaporated and the residue was purified by silica gel chromatography (dichloromethane/5% methanol, 0.35 M ammonia in dichloromethane gradient elution) to give the title compound as two yellow amorphous solids.

Isomer 1 (cis isomer, 1.97 g, 50%). FDMS m/e=256 ($M^++1$).

Isomer 2 (trans isomer, 1.51 g, 38%). FDMS m/e=256 ($M^++1$). $C_{17}H_{21}NO \cdot 0.5H_2O$.

| analysis: | calculated | found |
|---|---|---|
| C | 77.24 | 77.40 |
| H | 8.39 | 8.40 |
| N | 5.30 | 5.69 |

Preparation of cis-(2S)-(−)-3-(4-(6-Methoxynaphth-2-yl)-2-methylpiperidin-1-yl)-1-(2-methylindol-4-yl)oxy-2-propanol succinate.

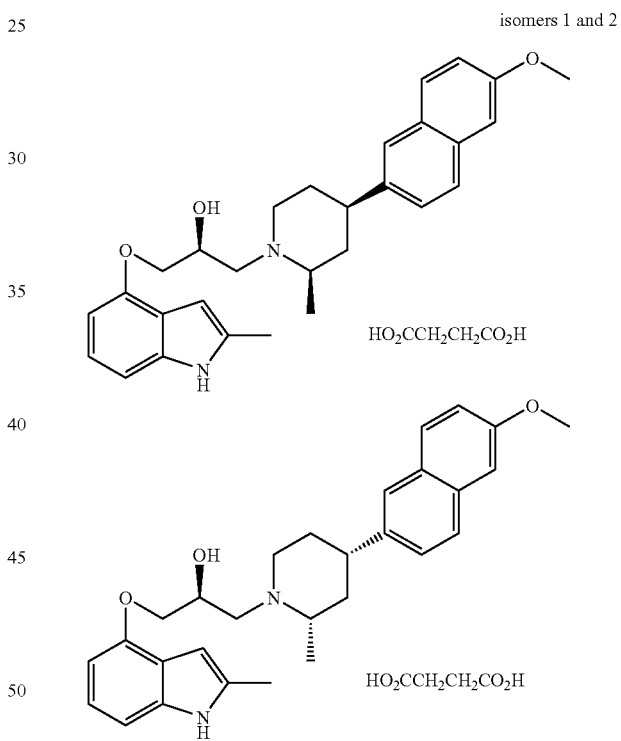

Scheme IV, step B: A solution of cis-4-(6-methoxynaphth-2-yl)-2-methyl-piperidine (1.569 g, 6.14 mmol, isomer 1) and (2S)-4-glycidyloxy-2-methylindole (1.249 g, 6.14 mmol) in methanol (30 mL) was heated at reflux for 18 hours and then cooled and evaporated. The residue was purified by silica gel chromatography (dichloromethane/2% methanol, 0.15 M ammonia in dichloromethane gradient elution) to give the free bases of the title compounds as two clear colorless oils. The succinate salts were prepared to give the title compounds.

Isomer 1 (0.801 g, 28%, free base). FDMS m/e=459 ($M^++1$ of free base). $[\alpha]_D = -18.05$ (c 0.554, methanol). $C_{29}H_{34}N_2O_3 \cdot C_4H_6O_4$.

| analysis: | calculated | found |
|---|---|---|
| C | 68.73 | 68.72 |
| H | 6.99 | 6.93 |
| N | 4.86 | 5.23 |

Isomer 2 (1.144 g, 41%, free base). FDMS m/e=459 (M⁺+1 of free base). [α]$_D$=−7.27 (c 0.55, methanol).

Preparation of trans-(2S)-(−)-3-(4-(6-Methoxynaphth-2-yl)-2-methylpiperidin-1-yl)-1-(2-methylindol-4-yl)oxy-2-propanol succinate.

isomers 3 and 4

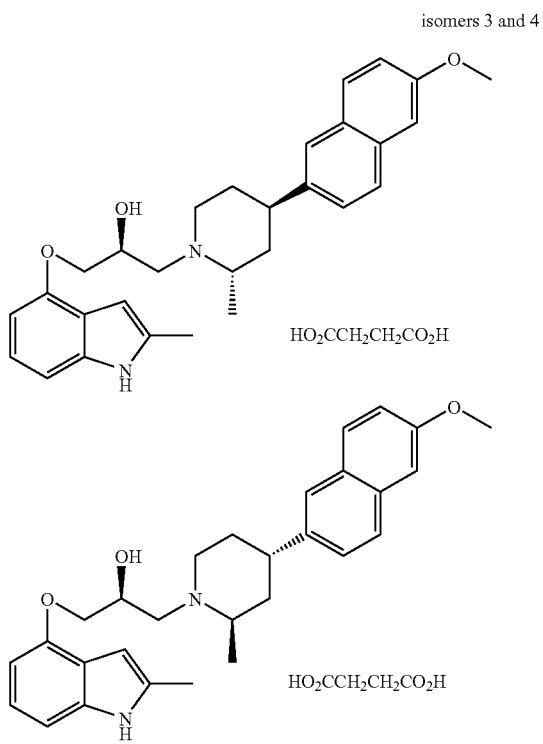

Scheme IV, step B: A solution of trans-4-(6-methoxynaphthyl)2-methylpiperidine (1.494 g, 5.85 mmol, isomer 2) and (2S)-4-glycidyloxy-2-methylindole (1.189 g, 5.85 mmol) in methanol (30 mL) was heated at reflux for 18 hours and then cooled and evaporated. The residue was purified by silica gel chromatography (dichloromethane/2% methanol, 0.15 M ammonia in dichloromethane gradient elution) to give the free bases of the title compounds as two clear colorless oils. The succinate salts were prepared to give the title compounds.

Isomer 3 (1.089 g, 41%, free base). FDMS m/e=459 (M⁺+1 of free base). [α]$_D$=−8.91 (c 0.449, methanol). $C_{29}H_{34}N_2O_3 \cdot C_4H_6O_4$.

| analysis: | calculated | found |
|---|---|---|
| C | 68.73 | 68.55 |
| H | 6.99 | 6.64 |
| N | 4.86 | 4.90 |

Isomer 4 (1.041 g, 39%, free base). FDMS m/e=459 (M⁺+1 of free base). [α]$_D$=−3.64 (c 0.549, methanol). $C_{29}H_{34}N_2O_3 \cdot C_4H_6O_4 \cdot 0.5H_2O$.

| analysis: | calculated | found |
|---|---|---|
| C | 67.67 | 67.97 |
| H | 7.06 | 6.90 |
| N | 4.78 | 4.90 |

EXAMPLE 119

Preparation of (2S)-(−)-3-[(2R,4R)-4-(7-Fluorobenzo[b]thiophen-2-yl)-2-methylpiperidin-1-yl]-1-(1H-2-methylindol-4-yl)oxy-2-propanol

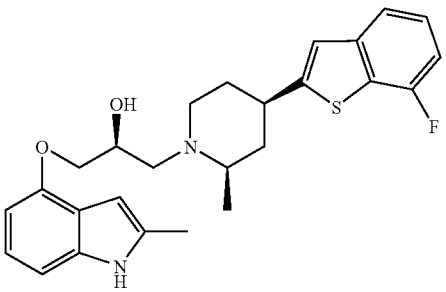

Preparation of 2-Fluorobenzenethioacetaldehyde diethyl acetal.

The title compound was prepared in quantitative crude yield from 2-fuorobenzenethiol by essentially following the procedures detailed in (Graham, S. L., et. al. J. Med. Chem. 1989,32, 2548–2554).

Preparation of 7-Fluorobenzo[b]thiophene.

To a biphasic mixture of polyphosphoric acid (PPA; 43.0 g) and 385 mL of dry chlorobenzene heated to reflux, was added dropwise 2-fluorobenzenethioacetaldehyde diethyl acetal (19.1 g, 78.1 mmol) in 60 mL of chlorobenzene over a period of 2.5 h. The reaction mixture was cooled to room temperature and the organic layer was decanted off the PPA layer. The PPA layer was cooled to 0° C. and diluted with 400 mL of H$_2$O. This aqueous layer was extracted with Et$_2$O (2×500 mL). The combined organic layers were dried over MgSO$_4$ and concentrated under reduced pressure. The residue was purified by a medium pressure chromatography system (silica gel, 100% hexanes) to afford 7-fluorobenzo [b]thiophene as a yellow oil (5.42 g, 46%). FDMS m/e=152 (M⁺).

¹HNMR (CDCl$_3$) 7.59 (d, J=7.8 Hz, 1H), 7.46 (d, J=5.4 Hz, 1H), 7.36 (dd, J=5.4, 3.9 Hz, 1H), 7.31 (dt, J=7.8, 4.9 Hz, 1H), 7.03 (dd, J=9.8, 7.8 Hz, 1H).

Preparation of N-t-Butoxycarbonyl-4-(7-fluorobenzo[b]thiophen-2-yl)-2-methyl-4-piperidinol.

Scheme IA, step A: To a solution of 7-fluorobenzo[b]thiophene (4.00 g, 26.3 mmol) in dry THF (130 mL) at −78° C. was added 1.6 M n-BuLi in hexanes (18.1 mL, 28.9 mmol). The solution was stirred at −78° C. for 50 min. N-t-Butoxycarbonyl-2-methyl-4-piperidone (5.61 g, 26.3 mmol) dissolved in THF (20 mL) was added via a cannula at −78° C. The reaction mixture was stirred at −78° C. for 2 h. The reaction was then quenched with 110 mL of saturated aqueous NH$_4$Cl solution. The mixture was extracted with EtOAc (2×400 mL). The combined organic layers were then dried over MgSO$_4$ and filtered. The filtrate was concentrated and purified by medium pressure chromatography (15% EtOAc/hexanes) to give N-t-butoxycarbonyl-4-(7-fluorobenzo[b]thiophen-2-yl)-2-methyl-4-piperidinol as a white foam (5.90 g, 61%). IR (CHCl$_3$) 3350 (br), 1680 cm$^{-1}$. Ion Spray MS 205 (M−160)$^+$; 366 (M+H)$^+$; 424 (M+CH$_3$COO$^−$)$^−$. C$_{19}$H$_{24}$FNO$_3$S

| analysis: | calculated | found |
|---|---|---|
| C | 62.44 | 62.14 |
| H | 6.62 | 6.92 |
| N | 3.83 | 3.90 |

Preparation of (±)-cis-4-(7-Fluorobenzo[b]thiophen-2-yl)-2-methylpiperidine.

Scheme IA, steps B and C: To a solution of N-t-butoxycarbonyl-4-(7-fluorobenzo[b]thiophen-2-yl)-2-methyl-4-piperidinol (5.90 g, 16.1 mmol),in dry CH$_2$Cl$_2$ (56 mL) at 0° C. was added 24 mL of trifluoroacetic acid. The solution was stirred at 0° C. for 1 h. The reaction was then quenched at room temperature with saturated aqueous NaHCO$_3$ solution (280 mL). The mixture was extracted with CH$_2$Cl$_2$ (2×500 mL). The combined organic layers were dried over MgSO$_4$ and concentrated to yield 3.84 g of crude regioisomeric olefins. To a solution of the crude olefins (3.84 g) in a 3:1 mixture of ethanol (110 mL) and 2,2,2-trifluoroethanol (37 mL) was added 10% Pd/C (4.00 g). The black slurry was stirred vigorously at room temperature under hydrogen (balloon pressure) for 16 h. The black slurry was then filtered over a pad of diatomaceous earth and washed with ethanol. The filtrate was concentrated, and the residue was purified by medium pressure chromatography [silica gel, 4–5% (3.5 M NH$_3$ in MeOH)/CH$_2$Cl$_2$] to give cis-(±)-4-(7-fluorobenzo[b]thiophen-2-yl)-2-methylpiperidine as a brown solid (1.45 g, 36%). mp 55–57° C. IR (KBr) 3246 cm$^{-1}$. Ion Spray MS 250 (M+H)$^+$. C$_{14}$H$_{16}$FNS

| analysis: | calculated | found |
|---|---|---|
| C | 67.44 | 67.76 |
| H | 6.47 | 6.76 |
| N | 5.62 | 5.62 |

Preparation of (±)-trans-4-(7-Fluorobenzo[b]thiophen-2-yl)-2-methylpiperidine.

Scheme IA, steps B and C: To a solution of N-t-butoxycarbonyl-4-(7-fluorobenzo[b]thiophen-2-yl)-2-methyl-4-piperidinol (5.90 g, 16.1 mmol) in dry CH$_2$Cl$_2$ (56 mL) at 0° C. was added 24 mL of trifluoroacetic acid. The solution was stirred at 0° C. for 1 h. The reaction was then quenched at room temperature with saturated aqueous NaHCO$_3$ solution (280 mL). The mixture was extracted with CH$_2$Cl$_2$ (2×500 mL). The combined organic layers were dried over MgSO$_4$ and concentrated to yield 3.84 g of crude regioisomeric olefins. To a solution of the crude olefins (3.84 g) in a 3:1 mixture of ethanol (110 mL) and 2,2,2-trifluoroethanol (37 mL) was added 10% Pd/C (4.00 g). The black slurry was stirred vigorously at room temperature under hydrogen (balloon pressure) for 16 h. The black slurry was then filtered over a pad of diatomaceous earth and washed with ethanol. The filtrate was concentrated, and the residue was purified by medium pressure chromatography [silica gel, 4–5% (3.5 M NH$_3$ in MeOH)/CH$_2$Cl$_2$] to give trans-(±)-4-(7-fluorobenzo[b]thiophen-2-yl)-2-methylpiperidine as a brown solid (0.594 g, 15%). mp 45–47° C. IR (KBr) 3226 cm$^{-1}$. Ion Spray MS 250 (M+H)$^+$. C$_{14}$H$_{16}$FNS

| analysis: | calculated | found |
|---|---|---|
| C | 67.44 | 67.69 |
| H | 6.47 | 6.79 |
| N | 5.62 | 5.66 |

Preparation of Final Title Compound.

Scheme IV, step B: A solution of (±)-cis-4-(7-fluorobenzo[b]thiophen-2-yl)-2-methylpiperidine (0.700 g, 2.81 mmol) and (2S)-4-glycidyloxy-2-methylindole (0.571 g, 2.81 mmol) in MeOH (35mL) was heated at reflux for 48 h and then cooled and evaporated. The residue was purified by silica gel chromatography [1% (3.5 M NH$_3$ in MeOH)/CH$_2$Cl$_2$] to give the final title compound as an off-white foam (0.434 g, 34%). The hydrochloride salt was prepared with 1 equiv. of HCl in EtOAc. mp (HCl) 135–140° C. IR (CHCl$_3$) 3474, 3350 (br), 1246 cm$^{-1}$. Ion Spray MS 453 (M+H)$^+$; 451 (M−H)$^−$ 511 (M+CH$_3$COO$^−$)$^−$. [ ]$_D$=−11.43 (c 0.53, MeOH). C$_{26}$H$_{29}$FN$_2$O$_2$S.HCl.0.5H$_2$O

| analysis: | calculated | found |
|---|---|---|
| C | 62.70 | 62.45 |
| H | 6.27 | 6.35 |
| N | 5.62 | 5.46 |

EXAMPLE 120

Preparation of (2S)-(+)-3-[(2S,4S)-4-(7-Fluorobenzo[b]thiophen-2-yl)-2-methylpiperidin-1-yl]-1-(1H-2-methylindol-4-yl)oxy-2-propanol

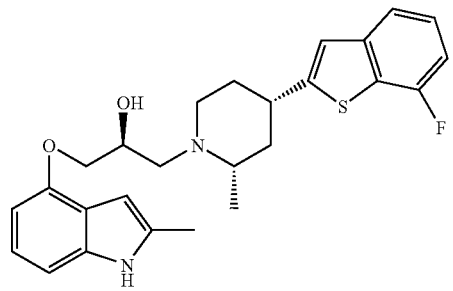

Scheme IV, step B: A solution of (±)-cis-4-(7-fluorobenzo[b]thiophen-2-yl)-2-methylpiperidine (0.700 g, 2.81 mmol) and (2S)4-glycidyloxy-2-methylindole (0.571 g, 2.81 mmol) in MeOH (35mL) was heated at reflux for 48 h and then cooled and evaporated. The residue was purified by silica gel chromatography [1% (3.5 M NH$_3$ in MeOH)/CH$_2$Cl$_2$] to give the title propanol as an off-white foam (0.338 g, 27%). The hydrochloride salt was prepared with 1 equiv. of HCl in EtOAc. mp (HCl) 162–166° C. IR (CHCl$_3$) 3474, 3350 (br), 1246 cm$^{-1}$. Ion Spray MS 453 (M+H)$^+$; 451 (M−H)$^−$ 511 (M+CH$_3$COO$^−$)$^−$. [ ]$_D$=27.07 (c 0.52, MeOH). C$_{26}$H$_{29}$FN$_2$O$_2$S.HCl

| analysis: | calculated | found |
|---|---|---|
| C | 63.86 | 63.60 |
| H | 6.18 | 6.11 |
| N | 5.73 | 5.74 |

EXAMPLE 121

Preparation of (2S)-3-[(2S,4R)-4-(7-Fluorobenzo[b]thiophen-2-yl)-2-methylpiperidin-1-yl]-1-(1H-2-methylindol-4-yl)oxy-2-propanol

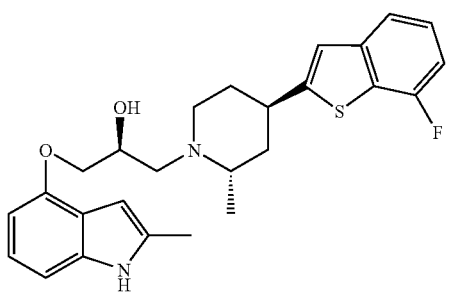

Scheme IV, step B: A solution of (±)-trans-4-(7-fluorobenzo[b]thiophen-2-yl)-2-methylpiperidine (0.400 g, 1.60 mmol) and (2S)-4-glycidyloxy-2-methylindole (0.326 g, 1.60 mmol) in MeOH (20 mL) was heated at reflux for 20 h and then cooled and evaporated. The residue was purified by silica gel chromatography [1–2% (3.5 M NH$_3$ in MeOH)/CH$_2$Cl$_2$] to give the title compound as a white foam (0.292 g, 40%). The hydrochloride salt was prepared with 1 equiv. of HCl in EtOAc. mp (HCl) 158–161° C. IR (CHCl$_3$) 3474, 3350 (br), 1246 cm$^{-1}$. Ion Spray MS 453 (M+H)$^+$; 451 (M−H)$^-$; 487 (M+Cl)$^-$. [ ]$_D$=0 (c 0.50, MeOH). C$_{26}$H$_{29}$FN$_2$O$_2$S.HCl

| analysis: | calculated | found |
|---|---|---|
| C | 63.86 | 64.12 |
| H | 6.18 | 6.14 |
| N | 5.73 | 5.63 |

EXAMPLE 122

Preparation of (2S)-(+)-3-[(2R,4S)-4-(7-Fluorobenzo[b]thiophen-2-yl)-2-methylpiperidin-1-yl]-1-(1H-2-methylindol-4-yl)oxy-2-propanol

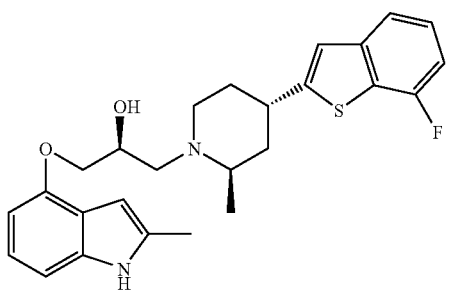

Scheme IV, step B: A solution of (±)-trans-4-(7-fluorobenzo[b]thiophen-2-yl)-2-methylpiperidine (0.400 g, 1.60 mmol) and (2S)-4-glycidyloxy-2-methylindole (0.326 g, 1.60 mmol) in MeOH (20 mL) was heated at reflux for 20 h and then cooled and evaporated. The residue was purified by silica gel chromatography [1–2%; (3.5 M NH$_3$ in MeOH)/CH$_2$Cl$_2$] to give the title compound as a white foam (0.276 g, 38%). The hydrochloride salt was prepared with 1 equiv. of HCl in EtOAc. mp (HCl) 155–158° C. IR (CHCl$_3$) 3473, 3300 (br), 1245 cm$^{-1}$. Ion Spray MS 453 (M+H)$^+$; 451 (M−H)$^-$ 487 (M+Cl)$^-$. [ ]$_D$=17.57. (c 0.57, MeOH). C$_{26}$H$_{29}$FN$_2$O$_2$S.HCl.0.4H$_2$O

| analysis: | calculated | found |
|---|---|---|
| C | 62.93 | 62.57 |
| H | 6.26 | 6.26 |
| N | 5.65 | 5.42 |

EXAMPLE 123

Preparation of (2S)-(−)-3-[(2R,4R)-4-(7-Fluorobenzo[b]thiophen-2-yl)2-methylpiperidin-1-yl]-1-(1H-indol-4-yl)oxy-2-propanol

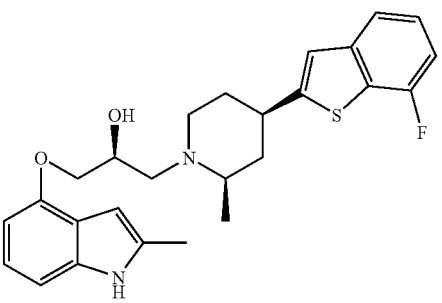

Scheme IV, step B: A solution of (±)-cis-4-(7-fluorobenzo[b]thiophen-2-yl)-2-methylpiperidine (0.600 g, 2.41 mmol) and (S)-4-(oxiranylmethoxy)indole (0.455 g, 2.41 mmol) in MeOH (30 mL) was heated at reflux for 24 h and then cooled and evaporated. The residue was purified by silica gel chromatography [1% (2.0 M NH$_3$ in MeOH)/CH$_2$Cl$_2$] to give the title compound as a white foam (0.341 g, 32%). The hydrochloride salt was prepared with 1 equiv. of HCl in EtOAc. mp (HCl) 147–150° C. IR (KBr) 3404, 3300 (br), 1243 cm$^{-1}$. Ion Spray MS 439 (M+H)$^+$; 437 (M−H)$^-$; 497 (M+CH$_3$COO$^-$)$^-$. [ ]$_D$=−11.72 (c 0.51, MeOH). C$_{25}$H$_{27}$FN$_2$O$_2$S.0.1H$_2$O

| analysis: | calculated | found |
|---|---|---|
| C | 68.19 | 67.92 |
| H | 6.23 | 6.14 |
| N | 6.36 | 6.36 |

EXAMPLE 124

Preparation of (2S)-(+)-3-[(2S,4S)-4-(7-Fluorobenzo[b]thiophen-2-yl)-2-methylpiperidin-1-yl]-1-(1-H-indol-4-yl)oxy-2-propanol

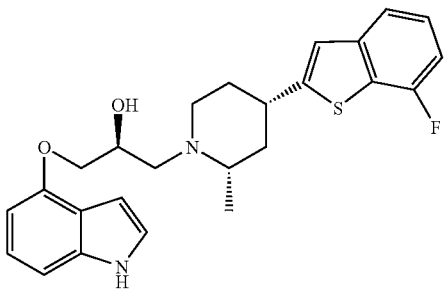

Scheme IV, step B: A solution of (±)-cis-4-(7-fluorobenzo[b]thiophen-2-yl)-2-methylpiperidine (0.600 g, 2.41 mmol) and (S)-4-(oxiranylmethoxy)indole (0.455 g, 2.41 mmol) in MeOH (30 mL) was heated at reflux for 24 h and then cooled and evaporated. The residue was purified by silica gel chromatography [1% (2.0 M $NH_3$ in MeOH)/$CH_2Cl_2$] to give the title compound as a white foam (0.396 g, 38%). The hydrochloride salt was prepared with 1 equiv. of HCl in EtOAc. mp (HCl) 150–153° C. IR (KBr) 3408, 3300 (br), 1242 $cm^{-1}$. Ion Spray MS 439 $(M+H)^+$; 437 $(M-H)^-$; 497 $(M+CH_3COO^-)^-$. [ ]$_D$=29.20 (c 0.55, MeOH). $C_{25}H_{27}FN_2O_2S$

| analysis: | calculated | found |
|---|---|---|
| C | 68.47 | 68.08 |
| H | 6.21 | 6.18 |
| N | 6.39 | 6.58 |

EXAMPLE 125

Preparation of (2S)-3-[(2S,4R)-4-(7-Fluorobenzo[b]thiophen-2-yl)-2-methylpiperidin-1-yl]-1-(1-H-indol-4-yl)oxy-2-propanol

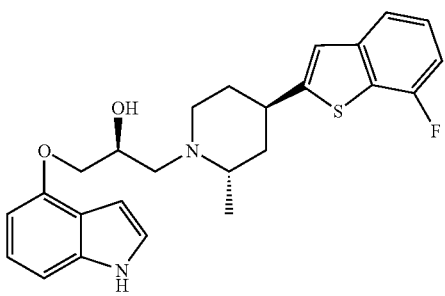

Scheme IV, step B: A solution of (±)-trans-4-(7-fluorobenzo[b]thiophen-2-yl)-2-methylpiperidine (0.171 g, 0.686 mmol) and (S)-4-(oxiranylmethoxy)indole (0.130 g, 0.686 mmol) in MeOH (9 mL) was heated at reflux for 17 h and then cooled and evaporated. The residue was purified by silica gel chromatography [1% (2.0 M $NH_3$ in MeOH)/$CH_2Cl_2$] to give the title compound as a white foam (0.122 g, 41%). The hydrochloride salt was prepared with 1 equiv. of HCl in EtOAc. IR (KBr) 3406, 3300 (br), 1243 $cm^{-1}$. Ion Spray MS 439 $(M+H)^+$; 437 $(M-H)^-$. [ ]$_D$=0 (c 0.49, MeOH). $C_{25}H_{27}FN_2O_2S$

| analysis: | calculated | found |
|---|---|---|
| C | 68.47 | 68.36 |
| H | 6.21 | 6.34 |
| N | 6.39 | 6.33 |

EXAMPLE 126

Preparation of (2S)-(+)-3-[(2R,4S)-4-(7-Fluorobenzo[b]thiophen-2-yl)-2-methylpiperidin-1-yl]-1-(1-H-indol-4-yl)oxy-2-propanol

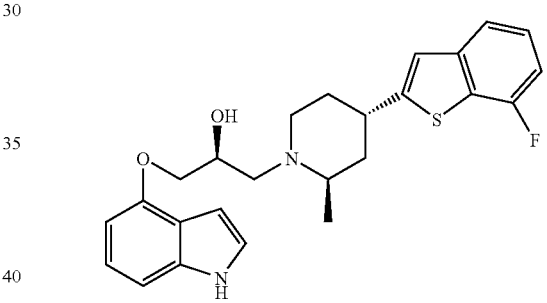

Scheme IV, step B: A solution of (±)-trans-4-(7-fluorobenzo[b]thiophen-2-yl)-2-methylpiperidine (0.171 g, 0.686 mmol) and (S)-4-(oxiranylmethoxy)indole (0.130 g, 0.686 mmol) in MeOH (9 mL) was heated at reflux for 17 h and then cooled and evaporated. The residue was purified by silica gel chromatography [1% (2.0 M $NH_3$ in MeOH)/$CH_2Cl_2$] to give the title compound as a white foam (0.115 g, 38%). The hydrochloride salt was prepared with 1 equiv. of HCl in EtOAc. mp (HCl) 146–149° C. IR (KBr) 3405, 3300 (br), 1242 $cm^{-1}$. Ion Spray MS 439 $(M+H)^+$; 437 $(M-H)^-$; 497 $(M+CH_3COO^-)^-$. [ ]$_D$=10.42 (c 0.58, MeOH). $C_{25}H_{27}FN_2O_2S$

| analysis: | calculated | found |
|---|---|---|
| C | 68.47 | 68.07 |
| H | 6.21 | 6.55 |
| N | 6.39 | 6.38 |

EXAMPLE 127

Preparation of (2S)-(−)-3-[(2R,4R)-4-(4-Ethylbenzo[b]thiophen-2-yl)-2-methylpiperidin-1-yl]-1-(1H-2-methylindol-4-yl)oxy-2-propanol

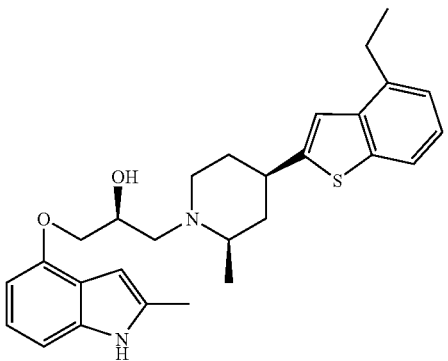

Preparation of ( )-N,N-Dimethyl-2-(2-ethylphenyl)-2-hydroxythioacetamide.

A solution of 30.11 g of 1-bromo-2-ethylbenzene in ca. 500 mL of freshly distilled THF was treated with 112 mL of 1.6 M n-BuLi in hexanes at −78° C. over a period of ca. 3 h. To this was added 15 mL of anhydrous DMF, and the mixture was stirred at −78° C. for 30 min. The cold bath was removed, and the reaction was quenched with ca. 300 mL of saturated aqueous $NH_4Cl$. The layers were separated, and the organic layer was washed with ca. 300 mL of brine. The aqueous layers were back extracted with 2×500 mL of EtOAc. Combined organic layers were dried over $MgSO_4$, concentrated, and dried under house vacuum to yield 20.89 g (96%) of fairly clean crude 2-ethylbenzaldehyde.

To 29.0 mL of diisopropylamide in ca. 500 mL of freshly distilled THF at −70° C. was added 117 mL of 1.6 M n-BuLi in hexanes, and the yellow solution was stirred at −70° C. for 20 min, for 15 min without the cold bath, then re-cooled to −73° C. To this was added a pre-cooled (−70° C.) mixture of 20.89 g of the crude benzaldehyde and 16 mL of N,N-dimethylthioformamide in 70 mL of freshly distilled THF via a cannula over 15 min. The reddish clear solution was stirred at −75° C. for 45 min, then the cold bath was removed, and the mixture was stirred for another 30 min. The reaction was quenched with ca. 300 mL of saturated aqueous $NH_4Cl$, and the layers were separated. The aqueous layer was extracted with 3×500 mL of EtOAc. The organic layers were washed with ca. 300 mL of brine, combined, dried over $MgSO_4$, and concentrated. The residue was crystallized from EtOAc-hexanes to afford 25.20 g (73%) of yellowish crystalline solid. IR ($CHCl_3$) ~3200 (br), 3009, 1529, 1387 $cm^{-1}$. mp 104–105° C. Ion Spray MS 223.9 $(M+H)^+$. $C_{12}H_{17}NOS$

| analysis: | calculated | found |
|---|---|---|
| C | 64.54 | 64.70 |
| H | 7.67 | 7.73 |
| N | 6.27 | 6.31 |

Preparation of 4-Ethyl-2-(N,N-dimethylamino)benzo[b]thiophene.

N,N-Dimethyl-2-(2-ethylphenyl)-2-hydroxythioacetamide (25.1 g, 112 mmol) was dissolved in Eaton's reagent (7.5% w/w $P_2O_5$/$MeSO_3H$) (330 mL). The reaction mixture was heated to 80° C. and stirred for 1 h. The reaction mixture was then cooled to room temperature and stirred for an additional 1.5 h. The reaction was quenched by pouring the reaction mixture slowly into cooled (0° C.) 5.0 N NaOH (1.60 L). The mixture was extracted with EtOAc (2×1.50 L). The combined organic layers were then dried over $MgSO_4$ and concentrated to yield the title benzo[b]thiophene (21.66 g, 94% crude yield) as a red oil. EIMS 205 $M^+$; 190 $(M-15)^+$ (base peak).

$^1HNMR$ ($CDCl_3$) 7.42 (d, J=7.8 Hz, 1H), 7.04 (d, J=7.3 Hz, 1H), 6.98 (t, J=7.6 Hz, 1H), 5.98 (s, 1H), 3.01 (s, 6H), 2.82 (q, J=7.8 Hz, 2H), 1.30 (t, J=7.8 Hz, 3H).

Preparation of 4-Etylthianapthen-2-one.

4-ethyl-2-dimethylaminobenzo[b]thiophene (11.10 g, 54.0 mmol) was dissolved in a 1:1 mixture of THF/1.0 N HCl (380 mL). The biphasic mixture was stirred vigorously and heated at reflux for 3 h 15 min. The reaction mixture was then cooled to room temperature and the layers were separated. The aqueous layer was extracted with EtOAc (2×400 mL). The combined organic layers were dried over $MgSO_4$ and concentrated to give 4-ethylthianapthen-2-one (9.63 g, quantitative crude yield) as a dark red solid.

$^1HNMR$ ($CDCl_3$) 7.19 (t, J=7.8 Hz, 1H), 7.11 (d, J=6.8 Hz, 1H), 7.00 (d, J=7.3 Hz, 1H), 3.82 (s, 2H), 2.51 (q, J=7.8 Hz, 2H), 1.17 (t, J=7.8 Hz, 3H).

Preparation of 4-Ethylbenzo[b]thiophene.

To a solution of 4-ethylthianapthen-2-one (19.5 g, 110 mmol) in $CH_2Cl_2$ (1.15 L) was added dropwise 1.0 M diisobutylaluminum hydride in toluene (150 mL, 150 mmol) at 0° C. The solution was stirred at 0° C. for 2 h. The reaction was quenched with conc. HCl (700 mL) added dropwise over a period of 1.5 h. This mixture was then stirred vigorously for 2 h. The layers were separated, and the organic layer was washed with brine (1×500 mL), dried over $MgSO_4$ and concentrated. The residue was purified by medium pressure chromatography (100% hexanes) to give 4-ethylbenzo[b]thiophene as a yellow oil (6.37 g, 37%). EIMS 162 $M^+$.

$^1HNMR$ ($CDCl_3$) 7.53 (d, J=7.8 Hz, 1H), 7.09 (t, J=7.8 Hz, 1H), 7.05 (d, J=6.4 Hz, 1H), 6.98 (distorted d, 2H), 2.80 (q, J=7.8 Hz, 2H), 1.15 (t, J=7.8 Hz, 3H).

Preparation of N-t-Butoxycarbonyl-4-(4-ethylbenzo[b]thiophen-2-yl)-2-methyl-4-piperidinol.

Scheme IA, step A: To a solution of 4-ethylbenzo[b]thiophene (6.37 g, 39.2 mmol) in dry THF (200 mL) at −78° C. was added 1.6 M n-BuLi in hexanes (27.0 mL, 43.2 mmol). The solution was stirred at −78° C. for 2 h. N-t-Butoxycarbonyl-2-methyl-4-piperidone (6.70 g, 31.4 mmol) dissolved in THF (20 mL) was added via a cannula at −78° C. The reaction mixture was stirred at −78° C. for 3 h. The reaction was then quenched with 200 mL of saturated aqueous $NH_4Cl$ solution. The mixture was extracted with EtOAc (1×200 mL). The combined organic layers were then dried over $MgSO_4$ and filtered. The filtrate was concentrated and purified by medium pressure chromatography (20% EtOAc/hexanes) to give N-t-butoxycarbonyl-4-(4-ethylbenzo[b]thiophen-2-yl)-2-methyl-4-piperidinol as a white foam (6.58 g, 56%). IR ($CHCl_3$) 3425 (br), 1664, 1692 $cm^{-1}$. Ion Spray MS 376 $(M+H)^+$; 302 $(M-73)^+$ (base peak); 434 $(M+CH_3COO^-)^-$. $C_{21}H_{29}NO_3S$

| analysis: | calculated | found |
|---|---|---|
| C | 67.17 | 66.94 |
| H | 7.78 | 7.91 |
| N | 3.73 | 3.91 |

Preparation of (±)-cis-4-(4-Ethylbenzo[b]thiophen-2-yl)-2-methylpiperidine.

Scheme IA, step B and C: To a solution of N-t-butoxycarbonyl-4-(4-ethylbenzo[b]thiophen-2-yl)-2-methyl-4-piperidinol (6.58 g, 17.5 mmol) in dry $CH_2Cl_2$ (60 mL) at 0° C. was added 25 mL of trifluoroacetic acid. The solution was stirred at 0° C. for 1.5 h. The reaction was then quenched at room temperature with saturated aqueous $NaHCO_3$ solution (260 mL). The mixture was extracted with $CH_2Cl_2$ (1×300 mL). The combined organic layers were dried over $MgSO_4$ and concentrated to yield 5.90 g of crude regioisomeric olefins. To a solution of the crude olefins (5.90 g) in a 3:1 mixture of ethanol (135 mL) and 2,2,2-trifluoroethanol (40 mL) was added 10% Pd/C (4.50 g). The black slurry was stirred vigorously at room temperature under hydrogen (balloon pressure) for 72 h. The black slurry was then filtered over a pad of diatomaceous earth and washed with ethanol. The filtrate was concentrated, and the residue was purified by medium pressure chromatography [silica gel, 4% (3.5 M $NH_3$ in MeOH)/$CH_2Cl_2$] to give cis-(±)-4-(4-ethylbenzo[b]thiophen-2-yl)-2-methylpiperidine as a yellow semi-solid (2.37 g, 52%). IR ($CHCl_3$) 3100 (br) $cm^{-1}$. Ion Spray MS 260 $(M+H)^+$. $C_{16}H_{21}NS$

| analysis: | calculated | found |
|---|---|---|
| C | 74.08 | 74.06 |
| H | 8.16 | 8.15 |
| N | 5.40 | 5.53 |

Preparation of (±)-trans-4-(4-ethylbenzo[b]thiophen-2-yl)-2-methylpiperidine.

Scheme IA, steps B and C: To a solution of N-t-butoxycarbonyl-4-(4-ethylbenzo[b]thiophen-2-yl)-2-methyl-4-piperidinol (6.58 g, 17.5 mmol) in dry $CH_2Cl_2$ (60 mL) at 0° C. was added 25 mL of trifluoroacetic acid. The solution was stirred at 0° C. for 1.5 h. The reaction was then quenched at room temperature with saturated aqueous $NaHCO_3$ solution (260 mL). The mixture was extracted with $CH_2Cl_2$ (1×300 mL). The combined organic layers were dried over $MgSO_4$ and concentrated to yield 5.90 g of crude regioisomeric olefins. To a solution of the crude olefins (5.90 g) in a 3:1 mixture of ethanol (135 mL) and 2,2,2-trifluoroethanol (40 mL) was added 10% Pd/C (4.50 g). The black slurry was stirred vigorously at room temperature under hydrogen (balloon pressure) for 72 h. The black slurry was then filtered over a pad of diatomaceous earth and washed with ethanol. The filtrate was concentrated, and the residue was purified by medium pressure chromatography [silica gel, 4% (3.5 M $NH_3$ in MeOH)/$CH_2Cl_2$] to give trans-(±)-4-(4-ethylbenzo[b]thiophen-2-yl)-2-methylpiperidine as a yellow semi-solid (0.855 g, 19%). Ion Spray MS 260 $(M+H)^+$. $C_{16}H_{21}NS$

| analysis: | calculated | found |
|---|---|---|
| C | 74.08 | 73.86 |
| H | 8.16 | 8.18 |
| N | 5.40 | 5.62 |

Preparation of Final Title Compound.

Scheme IV, step B: A solution of (±)-cis-4-(4-ethylbenzo[b]thiophen-2-yl)-2-methylpiperidine (1.15 g, 4.43 mmol) and (2S4-glycidyloxy-2-methylindole (0.900 g, 4.43 mmol) in MeOH (58 mL) was heated at reflux for 24 h and then cooled and evaporated. The residue was purified by silica gel chromatography [0.5–1.5% (3.5 M $NH_3$ in MeOH)/$CH_2Cl_2$] to give the final title compound as an off-white foam (0.568 g, 28%). The hydrochloride salt was prepared with 1 equiv. of HCl in EtOAc. IR (KBr) 3399, 3350 (br) $cm^{-1}$. Ion Spray MS 463 $(M+H)^+$; 461 $(M-H)^-$ 521 $(M+CH_3COO^-)^-$. $[\ ]_D = -11.90$ (c 0.50, MeOH). $C_{28}H_{34}N_2O_2S$

| analysis: | calculated | found |
|---|---|---|
| C | 72.69 | 72.63 |
| H | 7.41 | 7.36 |
| N | 6.05 | 6.05 |

EXAMPLE 128

Preparation of (2S)-(+)-3-[(2S, 4S)-4-(4-Ethylbenzo[b]thiophen-2-yl)-2-methylpiperidin-1-yl]-1-(1H-2-methylindol-4-yl)oxy-2-propanol

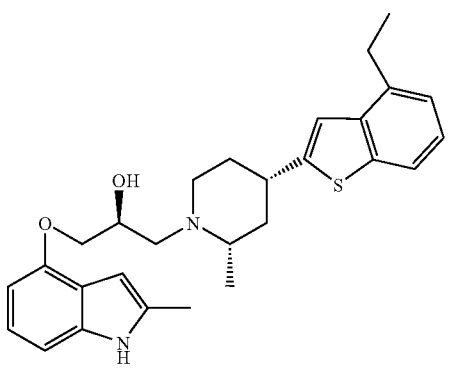

Scheme IV, step B: A solution of (±)-cis4-(4-ethylbenzo[b]thiophen-2-yl)-2-methylpiperidine (1.15 g, 4.43 mmol) and (2S)-4-glycidyloxy-2-methylindole (0.900 g, 4.43 mmol) in MeOH (58 mL) was heated at reflux for 24 h and then cooled and evaporated. The residue was purified by silica gel chromatography [0.5–1.5% (3.5 M $NH_3$ in MeOH)/$CH_2Cl_2$] to give the title compound as an off-white foam (0.713 g, 35%). The hydrochloride salt was prepared with 1 equiv. of HCl in EtOAc. IR (KBr) 3403, 3300 (br) $cm^{-1}$. Ion Spray MS 463 $(M+H)^+$; 461 $(M-H)^-$. $[\ ]_D = 26.03$ (c 0.46, MeOH). $C_{28}H_{34}N_2O_2S$

| analysis: | calculated | found |
|---|---|---|
| C | 72.69 | 72.49 |
| H | 7.41 | 7.36 |
| N | 6.05 | 6.04 |

EXAMPLE 129

Preparation of (2S)-3-[(2S,4R)4-(4-Ethylbenzo[b]thiophen-2-yl)-2-methylpiperidin-1-yl]-1-(1H-2-methylindol-4-yl)oxy-2-propanol

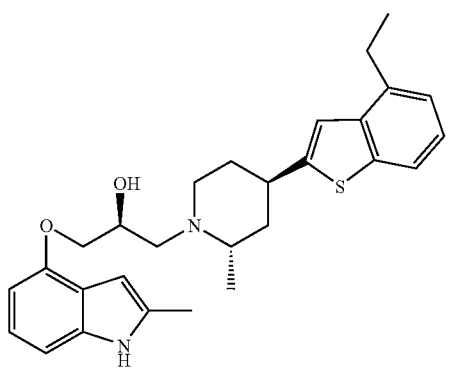

Scheme IV, step B: A solution of (±)-trans-4-(4-ethylbenzo[b]thiophen-2-yl)-2-methylpiperidine (0.511 g, 1.97 mmol) and (2S)-4-glycidyloxy-2-methylindole (0.400 g, 1.97 mmol) in MeOH (26 mL) was heated at reflux for 16 h and then cooled and evaporated. The residue was purified by silica gel chromatography [1% (3.5 M $NH_3$ in MeOH)/$CH_2Cl_2$] to give the title compound as a white foam (0.233 g, 26%). The hydrochloride salt was prepared with 1 equiv. of HCl in EtOAc. IR (KBr) 3399, 3300 (br) $cm^{-1}$. Ion Spray MS 463 (M+H)$^+$; 461 (M–H)$^-$. [ ]$_D$=0.00 (c 0.57, MeOH). $C_{28}H_{34}N_2O_2S$.HCl

| analysis: | calculated | found |
|---|---|---|
| C | 67.38 | 67.54 |
| H | 7.07 | 7.10 |
| N | 5.61 | 5.85 |

EXAMPLE 130

Preparation of (2S)-(+)-3-[(2R,4S)-4-(4-Ethylbenzo[b]thiophen-2-yl)-2-methylpiperidin-1-yl]-1-(1H-2-methylindol-4-yl)oxy-2-propanol

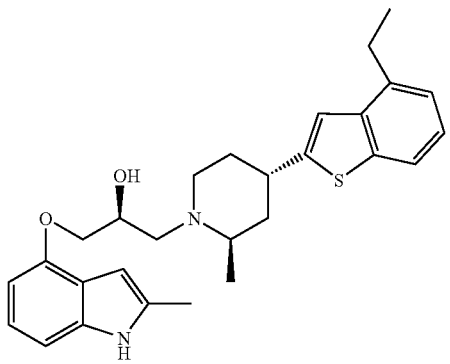

Scheme IV, step B: A solution of (±)-trans-4-(4-ethylbenzo[b]thiophen-2-yl)-2-methylpiperidine (0.511 g, 1.97 mmol) and (2S)-4-glycidyloxy-2-methylindole (0.400 g, 1.97 mmol) in MeOH (26 mL) was heated at reflux for 16 h and then cooled and evaporated. The residue was purified by silica gel chromatography [1% (3.5 M $NH_3$ in MeOH)/$CH_2Cl_2$] to give the title compound as a white foam (0.261 g, 29%). The hydrochloride salt was prepared with 1 equiv. of HCl in EtOAc. IR (KBr) 3400, 3250 (br) $cm^{-1}$. mp 153–158° C. Ion Spray MS 463 (M+H)$^+$; 461 (M–H)$^-$. [ ]$_D$=13.22 (c 0.61, MeOH). $C_{28}H_{34}N_2O_2S$.HCl.0.1$H_2O$

| analysis: | calculated | found |
|---|---|---|
| C | 67.14 | 66.80 |
| H | 7.08 | 7.14 |
| N | 5.59 | 5.60 |

EXAMPLE 131

Preparation of (2S)-(–)-3-[(2R;4R)-4-(4-Ethylbenzo[b]thiophen-2-yl)-2-methylpiperidin-1-yl]-1-(1H-indol-4-yl)oxy-2-propanol

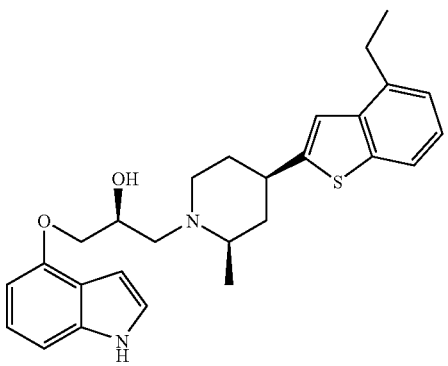

Scheme IV, step B: A solution of (±)-cis-4-(4-ethylbenzo[b]thiophen-2-yl)-2-methylpiperidine (1.17 g, 4.52 mmol) and (S)-4-(oxiranylmethoxy)indole (0.856 g, 4.52 mmol) in MeOH (59 mL) was heated at reflux for 18 h and then cooled and evaporated. The residue was purified by silica gel chromatography [0.75–2% (2.0 M $NH_3$ in MeOH)/$CH_2Cl_2$] to give the title compound as a white foam (0.712 g, 35%). The hydrochloride salt was prepared with 1 equiv. of HCl in EtOAc. IR (KBr) 3410, 3400 (br) $cm^{-1}$. Ion Spray MS 449 (M+H)$^+$; 447 (M–H)$^-$; 507 (M+$CH_3COO^-$)$^-$. [ ]$_D$=–13.70 (c 0.58, MeOH). $C_{27}H_{32}N_2O_2S$

| analysis: | calculated | found |
|---|---|---|
| C | 72.29 | 72.53 |
| H | 7.19 | 7.00 |
| N | 6.24 | 6.05 |

EXAMPLE 132

Preparation of (2S)-(+)-3-[(2S,4S)-4-(4-Ethylbenzo[b]thiophen-2-yl)-2-methylpiperidin-1-yl]-1-(1H-indol-4-yl)oxy-2-propanol

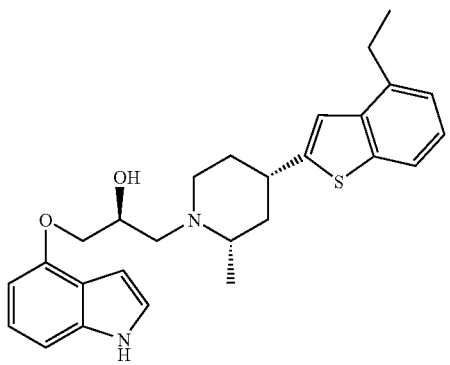

Scheme IV, step B: A solution of (±)-cis-4-(4-ethylbenzo[b]thiophen-2-yl)-2-methylpiperidine (1.17 g, 4.52 mmol) and (S)-4-(oxiranylmethoxy)indole (0.856 g, 4.52 mmol) in MeOH (59 mL) was heated at reflux for 18 h and then cooled and evaporated. The residue was purified by silica gel chromatography [0.75–2% (2.0 M $NH_3$ in MeOH)/$CH_2Cl_2$] to give the title compound as a white foam (0.498 g, 25%). The hydrochloride salt was prepared with 1 equiv. of HCl in EtOAc. IR (KBr) 3416, 3400 (br) $cm^{-1}$. Ion Spray MS 449 $(M+H)^+$; 447 $(M-H)^-$; 507 $(M+CH_3COO^-)^-$. $[\ ]_D$=25.64 (c 0.54, MeOH). $C_{27}H_{32}N_2O_2S$

| analysis: | calculated | found |
|---|---|---|
| C | 72.29 | 72.32 |
| H | 7.19 | 7.05 |
| N | 6.24 | 6.16 |

EXAMPLE 133

Preparation of (2S)-3-[(2S,4R)-4-(4-Ethylbenzo[b]thiophen-2-yl)-2-methylpiperidin-1-yl]-1-(1H-indol-4-yl)oxy-2-propanol

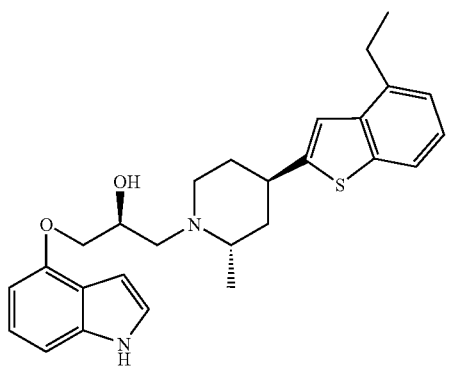

Scheme IV, step B: A solution of (±)-trans-4-(4-ethylbenzo[b]thiophen-2-yl)-2-methylpiperidine (0.462 g, 1.78 mmol) and (S)-4-(oxiranylmethoxy)indole (0.337 g, 1.78 mmol) in MeOH (24 mL) was heated at reflux for 18 h and then cooled and evaporated. The residue was purified by silica gel chromatography [1% (2.0 M $NH_3$ in MeOH)/$CH_2Cl_2$] to give the title compound as a white foam (0.286 g, 36%). The hydrochloride salt was prepared with 1 equiv. of HCl in EtOAc. IR (KBr) 3414, 3400 (br) $cm^{-1}$. Ion Spray MS 449 $(M+H)^+$; 447 $(M-H)^-$; 483 $(M+Cl)^-$; 507 $(M+CH_3COO^-)^-$. $[\ ]_D$=0.00 (C 0.57, MeOH). $C_{27}H_{32}N_2O_2S \cdot HCl$

| analysis: | calculated | found |
|---|---|---|
| C | 66.85 | 66.52 |
| H | 6.86 | 6.85 |
| N | 5.77 | 5.85 |

EXAMPLE 134

Preparation of (2S)-(+)-3-[(2R,4S)-4-(4-Ethylbenzo[b]thiophen-2-yl)-2-methylpiperidin-1-yl]-1-(1H-indol-4-yl)oxy-2-propanol

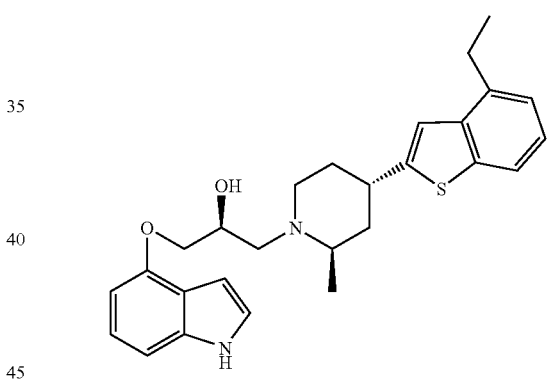

Scheme IV, step B: A solution of (±)-trans-4-(4-ethylbenzo[b]thiophen-2-yl)-2-methylpiperidine (0.462 g, 1.78 mmol) and (S)-4-(oxiranylmethoxy)indole (0.337 g, 1.78 mmol) in MeOH (24 mL) was heated at reflux for 18 h and then cooled and evaporated. The residue was purified by silica gel chromatography. [1% (2.0 M $NH_3$ in MeOH)/$CH_2Cl_2$] to give the title compound as a white foam (0.223 g, 28%). The hydrochloride salt was prepared with 1 equiv. of HCl in EtOAc. IR (KBr) 3416, 3400 (br) $cm^{-1}$. Ion Spray MS 449 $(M+H)^+$; 447 $(M-H)^-$; 507 $(M+CH_3COO^-)^-$. $[\ ]_D$=11.19 (c 0.54, MeOH). $C_{27}H_{32}N_2O_2S$

| analysis: | calculated | found |
|---|---|---|
| C | 72.29 | 72.01 |
| H | 7.19 | 7.14 |
| N | 6.24 | 6.13 |

EXAMPLE 135

Preparation of (2S)-3-[(2S,4R)-4-(4-Hydroxybenzo[b]thiophen-2-yl)-2-methylpiperidin-1-yl]-1-(1H-indol4-yl)oxy-2-propanol

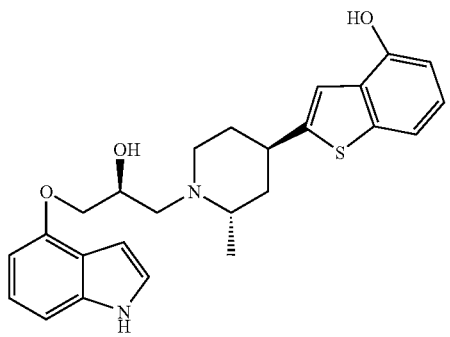

A solution of (2S)-3-[(2S,4R)-4-(4-methoxybenzo[b]thiophen-2-yl)-2-methylpiperidin-1-yl]-1-(1H-indol-4-yl)oxy-2-propanol (0.070 g, 0.155 mmol) and sodium thioethoxide (0.039 g, 0.464 mmol) in DMF (2 mL) was heated to 80° C. and stirred for 8 h. Another portion of sodium thioethoxide (0.039 g, 0.464 mmol) was added and the reaction was stirred at 80° C. for another 16 h. The reaction was cooled to room temperature and quenched with $H_2O$ (9 mL). The mixture was diluted with EtOAc (15 mL) and the layers were separated. The aqueous layer was extracted with EtOAc (1×30 mL). The combined organic layers were dried over $MgSO_4$, filtered and concentrated. The residue was purified by silica gel chromatography [4% (3.5 M $NH_3$ in MeOH)/$CH_2Cl_2$] to give the title compound as a white solid (0.035 g, 52%). The hydrochloride salt was prepared with 1 equiv. of HCl in EtOAc. Ion Spray MS 437 (M+H)$^+$; 435 (M−H)$^−$. $C_{25}H_{28}N_2O_3S.HCl.0.8H_2O$

| analysis: | calculated | found |
|---|---|---|
| C | 61.60 | 61.34 |
| H | 6.33 | 6.14 |
| N | 5.75 | 5.72 |

EXAMPLE 136

Preparation of (2S)-(+)-3-[(2R,4S)4-(4-Hydroxybenzo[b]thiophen-2-yl)-2-methylpiperidin-1-yl]-1-(1H-indol-4-yl)oxy-2-propanol

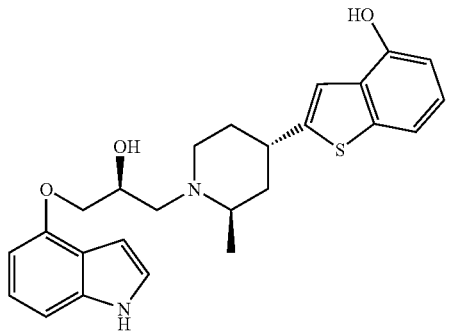

A solution of (2S)-(+)-3-[(2R,4S)-4-(4-methoxybenzo[b]thiophen-2-yl)-2-methylpiperidin-1-yl]-1-(1H-indol-4-yl)oxy-2-propanol (0.232 g, 0.515 mmol) and sodium thioethoxide (0.347 g, 4.12 mmol) in DMF (6.6 mL) was heated to 80° C. and stirred for 16 h. The reaction was cooled to room temperature and quenched with $H_2O$ (18 mL). The aqueous layer was extracted with EtOAc (3×50 mL). The combined organic layers were dried over $MgSO_4$, filtered and concentrated. The residue was purified by silica gel chromatography [4% (3.5 M $NH_3$ in MeOH)/$CH_2Cl_2$] to give the title compound as an off-white solid (0.109 g, 49%). The hydrochloride salt was prepared with 1 equiv. of HCl in EtOAc. IR (KBr) 3401, 3350 (br) cm$^{-1}$. Ion Spray MS 437 (M+H)$^+$; 435 (M−H)$^−$. [ ]$_D$=11.70 (c 0.51, MeOH). $C_{25}H_{28}N_2O_3S.0.1H_2O$

| analysis: | calculated | found |
|---|---|---|
| C | 68.50 | 68.25 |
| H | 6.48 | 6.52 |
| N | 6.39 | 6.24 |

EXAMPLE 137

Preparation of (2S)-(+)-3-[(2R,4R)-4-(4-Hydroxybenzo[b]thiophen-2-yl)-2-methylpiperidin-1-yl]-1-(1H-indol-4-yl)oxy-2-propanol

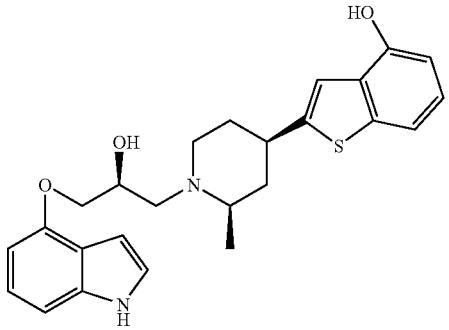

Preparation of cis-(±)-4-(4-Hydroxybenzo[b]thiophen-2-yl)-2-methylpiperidine.

A solution of cis-( )-4-(4-methoxybenzo[b]thiophen-2-yl)-2-methylpiperidine (1.01 g, 3.86 mmol) and ethanethiol (2.28 mL, 30.86 mmol) in dichloroethane (38 mL) was treated with $AlCl_3$ (2.06 g, 15.45 mmol). After stirring for 6 h, the slurry was poured into a solution of saturated aqueous Rochelle's salt (potassium sodium tartrate, 100 mL), MeOH (5 mL), and 2 N NaOH (50 mL), and then extracted with $CH_2Cl_2$ (3×100 mL). The organic layers were dried over $MgSO_4$, filtered and concentrated under reduced pressure. The residue was purified by silica gel chromatography [0 to 20% (2.0 M $NH_3$ in MeOH)/$CH_2Cl_2$] to give cis-(±)-4-(4-hydroxybenzo[b]thiophen-2-yl)-2-methylpiperidine as an off-white powder (0.4704 g, 49%).

IR (KBr) 3278, 2938, 1571, 1450, 1247,763 cm$^{-1}$. Ion Spray MS 248.3 (M+H)$^-$, 246.3 (M−H)$^-$, 493.2 (2M−H)$^-$. $C_{14}H_{17}NOS$

| analysis | calculated | found |
|---|---|---|
| C | 67.97 | 67.63 |
| H | 6.92 | 7.03 |
| N | 5.66 | 5.70 |

Preparation of Final Title Compound.

Scheme IV, step B: A solution of cis-(±)-4-(4-hydroxybenzo[b]thiophen-2-yl)-2-methylpiperidine (0.218 g, 0.884 mmol) and (2S)-4-glycidyloxyindole (0.1672 g, 0.884 mmol) in MeOH (12 mL) was heated at reflux for 19 h and then cooled and evaporated. The residue was purified by silica gel chromatography [2 to 9% (2.0 M $NH_3$ in MeOH)/$CH_2Cl_2$] to give the final title compound as a transparent solid (0.1615 g, 42%). The hydrochloride salt was prepared by dripping 1 equivalent of 1.0 M HCl in ether into a solution of the free base in 2 mL of EtOAc. mp 164.5° C. (dec). IR (KBr) 3397, 2927, 1276, 1089 cm$^{-1}$. Ion Spray MS 437.2 (M+H)$^+$. [ ]$_D$=−27.26 (c 0.587, MeOH). $C_{25}H_{28}N_2O_3S \cdot 0.2CH_2Cl_2$

| analysis | calculated | found |
|---|---|---|
| C | 66.73 | 67.00 |
| H | 6.31 | 6.43 |
| N | 6.18 | 6.20 |

EXAMPLE 138

Preparation of (2)-(−)-3-[(2S,4S)-4-(4-Hydroxybenzo[b]thiophen-2-yl)-2-methylpiperidin-1-yl]-1-(1H-indol-4-yl)oxy-2-propanol

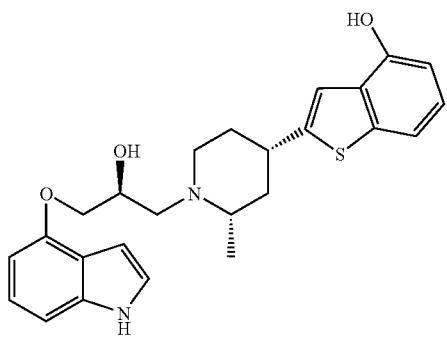

Scheme IV, step B: A solution of cis-(±)-4-(4-hydroxybenzo[b]thiophen-2-yl)-2-methylpiperidine (0.218 g, 0.884 mmol) and (2S)-4-glycidyloxyindole (0.1672 g, 0.884 mmol) in MeOH (12 mL) was heated at reflux for 19 h and then cooled and evaporated. The residue was purified by silica gel chromatography [2 to 9% (2.0 M $NH_3$ in MeOH)/$CH_2Cl_2$] to give the title compound as a transparent solid (0.1579 g, 41%). The hydrochloride salt was prepared by dripping 1 equivalent of 1.0 M HCl in ether, into a solution of the free base in 2 mL of EtOAc. mp 160.2° C. (dec). IR (KBr) 3407, 2926, 1242, 1086 cm$^{-1}$. Ion Spray MS 437.2 (M+H)$^+$; 435.4 (M−H)$^-$. [ ]$_D$=−9.9 (c 0.606, MeOH). $C_{25}H_{28}N_2O_3S \cdot 0.2CH_2Cl_2$

| analysis | calculated | found |
|---|---|---|
| C | 66.73 | 66.49 |
| H | 6.31 | 6.39 |
| N | 6.18 | 6.15 |

EXAMPLE 139

Preparation of (2S)-(−)-3-[(2R,4R)-4-(4-Hydroxybenzo[b]thiophen-2-yl)-2-methylpiperidin-1-yl]-1-(1H-2-methylindol-4-yl)oxy-2-propanol

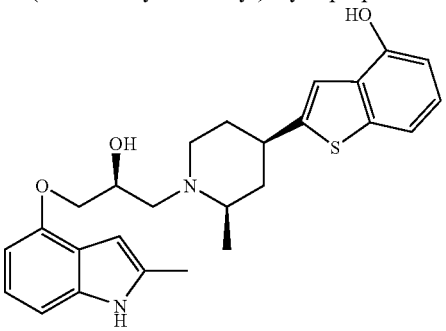

Scheme IV, step B: A solution of cis-(±)-4-(4-hydroxybenzo[b]thiophen-2-yl)-2-methylpiperidine (0.214 g, 0.865 mmol) and (2S)-4-glycidyloxy-2-methylindole (0.175 g, 0.865 mmol) in MeOH (40 mL) was heated at reflux for 40 h and then cooled and evaporated. The residue was purified by silica gel chromatography [2 to 25% (2.0 M $NH_3$ in MeOH)/$CH_2Cl_2$] to give the title compound as an off-white solid (0.1589 g, 41%). The hydrochloride salt was prepared by dripping 1 equivalent of 1.0 M HCl in ether into a solution of the free base in MeOH. mp 145.8° C. (dec). IR (KBr) 3473, 3008, 1246, cm$^{-1}$. Ion Spray MS 451.2 (M+H)$^+$; 449.1 (M−H)$^-$. [ ]$_D$=−11.98 (c 0.501, MeOH). $C_{26}H_{30}N_2O_3S \cdot 0.4CH_2Cl_2$

| analysis | calculated | found |
|---|---|---|
| C | 65.44 | 65.59 |
| H | 6.41 | 6.36 |
| N | 5.78 | 6.17 |

EXAMPLE 140

Preparation of (2S)-(+)-3-[(2S,4S)-4-(4-Hydroxybenzo[b]thiophen-2-yl)-2-methylpiperidin-1-yl]-1-(1H-2-methylindol-4-yl)oxy-2-propanol

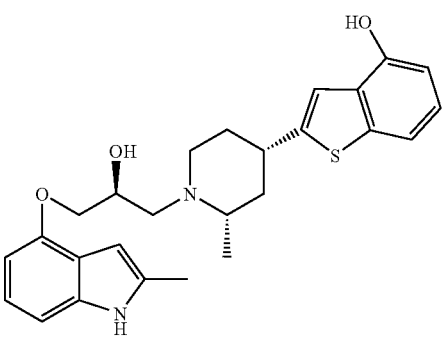

Scheme IV, step B: A solution of cis-(+)-4-(4-hydroxybenzo[b]thiophen-2-yl)-2-methylpiperidine (0.214 g, 0.865 mmol) and (2S)4-glycidyloxy-2-methylindole (0.175 g, 0.865 mmol) in MeOH (40 mL) was heated at reflux for 40 h and then cooled and evaporated. The residue was purified by silica gel chromatography [2 to 25% (2.0 M $NH_3$ in MeOH)/$CH_2Cl_2$] to give the title compound as an off-white solid (0.1589 g, 41%). The hydrochloride salt was prepared by dripping 1 equivalent of 1.0 M HCl in ether into a solution of the free base in MeOH. mp 150.2° C. (KBr) 3473, 2936, 1246 cm$^{-1}$. Ion Spray MS 451.2 (M+H)$^+$; 449.1 (M−H)$^-$. [ ]$_D$=27.72 (c 0.505, MeOH). $C_{26}H_{30}N_2O_3S \cdot 0.1H_2O \cdot 0.2CH_2Cl_2$

| analysis | calculated | found |
|---|---|---|
| C | 67.04 | 66.84 |
| H | 6.57 | 6.52 |
| N | 5.97 | 6.24 |

EXAMPLE 141

Preparation of (2S)-(+)-3-[(2S,4R)-4-(4-Hydroxybenzo[b]thiophen-2-yl)-2-methylpiperidin-1-yl]-1-(1H-2-methylindol-4-yl)oxy-2-pronanol.

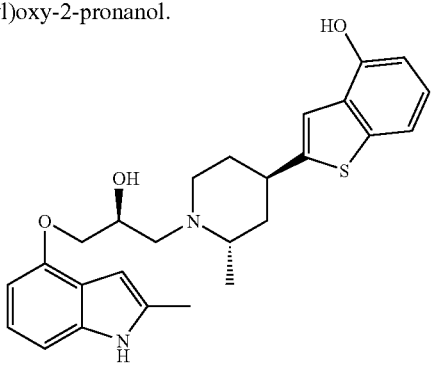

A solution of (2S)-(−)-3-[(2S,4R)-4-(4-methoxybenzo[b]thiophen-2-yl)-2-methylpiperidin-1-yl]-1-(1H-2-methylindol-4-yl)oxy-2-propanol (0.2903 g, 0.624 mmol) and sodium ethanethiolate (0.840 g, 9.99 mmol) in DMF (10 mL) was heated at reflux for 16 h and then cooled and evaporated. The residue was diluted with 25 mL of saturated aqueous NaHCO$_3$ and extracted with CH$_2$Cl$_2$ (2×25 mL). The organic layers were dried over MgSO$_4$, filtered and concentrated under reduced pressure. The residue was purified by silica gel chromatography [2 to 12% (2.0 M NH$_3$ in MeOH)/CH$_2$Cl$_2$] to give the title compound as an off-white foam (0.0904 g, 32%). The hydrochloride salt was prepared by dripping 1 equivalent of 1.0 M HCl in ether into a solution of the free base in MeOH (2 mL). IR (KBr) 3472, 2936, 1246 cm$^{-1}$. Ion Spray MS 449.1 (M−H)$^-$. [ ]$_D$=2.47 (c 0.809, MeOH). C$_{26}$H$_{30}$N$_2$O$_3$S.0.4CH$_2$Cl$_2$

| analysis | calculated | found |
|---|---|---|
| C | 65.44 | 65.71 |
| H | 6.41 | 6.52 |
| N | 5.78 | 5.59 |

EXAMPLE 142

Preparation of (2S)-(+)-3-[(2R,4S)-4-(4-Hydroxybenzo[b]thiophen-2-yl)-2-methylpiperidin-1-yl]-1-(1H-2-methylindol4-yl)oxy-2-propanol

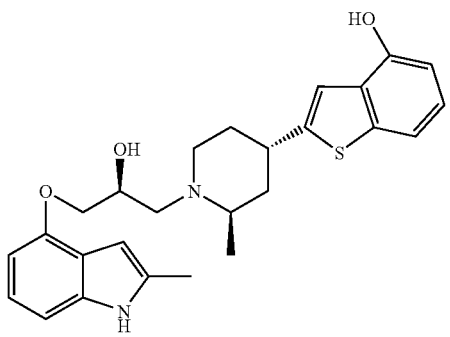

A solution of (2S)-(−)-3-[(2R,4S)-4-(4-methoxybenzo[b]thiophen-2-yl)-2-methylpiperidin-1-yl]-1-(1H-2-methylindol-4-yl)oxy-2-propanol (0.300 g, 0.645 mmol) and sodium ethanethiolate (0.650 g, 7.74 mmol) in DMF (10 mL) was heated at reflux for 55 h and then diluted with 50 mL of brine and 50 mL H$_2$O. The solution was then extracted with EtOAc (3×50 mL). The organic layers were washed with 50/50 mixture of brine and H$_2$O (4×75 mL). The organic layers were then dried over MgSO$_4$, filtered and concentrated under reduced pressure. The residue was purified by silica gel chromatography [3% (2.0 M NH$_3$ in MeOH)/CH$_2$Cl$_2$] to give the title compound as a yellow solid (0.1071 g, 37%). The hydrochloride salt was prepared by dripping 1 equivalent of 1.0 M HCl in ether into a solution of the free base in MeOH (2 mL). mp 131.4° C. IR (KBr) 3473, 3008, 2936, 1245 cm$^{-1}$. Ion Spray MS 451.2 (M+H)$^+$; 449.2 (M−H)$^-$. [ ]$_D$=12 (c 0.500, MeOH). C$_{26}$H$_{30}$N$_2$O$_3$S.0.8H$_2$O

| analysis | calculated | found |
|---|---|---|
| C | 67.16 | 66.94 |
| H | 6.85 | 6.65 |
| N | 6.02 | 6.09 |

EXAMPLE 143

Preparation of (2S)-3-[(2S,4R)-4-(7-t-Butyl-4-methoxybenzo[b]thiophen-2-yl)-2-methylpiperidin-1-yl]-1-(1H-2-methylindol-4-yl)oxy-2-propanol

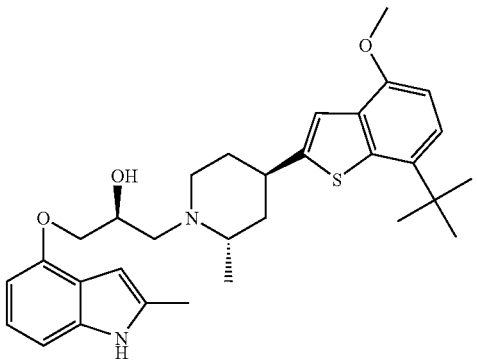

Scheme IV, step B: A solution of trans-( )-4-(4-methoxybenzo[b]thiophen-2-yl)-2-methylpiperidine (2.03 g, 7.78 mmol) and (2S)-4-glycidyloxy-2-methylindole (1.58 g, 7.78 mmol) in MeOH (100 mL) was heated at reflux for 15 h and then cooled and evaporated. The residue was purified by silica gel chromatography [1% (2.0 M NH$_3$ in MeOH)/CH$_2$Cl$_2$]and then by reverse phase chromatography [40% CH$_3$CN/60% 0.01 N HCl]. The fractions collected and concentrated were taken up in 30 mL of CH$_2$Cl$_2$ and 30 mL 2.0 N NaOH, and then extracted with CH$_2$Cl$_2$ (3×30 mL). The organic layers were dried over MgSO$_4$, filtered and concentrated under reduced pressure to give the title compound (0.0292 g, 0.8%). The hydrochloride salt was prepared by dripping 1 equivalent of 1.0 M HCl in ether into a solution of the free base in EtOAc (2 mL). Ion Spray MS 521.2 (M+H)$^+$. C$_{31}$H$_{40}$N$_2$O$_3$S.1.0HCl.0.7H$_2$O

| analysis | calculated | found |
|---|---|---|
| C | 65.34 | 65.13 |
| H | 7.50 | 7.33 |
| N | 4.92 | 4.73 |

EXAMPLE 144

Preparation of (2S)-3-[2,2-Dimethyl-4-(4-methoxybenzo[b]thiophen-2-yl)piperidin-1-yl]-1-(1H-2-methylindol-4-yl)oxy-2-propanol

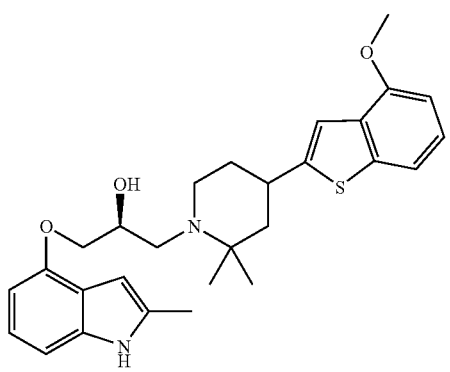

Preparation of 2,2-Dimethyl-4-(4-methoxybenzo[b]thiophen-2-yl)piperidine.

A solution of cis-(±)-4-(4-methoxybenzo[b]thiophen-2-yl)-2-methylpiperidine in THF (35 mL) was cooled to 0° C. (ice-water bath), then treated with NCS (2.26 g, 16.94 mol). After stirring 15 minutes, the ice-water bath was removed and the mixture was stirred at room temperature for 45 minutes. The mixture was then concentrated under reduced pressure and diluted with Et$_2$O (100 mL), saturated aqueous NaHCO$_3$ (50 mL) and H$_2$O (50 mL). The mixture was shaken and partitioned in a separatory funnel. The aqueous layer was separated and extracted once with Et$_2$O. The combined organic layers were washed once with H$_2$O (50 mL), dried over MgSO$_4$, filtered and concentrated under reduced pressure to give the cis-(±)-N-chloro-4-(4-methoxybenzo[b]thiophen-2-yl)-2-methylpiperidine as a yellow oil (4.78 g, 99%).

A solution of the crude cis-(±)-N-chloro-4-(4-methoxybenzo[b]thiophen-2-yl)-2-methylpiperidine (2.348 g, 7.93 mmol) in THF (80 mL) was treated with DBU (1.18 mL, 7.93 mmol). After stirring 17 h, the DBU salt was filtered off through a sintered funnel, rinsed with Et$_2$O, and the filtrate was concentrated under reduced pressure to give 4-(4-methoxybenzo[b]thiophen-2-yl)-2-methyl-3,4,5,6-tetrahydropyridine as a golden oil (2. 3 g, 99%) that was immediately used in the next step.

To a solution of the crude 4-(4-methoxybenzo[b]thiophen-2-yl)-2-methyl-3,4,5,6-tetrahydropyridine (2.19 g, 8.44 mmol) in THF (38 mL) cooled to −78° C. in a dry ice/acetone bath, was added dropwise BF$_3$Et$_2$O (48%) (3.34 mL, 12.6 mmol) via a syringe. After stirring ten minutes, the solution was treated with 24.1 mL (33.77 mmol) of 1.4 M MeLi. The mixture was stirred for 16 h, then quenched with 100 mL of saturated aqueous NH$_4$Cl and 50 mL of H$_2$O. The mixture was then extracted with CH$_2$Cl$_2$ (3×100 mL). The organic layers were dried over MgSO$_4$, filtered and concentrated under reduced pressure. The residue was purified by silica gel chromatography [2.5 to 7% (2.0 M NH$_3$ in MeOH)/CH$_2$Cl$_2$] to give the title compound as an orange oil (0.713 g, 30%). IR (KBr) 2936, 1571, 1471, 1259, 1049 cm$^{-1}$. Ion Spray MS 276.2 (M+H)$^+$. [ ]$_D$=0 (c 0.578, MeOH). C$_{16}$H$_{21}$NOS.0.1H$_2$O0.1CH$_2$Cl$_2$

| Analysis | calculated | found |
|---|---|---|
| C | 67.68 | 0.02 |
| H | 7.55 | 0.18 |
| N | 4.90 | 0.17 |

Preparation of Final Title Compound.

Scheme IV, step B: A solution of 2,2-dimethyl-4-(4-methoxybenzo[b]thiophen-2-yl)piperidine (0.352 g, 1.27 mmol) and (2S)-4-glycidyloxy-2-methylindole (0.259 g, 1.27 mmol) in MeOH (20 mL) was heated at reflux for 16 h and then cooled and evaporated. The residue was purified by silica gel chromatography [1.5% (2.0 M NH$_3$ in MeOH)/CH$_2$Cl$_2$] to give the title compound as a yellow foam (0.2719 g, 44%). The hydrochloride salt was prepared by dripping 1 equivalent of 1.0 M HCl in ether into a solution of the free base in EtOAc (3 mL). mp 142.6° C. IR (KBr) 3473, 3008, 2965,1258, 1247 cm$^{-1}$. Ion Spray MS 479.2 (M+H)$^+$; 477.3 (M−H)$^-$; 537.4(M+CH$_3$COO$^-$)$^-$. [ ]$_D$=0 (c 0.510, MeOH). C$_{28}$H$_{34}$N2O$_3$S.1.0HCl.0.6H$_2$O

| analysis | calculated | found |
|---|---|---|
| C | 63.78 | 63.50 |
| H | 6.97 | 6.61 |
| N | 5.29 | 5.32 |

EXAMPLE 145

Preparation of (2S)-(+)3-[2,2-Dimethyl-4-(4-methoxybenzo[b]thiophen-2-yl)piperidin-1-yl]-1-(1H-2-methylindol-4-yl)oxy-2-propanol

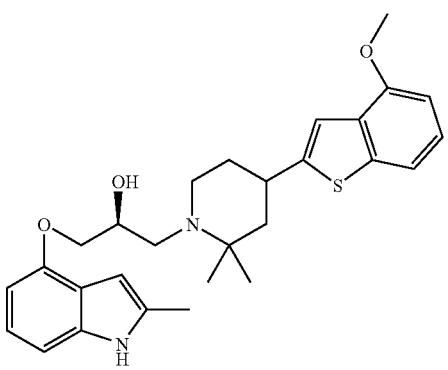

Scheme IV, step B: A solution of 2,2-dimethy-4-(4-methoxybenzo[b]thiophen-2-yl)piperidine (0.352 g, 1.27 mmol) and (2S)-4-glycidyloxy-2-methylindole (0.259 g, 1.27 mmol) in MeOH (20 mL) was heated at reflux for 16 h and then cooled and evaporated. The residue was purified by silica gel chromatography [1.5% (2.0 M NH₃ in MeOH)/CH₂Cl₂] to give the title compound as an orange solid (0.246 g, 40%). The hydrochloride salt was prepared by dripping 1 equivalent of 1.0 M HCl in ether into a solution of the free base in EtOAc (3 mL). mp 99.5° C. IR (KBr) 3473, 3008, 2937, 1258, 1246 cm⁻¹. Ion Spray MS 479.3 (M+H)⁺; 477.2 (M−H)⁻; 457.5 (M+CH₃COO⁻)⁻. [ ]$_D$=39.22 (c 0.510, MeOH). $C_{28}H_{34}N_2O_3S \cdot 0.2CH_2Cl_2$

| analysis | calculated | found |
|---|---|---|
| C | 68.34 | 68.03 |
| H | 7.00 | 6.97 |
| N | 5.65 | 5.86 |

EXAMPLE 146

Preparation of (2S)-3-[2,2-Dimethyl-4-(4-hydroxybenzo[b]thiophen-2-yl)piperidin-1-yl]-1-(1H-2-methylindol-4-yl)oxy-2-propanol

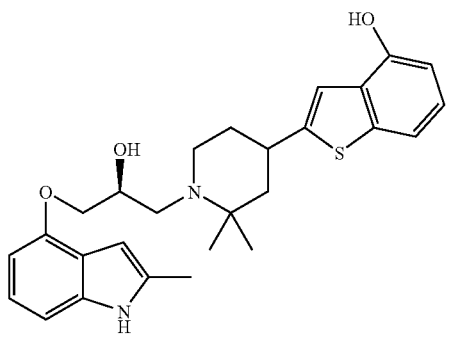

A solution of (2S)-3-[2,2-dimethyl-4-(4-methoxybenzo[b]thiophen-2-yl)piperidin-1-yl]-1-(1H-2-methylindol4-yl)oxy-2-propanol (0.6452 g, 1.34 mmol) and sodium ethanethiolate (1.81 g, 21.56 mmol) in DMF (22 mL) was heated at reflux for 20 h, and concentrated under reduced pressure The residue was diluted with 100 mL of saturated aqueous NaHCO₃ and 75 mL of CH₂Cl₂. After separating the layers, the aqueous layer was extracted with CH₂Cl₂ (2×75 mL). Combined organic layers were then dried over MgSO₄, filtered and concentrated under reduced pressure. The residue was purified by silica gel chromatography [1 to 4.5% (2.0 M NH₃ in MeOH)/CH₂Cl₂] to give the title compound as a brown foam (0.3014 g, 48%). The hydrochloride salt was prepared by dripping 1 equivalent of 1.0 M HCl in ether into a solution of the free base in MeOH (2 mL). mp 172.9° C. IR (KBr) 3591, 3472, 3008, 2931, 1246 cm⁻. Ion Spray MS 465.2 (M+H)+; 463.3 (M−H)⁻. [ ]$_D$=0 (c 0.487, MeOH). $C_{27}H_{32}N_2O_3S \cdot 0.3CH_2Cl_2$

| analysis | calculated | found |
|---|---|---|
| C | 66.90 | 66.86 |
| H | 6.70 | 6.80 |
| N | 5.72 | 5.58 |

EXAMPLE 147

Preparation of (2S)-(+)-3-[2,2-Dimethyl-4-(4-hydroxybenzo[b]thiophen-2-yl)piperidin-1-yl]-1-(1H-2-methylindol-4-yloxy-2-propanol

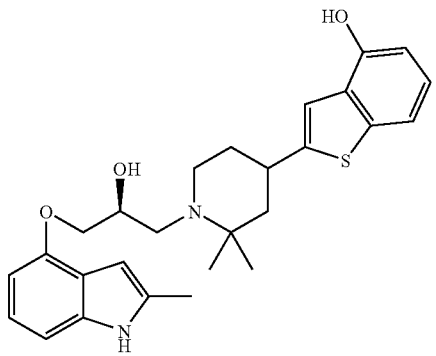

A solution of (2S)-3-[2,2-dimethyl-4-(4-methoxybenzo[b]thiophen-2-yl)piperidin-1-yl]-1-(1H-2-methylindol-4-yl)oxy-2-propanol (0.7319 g, 1.52 mmol) and sodium ethanethiolate (2.05 g, 24.4 mmol) in DMF (25 mL) was heated at reflux for 20 h, and concentrated under reduced pressure. The residue was diluted with 75 mL of saturated aqueous NaHCO₃ and 75 mL of CH₂Cl₂. After separating the layers, the aqueous layer was extracted with CH₂Cl₂ (2×75 mL). Combined organic layers were then dried over MgSO₄, filtered and concentrated under reduced pressure. The residue was purified by silica gel chromatography [1 to 10% (2.0 M NH₃ in MeOH)/CH₂Cl₂] to give the title compound as a tan solid (0.200 g, 28%). IR (KBr) 3473, 3018, 2933, 1245 cm⁻¹. Ion Spray MS 465.2 (M+H)⁺; 463.3 (M−H)⁺. [ ]$_D$=38.86 (c 0.5147, MeOH). $C_{27}H_{32}N_2O_3S \cdot 0.4CH_2Cl_2$

| analysis | calculated | found |
|---|---|---|
| C | 66.00 | 66.22 |
| H | 6.63 | 6.85 |
| N | 5.62 | 5.59 |

EXAMPLE 148

Preparation of cis-(2S )-1-(4-(2-Methyl)indolyloxy)-3-(4-(5-benzo[b]thiophenyl)-2-methylpiperidine-1-yl)-2-propanol Isomer 1 Succinate.

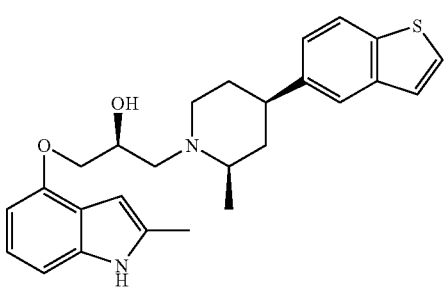

Preparation of 4-Hydroxy-4-(5-benzo[b]thiophenyl)-2-methyl-1-t-butyloxycarbonyl-piperidine.

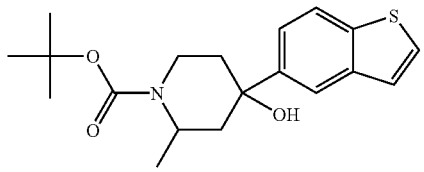

To a solution of 5-bromobenzothiophene (prepared according to J. Het. Chem. 1988, 25, 1271) (14.332 g, 67.3 mmol) in diethyl ether (300 mL) was added magnesium (3.27 g, 135 mmol) and 1,2-dibromoethane (5.8 mL, 67.3 mmol). The mixture was refluxed for 4 hours then cooled to 20° C. for 18 hours. A solution of 1-t-butyloxycarbonyl-2-methyl-4-piperidone (15.78 g, 73.98 mmol) in tetrahydrofuran (75 mL) was added dropwise to the mixture. The mixture was stirred for 24 hours then diluted with saturated ammonium chloride and extracted with ethyl acetate three times. The combined organics were dried over sodium sulfate and then filtered and evaporated. The residue was purified using silica gel chromatography (dichloromethane/7% methanol in dichloromethane gradient eluent) to give 12.74 g (55%) of the intermediate title compound as a yellow amorphous solid. FDMS m/e=348 ($M^+$+1).

Preparation of 4-(5-Benzo[b]thiophenyl)-2-methyl piperidin-3-ene.

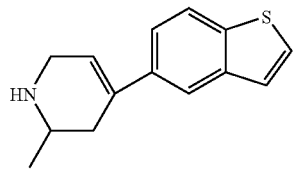

4-Hydroxy-4-(5-benzo[b]thiophenyl)-2-methyl-1-t-butyloxycarbonyl-piperidine (12.7 g, 36.5 mmol) was suspended in toluene (300 mL) and p-toluenesulphonic acid hydrate (20.9 g, 0.110 mol) was added. The mixture was refluxed for 3 hours then cooled to room temperature. The mixture was evaporated and the residue was diluted with 2N sodium hydroxide then extracted 3 times with ethyl acetate. The combined organics were dried over sodium sulfate, filtered and evaporated to give the intermediate title compound as a yellow amorphous solid (6.310 g, 75%). FDMS m/e=230 ($M^+$+1).

Preparation of 4-(5-Benzo[b]thiophenyl)-2-methyl piperidine.

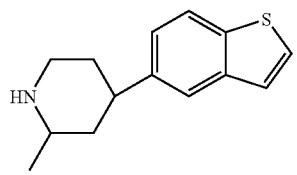

To a solution of 4-(5-benzo[b]thiophenyl)-2-methyl piperidin-3-ene (6.28 g, 27.4 mmol) in methanol (175 mL) was added 3% palladium on polyethylenimine/$SiO_2$ (6.25 g). The mixture was hydrogenated on a PARR shaker at 50° C. and 70 psi for 24 hours. At this time another 6 g of 3% palladium on polyethylenimine/$SiO_2$ was added and the mixture was hydrogenated for 48 hours at 50° C. and 65 psi. The mixture was cooled and then filtered and the catalyst was washed with boiling methanol. The combined organics were evaporated and the residue was purified using silica gel chromatography (dichloromethane/7% methanol, 0.35 M ammonia in dichloromethane gradient elution) to give the intermediate title compound as two yellow oils.

Isomer 1 (cis isomer, 1.445 g, 23%). FDMS m/e=232 ($M^+$+1).

Isomer 2 (trans isomer, 1.273 g, 20%). FDMS m/e=232 ($M^+$+1).

Preparation of Final Title Compound.

A solution cis-4-(5-benzo[b]thiophenyl)-2-methylpiperidine (1.44 g, 6.22 mmol, isomer 1) and (S)-(+)-4-(oxiranylmethoxy)-2-methyl-1H-indole (1.26 g, 6.22 mmol) in methanol (30 mL) was refluxed for 19 hours and then cooled and evaporated. The residue was purified using silica gel chromatography (dichloromethane/5% methanol, 0.35M ammonia in dichloromethane gradient elution) to give two yellow amorphous solids. The succinate salt of isomer 1 was prepared to give the title compound.

Isomer 1 (1.197 g, 44%, free base). FDMS m/e=435 ($M^+$+1 of free base). $[D]_{589}$=−11.15 (c=0.538, methanol). $C_{26}H_{30}N_2O_2S \cdot C_4H_6O_4$.

| analysis: | calculated | found |
|---|---|---|
| C | 65.20 | 65.44 |
| H | 6.57 | 6.50 |
| N | 5.07 | 5.03 |

EXAMPLE 149

Preparation of cis-(2S)-1-(4-(2-Methyl)indolyloxy)-3-(4-(2-naphthyl)-2-methylpiperidine-1-yl)-2-propanol Isomer 1 Oxalate.

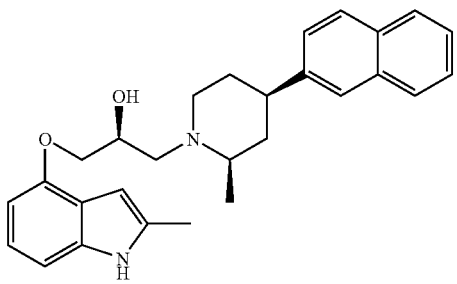

A solution cis-4-(2-naphthyl)-2-methyl piperidine (0.191 g, 0.848 mmol, isomer 1) and (S)-(+)-4-(oxiranylmethoxy)-2-methyl-1H-indole (0.172 g, 0.848 mmol) in methanol (10 mL) was refluxed for 20 hours and then cooled and evaporated. The residue was purified using silica gel chromatography (dichloromethane/2% methanol, 0.15M ammonia in dichloromethane gradient elution) to give two clear colorless oils. The oxalate salt was prepared of isomer 1 to give the title compound.

Isomer 1 (0.118 g, 33%, free base). FDMS m/e=429 ($M^+$+1 of free base). $C_{28}H_{32}N_2O_2 \cdot C_2H_2O_4$.

| analysis: | calculated | found |
|---|---|---|
| C | 69.48 | 69.61 |
| H | 6.61 | 6.42 |
| N | 5.40 | 5.63 |

Serotonin $1_A$ Receptor Activity

The compounds of the present invention are active at the serotonin $1_A$ receptor, particularly as antagonists and as partial agonists at that receptor, and are distinguished by their selectivity. It is now well understood by pharmacologists and physicians that pharmaceuticals which have a single physiological activity, or which are much more active in the desired activity than in their other activities, are much more desirable for therapy than are compounds which have multiple activities at about the same dose.

The 5-$HT_{1A}$ receptor binding potency of the present compounds are measured by a modification of the binding assay described by Taylor, et al. (*J. Pharmacol. Exp. Ther.* 236, 118–125, 1986); and Wong, et al., *Pharm. Biochem. Behav.* 46, 173–77 (1993). Membranes for the binding assay are prepared from male Sprague-Dawley rats (150–250 g). The animals are killed by decapitation, and the brains are rapidly chilled and dissected to obtain the hippocampi. Membranes from the hippocampi are either prepared that day, or the hippocampi are stored frozen (−70° C.) until the day of preparation. The membranes are prepared by homogenizing the tissue in 40 volumes of ice-cold Tris-HCl buffer (50 mM, pH 7.4 at 22° C.) using a homogenizer for 15 sec., and the homogenate is centrifuged at 39800×g for 10 min. The resulting pellet is then resuspended in the same buffer, and the centrifugation and resuspension process is repeated three additional times to wash the membranes. Between the second and third washes the resuspended membranes are incubated for 10 min. at 37° C. to facilitate the removal of endogenous ligands. The final pellet is resuspended in 67 mM Tris-HCl, pH 7.4, to a concentration of 2 mg of tissue original wet weight/200 μL. This homogenate is stored frozen (−70° C.) until the day of the binding assay. Each tube for the binding assay has a final volume of 800 μL and contains the following: Tris-HCl (50 mM), pargyline (10 μM), $CaCl_2$ (3 mM), [$^3$H]8-OH-DPAT (1.0 nM), appropriate dilutions of the drugs of interest, and membrane resuspension equivalent to 2 mg of original tissue wet weight, for a final pH of 7.4. The assay tubes are incubated for either 10 min. or 15 min. at 37° C., and the contents are then rapidly filtered through GF/B filters (pretreated with 0.5% polyethylenimine), followed by four one-mL washes with ice-cold buffer. The radioactivity trapped by the filters is quantitated by liquid scintillation spectrometry, and specific [$^3$H]8-OH-DPAT binding to the 5-$HT_{1A}$ sites is defined as the difference between [$^3$H]8-OH-DPAT bound in the presence and absence of 10 μM 5-HT.

$IC_{50}$ values, i.e., the concentration required to inhibit 50% of the binding, are determined from 12-point competition curves using nonlinear regression (SYSTAT, SYSTAT, Inc., Evanston, Ill.). $IC_{50}$ values are converted to $K_i$ values using the Cheng-Prusoff equation (*Biochem. Pharmacol.* 22, 3099–3108 (1973).

Additional binding assays of some of the present compounds are carried out by an assay method which uses a cloned cell line which expresses the serotonin $1_A$ receptor, rather than the hippocampal membranes. Such cloned cell lines have been described by Fargin, et al., *J. Bio. Chem.,* 264, 14848–14852 (1989), Aune, et al., *J. Immunology,* 151, 1175–1183 (1993), and Raymond, et al., *Naunyn-Schmiedeberg's Arch. Pharmacol.,* 346,127–137 (1992). Results from the cell line assay are substantially in agreement with results from the hippocampal membrane assay.

As was reported by R. L. Weinshank, et al., WO93/14201, the 5-$HT_{1A}$ receptor is functionally coupled to a G-protein as measured by the ability of serotonin and serotonergic drugs to inhibit forskolin stimulated cAMP production in NIH3T3 cells transfected with the 5-$HT_{1A}$ receptor. Adenylate cyclase activity is determined using standard techniques. A maximal effect is achieved by serotonin. An $E_{max}$ is determined by dividing the inhibition of a test compound by the maximal effect and determining a percent inhibition. (N. Adham, et al., supra,; R. L. Weinshank, et al., *Proceedings of the National Academy of Sciences* (*USA*), 89,3630–3634 (1992)), and the references cited therein.

Measurement of cAMP Formation

Transfected NIH3T3 cells (estimated Bmax from one point competition studies=488 fmol/mg of protein) are incubated in DMEM, 5 mM theophylline, 10 mM HEPES (4-[2-hydroxyethyl]-1-piperazineethanesulfonic acid) and 10 μM pargyline for 20 minutes at 37° C., 5% carbon dioxide. Drug dose-effect curves are then conducted by adding 6 different final concentrations of drug, followed immediately by the addition of forskolin (10 mM). Subsequently, the cells are incubated for an additional 10 minutes at 37° C., 5% carbon dioxide. The medium is aspirated and the reaction is stopped by the addition of 100 mM hydrochloric acid. To demonstrate competitive antagonism, a dose-response curve for 5-HT is measured in parallel, using a fixed dose of methiothepin (0.32 mM). The plates are stored at 4° C. for 15 minutes and then centrifuged for 5 minutes at 500×g to pellet cellular debris, and the supernatant is aliquoted and stored at −20° C. before assessment of cAMP formation by radioimmunoassay (cAMP radioimmunoassay kit; Advanced Magnetics, Cambridge, Mass.). Radioactivity is quantified using a Packard COBRA Auto Gamma counter, equipped with data reduction software. Representative compounds are tested for 5-$HT_{1A}$ receptor antagonist activity in the cAMP assay.

5$HT_{1A}$ Antagonist, In Vivo Tests a) 5$HT_{1A}$ Antagonism Subcutaneous Test

Compounds are tested over a range of subcutaneous doses for activity in blocking the 8-OH-DPAT induced behaviors and hypothermia. Lower lip retraction (LLR) and flat body posture (FBP) are recorded in male Sprague Dawley rats (~250 grams from Harlan Sprague Dawley). Both LLR and FBP are measured on a scale of 0–3 (Wolff et al, 1997). In the LLR behavioral assay, "0" indicates normal lip position; "1" indicates a slight separation of the lips; "2" indicates that the lips are open with some teeth visible; "3" indicates that the lips are fully open with all the front teeth exposed. In the FBP assay, a score of "0" indicates normal body posture; "1" indicates that the stomach is on the floor with the back in its normal rounded position; "2" indicates that the stomach is on the floor with the back straightened and rising from the shoulders to the hips; "3" indicates that the stomach is pressed into the floor and the back is flattened with the shoulders and hips even. Core body temperature is recorded by rectal probe inserted 5.0 cm immediately after the behavioral measures. Rats are injected subcutaneous with compound (at 0, 0.3, 1.0 and 3.0 mg/kg) 35 minutes before scoring and the 8-OH-DPAT (0.1 mg/kg subcutaneous) is injected 20 minutes before scoring.

b) 5HT$_{1A}$ Agonist Subcutaneous Test

The compounds are also tested at a high dose of 10 mg/kg subcutaneous alone to see if they induced 5HT$_{1A}$ agonist-like hypothermia.

The efficacy of the compounds of the invention to inhibit the reuptake of serotonin is determined by a paroxetine binding assay, the usefulness of which is set out by Wong, et al., *Neuropsychopharmacology*, 8, 23–33 (1993). Synaptosomal preparations from rat cerebral cortex are made from the brains of 100–150 g Sprague-Dawley rats which are killed by decapitation. The cerebral cortex is homogenized in 9 volumes of a medium containing 0.32 M sucrose and μM glucose. The preparations are resuspended after centrifugation by homogenizing in 50 volumes of cold reaction medium (50 μM sodium chloride, 50 μM potassium chloride, pH 7.4) and centrifuging at 50,000 g for 10 minutes. The process is repeated two times with a 10-minute incubation at 37° C. between the second and third washes. The resulting pellet is stored at −70° C. until use. Binding of $^3$H-paroxetine to 5-HT uptake sites is carried out in 2 ml reaction medium containing the appropriate drug concentration, 0.1 nM $^3$H-paroxetine, and the cerebral cortical membrane (50 μg protein/tube). Samples are incubated at 37° C. for 30 minutes; those containing 1 μM fluoxetine are used to determine nonspecific binding of $^3$H-paroxetine. After incubation, the tubes are filtered through Whatman GF/B filters, which are soaked in 0.05% polyethylenimine for 1 hour before use, using a cell harvester by adding about 4 ml cold Tris buffer (pH 7.4), aspirating, and rinsing the tubes three additional times. Filters are then placed in scintillation vials containing 10 mL scintillation fluid, and the radioactivity is measured by liquid scintillation spectrophotometry.

The pharmacological activities which have been described immediately above provide the mechanistic basis for the pharmaceutical utility of the compounds described in this document. A number of pharmaceutical utilities will be described below.

The activity of the compounds at the serotonin 1$_A$ receptor provides a method of affecting the serotonin 1$_A$ receptor which comprises administering to a patient in need of such treatment an effective amount of a compound of formula 1. Reasons for the necessity of affecting the serotonin 1$_A$ receptor will be described in detail below, but in all cases the effect on the serotonin 1$_A$ receptor is brought about through the compounds' potency as antagonists or partial agonists at that receptor. A patient in need of a modification of the effects. of the 5-HT$_{1A}$ receptor is one having one, or more of the specific conditions and problems to be further described, or a condition or problem not yet recognized as created by an imbalance or malfunction of the 5-HT$_{1A}$ receptor, since research on the central nervous system is presently ongoing in many fields and newly discovered relationships between receptors and therapeutic needs are continually being discovered. In all cases, however, it is the compounds' ability to affect the serotonin 1$_A$ receptor which creates their physiological or therapeutic effects.

Further, the activity of compounds of formula I in the inhibition of the reuptake of serotonin provides a method of inhibiting the reuptake of serotonin comprising administering to a patient in need of such treatment an effective amount of a compound of that formula. The treatment of depression with drugs of the class of which fluoxetine is the leader has become perhaps the greatest medical breakthrough of the past decade. Numerous other treatment methods carried out by the administration of the compounds of formula I will be set out in detail below.

The unique combination of 5-HT$_{1A}$ receptor activity and serotonin reuptake inhibition possessed by the compounds of the invention afford a method of providing to a patient both physiological activities with a single administration of a compound of that formula. As discussed in the Background section of this document, the value of combining the two effects has been discussed in the literature, and it is believed that the present compounds are advantageous in that they provide both physiological effects in a single drug. It is presently believed that the result of administration of a compound of formula I is to provide physiological and therapeutic treatment methods which are typical of those provided by presently known serotonin reuptake inhibitors, but with enhanced efficacy and quicker onset of action.

The activities of compounds of formula I at the 5-HT$_{1A}$ receptor and in reuptake inhibition are of comparable potencies, so an effective amount as defined hereinabove for affecting the serotonin 1$_A$ receptor or for inhibiting the reuptake of serotonin, is effective for affecting the serotonin 1$_A$ receptor and for inhibiting the reuptake of serotonin in a patient.

Further discussion of specific therapeutic methods provided by the dual activity compounds of formula I, and the diseases and conditions advantageously treated therewith, are provided below.

The compounds of the present invention are useful for binding, blocking or modulating the serotonin 1$_A$ receptor, and for the treatment of conditions caused by or influenced by defective function of that receptor. In particular, the compounds are useful for antagonism at the serotonin 1$_A$ receptor, and accordingly, are useful for the treatment of conditions caused by or affected by excessive activity of that receptor.

More particularly, the compounds are useful in the treatment of anxiety, depression, hypertension, cognitive disorders, Alzheimer's disease, psychosis, sleep disorders, gastric motility disorders, sexual dysfunction, brain trauma, memory loss, appetite disorders, bulimia, obesity, substance abuse, obsessive-compulsive disease, panic disorder and migraine.

Depression in its many variations has recently become much more visible to the general public than it has previously been. It is now recognized as an extremely damaging disorder, and one that afflicts a surprisingly large fraction of the human population. Suicide is the most extreme symptom of depression, but millions of people, not quite so drastically afflicted, live in misery and partial or complete uselessness, and afflict their families as well by their affliction. The introduction of fluoxetine was a breakthrough in the treatment of depression, and depressives are now much more likely to be diagnosed and treated than they were only a decade ago.

Depression is often associated with other diseases and conditions, or caused by such other conditions. For example, it is associated with Parkinson's disease; with HIV; with Alzheimer's disease; and with abuse of anabolic steroids. Depression may also be associated with abuse of any substance, or may be associated with behavioral problems resulting from or occurring in combination with head injuries, mental retardation or stroke. Depression in all its variations is a preferred target of treatment with the compounds of the present invention.

Obsessive-compulsive disease appears in a great variety of degrees and symptoms, generally linked by the victim's uncontrollable urge to perform needless, ritualistic acts. Acts of acquiring, ordering, cleansing and the like, beyond any rational need or rationale, are the outward characteristic of the disease. A badly afflicted patient may be unable to do anything but carry out the rituals required by the disease. Fluoxetine is approved in the United States and other countries for the treatment of obsessive-compulsive disease and has been found to be effective.

Obesity is a frequent condition in the American population. It has been found that fluoxetine will enable an obese patient to lose weight, with the resulting benefit to the circulation and heart condition, as well as general well is being and energy.

Urinary incontinence is classified generally as stress or urge incontinence, depending on whether its root cause is the inability of the sphincter muscles to keep control, or the overactivity of the bladder muscles.

The present treatment methods are useful for treating many other diseases, disorders and conditions as well, as set out below. In many cases, the diseases to be mentioned here are classified in the International Classification of Diseases, 9th Edition (ICD), or in the Diagnostic and Statistical Manual of Mental Disorders, 3rd Version Revised, published by the American Psychiatric Association (DSM). In such cases, the ICD or DSM code numbers are supplied below for the convenience of the reader.

depression, ICD 296.2 & 296.3, DSM 296, 294.80, 293.81, 293.82, 293.83, 310.10, 318.00, 317.00
migraine
pain, particularly neuropathic pain
bulimia, ICD 307.51, DSM 307.51
premenstrual syndrome or late luteal phase syndrome, DSM 307.90
alcoholism, ICD 305.0, DSM 305.00 & 303.90
tobacco abuse, ICD 305.1, DSM 305.10 & 292.00
panic disorder, ICD 300.01, DSM 300.01 & 300.21
anxiety, ICD 300.02, DSM 300.00
post-traumatic syndrome, DSM 309.89
memory loss, DSM 294.00
dementia of aging, ICD 290
social phobia, ICD 300.23, DSM 300.23
attention deficit hyperactivity disorder, ICD 314.0
disruptive behavior disorders, ICD 312
impulse control disorders, ICD 312, DSM 312.39 & 312.34
borderline personality disorder, ICD 301.83, DSM 301.83
chronic fatigue syndrome
premature ejaculation, DSM 3.02.75
erectile difficulty, DSM 302.72
anorexia nervosa, ICD 307.1, DSM 307.10
disorders of sleep, ICD 307.4
autism
mutism
trichotillomania Anxiety and its frequent concomitant, panic disorder, may be particularly mentioned in connection with the present compounds. The subject is carefully explained by the Diagnostic and Statistical Manual of Mental Disorders, published by the American Psychiatric Association, which classifies anxiety under its category 300.02.

In addition, the unique combination of pharmacological properties possessed by the compounds of formula I permit those compounds to be used in a method of simultaneously treating anxiety and depression. The anxiety portion of the combined syndrome is believed to be attacked by the 5-HT$_{1A}$ receptor-affecting property of the compounds, and the depression portion of the condition is believed to be addressed by the serotonin reuptake inhibition property. Thus, administration of an effective amount, which is determined in an analogous manner as discussed hereinabove, of a compound of formula I, will provide a method of simultaneously treating anxiety and depression.

It is well known that the chronic administration of nicotine results in tolerance and, eventually, dependence. The use of tobacco has become extremely widespread in all countries, despite the well known adverse effects of the use of tobacco in all its forms. Thus, it is clear that tobacco use is extremely habit-forming, if not addictive, and that its use provides sensations to the user which are pleasant and welcome, even though the user may be fully aware of the drastic long term ill effects of its use.

Rather recently, vigorous campaigns against the use of tobacco have taken place, and it is now common knowledge that the cessation of smoking brings with it numerous unpleasant withdrawal symptoms, which include irritability, anxiety, restlessness, lack of concentration, lightheadedness, insomnia, tremor, increased hunger and weight gain, and, of course, a craving for tobacco.

At the present time, probably the most widely used therapy to assist the cessation of tobacco use is nicotine replacement, by the use of nicotine chewing gum or nicotine-providing transdermal patches. It is widely known, however, that nicotine replacement is less effective without habit-modifying psychological treatment and training.

Thus, the present method of preventing or alleviating the symptoms caused by withdrawal or partial withdrawal from the use of tobacco or of nicotine comprises the previously discussed method of affecting the serotonin $1_A$ receptor, in that the treatment method comprises the administration to a patient an effective amount of a compound of formula I. The method of the present invention is broadly useful in assisting persons who want to cease or reduce their use of tobacco or nicotine. Most commonly, the form of tobacco use is smoking, most commonly the smoking of cigarettes. The present invention is also helpful, however, in assisting in breaking the habit of all types of tobacco smoking, as well as the use of snuff, chewing tobacco, etc. The present method is also helpful to those who have replaced, or partially replaced, their use of tobacco with the use of nicotine replacement therapy. Thus, such patients can be assisted to reduce and even eliminate entirely their dependence on nicotine in all forms.

A particular benefit of therapy with the present compounds is the elimination or reduction of the weight gain which very often results from reducing or withdrawing from use of tobacco or nicotine.

It will be understood that the present invention is useful for preventing or alleviating the withdrawal symptoms which afflict patients who are trying to eliminate or reduce their use of tobacco or nicotine. The common withdrawal symptoms of such people include, at least, irritability, anxiety, restlessness, lack of concentration, insomnia, nervous tremor, increased hunger and weight gain, light-headedness, and the craving for tobacco or nicotine. The prevention or alleviation of such symptoms, when they are caused by or occur in conjunction with ceasing or reducing the patient's use of tobacco or nicotine, is a desired result of the present invention and an important aspect of it.

The invention is carried out by administering an effective amount of a compound of formula I to a patient who is in need of or carrying out a reduction or cessation of tobacco or nicotine use.

As used herein, the term "Patient" refers to a mammal such as a dog, cat, guinea pig, mouse, rat, monkey, or human being. It is understood that a human being is the preferred patient.

As used herein, the terms "treating" or "to treat" each mean to alleviate symptoms, eliminate the causation either on a temporary or permanent basis, or to prevent or slow the appearance of symptoms of the named disorder.

As used herein, the term "effective amount" refers to the amount of a compound of formula (I) which is effective, upon single or multiple dose administration to a patient, in treating the patient suffering from the named disorder. The effective amount of compound to be administered, in general, is from about 1 to about 200 mg/day. The daily dose may be administered in a single bolus, or in divided doses, depending on the judgment of the physician in charge of the case. A more preferred range of doses is, from about 5 to about 100 mg/day; other dosage ranges which may be preferred in certain circumstances are from about 10 to about 50 mg/day; from about 5 to about 50 mg/day; from about 10 to about 25 mg/day; and a particularly preferred range is from about 20 to about 25 mg/day.

An effective amount can be readily determined by the attending diagnostician, as one skilled in the art, by the use of known techniques and by observing results obtained under analogous circumstances. In determining the effective amount or dose, a number of factors are considered by the attending diagnostician, including, but not limited to: the species of mammal; its size, age, and general health; the specific disease or disorder involved; the degree of or involvement or the severity of the disease or disorder; the response of the individual patient; the particular compound administered; the mode of administration; the bioavailability characteristics of the preparation administered; the dose regimen selected; the use of concomitant medication; and other relevant circumstances.

In effecting treatment of a patient afflicted with a condition, disease or disorder described above, a compound of formula (I) can be administered in any form or mode which makes the compound bioavailable in effective amounts, including oral and parenteral routes. For example, compounds of formula (I) can be administered orally, subcutaneously, intramuscularly, intravenously, transdermally, intranasally, rectally, and the like. Oral administration is generally preferred. One skilled in the art of preparing formulations can readily select the proper form and mode of administration depending upon the particular characteristics of the compound selected, the disease state to be treated, the stage of the disease, and other relevant circumstances.

It is understood that, while the compounds of formula I individually provide the benefit of the combination of serotonin reuptake inhibitors and serotonin $1_A$ antagonists, it is entirely possible to administer a compound of formula I in combination with a conventional serotonin reuptake inhibitor in order to obtain still further enhanced results in potentiating serotonin reuptake inhibition. Examples of representative serotonin reuptake inhibitors include but are not limited to the following:

Fluoxetine, N-methyl-3-(p-trifluoromethylphenoxy)-3-phenylpropylamine, is marketed in the hydrochloride salt form, and as the racemic mixture of its two enantiomers. U.S. Pat. No. 4,314,081 is an early reference on the compound. Robertson, et al., *J. Med. Chem.* 31, 1412 (1988), taught the separation of the R and S enantiomers of fluoxetine and showed that their activity as serotonin uptake inhibitors is similar to each other. In this document, the word "fluoxetine" will be used to mean any acid addition salt or the free base, and to include either the racemic mixture or either of the R and S enantiomers.

Duloxetine, N-methyl-3-(1-naphthalenyloxy)-3-(2-thienyl)propanamine, is usually administered as the hydrochloride salt and as the (+) enantiomer. It was first taught by U.S. Pat. No. 4,956,388, which shows its high potency. The word "duloxetine" will be used here to refer to any acid addition salt or the free base of the molecule.

Venlafaxine is known in the literature, and its method of synthesis and its activity as an inhibitor of serotonin and norepinephrine uptake are taught by U.S. Pat. No. 4,761,501. Venlafaxine is identified as compound A in that patent.

Milnacipran (N,N-diethyl-2-aminomethyl-1-phenylcyclopropanecarboxamide) is taught by U.S. Pat. No. 4,478,836, which prepared milnacipran as its Example 4. The patent describes its compounds as antidepressants. Moret, et al., *Neuropharmacology* 24, 1211–19 (1985), describe its pharmacological activities.

Citalopram, 1-[3-(dimethylamino)propyl]-1-(4-fluorophenyl)-1,3-dihydro-5-isobenzofurancarbonitrile, is disclosed in U.S. Pat. No. 4,136,193 as a serotonin reuptake inhibitor. Its pharmacology was disclosed by Christensen, et al., *Eur. J. Pharmacol.* 41, 153 (1977), and reports of its clinical effectiveness in depression may be found in Dufour, et al., *Int. Clin. Psychopharmacol.* 2, 225 (1987), and Timmerman, et al., ibid., 239.

Fluvoxamine, 5-methoxy-1-[4-(trifluoromethyl)phenyl]-1-pentanone O-(2-aminoethyl)oxime, is taught by U.S. Pat. No. 4,085,225. Scientific articles about the drug have been published by Claassen, et al., *Brit. J. Pharmacol.* 60, 505 (1977); and De Wilde, et al., *J. Affective Disord.* 4, 249 (1982); and Benfield, et al., *Drugs* 32, 313 (1986).

Sertraline, 1-(3,4-dichlorophenyl)-4-methylaminotetralin, is disclosed in U.S. Pat. No. 4,536,518.

Paroxetine, trans-(−)-3-[(1,3-benzodioxol-5-yloxy)methyl]-4-(4-fluorophenyl)piperidine, may be found in U.S. Pat. Nos. 3,912,743 and 4,007,196. Reports of the drug's activity are in Lassen, *Eur. J. Pharmacol.* 47, 351 (1978); Hassan, et al., *Brit. J. Clin. Pharmacol.* 19, 705 (1985); Laursen, et al., *Acta Psychiat. Scand.* 71, 249 (1985); and Battegay, et al., *Neuropsychobiology* 13, 31 (1985).

All of the U.S. patents which have been mentioned above in connection with compounds used in the present invention are incorporated herein by reference.

Fluoxetine or duloxetine are the preferred SRIs in pharmaceutical compositions combining a compound of formula I and an SRI, and the corresponding methods of treatment.

It will be understood by the skilled reader that all of the compounds used in the present invention are capable of forming salts, and that the salt forms of pharmaceuticals are commonly used, often because they are more readily crystallized and purified than are the free bases. In all cases, the use of the pharmaceuticals described above as salts is contemplated in the description herein, and often is preferred, and the pharmaceutically acceptable salts of all of the compounds are included in the names of them.

The dosages of the drugs used in the present combination must, in the final analysis, be set by the physician in charge of the case, using knowledge of the drugs, the properties of the drugs in combination as determined in clinical trials, and the characteristics of the patient, including diseases other than that for which the physician is treating the patient. General outlines of the dosages, and some preferred human dosages, can and will be provided here. Dosage guidelines for some of the drugs will first be given separately; in order to create a guideline for any desired combination, one would choose the guidelines for each of the component drugs.

Fluoxetine: from about 1 to about 80 mg, once/day; preferred, from about 10 to about 40 mg once/day; preferred for bulimia and obsessive-compulsive disease, from about 20 to about 80 mg once/day;

Duloxetine: from about 1 to about 30 mg once/day; preferred, from about 5 to about 20 mg once/day;

Venlafaxine: from about 10 to about 150 mg once-thrice/day; preferred, from about 25 to about 125 mg thrice/day;

Milnacipran: from about 10 to about 100 mg once-twice/day; preferred, from about 25 to about 50 mg twice/day;

Citalopram: from about 5 to about 50 mg once/day; preferred, from about 10 to about 30 mg once/day;

Fluvoxamine: from about 20 to about 500 mg once/day; preferred, from about 50 to about 300 mg once/day;

Paroxetine: from about 5 to about 100 mg once/day; preferred, from about 50 to about 300 mg once/day.

In more general terms, one would create a combination of the present invention by choosing a dosage of SRI according to the spirit of the above guideline, and choosing a dosage of the compound of formula I in the ranges taught above.

The adjunctive therapy of the present invention is carried out by administering a SRI together with a compound of formula I in any manner which provides effective levels of the two compounds in the body at the same time. All of the compounds concerned are orally available and are normally administered orally, and so oral administration of the adjunctive combination is preferred. They may be administered together, in a single dosage form, or may be administered separately.

However, oral administration is not the only route or even the only preferred route. For example, transdermal administration may be very desirable for patients who are forgetful or petulant about taking oral medicine. One of the drugs may be administered by one route, such as oral, and the other may be administered by the trans-dermal, percutaneous, intravenous, intramuscular, intranasal or intrarectal route, in particular circumstances. The route of administration may be varied in any way, limited by the physical properties of the drugs and the convenience of the patient and the caregiver.

It is particularly preferred, however, for the adjunctive combination to be administered as a single pharmaceutical composition, and so pharmaceutical compositions incorporating both a SRI and a compound of formula I are important embodiments of the present invention. Such compositions may take any physical form which is pharmaceutically acceptable, but orally usable pharmaceutical compositions are particularly preferred. Such adjunctive pharmaceutical compositions contain an effective amount of each of the compounds, which effective amount is related to the daily dose of the compounds to be administered. Each adjunctive dosage unit may contain the daily doses of both compounds, or may contain a fraction of the daily doses, such as one-third of the doses. Alternatively, each dosage unit may contain the entire dose of one of the compounds, and a fraction of the dose of the other compound. In such case, the patient would daily take one of the combination dosage units, and one or more units containing only the other compound. The amounts of each drug to be contained in each dosage unit depends on the identity of the drugs chosen for the therapy, and other factors such as the indication for which the adjunctive therapy is being given.

As stated above, the benefit of the adjunctive therapy is its ability to augment the increase in availability of serotonin, norepinephrine and dopamine caused by the SRI compounds, resulting in improved activity in treating the various conditions described below in detail. The increase in availability of serotonin is particularly important and is a preferred aspect of the invention. Further, the invention provides a more rapid onset of action than is usually provided by treatment with the SRI alone.

Pharmaceutical Compositions

The present invention provides pharmaceutical compositions of compounds of formula I, including the hydrates thereof, comprising, as an active ingredient, a compound of formula I in admixture or otherwise in association with one or more pharmaceutically acceptable carriers, diluents or excipients. It is customary to formulate pharmaceuticals for administration, to provide control of the dosage and stability of the product in shipment and storage, and the usual methods of formulation are entirely applicable to the compounds of formula 1. Such pharmaceutical compositions are valuable and novel because of the presence of the compounds of formula I therein. Although pharmaceutical chemists are well aware of many effective ways to formulate pharmaceuticals, which technology is applicable to the present compounds, some discussion of the subject will be given here for the convenience of the reader.

The usual methods of formulation used in pharmaceutical science and the usual types of compositions may be used according to the present invention, including tablets, chewable tablets, capsules, solutions, parenteral solutions, intranasal sprays or powders, troches, suppositories, transdermal patches and suspensions. In general, pharmaceutical compositions contain from about 0.5% to about 50% of the compound of formula (I) in total, depending on the desired dose and the type of composition to be used. The amount of the compound of formula (I), however, is best defined as the effective amount, that is, the amount of each compound which provides the desired dose to the patient in need of such treatment. The activity of the compounds do not depend on the nature of the composition, so the compositions are chosen and formulated solely for convenience and economy. Any compound may be formulated in any desired form of composition. Some discussion of different compositions will be provided, followed by some typical formulations.

Capsules are prepared by mixing the compound with a suitable diluent and filling the proper amount of the mixture in capsules. The usual diluents include inert powdered substances such as starch of many different kinds, is powdered cellulose, especially crystalline and microcrystalline cellulose, sugars such as fructose, mannitol and sucrose, grain flours and similar edible powders.

Tablets are prepared by direct compression, by wet granulation, or by dry granulation. Their formulations usually incorporate diluents, binders, lubricants and disintegrators as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant is necessary in a tablet formulation to prevent the tablet and punches from sticking in the die. The lubricant is chosen from such slippery solids as talc, magnesium and calcium stearate, stearic acid and hydrogenated vegetable oils.

Tablet disintegrators are substances which swell when wetted to break up the tablet and release the compound. They include starches, clays, celluloses, algins and gums. More particularly, corn and potato starches, methylcellulose, agar, bentonite, wood cellulose, powdered natural sponge, cation-exchange resins, alginic acid, guar gum, citrus pulp and carboxymethylcellulose, for example, may be used, as well as sodium lauryl sulfate.

Enteric formulations are often used to protect an active ingredient from the strongly acidic contents of the stomach. Such formulations are created by coating a solid dosage form with a film of a polymer which is insoluble in acidic environments, and soluble in basic environments. Exemplary films are cellulose acetate phthalate, polyvinyl acetate phthalate, hydroxypropyl methylcellulose phthalate and hydroxypropyl methylcellulose acetate succinate.

Tablets are often coated with sugar as a flavor and sealant, or with film-forming protecting agents to modify the dissolution properties of the tablet. The compounds may also be formulated as chewable tablets, by using large amounts of pleasant-tasting substances such as mannitol in the formulation, as is now well-established practice. Instantly dissolving tablet-like formulations are also now frequently used to assure that the patient consumes the dosage form, and to avoid the difficulty in swallowing solid objects that bothers some patients.

When it is desired to administer the combination as a suppository, the usual bases may be used. Cocoa butter is a traditional suppository base, which may be modified by addition of waxes to raise its melting point slightly. Water-miscible suppository bases comprising, particularly, polyethylene glycols of various molecular weights are in wide use, also.

Transdermal patches have become popular recently. Typically they comprise a resinous composition in which the drugs will dissolve, or partially dissolve, which is held in contact with the skin by a film which protects the composition. Many patents have appeared in the field recently. Other, more complicated patch compositions are also in use, particularly those having a membrane pierced with pores through which the drugs are pumped by osmotic action.

The following typical formulae are provided for the interest and information of the pharmaceutical scientist.

Formulation 1

Hard gelatin capsules are prepared using the following ingredients:

|  | Quantity (mg/capsule) |
| --- | --- |
| Example #1 | 20 mg |
| Starch, dried | 200 mg |
| Magnesium stearate | 10 mg |
| Total | 230 mg |

As with any group of structurally related compounds which possess a particular generic utility, certain groups and configurations are preferred for compounds of formula I or formula Ia.

With respect to substituent $R^1$, compounds wherein $R^1$ is hydrogen, F, methyl, ethyl, —C(=O)NR$^8$R$^9$, or CN are preferred, with hydrogen, methyl, and —C(=O)NH$_2$ being especially preferred.

With respect to substituent A, compounds wherein A is hydroxy are preferred. In addition, it is further preferred that when A is hydroxy, it is in the (S)-configuration.

With respect to substituent m, compounds wherein m is 0 or 1 are preferred.

With respect to substituent n, compounds wherein n is 1 or 2 are preferred.

With respect to substituents p and q, compounds wherein p and q are both one are preferred.

With respect to substituent X, compounds wherein X is hydrogen are preferred.

With respect to substituent $R^2$, compounds wherein $R^2$ is hydrogen, F, Cl, Br, methyl or methoxy are preferred, with hydrogen being especially preferred.

With respect to substituent $R^3$, compounds wherein $R^3$ is hydrogen, methyl, ethyl or propyl are preferred with hydrogen and methyl being especially preferred.

With respect to substituent $R^4$, compounds wherein $R^4$ is hydrogen, methyl, ethyl or propyl are preferred, with hydrogen and methyl being especially preferred.

With respect to substituent $R^5$, compounds wherein $R^5$ is hydrogen, F, Cl, Br, I OH, $C_1$–$C_6$ alkyl, $C_1$–$C_6$ alkoxy, halo($C_1$–$C_6$) alkyl, phenyl, substituted phenyl, C(=O)NR$_8$R$_9$, NO$_2$, NH$_2$, and CN are preferred, with hydrogen, F, Cl, Br, methyl, ethyl, propyl, isopropyl, methoxy, ethoxy, propoxy and isopropoxy being especially preferred.

With respect to substituent $R^6$, compounds wherein $R^6$ is hydrogen, F, Cl, Br, I OH, $C_1$–$C_6$ alkyl, $C_1$–$C_6$ alkoxy, halo($C_1$–$C_6$) alkyl, phenyl, substituted phenyl, C(=O)NR$_8$R$_9$, NO$_2$, NH$_2$, and CN are preferred, with hydrogen, F, Cl, Br, methyl, ethyl, propyl, isopropyl, methoxy, ethoxy, propoxy and isopropoxy being especially preferred.

With respect to substituent $R^7$, compounds wherein $R^7$ is hydrogen, F, Cl, Br, methyl, ethyl, propyl, isopropyl or butyl are preferred, with methyl, ethyl, and propyl being especially preferred.

With respect to substituent $R^8$, compounds wherein $R^8$ is hydrogen, methyl, ethyl, propyl, isopropyl or butyl are preferred.

With respect to substituent $R^9$, compounds wherein $R^9$ is hydrogen, methyl, ethyl, propyl, isopropyl or butyl are preferred.

With respect to the piperidine portion of formula I, compounds with the following substitutions are preferred:

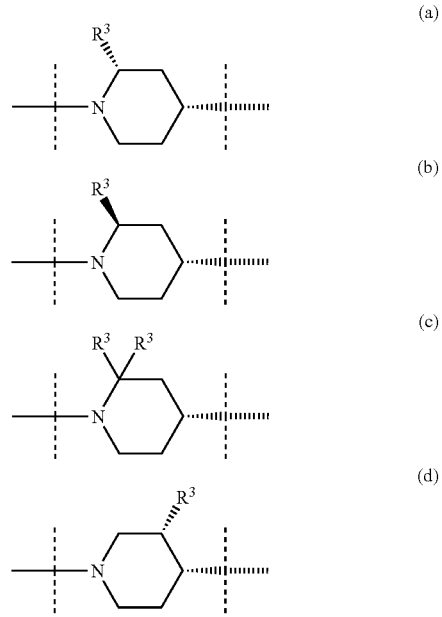

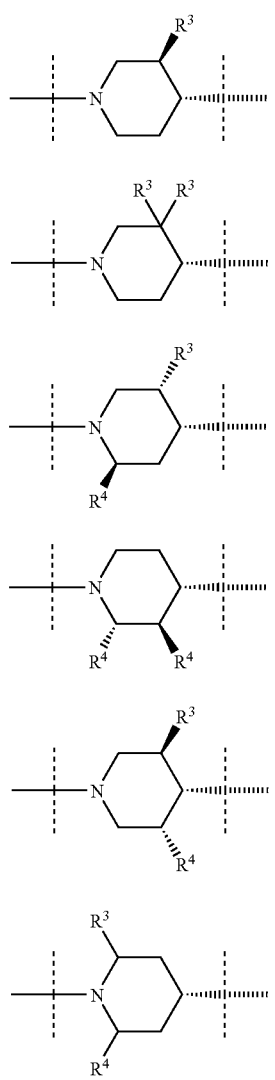
With respect substituent B, compounds with the following substitutions are preferred:
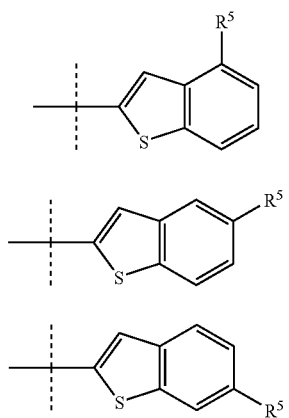
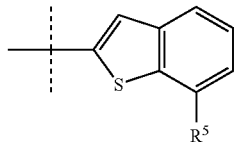
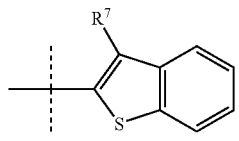
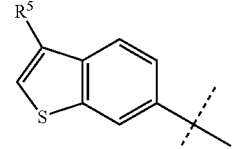
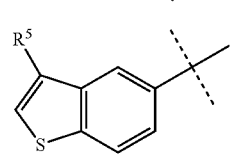
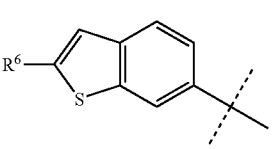
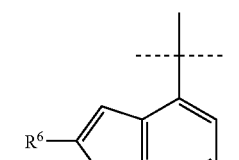
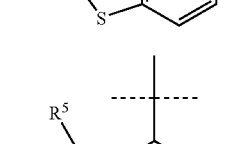
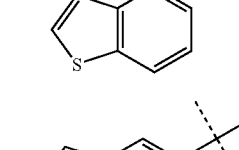
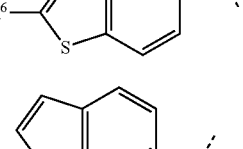
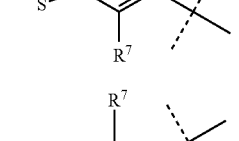
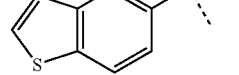

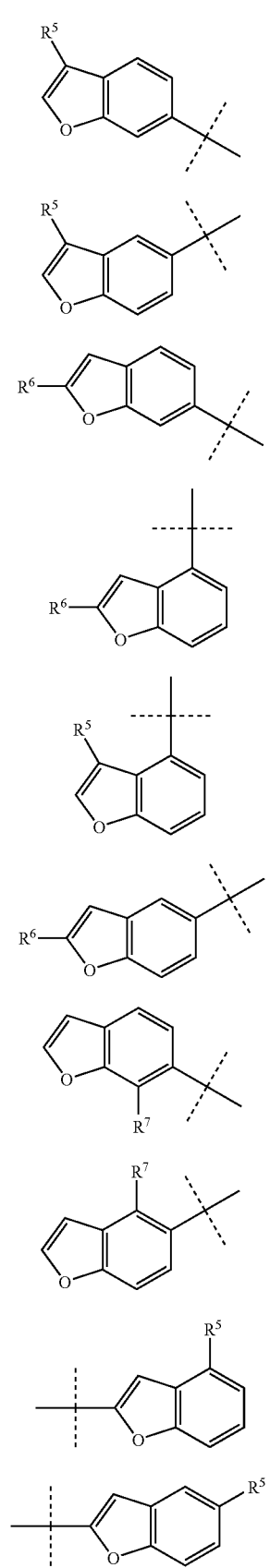
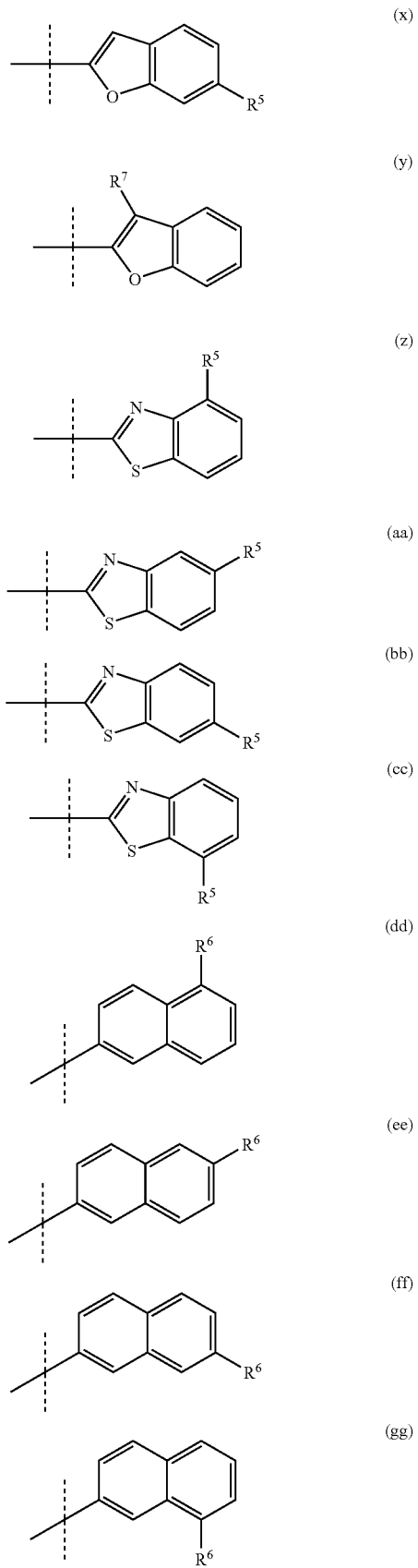

-continued
(hh) 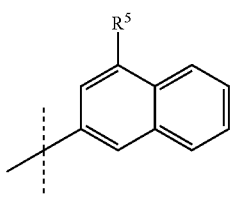
(ii) 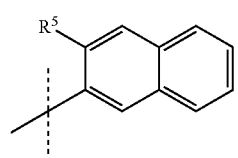
(jj) 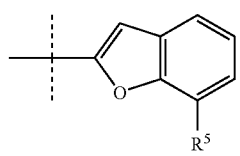
More specifically, as shown in Table I, the following substituents represented by B are especially preferred:
TABLE I
| | Substituent B |
|---|---|
| a | 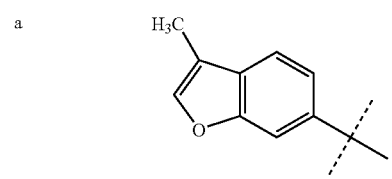 |
| b | 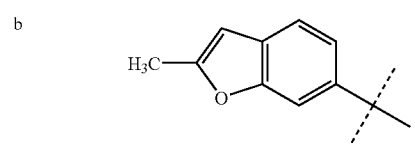 |
| c | 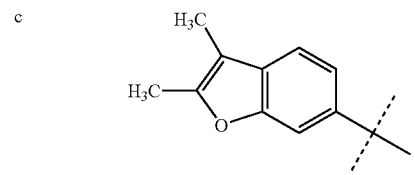 |
| d | 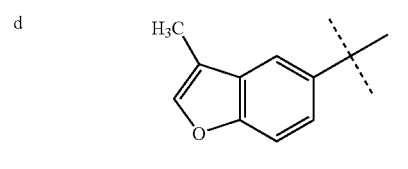 |
| e | 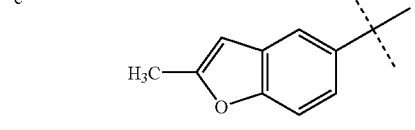 |
TABLE I-continued
| | Substituent B |
|---|---|
| f | |
| g | |
| h | |
| i | |
| j | |
| k | |
| l | |
| m | |
| n | |
| o | |

TABLE I-continued
| | Substituent B | | Substituent B |
|---|---|---|---|
| p | 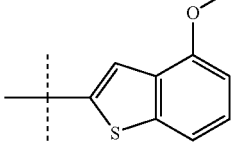 | aa | 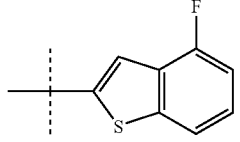 |
| q | 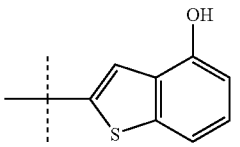 | bb | 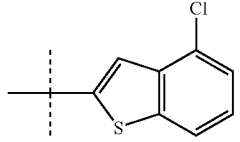 |
| r | 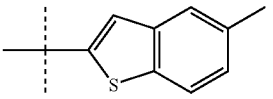 | cc | 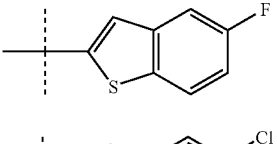 |
| s | 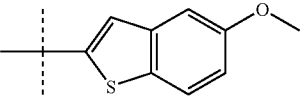 | dd | 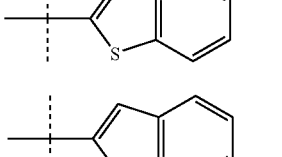 |
| t | 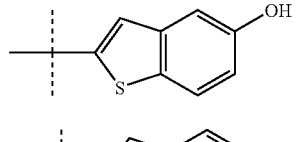 | ee | 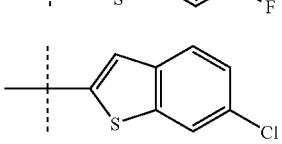 |
| u | 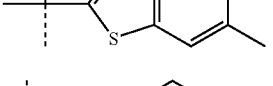 | ff | 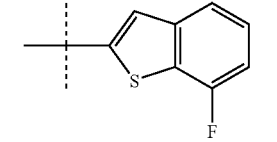 |
| v | 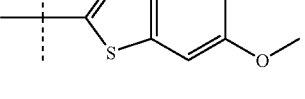 | gg | 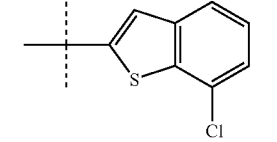 |
| w | 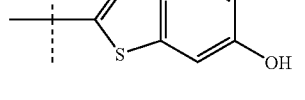 | hh | 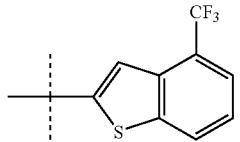 |
| x | 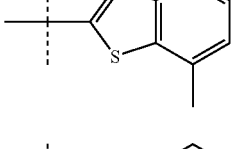 | ii | 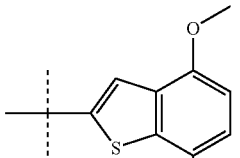 |
| y | 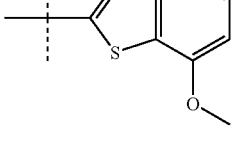 | jj |  |
| z | 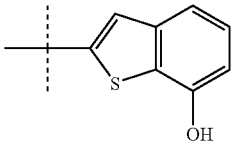 | | |

In addition, compounds of formula Ia'
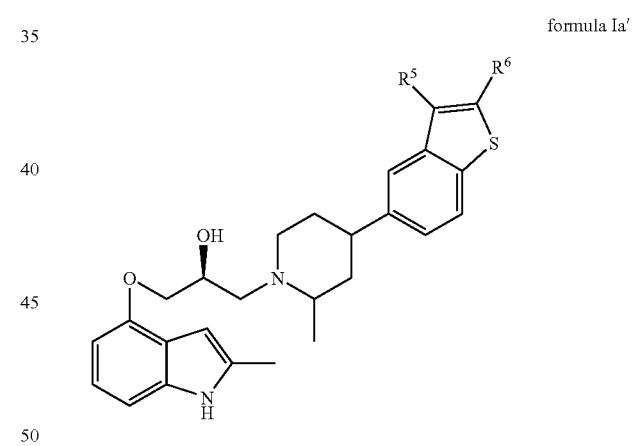
formula Ia'
wherein $R^5$ and $R^6$ are each independently hydrogen or $C_1$–$C_4$ alkyl, with the, proviso that at least one of $R^5$ and $R^6$ are other than hydrogen are most especially preferred.
We claim:
1. A compound of the formula:
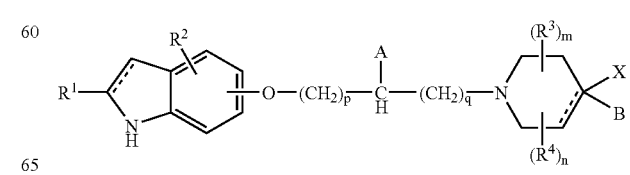

wherein
A is hydrogen or OH:
B is selected from the group consisting of:

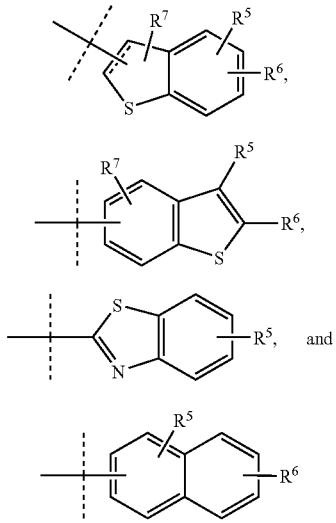

(a)

(b)

(c)

(d)

- - - - - represents a single or a double bond;
X is hydrogen, OH or $C_1$–$C_6$ alkoxy when - - - - - represents a single bond in the piperidine ring, and X is nothing when - - - - - represents a double bond piperidine ring;
$R^1$ is hydrogen, F, $C_1$–$C_{20}$ alkyl, —C(=O)NR$^8$R$^9$, or CN;
$R^2$ is hydrogen, F, Cl, Br, I, OH, $C_1$–$C_6$ alkyl or $C_1$–$C_6$ alkoxy;
$R^3$ and $R^4$ are each independently hydrogen or $C_1$–$C_4$ alkyl;
$R^5$ and $R^6$ are each independently hydrogen, F, Cl, Br, I, OH, $C_1$–$C_6$ alkyl, $C_1$–$C_6$alkoxy, halo($C_1$–$C_6$)alkyl, phenyl, —C(=O)NR$^8$R$^9$, NO$_2$, NH$_2$, CN, or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, NO$_2$, NH$_2$, CN, and phenyl;
$R^7$ is hydrogen, F, Cl, Br, I, OH, $C_1$–$C_6$ alkyl or ($C_1$–$C_6$ alkyl)NR$^8$R$^9$;
$R^8$ and $R^9$ are each independently hydrogen or $C_1$–$C_{10}$ alkyl;
m is 0, 1, or 2;
n is 0, 1, or 2;
p is 0, 1, 2, 3 or 4; and
q is 0, 1, 2 or 3; or a pharmaceutically acceptable salt thereof;
with the proviso that if both $R^3$ and $R^4$ represent hydrogen, then $R^1$ is F, $C_1$–$C_{20}$ alkyl, —C(=O)NR$^8$R$^9$, or CN.

2. A compound of the formula:

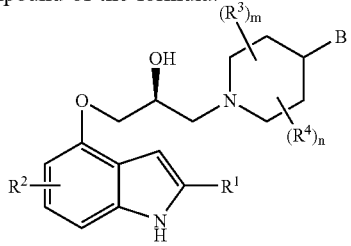

wherein
B is selected from the group consisting of:

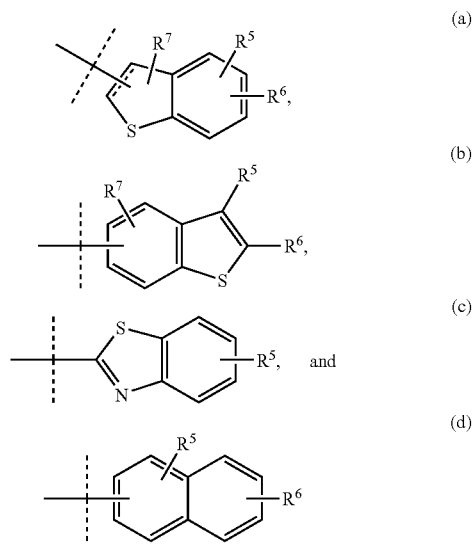

(a)

(b)

(c)

(d)

$R^1$ is hydrogen, F, $C_1$–$C_{20}$ alkyl, —C(=O)NR$^8$R$^9$, or CN;
$R^2$ is hydrogen, F, Cl, Br, I, OH, $C_1$–$C_6$ alkyl or $C_1$–$C_6$ alkoxy;
$R^3$ and $R^4$ are each independently hydrogen or $C_1$–$C_4$ alkyl;
$R^5$ and $R^6$ are each independently hydrogen, F, Cl, Br, I, OH, $C_1$–$C_6$ alkyl, $C_1$–$C_6$ alkoxy, halo($C_1$–$C_6$)alkyl, phenyl, —C(=O)NR$^8$R$^9$, NO$_2$, NH$_2$, CN, or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, NO$_2$, NH$_2$, CN, and phenyl;
$R^7$ is hydrogen, F, Cl, Br, I, OH, $C_1$–$C_6$ alkyl or ($C_1$–$C_6$ alkyl)NR$^8$R$^9$;
$R^8$ and $R^9$ are each independently hydrogen or $C_1$–$C_{10}$ alkyl;
m is 0, 1, or 2; and
n is 0, 1, or 2; or a pharmaceutically acceptable salt thereof;
with the proviso that if both $R^3$ and $R^4$ represent hydrogen, then $R^1$ is F, $C_1$–$C_{20}$ alkyl, —C(=O)NR$^8$R$^9$, or CN.

3. A compound according to claim 2 wherein $R^2$ is hydrogen.

4. A compound according to claim 3 wherein $R^1$ is hydrogen, methyl, or —C(=O)NH$_2$.

5. A compound according to claim 2 wherein $R^1$ is hydrogen or methyl.

6. A compound according to claim 2 wherein m is 0 and n is 1.

7. A compound according to claim 2 wherein $R^3$ is hydrogen and $R^4$ is methyl.

8. A compound according to claim 2 wherein B is:

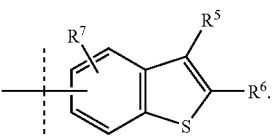

9. A compound according to claim 2 wherein $R^6$ and $R^7$ are hydrogen.

10. A compound according to claim 2 wherein B is:

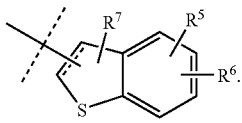

11. A compound according to claim 10 wherein $R^6$ and $R^7$ are hydrogen, and $R^5$ is methyl, methoxy, F, or Cl.

12. A method of treating depression comprising administering to a patient in need thereof an effective amount of a compound of formula:

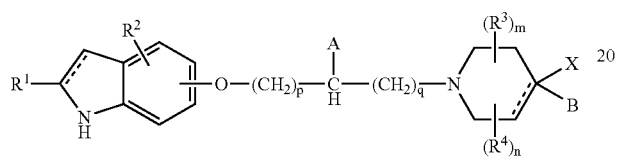

wherein
A is hydrogen or OH:
B is selected from the group consisting of:

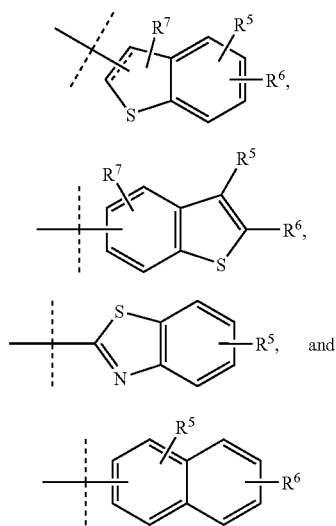

-----represents a single or a double bond;

X is hydrogen, OH or $C_1$–$C_6$ alkoxy when -----represents a single bond in the piperidine ring, and X is nothing when -----represents a double bond piperidine ring;

$R^1$ is hydrogen, F, $C_1$–$C_{20}$ alkyl, —C(=O)$NR^8R^9$, or CN;

$R^2$ is hydrogen, F, Cl, Br, I, OH, $C_1$–$C_6$ alkyl or $C_1$–$C_6$ alkoxy;

$R^3$ and $R^4$ are each independently hydrogen or $C_1$–$C_4$ alkyl;

$R^5$ and $R^6$ are each independently hydrogen, F, Cl, Br, I, OH, $C_1$–$C_6$ alkyl, $C_1$–$C_6$ alkoxy, halo($C_1$–$C_6$)alkyl, phenyl, —C(=O)$NR^8R^9$, $NO_2$, $NH_2$, CN, or phenyl substituted with from 1 to 3 substituents selected from the group consisting of F, Cl, Br, I, OH, $C_1$–$C_6$ alkyl, $C_1$–$C_6$ alkoxy, halo($C_1$–$C_6$)alkyl, $NO_2$, $NH_2$, CN, and phenyl;

$R^7$ is hydrogen, F, Cl, Br, I, OH, $C_1$–$C_6$ alkyl or ($C_1$–$C_6$ alkyl)$NR^8R^9$;

$R^8$ and $R^9$ are each independently hydrogen or $C_1$–$C_{10}$ alkyl;

m is 0, 1, or 2;

n is 0, 1, or 2;

p is 0, 1, 2, 3 or 4; and q is 0, 1, 2 or 3; or a pharmaceutically acceptable salt thereof;

with the proviso that if both $R^3$ and $R^4$ represent hydrogen, then $R^1$ is F, $C_1$–$C_{20}$ alkyl, —C(=O)$NR^8R^9$, or CN.

13. A pharmaceutical composition comprising an effective amount of a compound according to claim 1 in combination with a pharmaceutically acceptable carrier, diluent or excipient.

14. A compound which is trans-(2S,4R)-2-methyl-4-(3-methylbenzo[b]-thiophen-5-yl)piperidine D-(-)-tartrate.

15. A compound which is trans-(2S,4R)-2-methyl-4-(3-methylbenzo[b]-thiophen-5-yl)piperidine.

16. A compound which is cis-(2S)-(-)-3-(2-Methyl-4-(3-methylbenzo[b]thiophen-5-yl)piperidin-1-yl)-1-(2-methylindol-4-yl)oxy-2-propanol succinate.

17. A compound which is cis-(2S)-(-)-3-(2-Methyl-4-(3-methylbenzo[b]thiophen-5-yl)piperidin-1-yl)-1-(2-methylindol-4-yl)oxy-2-propanol.

18. A compound which is cis-(2S)-(-)-3-(2-Methyl-4-(3-methylbenzo[b]thiophen-5-yl)piperidin-1-yl)-1-(2-methylindol-4-yl)oxy-2-propanol succinate.

19. A compound which is cis-(2S)-(-)-3-(2-Methyl-4-(3-methylbenzo[b]thiophen-5-yl)piperidin-1-yl)-1-(2-methylindol-4-yl)oxy-2-propanol.

* * * * *